(12) United States Patent
Andersen et al.

(10) Patent No.: US 7,019,026 B1
(45) Date of Patent: Mar. 28, 2006

(54) MODULATORS OF PROTEIN TYROSINE PHOSPHATASES (PTPASES)

(75) Inventors: Henrik Sune Andersen, Lyngby (DK); Thomas Kruse Hansen, Herlev (DK); Jesper Lau, Farum (DK); Niels Peter Hundahl Møller, København Ø (DK); Ole Hvilsted Olsen, Brønshøj (DK); Frank Urban Axe, Escondido, CA (US); Yu Ge, San Diego, CA (US); Daniel Dale Holsworth, San Diego, CA (US); Todd Kevin Jones, Solana Beach, CA (US); Luke Milburn Judge, Seattle, WA (US); Wiliam Charles Ripka, San Diego, CA (US); Barry Zvi Shapira, La Jolla, CA (US); Roy Teruyuki Uyeda, San Diego, CA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/662,457

(22) Filed: Sep. 11, 2000

Related U.S. Application Data

(60) Provisional application No. 60/156,586, filed on Sep. 29, 1999.

(30) Foreign Application Priority Data

Sep. 10, 1999 (DK) ................ 1999 01278

(51) Int. Cl.
*A61K 31/381* (2006.01)
*C07D 409/04* (2006.01)

(52) U.S. Cl. ............ 514/443; 514/453; 514/456; 548/250; 548/452; 549/50

(58) Field of Classification Search ........... 549/23
See application file for complete search history.

(56) References Cited

U.S. PATENT DOCUMENTS 3,953,468 A  4/1976  Wechter et al. ....... 260/332.2 R 6,262,044 B1 *  7/2001  Moller ............... 514/202

FOREIGN PATENT DOCUMENTS

| GB | 1 583 679 | 1/1981 |
| WO | WO 99/46237 | 9/1999 |
| WO | WO 99/46267 | 9/1999 |
| WO | WO 99/46268 | 9/1999 |

OTHER PUBLICATIONS

Iversen et al., The Journal of Biological Chemistry, vol. 275, pp. 10300-10307 (2000).
Peters et al., The Journal of Biological Chemistry, vol. 275, pp. 18201-18209 (2000).

* cited by examiner

*Primary Examiner*—Kamal A. Saeed
(74) *Attorney, Agent, or Firm*—Marc A. Began, Esq.; Richard W. Bork, Esq.; Rosemarie R. Wilk-Orescan, Esq.

(57) ABSTRACT

Disclosed are novel compounds, novel compositions, methods of their use, and methods of their manufacture, where such compounds of Formula 1 are pharmacologically useful inhibitors of Protein Tyrosine Phosphatases (PTPases) such as PTP1B, CD45, SHP-1, SHP-2, PTPα, LAR and HePTP or the like, Formula 1

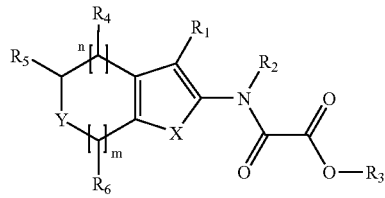

wherein n, m, X, Y, $R_1$, $R_2$, $R_3$, $R_4$, $R_5$ and $R_6$ are defined more fully in the description. The compounds are useful in the treatment of type I diabetes, type II diabetes, impaired glucose tolerance, insulin resistance, obesity, and other diseases.

74 Claims, No Drawings

MODULATORS OF PROTEIN TYROSINE PHOSPHATASES (PTPASES)

CROSS-REFERENCE-TO RELATED APPLICATIONS

This application claims priority under 35 USC 119 of U.S. provisional application No. 60/156,586 filed on Sep. 29, 1999 and Danish application no. PA 1999 01278 filed on Sep. 10, 1999, the contents of which are fully incorporated herein by reference.

FIELD OF THE INVENTION

The present invention relates to novel compounds, to methods for their preparation, to compositions comprising the compounds, to the use of these compounds as medicaments and their use in therapy, where such compounds of Formula 1 are pharmacologically useful inhibitors of Protein Tyrosine Phosphatases (PTPases) such as PTP1 B, CD45, SHP-1, SHP-2, PTPα, LAR and HePTP or the like,

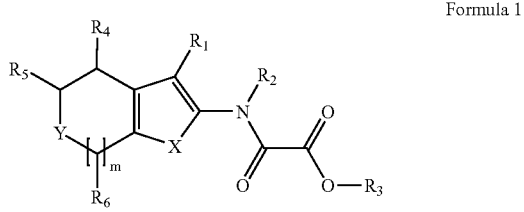

Formula 1 wherein n, m, X, Y, $R_1$, $R_2$, $R_3$, $R_4$, $R_5$ and $R_6$ are defined more fully below.

It has been found that PTPases plays a major role in the intracellular modulation and regulation of fundamental cellular signaling mechanisms involved in metabolism, growth, proliferation and differentiation (Hunter, Phil. Trans. R. Soc. Lond. B 353: 583–605 (1998); Chan et al., *Annu. Rev. Immunol.* 12: 555–592 (1994); Zhang, Curr. Top. Cell. Reg. 35: 21–68 (1997); Matozaki and Kasuga, *Cell, Signal* 8: 113–19 (1996, Flint et al., *The EMBO J.* 12: 1937–46 (1993); Fischer et al, *Science* 253:401–6 (1991)). Overexpression or altered activity of tyrosine phosphatases can also contribute to the symptoms and progression of various diseases (Wiener, et al., *J. Natl. Cancer Inst.* 86:372–8 (1994); Hunter and Cooper, *Ann. Rev. Biochem,* 54:897–930 (1985)). Furthermore, there is increasing evidence which suggests that inhibition of these PTPases may help treat certain types of diseases such as diabetes type I and II, autoimmune disease, acute and chronic inflammation, osteoporosis and various forms of cancer.
5252–263:1397-b-PTP-PTP-colony-270: 20824–16104 (1993), Brady—

BACKGROUND OF THE INVENTION

Protein phosphorylation is now well recognized as an important mechanism utilized by cells to transduce and regulate signals during different stages of cellular function (Hunter, *Phil. Trans. R. Soc. Lond.* B 353: 583–605 (1998); Chan et al., *Annu. Rev. Immunol.* 12: 555–592 (1994); Zhang, *Curr. Top. Cell. Reg.* 35: 21–68 (1997); Matozaki and Kasuga, *Cell. Signal.* 8: 113–19 (1996); Fischer et al, *Science* 253:401–6 (1991); Flint et al., *EMBO J.* 12:1937–46 (1993)). There are at least two major classes of phosphatases: (1) those that dephosphorylate proteins (or peptides) that contain a phosphate group(s) on a serine or threonine moiety (termed Ser/Thr phosphatases) and (2) those that remove a phosphate group(s) from the amino acid tyrosine (termed protein tyrosine phosphatases or PTPases or PTPs).

The PTPases are a family of enzymes that can be classified into two groups: a) intracellular or nontransmembrane PTPases and b) receptor-type or transmembrane PTPases.

Intracellular PTPases: Most known intracellular type PTPases contain a single conserved catalytic phosphatase domain consisting of 220–240 amino acid residues. The regions outside the PTPase domains are believed to play important roles in localizing the intracellular PTPases subcellularly (Mauro, L. J. and Dixon, J. E. *TIBS* 19: 151–155 (1994)). The first intracellular PTPase to be purified and characterized was PTP-1B, which was isolated from human placenta (Tonks et al., *J. Biol. Chem.* 263: 6722–6730 (1988)). Shortly after, PTP1B was cloned (Charbonneau et al, *Proc. Natl. Acad. Sci. USA* 86: 5252–5256 (1989); Chernoff et al., *Proc. Natl. Acad. Sci. USA* 87: 2735–2789 (1989)). Other examples of intracellular PTPases include (1) T-cell PTPase/TC-PTP (Cool et al. *Proc. Natl. Acad. Sci. USA* 86: 5257–5261 (1989)), (2) rat brain PTPase (Guan et al., *Proc. Natl. Acad. Sci. USA* 87: 1501–1502 (1990)), (3) neuronal phosphatase STEP (Lombroso et al., *Proc. Natl Sci. USA* 88: 7242–7246 (1991)), (4) ezrin-domain containing PTPases: PTPMEG1 (Guet al., *Proc. Natl. Acad. Sci. USA* 88: 5867–57871 (1991)), PTPH1 (Yang and Tonks, *Proc. Natl. Acad. Sci. USA* 88: 5949–5953 (1991)), PTPD1 and PTPD2 (Møller et al, *Proc. Natl. Acad. Sci. USA* 91: 7477–7481 (1994)), FAP-1/BAS (Sato et al., *Science* 268: 411–415 (1995); Banville et al., *J. Biol. Chem.* 269: 22320–22327 (1994); Maekawa et al., *FEBS Letters* 337: 200–206 (1994)), and SH2 domain containing PTPases: PTP1C/SH-PTP1/SHP-1 (Plutzky et al., *Proc. Natl. Acad. Sci. USA* 89:1123–1127 (1992); Shen et al., *Nature Lond.* 352: 736–739 (1991)) and PTP1D/Syp/SH-PTP2/SHP-2 (Vogel et al., *Science* 259: 1611–1614 (1993); Feng et al., *Science* 259: 1607–1611 (1993); Bastein et al., *Biochem. Biophys. Res. Comm.* 196:124–133 (1993)).

Receptor-type PTPases consist of a) a putative ligand-binding extracellular domain, b) a transmembrane segment, and c) an intracellular catalytic region. The structures and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains.

The first receptor-type PTPases to be identified were (1) CD45/LCA (Ralph, S. J., *EMBO J.* 6: 1251–1257 (1987)) and (2) LAR (Streuli et al., *J. Exp. Med.* 168: 1523–1530 (1988)) that were recognized to belong to this class of enzymes based on homology to PTP1 B (Charbonneau et al., *Proc. Natl. Acad. Sci. USA* 86: 5252–5256 (1989)). CD45 is a family of high molecular weight glycoproteins and is one of the most abundant leukocyte cell surface glycoproteins and appears to be exclusively expressed upon cells of the hematopoietic system (Trowbridge and Thomas, *Ann. Rev. Immunol.* 12: 85–116 (1994)).

The identification of CD45 and LAR as members of the PTPase family was quickly followed by identification and cloning of several different members of the receptor-type PTPase group. Thus, 5 different PTPases, (3) PTPα, (4) PTPβ, (5) PTPδ, (6) PTPε, and (7) PTPζ, were identified in one early study (Krueger et al., *EMBO J.* 9: 3241–3252

(1990)). Other examples of receptor-type PTPases include (8) PTPγ (Barnea et al., *Mol. Cell. Biol.* 13: 1497–1506 (1995)) which, like PTPζ(Krueger and Saito, *Proc. Natl. Acad. Sci. USA* 89: 7417–7421 (1992)) contains a carbonic anhydrase-like domain in the extracellular region, (9) PTPμ (Gebbink et al., *FEBS Letters* 290: 123–130 (1991)), (10) PTPκ (Jiang et al., *Mol. Cell. Biol.* 13: 2942–2951 (1993)). Based on structural differences the receptor-type PTPases may be classified into subtypes (Fischer et al., *Science* 253: 401–406 (1991)): (I) CD45; (II) LAR, PTPδ, (11) PTPσ; (III) PTP□, (12) SAP-1 (Matozaki et al., *J. Biol. Chem.* 269: 2075–2081 (1994)), (13) PTP-U2/GLEPP1 (Seimiya et al., *Oncogene* 10: 1731–1738 (1995); Thomas et al., *J. Biol. Chem.* 269: 19953–19962 (1994)), and (14) DEP-1; (IV) PTPα, PTPε. All receptor-type PTPases except Type III contain two PTPase domains. Novel PTPases are continuously identified. In the early days of PTPase research, it was believed that the number of PTPs would match that of protein tyrosine kinases (PTKs) (Hanks and Hunter, FASEB J. 9: 576–596 (1995)). However, although about 90 open reading frames in *C. elegans* contain the hallmark motif of PTPs, it now seems that the estimate of 'classical' PTPases must be downsized, perhaps to between 100 and 200 in humans.

PTPases are the biological counterparts to protein tyrosine kinases Therefore, one important function of PTPases is to control, down-regulate, the activity of PTKs. However, a more complex picture of the function of PTPases has emerged. Thus, several studies have shown that some PTPases may actually act as positive mediators of cellular signaling. As an example, the SH2 domain-containing SHP-2 seems to act as a positive mediator in insulin-stimulated Ras activation (Noguchi et al., *Mol. Cell. Biol.* 14: 6674–6682 (1994)) and of growth factor-induced mitogenic signal transduction (Xiao et al., *J. Biol. Chem.* 269: 21244–21248 (1994)), whereas the homologous SHP-1 seems to act as a negative regulator of growth factor-stimulated proliferation (Bignon and Siminovitch, *Clin. Immunol. Immunopathol.* 73: 168–179 (1994)). Another example of PTPases as positive regulators has been provided by studies designed to define the activation of the Src-family of tyrosine kinases. In particular, several lines of evidence indicate that CD45 is positively regulating the activation of hematopoietic cells, possibly through dephosphorylation of the C-terminal tyrosine of Fyn and Lck (Chan et al., *Annu. Rev. Immunol.* 12: 555–592 (1994)).

PTPases were originally identified and purified from cell and tissue lysates using a variety of artificial substrates and, therefore, their natural function of dephosphorylation was not well known. Since tyrosine phosphorylation by tyrosine kinases is usually associated with cell proliferation, cell transformation and cell differentiation, it was assumed that PTPases were also associated with these events. This association has now been proven to be the case with many PTPases. PTP1 B, a phosphatase whose structure was the first PTPase to be elucidated (Barford et al., *Science* 263: 1397–1404 (1994)) has been shown to be involved in insulin-induced oocyte maturation (Flint et al., *The EMBO J.* 12:1937–46 (1993)) and it has been suggested that the overexpression of this enzyme may be involved in $p185^{c\text{-}erb\,B2}$ associated breast and ovarian cancers (Wiener, et al., *J. Natl. cancer Inst.* 86:372–8 (1994); Weiner et al, *Am. J. Obstet. Gynecol.* 170:1177–883 (1994)). The association with cancer is recent evidence which suggests that overexpression of PTP1 B is statistically correlated with increased levels of $p185^{c\text{-}erb\,B2}$ in ovarian and breast cancer. The role of PTP1 B in the etiology and progression of the disease has not yet been elucidated. Inhibitors of PTP1 B may therefore help clarify the role of PTP1 B in cancer and in some cases provide therapeutic treatment for certain forms of cancer.

PTPases: The Insulin Receptor Signaling Pathway/Diabetes

Insulin is an important regulator of different metabolic processes and plays a key role in the control of blood glucose. Defects related to its synthesis or signaling lead to diabetes mellitus. Binding of insulin to the insulin receptor (IR) causes rapid (auto)phosphorylation of several tyrosine residues in the intracellular part of the β-subunit. Three closely positioned tyrosine residues (the tyrosine-1150 domain) must all be phosphorylated to obtain full activity of the insulin receptor tyrosine kinase (IRTK) which transmits the signal further downstream by tyrosine phosphorylation of other cellular substrates, including insulin receptor substrate-1 (IRS-1) (Wilden et al., *J. Biol. Chem.* 267:16660–16668 (1992); Myers and White, *Diabetes* 42: 643–650 (1993); Lee and Pilch, *Am. J. Physiol.* 266: $C319-C_{334}$ (1994); White et al., *J. Biol. Chem.* 263: 2969–2980 (1988)). The structural basis for the function of the tyrosine-triplet has been provided by X-ray crystallographic studies of IRTK that showed tyrosine-1150 to be autoinhibitory in its unphosphorylated state (Hubbard et al., *Nature* 372: 746–754 (1994)) and of the activated IRTK (Hubbard, EMBO J. 16:5572–5581 (1997)).

Several studies clearly indicate that the activity of the auto-phosphorylated IRTK can be reversed by dephosphorylation in vitro (reviewed in Goldstein, *Receptor* 3: 1–15 (1993); Mooney and Anderson, *J. Biol. Chem.* 264: 6850–6857 (1989)), with the tri-phosphorylated tyrosine-1150 domain being the most sensitive target for protein-tyrosine phosphatases (PTPases) as compared to the di- and mono-phosphorylated forms (King et al., *Biochem. J.* 275: 413418 (1991)). This tyrosine-triplet functions as a control switch of IRTK activity and the IRTK appears to be tightly regulated by PTP-mediated dephosphorylation in vivo (Khan et al., *J. Biol. Chem.* 264: 12931–12940 (1989); Faure et al., *J. Biol. Chem.* 267: 11215–11221 (1992); Rothenberg et al., *J. Biol. Chem.* 266: 8302–8311 (1991)). The intimate coupling of PTPases to the insulin signaling pathway is further evidenced by the finding that insulin differentially regulates PTPase activity in rat hepatoma cells (Meyerovitch et al., *Biochemistry* 31: 10338–10344 (1992)) and in livers from alloxan diabetic rats (Boylan et al., *J. Clin. Invest.* 90: 174–179 (1992)).

Until recently, relatively little was known about the identity of the PTPases involved in IRTK regulation. However, the existence of PTPases with activity towards the insulin receptor can be demonstrated as indicated above. Further, when the strong PTPase-inhibitor pervanadate is added to whole cells an almost full insulin response can be obtained in adipocytes (Fantus et al., *Biochemistry* 28: 8864–8871 (1989); Eriksson et al., *Diabetologia* 39: 235–242 (1995)) and skeletal muscle (Leighton et al., *Biochem. J.* 276: 289–292 (1991)). In addition, other studies show that a new class of peroxovanadium compounds act as potent hypoglycemic compounds in vivo (Posner et al.,supra). Two of these compounds were demonstrated to be more potent inhibitors of dephosphorylation of the insulin receptor than of the EGF-receptor, thus indicating that even such relatively unselective inhibitors may convey some specificity in regulating different signal transduction pathways.

It was recently found by Montreal-based research groups that mice lacking the protein tyrosine phosphatase-1B gene (PTP1B) (Elchebly et al., *Science* 283: 1544–1548 (1999)) yielded healthy mice that showed increased insulin sensitivity and resistance to diet-induced obesity. Importantly, these results have been confirmed and extended independently by another research team from Boston (Klaman et al., *Mol. Cell. Biol.* 20: 5479–5489 (2000)). The enhanced insulin sensitivity of the PTP$^{-/+}$ mice was also evident in glucose and insulin tolerance tests. The PTP-1B knock-out mouse showed many characteristics which would be highly desirable to have for an anti-diabetes treatment. Most importantly, the knock-out mice grew normally and were fertile and have exhibited no increased incidence of cancer, as obviously there could have been concerns when one considers the mitogenic properties of insulin. From the diabetes perspective, the first notable features of the knock-out animals were that blood glucose and insulin levels were lowered, and the consequent marked increase in insulin sensitivity in the knock-out animals. Moreover, the insulin-stimulated tyrosine phosphorylation levels of IR and IRS-1 were found to be increased/prolonged in muscle and liver—but not in fat tissue. Thus, the main target tissues for this type of approach would appear to be insulin action in liver and muscle. This is in contrast to the main target tissue for the PPARγ agonist class of insulin sensitizers (the "-diones"), which is adipose tissue (Murphy & Nolan, *Exp. Opin. Invest. Drugs* 9: 1347–1361 (2000)). Several other "diabetic" parameters were also improved, such as plasma triglycerides being decreased in the knockout mice. However, perhaps even more remarkably and unexpectedly, the knock-out animals also exhibited a resistance to weight gain when placed on a high-fat diet. This is again in contrast to the action of the PPARγ agonist class of insulin sensitizers, which rather induce weight gain (Murphy & Nolan, supra), and would suggest that inhibition of PTP-1 B could be a particularly attractive option for treatment of obese Type II diabetics. This is also supported by the fact that the heterozygous mice from this study showed many of these desirable features. In the Montreal study, there appeared to be no gender differences, whereas in the Boston study in general the male animals had larger responses to PTP-1 B being knocked out. In both studies, the reduction in weight gain of the knock-out animals on the high fat diet was found to be due to a decreased fat cell mass, although differences were observed with respect to fat cell number. Leptin levels were also lower in the knock-out mice, presumably as a reflection of the decreased fat mass. Significantly, the Boston group also found that the knock-out animals had an increased energy expenditure of around 20% and an increased respiratory quotient compared to the wild-type; again, heterozygote animals displayed an intermediate level of energy expenditure. Whether this increase in metabolic rate is a reflection of the effects of PTP-1 B on insulin-signaling or on other cellular components remains to be established, but the bottom-line message that inhibition of this enzyme may be an effective anti-diabetic and perhaps also anti-obesity therapy is clear.

It should also be noted that in the PTP-1 B knock-out mice the basal tyrosine phosphorylation level of the insulin receptor tyrosine kinase does not appear to be increased, which is in contrast to the situation after insulin treatment where there is an increased or prolonged phosphorylation. This might indicate that other PTPs are controlling the basic phosphorylation state of the insulin receptor in the knock-out mice—and perhaps in man.

Previous findings are in accordance with the results reported by Elchebly et al. (supra) (recently reviewed in Kennedy, *Biomed. Pharmacother.* 53: 466–470 (1999)). Thus, it has been found that high glucose concentration induce insulin resistance and increase the expression of PTP1B in rat (fibroblasts expressing the human insulin receptor (Maegawa et al., *J. Biol. Chem.* 270: 7724–7730 (1995)). In rat L6 cells, insulin and insulin-like growth factor I (IGF-1) were found to induce increased PTPase activity, including increased PTP1 B expression (Kenner et al., *J. Biol. Chem.* 266: 25455–25462 (1993)). In addition, the same group has shown that PTP1 B may interact directly with the activated IR (Seely et al. *Diabetes* 45:1379–1385 (1996)) and act directly as a negative regulator of insulin and IGF-1-stimulated signaling (Kenner et a. J. Biol. Chem. 271: 19810–19816 (1996)). Osmotic loading of rat KRC-7 hepatoma cells with neutralizing anti-PTP1 B antibodies also indicated a role for PTP1 B in negative regulating of the insulin signaling pathway (Akmad et al. *J. Biol. Chem.* 270: 20503–20508 (1995)).

Also other PTPases have been implicated as regulators of the insulin signaling pathway. Thus, it was found that the ubiquitously expressed SH2 domain containing PTPase, PTP1 D/SHP-2 (Vogel et al., 1993, supra), associates with and dephosphorylates IRS-1, but apparently not the IR itself (Kuhné et al., *J. Biol. Chem.* 268: 11479–11481 (1993); (Kuhné et al., *J. Biol. Chem.* 269: 15833–15837 (1994)).

Other studies suggest that receptor-type or membrane-associated PTPases are involved in IRTK regulation (Faure et al., *J. Biol. Chem.* 267: 11215–11221 (1992), (Haring et al., *Biochemistry* 23: 3298–3306 (1984); Sale, *Adv. Prot. Phosphatases* 6: 159–186 (1991)). Hashimoto et al. have proposed that LAR might play a role in the physiological regulation of insulin receptors in intact cells (Hashimoto et al., *J. Biol. Chem.* 267: 13811–13814 (1992)). Their conclusion was reached by comparing the rate of dephosphorylation/Inactivation of purified IR using recombinant PTP1 B as well as the cytoplasmic domains of LAR and PTPα. Antisense inhibition was used to study the effect of LAR on insulin signaling in a rat hepatoma cell line (Kulas et al., *J. Biol. Chem.* 270: 2435–2438 (1995)). A suppression of LAR protein levels by about 60 percent was paralleled by an approximately 150 percent increase in insulin-induced autophosphorylation. However, only a modest 35 percent increase in IRTK activity was observed, whereas the insulin-dependent phosphatidylinositol 3-kinase (PI 3-kinase) activity was significantly increased by 350 percent. Reduced LAR levels did not alter the basal level of IRTK tyrosine phosphorylation or activity. The authors speculate that LAR could specifically dephosphorylate tyrosine residues that are critical for PI 3-kinase activation either on the insulin receptor itself or on a downstream substrate. Conflicting results have been reported for PTP-LAR knock-out mice. Thus, Goldstein and coworkers reported that transgenic mice deficient in PTP-LAR exhibit profound defects in glucose-homeostasis (Ren et al., *Diabetes* 47: 493–497 (1998)). However, it is difficult to fully assess the contribution of LAR deficiency to the glucose homeostasis in these mice due to the fact that the control mice were of a different genetic background than the knock-out mice. Moreover, normal glucose homeostasis was reported in a different strain of PTP-LAR knock-out mice (Sorensen et al., *Diabetologia* 40: A143 (1997)).

While previous reports indicate a role of PTPα in signal transduction through src activation (Zheng et al., *Nature* 359: 336–339 (1992); den Hertog et al., *EMBO J.* 12: 37893798 (1993)) and interaction with GRB-2 (den Hertog et al., *EMBO J.* 13: 3020–3032 (1994); Su et al., *J. Biol. Chem.* 269: 18731–18734 (1994)), Møller, Lammers and coworkers provided results that suggest a function for this phosphatase and its close relative PTP☐ as negative regulators of the insulin receptor signal (Møller et al., 1995 supra; Lammers, et al., *FEBS Lett.* 404:37–40 (1997). These studies also indicated that receptor-like PTPases might play a significant role in regulating the IRTK.

Other studies have shown that PTP1 B and TC-PTP are likely to be involved in the regulation of several other cellular processes in addition to the described regulatory roles in insulin signaling. Therefore, PTP1B and/or TC-PTP as well as other PTPases showing key structural features with PTP1 B and TC-PTP are likely to be important therapeutic targets in a variety of human and animal diseases. The compounds of the present invention are useful for modulating or inhibiting PTP1 B and/or TC-PTP and/or other PTPases showing key structural features with said PTPases and for treating diseases in which said modulation or inhibition is indicated. A few examples that are not intended in any way to limit the scope of the invention of substrates that may be regulated by PTP1 B will be given below.

Tonks and coworkers have developed an elegant 'substrate trapping' technique that has allowed identification of the epidermal growth factor receptor (EGF-R) as a major substrate of PTP1B in COS cells (Flint et al. *Proc. Natl. Acad. Sci. USA* 94: 1680–1685 (1997)). In addition, three other as yet unidentified substrates of PTP1 B were isolated. As an example of these studies, it has been found—using the above substrate-trapping technique—that PTP1 B in addition to the EGF-R associates with activated platelet-derived growth factor receptor (PDGF-R), but not with colony-stimulating factor 1 receptor (CSF-1R) (Liu & Chernoff, *Biochem. J.* 327: 139–145 (1997)).

Early studies have shown that the subcellular localization as well as the enzyme activity of PTP1 B may be regulated by agonist-induced calpain-catalyzed cleavage in human platelets (Frangioni et al. *EMBO J.* 12: 4843–4856 (1993)). Moreover, PTP1 B cleavage correlated with the transaction from reversible to irreversible platelet aggregation. Thus, as a non-limiting example compounds of the present invention might be used to prevent or induce irreversible platelet aggregation in individuals in need thereof. It was proposed that the cleavage-induced change in the subcellular localization of PTP1 B (from membrane to cytosol) results in different substrate specificity not only in platelet but also in other cell types (Frangioni et al., supra).

The above substrate trapping method has further been used to identify the protein tyrosine kinase $p210^{bcr-abl}$ as a substrate for PTP1 B (LaMontagne, Jr. et al. *Mol. Cell. Biol.* 18: 2965–2975 (1998)). These studies suggest that PTP1 B might function as a negative regulator of $p210^{bcr-abl}$ signaling in vivo. In addition, PTP1B was recently found to bind to and dephosphorylate the docking protein p130 Cas in rat fibroblasts and hereby suppress transformation by v-crk, v-src, and v-ras, but not by v-raf (Liu et al. *Mol. Cell. Biol.* 18: 250–259 (1998)).

The transmembrane PTPase CD45, which is believed to be hematopoietic cell-specific, was found to negatively regulate the insulin receptor tyrosine kinase in the human multiple myeloma cell line U266 (Kulas et al., *J. Biol. Chem.* 271: 755–760 (1996)).

Further, PTPases influences the following hormones or diseases or disease states: somatostatin, the immune system/autoimmunity, cell—cell interactions/cancer, platelet aggregation, osteoporosis, and microorganisms, as disclosed in PCT Publication WO 99/15529.

Somatostatin inhibits several biological functions including cellular proliferation (Lamberts et al., *Molec. Endocrinol.* 8: 1289–1297 (1994)). While part of the antiproliferative activities of somatostatin are secondary to its inhibition of hormone and growth factor secretion (e.g. growth hormone and epidermal growth factor), other anti-proliferative effects of somatostatin are due to a direct effect on the target cells. As an example, somatostatin analogs inhibit the growth of pancreatic cancer presumably via stimulation of a single PTPase, or a subset of PTPases, rather than a general activation of PTPase levels in the cells (Liebow et al., *Proc. Natl. Acad. Sci. USA* 86: 2003–2007 (1989); Colas et al., *Eur. J. Biochem.* 207:1017–1024 (1992)).

PTPases: the Immune System/Autoimmunity

Several studies suggest that the receptor-type PTPase CD45 plays a critical role not only for initiation of T cell activation, but also for maintaining the T cell receptor-mediated signaling cascade. These studies are reviewed in: (Weiss A., *Ann. Rev. Genet.* 25: 487510 (1991); Chan et al., *Annu. Rev. Immunol.* 12: 555–592 (1994); Trowbridge and Thomas, *Annu. Rev. Immunol.* 12: 85–116 (1994)).

CD45 is one of the most abundant of the cell surface glycoproteins and is expressed exclusively on hemopoetic cells. In T cells, it has been shown that CD45 is one of the critical components of the signal transduction machinery of lymphocytes. In particular, evidence has suggested that CD45 phosphatase plays a pivotal role in antigen-stimulated proliferation of T lymphocytes after an antigen has bound to the T cell receptor (Trowbridge, *Ann. Rev. Immunol,* 12: 85–116 (1994)). Several studies suggest that the PTPase activity of CD45 plays a role in the activation of Lck, a lymphocyte-specific member of the Src family protein-tyrosine kinase (Mustelin et al., *Proc. Natl. Acad. Sci. USA* 86: 6302–6306 (1989); Ostergaard et al., *Proc. Natl. Acad. Sci. USA* 86: 8959–8963 (1989)). These authors hypothesized that the phosphatase activity of CD45 activates Lck by dephosphorylation of a C-terminal tyrosine residue, which may, in turn, be related to T-cell activation. Thus, it was found that recombinant p56lck specifically associates with recombinant CD45 cytoplasmic domain protein, but not to the cytoplasmic domain of the related PTPα (Ng et al., *J. Biol. Chem.* 271: 1295–1300 (1996)). The p56lck-CD45 interaction seems to be mediated via a nonconventional SH2 domain interaction not requiring phosphotyrosine. In immature B cells, another member of the Src family protein-tyrosine kinases, Fyn, seems to be a selective substrate for CD45 compared to Lck and Syk (Katagiri et al., *J. Biol. Chem.* 270: 27987–27990 (1995)).

Studies using transgenic mice with a mutation for the CD45-exon6 exhibited lacked mature T cells. These mice did not respond to an antigenic challenge with the typical T cell mediated response (Kishihara et al., *Cell* 74:143–56 (1993)). Inhibitors of CD45 phosphatase would therefore be very effective therapeutic agents in conditions that are associated with autoimmune diseases with rheumatoid arthritis, systemic lupus erythematosus, type I diabetes, and inflammatory bowel disease as non-limiting examples. Another important use of CD45 inhibitors is for immunosuppression in connection with tissue or cell transplantation and other condtions with need for immunosuppressive treatment.

CD45 has also been shown to be essential for the antibody mediated degranulation of mast cells (Berger et al., *J. Exp. Med.* 180:471–6 (1994)). These studies were also done with mice that were CD45-deficient. In this case, an igE-mediated degranulation was demonstrated in wild type but not CD45-deficient T cells from mice. These data suggest that CD45 inhibitors could also play a role in the symptomatic or therapeutic treatment of allergic disorders with asthma, allergic rhinitis, food allergy, eczema, urticaria and anaphylaxis as nonlimiting examples.

Another PTPase, an inducible lymphoid-specific protein tyrosine phosphatase (HePTP) has also been implicated in the immune response. This phosphatase is expressed in both resting T and B lymphocytes, but not non-hemopoetic cells. Upon stimulation of these cells, mRNA levels from the HePTP gene increase 10–15 fold (Zanke et al., *Eur. J. Immunol.* 22: 235–239 (1992)). In both T and B cells HePTP may function during sustained stimulation to modulate the immune response through dephosphorylation of specific residues. Its exact role, however remains to be defined.

Likewise, the hematopoietic cell specific SHP-1 seems to act as a negative regulator and play an essential role in immune cell development. In accordance with the above-mentioned important function of CD45, HePTP and SHP-1, selective PTPase inhibitors may be attractive drug candidates both as immunosuppressors and as immunostimulants. Recent studies illustrate the potential of PTPase inhibitors as immunomodulators by demonstrating the capacity of the non-selective vanadium-based PTPase inhibitor, BMLOV, to induce apparent B cell selective apoptosis compared to T cells (Dawson et al., *FEBS Lett.* 478: 233–236; Schieven et al., *J. Biol. Chem.* 270: 20824–20831 (1995)).

PTPases: Cell—Cell Interactions/Cancer

Focal adhesion plaques, an in vitro phenomenon in which specific contact points are formed when fibroblasts grow on appropriate substrates, seem to mimic, at least in part, cells and their natural surroundings. Several focal adhesion proteins are phosphorylated on tyrosine residues when fibroblasts adhere to and spread on extracellular matrix (Gumbiner, *Neuron* 11: 551–564 (1993)). However, aberrant tyrosine phosphorylation of these proteins can lead to cellular transformation. The intimate association between PTPases and focal adhesions is supported by the finding of several intracellular PTPases with ezrin-like N-terminal domains, e.g. PTPMEG1 (Gu et al, *Proc. Natl. Acad. Sci. USA* 88: 5867–5871 (1991), PTPH1 (Yang and Tonks, *Proc. Natl. Acad. Sci. USA* 88: 5949–5953 (1991)) and PTPD1 (Møller et al., *Proc. Natl. Acad. Sci. USA* 91: 7477–7481 (1994)). The ezrin-like domain shows similarity to several proteins that are believed to act as links between the cell membrane and the cytoskeleton. PTPD1 was found to be phosphorylated by and associated with c-src in vitro and is hypothesized to be involved in the regulation of phosphorylation of focal adhesions (Møller et al., supra).

PTPases may oppose the action of tyrosine kinases, including those responsible for phosphorylation of focal adhesion proteins, and may therefore function as natural inhibitors of transformation. TC-PTP, and especially the truncated form of this enzyme (Cool et al., *Proc. Natl. Acad. Sci. USA* 87: 7280–7284 (1990)), can inhibit the transforming activity of v-erb and v-fms (Lammers et al., *J. Biol. Chem.* 268: 22456–22462 (1993), Zander et al., *Oncogene* 8: 1175–1182 (1993)). Moreover, it was found that transformation by the oncogenic form of the HER2/neu gene was suppressed in NIH 3T3 fribroblasts overexpressing PTP1 B (Brown-Shimer et al., *Cancer Res.* 52: 478482 (1992)).

The expression level of PTP1 B was found to be increased in a mammary cell line transformed with neu (Zhay et al., *Cancer Res.* 53: 2272–2278 (1993)). The intimate relationship between tyrosine kinases and PTPases in the development of cancer is further evidenced by the finding that PTPε is highly expressed in murine mammary tumors in transgenic mice over-expressing c-neu and v-Ha-ras, but not c-myc or int-2 (Elson and Leder, *J. Biol. Chem.* 270: 26116–26122 (1995)). Further, the human gene encoding PTPγ was mapped to 3p21, a chromosomal region, which is frequently deleted in renal and lung carcinomas (LaForgia et al., *Proc. Natl. Acad. Sci. USA* 88: 5036–5040 (1991)).

In this context, it seems significant that PTPases appear to be involved in controlling the growth of fibroblasts. Thus, it was found that Swiss 3T3 cells harvested at high density contain a membrane-associated PTPase whose activity on an average is 8-fold higher than that of cells harvested at low or medium density (Pallen and Tong, *Proc. Natl. Acad. Sci. USA* 88: 6996–7000 (1991)). It was hypothesized by the authors that density-dependent inhibition of cell growth involves the regulated elevation of the activity of the PTPase(s) in question. In accordance with this view, a membrane-bound, receptor-type PTPase, DEP-1, showed enhanced (>=10-fold) expression levels with increasing cell density of WI-38 human embryonic lung fibroblasts and in the AG1518 fibroblast cell line (Ostman et al., *Proc. Natl. Acad. Sci. USA* 91: 9680–9684 (1994)).

Two closely related receptor-type PTPases, PTPκ and PTPμ, can mediate homophilic cell—cell interaction when expressed in non-adherent insect cells, suggesting that these PTPases might have a normal physiological function in cell-to-cell signalling (Gebbink et al., *J. Biol. Chem.* 268: 16101–16104 (1993), Brady-Kalnay et al., *J. Cell Biol.* 122: 961–972 (1993); Sap et al., *Mol. Cell. Biol.* 14: 1–9 (1994)). Interestingly, PTPκ and PTPμ do not interact with each other, despite their structural similarity (Zondag et al., *J. Biol. Chem.* 270: 14247–14250 (1995)). From the studies described above it is apparent that PTPases may play an important role in regulating normal cell growth. However, as pointed out above, other studies indicate that PTPases may also function as positive mediators of intracellular signaling and thereby induce or enhance mitogenic responses. Increased activity of certain PTPases might therefore result in cellular transformation and tumor formation. Indeed, in one study over-expression of PTPμ was found to lead to transformation of rat embryo fibroblasts (Zheng, supra). In addition, SAP-1 was found to be highly expressed in pancreatic and colorectal cancer cells. SAP-1 is mapped to chromosome 19 region q13.4 and might be related to carcinoembryonic antigen mapped to 19q13.2 (Uchida et al., *J. Biol. Chem.* 269: 12220–12228 (1994)). Further, the dsPTPase, cdc25, dephosphorylates cdc2 at Thr14/Tyr-15 and thereby functions as positive regulator of mitosis (reviewed by Hunter, *Cell* 80: 225–236 (1995)). Inhibitors of specific PTPases are therefore likely to be of significant therapeutic value in the treatment of certain forms of cancer.

PTPases: Platelet Aggregation

PTPases seem to be centrally involved in platelet aggregation. Thus, agonist-induced platelet activation results in calpain catalyzed cleavage of PTP1B with a concomitant 2-fold stimulation of PTPase activity (Frangioni et al., *EMBO J.* 12: 4843–4856 (1993)). The cleavage of PTP1 B leads to subcellular relocation of the enzyme and correlates with the transition from reversible to irreversible platelet aggregation in platelet-rich plasma. In addition, the SH2 domain containing PTPase, SHP-1, was found to translocate to the cytoskeleton in platelets after thrombin stimulation in an aggregation-dependent manner (Li et al., *FEBS Lett* 343: 89–93 (1994)).

Although some details in the above two studies have been questioned, there is over-all agreement that PTP1 B and SHP-1 play significant functional roles in platelet aggregation (Ezumi et al., *J. Biol. Chem.* 270: 11927–11934 (1995)). In accordance with these observations, treatment of platelets with the PTPase inhibitor pervanadate leads to significant increase in tyrosine phosphorylation, secretion and aggregation (Pumiglia et al., *Biochem. J.* 286: 441449 (1992)).

PTPases: Osteoporosis

The rate of bone formation is determined by the number and the activity of osteoblasts, which in term are determined by the rate of proliferation and differentiation of osteoblast progenitor cells, respectively. Histomorphometric studies indicate that the osteoblast number is the primary determinant of the rate of bone formation in humans (Gruber et al., *Mineral Electrolyte Metab.* 12: 246–254 (1987), reviewed in Lau et al., *Biochem. J.* 257: 2336 (1989)). Acid phosphatases/PTPases may be involved in negative regulation of osteoblast proliferation. Thus, fluoride, which has phosphatase inhibitory activity, has been found to increase spinal bone density in osteoporotics by increasing osteoblast proliferation (Lau et al., supra). Consistent with this observation, an osteoblastic acid phosphatase with PTPase activity was found to be highly sensitive to mitogenic concentrations of fluoride (Lau et al., *J. Biol. Chem.* 260: 4653–4660 (1985), Lau et al., *J. Biol. Chem.* 262: 1389–1397 (1987), Lau et al., *Adv. Protein Phosphatases* 4: 165–198 (1987)). Interestingly, the level of membrane-bound PTPase activity was increased dramatically when the osteoblast-like cell line UMR 106.06 was grown on collagen type-I matrix compared to uncoated tissue culture plates. Since a significant increase in PTPase activity was observed in density-dependent growth arrested fibroblasts (Pallen and Tong, *Proc. Natl. Acad. Sci.* 88: 6996–7000 (1991)), it might be speculated that the increased PTPase activity directly inhibits cell growth The mitogenic action of fluoride and other phosphatase inhibitors (molybdate and vanadate) may thus be explained by their inhibition of acid phosphatases/PTPases that negatively regulate the cell proliferation of osteoblasts. The complex nature of the involvement of PTPases in bone formation is further suggested by the identification of a novel parathyroid regulated, receptor-like PTPase, OST-PTP, expressed in bone and testis (Mauro et al., *J. Biol. Chem.* 269: 30659–30667 (1994)). OST-PTP is up-regulated following differentiation and matrix formation of primary osteoblasts and subsequently down-regulated in the osteoblasts which are actively mineralizing bone in culture. It may be hypothesized that PTPase inhibitors may prevent differentiation via inhibition of OST-PTP or other PTPases thereby leading to continued proliferation. This would be in agreement with the above-mentioned effects of fluoride and the observation that the tyrosine phosphatase inhibitor orthovanadate appears to enhance osteoblast proliferation and matrix formation (Lau et al., *Endocrinology* 116: 2463–2468 (1988)). In addition, it was observed that vanadate, vanadyl and pervanadate all increased the growth of the osteoblast-like cell line UMR106. Vanadyl and pervanadate were stronger stimulators of cell growth than vanadate. Only vanadate was able to regulate the cell differentiation as measured by cell alkaline phosphatase activity (Cortizo et al., *Mol. Cell. Biochem.* 145: 97–102 (1995)). It is of particular interest to the current invention that several studies have shown that bisphosphonates, such as alendronate and tiludronate, inhibit the PTPase activity in osteoclasts, and that the inhibition of PTPase activity correlated with the inhibition of in vitro osteoclast formation and boneresorption (Schmidt et al., *Proc. Natl. Acad. Sci. U.S.A.* 93: 3068–3073 (1996); Murakami et al., *Bone* 20: 399404 (1997); Opas et al., *Biochem. Pharmacol.* 54: 721–727 (1997); Skorey et al., *J. Biol. Chem.* 272: 22472–22480 (1997)). Thus, PTPase inhibitors other than bisphosphonates—can potentially be effective for prevention and/or treatment of osteoporosis.

PTPases: Microorganisms

Dixon and coworkers have called attention to the fact that PTPases may be a key element in the pathogenic properties of *Yersinia* (reviewed in Clemens et al. *Molecular Microbiology* 5: 2617–2620 (1991)). This finding was rather surprising since tyrosine phosphate is thought to be absent in bacteria. The genus *Yersinia* comprises 3 species: *Y. pestis* (responsible for the bubonic plague), *Y. pseudoturberculosis* and *Y. enterocolitica* (causing enteritis and mesenteric lymphadenitis). Interestingly, a dual-specificity phosphatase, VH1, has been identified in Vaccinia virus (Guan et al., *Nature* 350: 359–253 (1991)). These observations indicate that PTPases may play critical roles in microbial and parasitic infections, and they further point to PTPase inhibitors as a novel, putative treatment principle of infectious diseases.

WO 99/46267 discloses compounds, which are pharmacologically useful inhibitors of PTPases. However, the present invention, which represents a novel selection under WO 99/46267, discloses a class of compounds which surprisingly are more potent against protein tyrosine phosphatases (e.g. PTP1 B) than those disclosed in WO 99/46267.

DESCRIPTION OF THE INVENTION

The present invention relates to Compounds of the Formula 1 wherein n, m, X, Y, $R_1$, $R_2$, $R_3$, $R_4$, $R_5$ and $R_6$ are defined below;

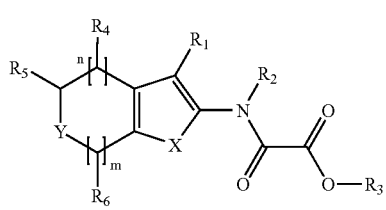

Formula 1

In the above Formula 1 n is 0, 1 or 2;

m is 1 or 2;

X is S, O, $NR_7$;

Y is O, S, SO, $SO_2$;

$R_1$ is hydrogen, $COOR_3$, or selected from the following 5-membered heterocycles:

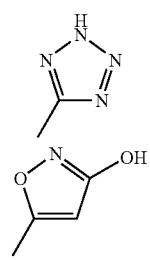

-continued

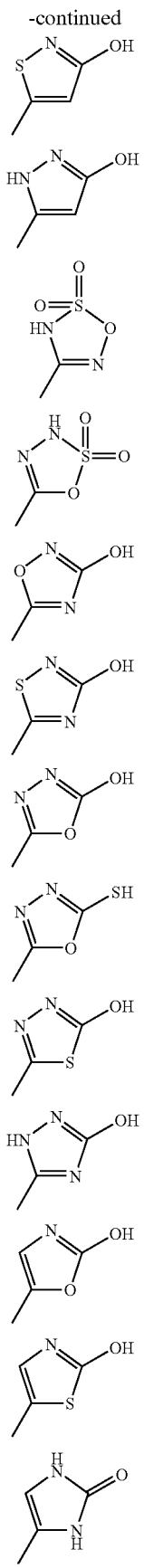

-continued

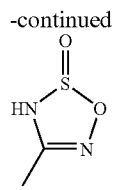

$R_2$ is hydrogen, $C_1$–$C_6$alkyl, hydroxy, $NR_7R_8$;

$R_3$ is hydrogen, $C_1$–$C_6$alkyl, aryl$C_1$–$C_6$alkyl, $C_1$–$C_6$alkylcarbonloxy$C_1$–$C_6$alkyl, $C_1$–$C_6$alkylcarbonyloxyaryl$C_1$–$C_6$alkyl;

$R_4$, $R_5$ and $R_6$ are independently hydrogen, trihalomethyl, $C_1$–$C_6$alkyl, aryl, aryl$C_1$–$C_6$alkyl, hydroxy, oxo, carboxy, carboxy$C_1$–$C_6$alkyl, $C_1$–$C_6$alkyloxycarbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy, aryloxy$C_1$–$C_6$alkyl aryl$C_1$–$C_6$alkyloxy, arl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio$C_1$–$C_6$alkyl, aryl$C_1$–$C_6$alkylthio, aryl$C_1$–$C_6$alkylthio$C_1$–$C_6$alkyl, $NR_8R_9$, $C_1$–$C_6$alkylamino$C_1$–$C_6$alkyl aryl$C_1$–$C_6$alkylamino$C_1$–$C_6$alkyl, di(aryl$C_1$–$C_6$alkyl) amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$-alkyl, arylcarboxy, arylcarboxy$C_1$–$C_6$alkyl, aryl$C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, -carbonyl$NR_8C_1$–$C_6$alkylCOR$_{11}$, aryl$C_1$–$C_6$alkylcarbonylamino, aryl$C_1$–$C_6$alkylcarbonylamino$C_1$–$C_6$alkyl, $CONR_7R_8$, $C_1$–$C_6$alkyl-$CONR_7R_8$ or arylaminocarbonylamino$C_1$–$C_6$alkyl wherein the alkyl and aryl groups are optionally substituted and $R_{11}$ is $NR_7R_8$, or $C_1$–$C_6$alkyl$NR_7R_8$;

$R_7$ and $R_8$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkyl-carboxy or aryl$C_1$–$C_6$alkylcarboxy wherein the alkyl and aryl groups are optionally substituted; or $R_7$ and $R_8$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulphur, the ring system can optionally be substituted with at least one $C_1$–$C_6$alkyl, aryl, aryl$C_1$–$C_6$alkyl, hydroxy, oxo, $C_1$–$C_6$alkyloxy, aryl$C_1$–$C_6$alkyloxy, $C_1$–$C_6$alkyloxy$C_1$–$C_6$alkyl, $C_1$–$C_6$alkylamino-$C_1$–$C_6$alkyl or $NR_9R_{10}$, wherein $R_9$ and $R_{10}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy; wherein the alkyl and aryl groups are optionally substituted; or $R_7$ and $R_8$ are independently a saturated or partial saturated cyclic 5, 6 or 7 membered amine, imide or lactam;

or a salt thereof with a pharmaceutically acceptable acid or base, or any optical isomer or mixture of optical isomers, including a racemic mixture, or any tautomeric form, or prodrug thereof.

The compounds of the invention can be further modified to act as prodrugs.

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver, poor uptake in cells. Although the factors determining bioavailability are not completely understood, there are many examples in the scientific literature—well known to those skilled in the art—of how to modify compounds, which are potent and selective in biochemical assays but show low or no activity in vivo, into drugs that are biologically active. It is within the scope of the invention to modify the compounds of the invention, termed the 'original compound', by attaching chemical groups that will improve the bioavailability of said compounds in such a way that the uptake in cells or mammals is facilitated. Examples of said modifications, which are not intended in any way to limit the scope of the invention, include changing of one or more carboxy groups to esters (for instance methyl esters, ethyl esters, acetoxymethyl esters or other acyloxymethyl esters). Compounds of the invention, original compounds, such modified by attaching chemical groups are termed 'modified compounds'. Said chemical groups may or may not be apparent in the claims of this invention. Other examples of modified compounds, which are not intended in any way to limit the scope of the invention, are compounds that have been cyclized at specific positions—socalled 'cyclic compounds'—which upon uptake in cells or mammals become hydrolyzed at the same specific position(s) in the molecule to yield the compounds of the invention, the original compounds, which are then said to be 'non-cyclic'. For the avoidance of doubt, it is understood that the latter original compounds in most cases will contain other cyclic or heterocyclic structures that will not be hydrolyzed after uptake in cells or mammals. Generally, said modified compounds will not show a behavior in biochemical assays similar to that of the original compound, i.e. the corresponding compounds of the invention without the attached chemical groups or said modifications. Said modified compounds may even be inactive in biochemical assays. However, after uptake in cells or mammals these attached chemical groups of the modified compounds may in turn be removed spontaneously or by endogenous enzymes or enzyme systems to yield compounds of the invention, original compounds. 'Uptake' is defined as any process that will lead to a substantial concentration of the compound inside cells or in mammals. After uptake in cells or mammals and after removal of said attached chemical group or hydrolysis of said cyclic compound, the compounds may have the same structure as the original compounds and thereby regain their activity and hence become active in cells and/or in vivo after uptake. A number of procedures, well known to those skilled in the art, may be used to verify that the attached chemical groups have been removed or that the cyclic compound has been hydrolyzed after uptake in cells or mammals. An example, which is not intended in any way to limit the scope of the invention, is given in the following. A mammalian cell line, which can be obtained from the American Tissue Type Collection or other similar governmental or commercial sources, is incubated with said modified compound. After incubation at conditions well known to those skilled in the art, the cells are washed appropriately, lysed and the lysate is isolated. Appropriate controls, well known to those skilled in the art, must be included. A number of different procedures, well known to those skilled in the art, may in turn be used to extract and purify said compound from said lysate. Said compound may or may not retain the attached chemical group or said cyclic compound may or may not have been hydrolyzed. Similarly, a number of different procedures—well known to those skilled in the art—may be used to structurally and chemically characterize said purified compound. Since said purified compound has been isolated from said cell lysate and hence has been taken up by said cell line, a comparison of said structurally and chemically characterized compound with that of the original unmodified compound (i.e. without said attached chemical group or said noncyclic compound) will immediately provide those skilled in the art information on whether the attached chemical group as been removed in the cell or if the cyclic compound has been hydrolyzed. As a further analysis, said purified compound may be subjected to enzyme kinetic analysis as described in detail in the present invention. If the kinetic profile is similar to that of the original compound without said attached chemical group, but different from said modified compound, this confirms that said chemical group has been removed or said cyclic compounds has been hydrolyzed. Similar techniques may be used to analyze compounds of the invention in whole animals and mammals.

A preferred prodrug is acetoxymethyl esters of the compounds of the present invention which may be prepared by the following general procedure (C. Schultz et al, *The Journal of Biological Chemistry*, 1993, 268, 6316–6322.):

A carboxylic acid (1 equivalent) is suspended in dry acetonitrile (2 ml per 0.1 mmol). Diisopropyl amine (3.0 equivalents) is added followed by bromomethyl acetate (1.5 equivalents). The mixture is stirred under nitrogen overnight at room temperature. Acetonitrile is removed under reduced pressure to yield an oil which is diluted in ethyl acetate and washed with water (3×). The organic layer is dried over anhydrous magnesium sulfate. Filtration followed by solvent removal under reduced pressure afford a crude oil. The product is purified by column chromatography on silica gel, using an appropriate solvent system.

Definitions

As used herein, the term "attached" or "–" (e.g. —$COR_{11}$ which indicates the carbonyl attachment point to the scaffold) signifies a stable covalent bond, certain preferred points of attachment points being apparent to those skilled in the art.

The terms "halogen" or "halo" include fluorine, chlorine, bromine, and iodine.

The term "alkyl" Includes $C_1$–$C_6$ straight chain saturated, methylene and $C_2$–$C_6$ unsaturated aliphatic hydrocarbon groups, $C_1$–$C_6$ branched saturated and $C_2$–$C_6$ unsaturated aliphatic hydrocarbon groups, $C_3$–$C_6$ cyclic saturated and $C_5$–$C_6$ unsaturated aliphatic hydrocarbon groups, and $C_1$–$C_6$ straight chain or branched saturated and $C_2$–$C_6$ straight chain or branched unsaturated aliphatic hydrocarbon groups substituted with $C_3$–$C_6$ cyclic saturated and unsaturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, ethenyl, propenyl, butenyl, pentenyl, hexenyl, isopropyl (i-Pr), isobutyl (I-Bu), tert-butyl (t-Bu), sec-butyl (s-Bu), isopentyl, neopentyl, cyclopropyl, cyclobutyl, cyclopentyl, cyclohexyl, cyclopentenyl, cyclohexenyl, methylcyclopropyl, ethylcyclohexenyl, butenylcyclopentyl, and the like.

The term "substituted alkyl" or "optionally substituted alkyl" represents an alkyl group as defined above wherein the substitutents are independently selected from halo, cyano, nitro, trihalomethyl, carbamoyl, hydroxy, oxo, $COOR_3$, $CONR_7R_8$, $-C_1-C_6$alkyl, $C_1-C_6$alkyloxy, aryloxy, aryl$C_1-C_6$alkyloxy, thio, $C_1-C_6$alkylthio, arylthio, aryl$C_1-C_6$alkylthio, $NR_7R_8$, $C_1-C_6$alkylamino, arylamino, aryl$C_1-C_6$alkylamino, di(aryl$C_1-C_6$alkyl)amino, $C_1-C_6$alkylcarbonyl, aryl$C_1-C_6$-alkylcarbonyl, $C_1-C_6$alkylcarboxy, arylcarboxy, aryl$C_1-C_6$alkylcarboxy, $C_1-C_6$alkylcarbonyl-amino, $-C_1-C_6$alkylamino$COR_{12}$, aryl$C_1-C_6$alkylcarbonylamino, tetrahydrofuranyl, morpholinyl, piperazinyl, $-CONR_7R_8$, $-C_1-C_6$alkyl$CONR_7R_8$, or a saturated or partial saturated cyclic 5, 6 or 7 membered amine, imide or lactam; wherein $R_1$, is hydroxy, $C_1-C_6$alkyl, aryl, aryl$C_1-C_6$alkyl, $C_1-C_6$alkyloxy, aryloxy, aryl$C_1-C_6$alkyloxy and $R_3$ is defined as above or $NR_7R_8$, wherein $R_7$, $R_8$ are defined as above.

The term "saturated, partially saturated or aromatic cyclic, bicyclic or tricyclic ring system" represents but are not limit to aziridinyl, pyrrolyl, pyrrolinyl, pyrrolidinyl, imidazolyl, 2-imidazolidinyl, pyrazolyl, 2-pyrazolinyl, 1,2,3-triazolyl, 1,2,4-triazolyl, morpholinyl, piperidinyl, thiomorpholinyl, piperazinyl, indolyl, isoindolyl, 1,2,3,4-tetrahydroquinolinyl, 1,2,3,4-tetrahydro-isoquinolinyl, 1,2,3,4-tetrahydroquinoxalinyl, indolinyl, indazolyl, benzimidazolyl, benzotriazolyl, purinyl, carbazolyl, acridinyl, phenothiazinyl, phenoxazinyl, iminodibenzyl, iminostilbenyl.

The term "alkyloxy" (e.g. methoxy, ethoxy, propyloxy, allyloxy, cyclohexyloxy) represents an "alkyl" group as defined above having the indicated number of carbon atoms attached through an oxygen bridge. The term "alkyloxyalkyl" represents an "alkyloxy" group attached through an alkyl group as defined above having the indicated number of carbon atoms.

The term "alkyloxyalkyloxy" represents an "alkyloxyalkyl" group attached through an oxygen atom as defined above having the indicated number of carbon atoms.

The term "aryloxy" (e.g. phenoxy, naphthyloxy and the like) represents an aryl group as defined below attached through an oxygen bridge.

The term "arylalkyloxy" (e.g. phenethyloxy, naphthylmethyloxy and the like) represents an "arylalkyl" group as defined below attached through an oxygen bridge.

The term "arylalkyloxyalkyl" represents an "arylalkyloxy" group as defined above attached through an "alkyl" group defined above having the indicated number of carbon atoms.

The term "arylthio" (e.g. phenylthio, naphthylthio and the like) represents an "aryl" group as defined below attached through an sulfur bridge.

The term "alkyloxycarbonyl" (e.g. methylformiat, ethylformiat and the like) represents an "alkyloxy" group as defined above attached through a carbonyl group.

The term "aryloxyalkyl" represents an "aryloxy" group as defined above attached through an "alkyl" group defined above having the indicated number of carbon atoms.

The term "aryloxycarbonyl" (e.g. phenylformiat, 2-thiazolylformiat and the like) represents an "aryloxy" group as defined above attached through a carbonyl group.

The term "arylalkyloxycarbonyl" (e.g. benzylformiat, phenyletylformiat and the like) represents an "arylalkyloxy" group as defined above attached through a carbonyl group.

The term "alkyloxycarbonylalkyl" represents an "alkyloxycarbonyl" group as defined above attached through an "alkyl" group as defined above having the indicated number of carbon atoms.

The term "arylalkyloxycarbonylalkyl" represents an "arylalkyloxycarbonyl" group as defined above attached through an "alkyl" group as defined above having the indicated number of carbon atoms.

The term "alkylthio" (e.g. methylthio, ethylthio, propylthio, cyclohexenylthio and the like) represents an "alkyl" group as defined above having the indicated number of carbon atoms attached through a sulfur bridge.

The term "arylalkylthio" (e.g. phenylmethylthio, phenylethylthio, and the like) represents an "arylalkyl" group as defined above having the indicated number of carbon atoms attached through a sulfur bridge.

The term "alkylthioalkyl" represents an "alkylthio" group attached through an alkyl group as defined above having the indicated number of carbon atoms.

The term "arylalkylthioalkyl" represents an "arylalkylthio" group attached through an alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, pyrrolidinyl, piperidinyl and the like) represents one or two "alkyl" groups as defined above having the indicated number of carbon atoms attached through an amine bridge. The two alkyl groups may be taken together with the nitrogen to which they are attached forming a saturated, partially saturated or aromatic cyclic, bicyclic or tricyclic ring system containing 3 to 14 carbon atoms and 0 to 3 additional heteroatoms selected from nitrogen, oxygen or sulfur, the ring system can optionally be substituted with at least one $C_1-C_6$alkyl, aryl, aryl$C_1-C_6$alkyl, hydroxy, oxo, $C_1-C_6$alkyloxy, $C_1-C_6$alkyloxy$C_1-C_6$alkyl, $NR_7R_8$, $C_1-C_6$alkylamino$C_1-C_6$alkyl substituent wherein the alkyl and aryl groups are optionally substituted as defined in the definition section and $R_7$ and $R_8$ are defined as above.

The term "arylalkylamino" (e.g. benzylamino, diphenylethylamino and the like) represents one or two "arylalkyl" groups as defined above having the indicated number of carbon atoms attached through an amine bridge. The two "arylalkyl" groups may be taken together with the nitrogen to which they are attached forming a saturated, partially saturated or aromatic cyclic, bicyclic or tricyclic ring system containing 3 to 14 carbon atoms and 0 to 3 additional heteroatoms selected from nitrogen, oxygen or sulfur, the ring system can optionally be substituted with at least one $C_1-C_6$alkyl, aryl, aryl$C_1-C_6$alkyl, hydroxy, oxo, $C_1-C_6$alkyloxy, $C_1-C_6$alkyloxy$C_1-C_6$alkyl, $NR_7R_8$, $C_1-C_6$alkylamino$C_1-C_6$alkyl substituent wherein the alkyl and aryl groups are optionally substituted as defined in the definition section and $R_7$ and $R_8$ are defined as above.

The term "alkylaminoalkyl" represents an "alkylamino" group attached through an alkyl group as defined above having the indicated number of carbon atoms.

The term "arylalkylaminoalkyl" represents an "arylalkylamino" group attached through an alkyl group as defined above having the indicated number of carbon atoms.

The term "arylalkyl" (e.g. benzyl, phenylethyl) represents an "aryl" group as defined below attached through an alkyl having the indicated number of carbon atoms or substituted alkyl group as defined above.

The term "alkylcarbonyl" (e.g. cyclooctylcarbonyl, pentylcarbonyl, 3-hexenylcarbonyl) represents an "alkyl" group as defined above having the indicated number of carbon atoms attached through a carbonyl group.

The term "arylcarbonyl" (benzoyl) represents an "aryl" group as defined above attached through a carbonyl group.

The term "arylalkylcarbonyl" (e.g. phenylcyclopropylcarbonyl, phenylethylcarbonyl and the like) represents an "arylalkyl" group as defined above having the indicated number of carbon atoms attached through a carbonyl group.

The term "alkylcarbonylalkyl" represents an "alkylcarbonyl" group attached through an "alkyl" group as defined above having the indicated number of carbon atoms.

The term "arylalkylcarbonylalkyl" represents an "arylalkylcarbonyl" group attached through an alkyl group as defined above having the indicated number of carbon atoms.

The term "arylamino" represents an "aryl" group as defined below attached through an amino group.

The term "arylaminocarbonyl" represents an "arylamino" group as defined above attached through a carbonyl group.

The term "arylaminocarbonylamino" represents an "arylaminocarbonyl" group as defined above attached through an amino group.

The term "arylaminocarbonylaminoalkyl" represents an "arylaminocarbonylamino" group as defined above attached through an "alkyl" group as defined above having the indicated number of carbon atoms.

The term "alkylcarboxy" (e.g. heptylcarboxy, cyclopropylcarboxy, 3-pentenylcarboxy) represents an "alkylcarbonyl" group as defined above wherein the carbonyl is in turn attached through an oxygen bridge.

The term "arylcarboxyalkyl" (e.g. phenylcarboxymethyl) represents an "arylcarbonyl" group defined above wherein the carbonyl is in turn attached through an oxygen bridge to an alkyl chain having the indicated number of carbon atoms.

The term "arylalkylcarboxy" (e.g. benzylcarboxy, phenylcyclopropylcarboxy and the like) represents an "arylalkylcarbonyl" group as defined above wherein the carbonyl is in turn attached through an oxygen bridge.

The term "alkylcarboxyalkyl" represents an "alkylcarboxy" group attached through an "alkyl" group as defined above having the indicated number of carbon atoms.

The term "arylalkylcarboxyalkyl" represents an "arylalkylcarboxy" group attached through an "alkyl" group as defined above having the indicated number of carbon atoms.

The term "alkylcarbonylamino" (e.g. hexylcarbonylamino, cyclopentylcarbonyl-aminomethyl, methylcarbonylaminophenyl) represents an "alkylcarbonyl" group as defined above wherein the carbonyl is in turn attached through the nitrogen atom of an amino group. The nitrogen atom may itself be substituted with an alkyl or aryl group.

The term "arylalkylcarbonylamino" (e.g. benzylcarbonylamino and the like) represents an "arylalkylcarbonyl" group as defined above wherein the carbonyl is in turn attached through the nitrogen atom of an amino group. The nitrogen atom may itself be substituted with an alkyl or aryl group.

The term "alkylcarbonylaminoalkyl" represents an "alkylcarbonylamino" group attached through an "alkyl" group as defined above having the indicated number of carbon atoms. The nitrogen atom may itself be substituted with an alkyl or aryl group.

The term "arylalkylcarbonylaminoalkyl" represents an "arylalkylcarbonylamino" group attached through an "alkyl" group as defined above having the indicated number of carbon atoms. The nitrogen atom may itself be substituted with an alkyl or aryl group.

The term "alkylcarbonylaminoalkylcarbonyl" represents an alkylcarbonylaminoalkyl group attached through a carbonyl group. The nitrogen atom may be further substituted with an "alkyl" or "aryl" group.

The term "aryl" represents an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g., 3-indolyl, 4-imidazolyl).

The definition of aryl includes but is not limited to phenyl, biphenyl, indenyl, fluorenyl, naphthyl (1-naphthyl, 2-naphthyl), pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), isoxazolyl (3-isoxazolyl, 4-isoxazolyl, 5-isoxazolyl), thiazolyl (2-thiazolyl, 4-thiazolyl, 5-thiazolyl), thiophenyl (2-thiophenyl, 3-thiophenyl, 4-thiophenyl, 5-thiophenyl), furanyl (2-furanyl, 3-furanyl, 4-furanyl, 5-furanyl, pyridyl (2-pyridyl, 3-pyridyl, 4-pyridyl, 5-pyridyl), 5-tetrazolyl, pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydrobenzo[b]furanyl), 5-(2,3-dihydro-benzo-[b]furanyl), 6-(2,3-dihydro-benzo-[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]-thiophenyl (2-(2,3-dihydro-benzo[b]thiophenyl), 3-(2,3-dihydro-benzo[b]-thiophenyl), 4-(2,3-dihydro-benzo[b]thiophenyl), 5-(2,3-dihydro-benzo[b]-thiophenyl), 6-(2,3-dihydro-benzo[b]thiophenyl), 7-(2,3-dihydro-benzo[b]-thiophenyl)), 4,5,6,7-tetrahydro-benzo[b]thiophenyl (2-(4,5,6,7-tetrahydro-benzo-[ [b]thiophenyl), 3-(4,5,6,7-tetrahydro-benzo-[b]thiophenyl), 4-(4,5,6,7-tetrahydrobenzo[b]thiophenyl), 5-(4,5,6,7-tetrahydro-benzo-[b]thiophenyl), 6-(4,5,6,7-tetrahydro-benzo-[b]thiophenyl), 7-(4,5,6,7-tetrahydro-benzo[b]thiophenyl)), 4,5,6,7-tetrahydro-thieno[2,3-c]pyridyl (4-(4,5,6,7-tetrahydro-thieno[2,3-c]pyridyl), 5-4,5,6,7-tetrahydro-thieno[2,3-c]pyridyl), 6-(4,5,6,7-tetrahydro-thieno[2,3-c]pyridyl), 7-(4,5,6,7-tetrahydro-thieno[2,3-c]pyridyl)), indolyl (1-indolyl, 2-indolyl, 3-indolyl, 4-indolyl, 5-indolyl, 6-indolyl, 7-indolyl), isoindolyl (1-isoindolyl, 2-isoindolyl, 3-isoindolyl, 4-isoindolyl, 5-isoindolyl, 6-isoindolyl, 7-isoindolyl), 1,3-dihydro-isoindolyl (1-(1,3-dihydro-isoindolyl), 2-(1,3-dihydro-isoindolyl), 3-(1,3-dihydro-isoindolyl), 4-(1,3-dihydro-isoindolyl), (1-(1,3-dihydro-isoindolyl), 6-(1,3-dihydro-isoindolyl), 7-(1,3-dihydro-isoindolyl)), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzo-thiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz-[b,f]azepin-1-yl, 5H-dibenz-[b,f]azepine-2-yl, 5H-dibenz[b,f]azepine-3-yl, 5H-dibenz-[b,f]azepine-4-yl, 5H-dibenz[b,f]-azepine-5-yl), 10,11-dihydro-5H-dibenz[b,f]azepine (10,11 dihydro-5H-dibenz[b,f]azepine-1-yl, 10,11-dihydro-5H-dibenz-[b,f] azepine-2-yl, 10,11-dihydro-5H-dibenz[b,f]azepine-3-yl, 10,11-dihydro-5H-dibenz-[b,f]azepine-4-yl, 10,11-dihydro-5H-dibenz[b,f]azepine-5-yl), piperidinyl (2-piperidinyl, 3-piperidinyl, 4-piperidinyl), pyrrolidinyl (1-pyrrolidinyl, 2-pyrrolidinyl, 3-pyrrolidinyl), phenylpyridyl (2-phenyl-pyridyl, 3-phenyl-pyridyl, 4-phenylpyridyl), phenylpyrimidinyl (2-phenylpyrimidinyl-4-phenyl-pyrimidinyl, 5-phenylpyrimidinyl, 6-phenylpyrimidinyl), phenylpyrazinyl, phenylpyridazinyl (3-phenylpyridazinyl, 4-phenylpyridazinyl, 5-phenyl-pyridazinyl).

The term "optionally substituted aryl" represents an aryl group as defined above where the substituents are independently selected from the group consisting of halo, nitro, cyano, trihalomethyl, $C_1$–$C_6$alkyl, aryl, aryl$C_1$–$C_6$alkyl, hydroxy, COOR$_3$, CONR$_7$R$_8$, $C_1$–$C_6$alkyloxy, $C_1$–$C_6$alkyloxyC$_1$–$C_6$alkyl, aryloxy, aryl$C_1$–$C_6$alkyloxy, aryl$C_1$–$C_6$alkyloxyC$_1$–$C_6$alkyl, thio, $C_1$–$C_6$alkylthio, $C_1$–$C_6$alkylthioC$_1$–$C_6$alkyl, arylthio, aryl$C_1$–$C_6$alkylthio, aryl$C_1$–$C_6$alkylthioC$_1$–$C_6$alkyl, NR$_7$R$_8$, $C_1$–$C_6$-alkylamino, $C_1$–$C_6$alkylaminoC$_1$–$C_6$alkyl, arylamino, aryl$C_1$–$C_6$alkylamino, aryl$C_1$–$C_6$alkyl-aminoC$_1$–$C_6$alkyl, di(aryl$C_1$–$C_6$alkyl)aminoC$_1$–$C_6$alkyl, $C_1$–$C_6$alkylcarbonyl, $C_1$–$C_6$alkylcarbonylC$_1$–$C_6$alkyl, aryl$C_1$–$C_6$alkylcarbonyl, aryl$C_1$–$C_6$alkylcarbonylC$_1$–$C_6$alkyl, $C_1$–$C_6$alkylcarboxy, $C_1$–$C_6$alkylcarboxyC$_1$–$C_6$alkyl, aryl$C_1$–$C_6$alkylcarboxy, aryl$C_1$–$C_6$alkylcarboxyC$_1$–$C_6$alkyl, carboxyC$_1$–$C_6$-alkyloxy, $C_1$–$C_6$alkylcarbonylamino, $C_1$–$C_6$alkylcarbonylaminoC$_1$–$C_6$alkyl, -carbonylNR$_7$C$_1$–$C_6$alkylCOR$_{11}$, aryl$C_1$–$C_6$alkylcarbonylamino, aryl$C_1$–$C_6$-alkylcarbonylaminoC$_1$–$C_6$alkyl, —CONR$_7$R$_8$, or —C$_1$–$C_6$alkylCONR$_7$R$_8$; wherein R$_3$, R$_7$, R$_8$, and R$_1$, are defined as above and the alkyl and aryl groups are optionally substituted as defined in the definition section;

The term "arylcarbonyl" (e.g. 2-thiophenylcarbonyl, 3-methoxy-anthrylcarbonyl, oxazolylcarbonyl) represents an "aryl" group as defined above attached through a carbonyl group.

The term "arylalkylcarbonyl" (e.g. (2,3-dimethoxyphenyl)propylcarbonyl, (2-chloronaphthyl)pentenylcarbonyl, imidazolylcyclopentylcarbonyl) represents an "arylalkyl" group as defined above wherein the "alkyl" group is in turn attached through a carbonyl.

The term "alkyl and aryl groups are optionally substituted" represents respectively an "optionally substituted alkyl" group and an "optionally substituted aryl" group as defined above.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the Compounds of Formula 1, where a basic or acidic group is present in the structure, are also included within the scope of this invention. When an acidic substituent is present, such as —COOH, 5-tetrazolyl or —P(O)(OH)$_2$, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethane sulfonate, picrate and the like, and include acids related to the pharmaceutically acceptable salts listed in Journal of Pharmaceutical Science, 66, 2 (1977) and incorporated herein by reference, can be used as the dosage form.

Also, in the case of the —COOH or —P(O)(OH)$_2$ being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other.

In a preferred embodiment, the present invention is concerned with compounds of Formula I

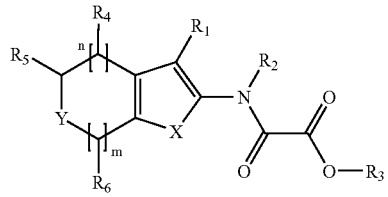

Formula 1 wherein n is 0, 1 or 2;

m is 1 or 2;

X is S or O;

Y is O, S, SO or SO$_2$;

R$_1$ is hydrogen or COOR$_3$, or R$_1$ is selected from the group consisting of the following 5-membered heterocycles:

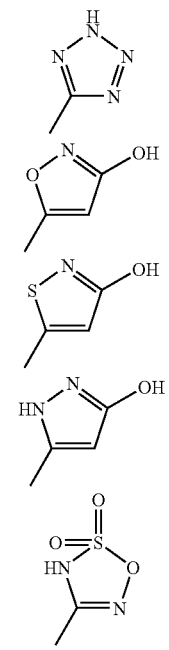

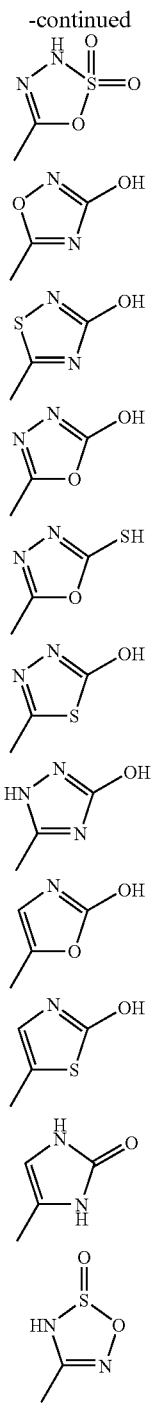

$R_2$ is hydrogen, $C_1$–$C_6$alkyl, hydroxy or $NR_7R_8$;

$R_3$ is hydrogen, $C_1$–$C_6$alkyl, aryl$C_1$–$C_6$alkyl, $C_1$–$C_6$alkylcarbonyloxy$C_1$–$C_6$alkyl or $C_1$–$C_6$alkylcarbonyloxyaryl$C_1$–$C_6$alkyl;

$R_4$, $R_5$ and $R_6$ are independently hydrogen, trihalomethyl, $C_1$–$C_6$alkyl, aryl, aryl$C_1$–$C_6$alkyl, hydroxy, oxo, carboxy, carboxy$C_1$–$C_6$alkyl, $C_1$–$C_6$alkyloxy-carbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$-alkyl, thio, $C_1$–$C_6$alkylthio, $C_1$–$C_6$alkylthio$C_1$–$C_6$alkyl, aryl-thio, aryl$C_1$–$C_6$alkyl-thio, aryl$C_1$–$C_6$alkylthio$C_1$–$C_6$alkyl, $NR_8R_9$, $C_1$–$C_6$alkylamino$C_1$–$C_6$alkyl, aryl-$C_1$–$C_6$alkylamino$C_1$–$C_6$alkyl, di(aryl$C_1$–$C_6$alkyl) amino$C_1$–$C_6$alkyl, $C_1$–$C_6$alkyl-carbonyl, $C_1$–$C_6$alkylcarbonyl, $C_1$–$C_6$alkyl, aryl$C_1$–$C_6$alkylcarbonyl, aryl$C_1$–$C_6$-alkylcarbonyl$C_1$–$C_6$alkyl, $C_1$–$C_6$alkylcarboxy, $C_1$–$C_6$alkylcarboxy$C_1$–$C_6$alkyl, arylcarboxy, arylcarboxy$C_1$–$C_6$alkyl, aryl $C_1$–$C_6$alkylcarboxy, aryl$C_1$–$C_6$alkyl-carboxy$C_1$–$C_6$alkyl, $C_1$–$C_6$alkylcarbonylamino, $C_1$–$C_6$alkylcarbonyl-amino$C_1$–$C_6$alkyl, -carbonyl$NR_8C_1$–$C_6$alkyl$COR_{11}$, aryl$C_1$–$C_6$alkylcarbonyl-amino, aryl$C_1$–$C_6$alkylcarbonylamino$C_1$–$C_6$alkyl, $CONR_7R_8$, or $C_1$–$C_6$alkyl$CONR_7R_8$ wherein the alkyl and aryl groups are optionally substituted and $R_1$, is $NR_7R_8$, or $C_1$–$C_6$alkyl$NR_7R_8$;

$R_7$ and $R_8$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein the alkyl and aryl groups are optionally substituted; or $R_7$ and $R_8$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulphur, the ring system can optionally be substituted with at least one $C_1$–$C_6$alkyl, aryl, aryl$C_1$–$C_6$alkyl hydroxy, oxo, $C_1$–$C_6$alkyloxy, aryl$C_1$–$C_6$alkyloxy, $C_1$–$C_6$-alkyloxy$C_1$–$C_6$alkyl, $C_1$–$C_6$alkylamino-$C_1$–$C_6$alkyl or $NR_9R_{10}$, wherein $R_9$ and $R_{10}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$-alkylcarboxy or aryl$C_1$–$C_6$alkylcarboxy; wherein the alkyl and aryl groups are optionally substituted; or $R_7$ and $R_8$ are independently a saturated or partial saturated cyclic 5, 6 or 7 membered amine, imide or lactam;

or a salt thereof with a pharmaceutically acceptable acid or base, or any optical isomer or mixture of optical isomers, including a racemic mixture, or any tautomeric form.

In another preferred embodiment, the present invention is concerned with compounds of Formula I wherein X is sulphur.

In another preferred embodiment, the present invention is concerned with compounds of Formula I wherein $R_1$ is $COOR_3$ and $R_2$ is hydrogen; wherein $R_3$ is defined as above.

In another preferred embodiment, the present invention is concerned with compounds of Formula I wherein n and m are 1.

In another preferred embodiment, the present invention is concerned with compounds of Formula I wherein Y is oxygen.

In another preferred embodiment, the present invention is concerned with compounds of Formula I wherein $R_5$ is $C_1$–$C_6$alkyl$NR_7R_8$.

In another preferred embodiment, the present invention is concerned with compounds of Formula I wherein $R_4$ and $R_6$ are hydrogen.

In another preferred embodiment, the present invention is concerned with compounds of Formula I wherein $R_1$ is 5-tetrazolyl, $R_2$ is hydrogen, $R_5$ is $C_1$–$C_6$alkyl$NR_7R_8$ and Y is oxygen.

In another preferred embodiment, the present invention is concerned with compounds of Formula I wherein $R_1$ is 5-tetrazolyl, $R_2$ is hydrogen, $R_6$ is $C_1$–$C_6$alkyl$NR_7R_8$ and Y is oxygen.

In another preferred embodiment, the present invention is concerned with compounds of Formula I wherein $R_6$ is $C_1$–$C_6$alkyl$NR_7R_8$.

In another preferred embodiment, the present invention is concerned with compounds of Formula I wherein $R_4$ and $R_5$ are hydrogen.

In another preferred embodiment, the present invention is concerned with compounds of Formula I wherein $R_7$ and $R_8$ are together with the nitrogen to which they are attached forming a saturated, partially saturated or aromatic cyclic, bicyclic or tricyclic ring system.

In a preferred embodiment of the invention X in formula 1 is sulphur and Y is oxygen.

In another preferred embodiment of the invention $R_1$ is COOR$_3$ and $R_2$ is hydrogen; wherein $R_3$ is hydrogen, $C_1$–$C_6$alkyl or aryl$C_1$–$C_6$alkyl.

In a further preferred embodiment of the invention n and m are 1.

In a further preferred embodiment of the invention $R_4$ and $R_6$ are both hydrogen and $R_5$ is CON$R_7R_8$, wherein $R_7$ and $R_8$ are independently selected from hydrogen, $C_1$–$C_6$alkyl or aryl.

Most preferred is $R_7$ hydrogen and $R_8$ is phenyl or benzyl.

In a further preferred embodiment of the invention $R_4$ and $R_6$ are both hydrogen and $R_5$ is $C_1$–$C_6$alkyl$NR_7R_8$, wherein $R_7$ and $R_8$ are together with the nitrogen to which they are attached forming a saturated, partially saturated or aromatic monocyclic, bicyclic or tricyclic ring system containing from 3 to 14 carbon atoms and from 0 to 3 additional heteroatoms selected from nitrogen, oxygen or sulphur, the ring system being optionally substituted as defined above for substituted alkyl and substituted aryl.

Preferably are $R_8$ and $R_9$ together with the nitrogen to which they are attached forming an isoindol, thiazolidine, pyrrolopyrazine, pyrrolopyridine, benzo[d]isoxazol, 1,3-dihydro-benzo[d]isothiazol or 1,1-dioxo-1,3-dihydro-benzo[d]isothiazol ring, the ring system being optionally substituted as defined above.

Most preferred ring systems are 1,3-dihydro-benzo[d]isothiazol or 1,1-dioxo-1,3-dihydro-benzo[d]isothiazol rings.

In a further preferred embodiment of the invention $R_4$ and $R_5$ are both hydrogen and $R_6$ is CON$R_7R_8$, wherein $R_7$ and $R_8$ are independently selected from hydrogen, $C_1$–$C_6$alkyl or aryl.

Most preferred is $R_7$ hydrogen and $R_6$ is phenyl or benzyl.

In a further preferred embodiment of the invention $R_4$ and $R_5$ are both hydrogen and $R_6$ is $C_1$–$C_6$alkyl$NR_7R_8$, wherein $R_7$ and $R_8$ are together with the nitrogen to which they are attached forming a saturated, partially saturated or aromatic monocyclic, bicyclic or tricyclic ring system containing from 3 to 14 carbon atoms and from 0 to 3 additional heteroatoms selected from nitrogen, oxygen or sulphur, the ring system being optionally substituted as defined above for substituted alkyl and substituted aryl.

Preferably are $R_8$ and $R_9$ together with the nitrogen to which they are attached forming an isoindol, thiazolidine, pyrrolopyrazine or pyrrolopyridine, benzo[d]isoxazol, 1,325 dihydro-benzo[d]isothiazol or 1,1-dioxo-1,3-dihydro-benzo[d]isothiazol ring, the ring system being optionally substituted as defined above for substituted aryl. Most preferred ring systems are 1,3-dihydro-benzo[d]isothiazol and 1,1-dioxo-1,3-dihydrobenzo[d]isothiazol rings.

In another preferred embodiment, the present invention is concerned with compounds of Formula I wherein the ring system is 1,3-dihydro-benzo[d]isothiazolyl, substituted with 2 or 3 oxo groups at the atom positions adjacent to the nitrogen atom.

In another preferred embodiment, the present invention is concerned with compounds of Formula I wherein the ring system is 1,3-dihydro-isoindol, substituted with 1 or 2 oxo groups at the atom positions adjacent to the nitrogen atom.

In another preferred embodiment, the present invention is concerned with compounds of Formula I wherein the ring system is optionally substituted with hydroxy, nitro, methoxy, benzyloxy, fluoro, chloro, $CH_3CH_2CH_2NHC(O)$— or $CH_3C(O)NH$—.

In another preferred embodiment, the present invention is concerned with compounds of Formula I wherein $R_7$ and $R_8$ are together with the nitrogen to which they are attached forming a saturated, partially saturated or aromatic monocyclic, bicyclic or tricyclic ring system.

In another preferred embodiment, the present invention is concerned with compounds of Formula I wherein the ring system is 1,3-dihydro-isoindol, substituted with 1 or 2 oxo groups at the atom positions adjacent to the nitrogen atom.

In another preferred embodiment, the present invention is concerned with compounds of Formula I wherein the ring system is optionally substituted with hydroxy, nitro, methoxy, benzyloxy, fluoro, chloro, $CH_3CH_2CH_2NHC(O)$— or $CH_3C(O)NH$—.

In another preferred embodiment, the present invention is concerned with compounds of Formula I wherein the ring system is thiazolidin-2,4-dione.

In another preferred embodiment, the present invention is concerned with compounds of Formula I wherein the ring system is 5-arylidene-thiazolidin-2,4-dione.

In another preferred embodiment, the present invention is concerned with compounds of Formula I wherein the aryl group is phenyl optionally substituted with methoxy or $CH_3C(O)$—.

In another preferred embodiment, the present invention is concerned with compounds of Formula I wherein the aryl group is pyridyl.

In another preferred embodiment, the present invention is concerned with compounds of Formula I wherein the aryl group is 4(5)-imidazolyl.

In another preferred embodiment, the present invention is concerned with compounds of Formula I wherein the ring system is 5-(aryl-methyl)-thiazolidin-2,4-dione.

In another preferred embodiment, the present invention is concerned with compounds of Formula I wherein the aryl group is pyridyl.

In another preferred embodiment, the present invention is concerned with compounds of Formula I wherein $R_7$ is hydrogen and $R_5$ is —C(O)-aryl.

In another preferred embodiment, the present invention is concerned with compounds of Formula I wherein the aryl group is phenyl optionally substituted as defined above for aryl.

In another preferred embodiment, the present invention is concerned with compounds of Formula I wherein the aryl group is benzo[1,3]dioxole.

In another preferred embodiment, the present invention is concerned with compounds of Formula I wherein $R_7$ is hydrogen and $R_8$ is —C(O)—$C_1$–$C_6$alkylaryl.

In another preferred embodiment, the present invention is concerned with compounds of Formula I wherein the aryl group is phenyl optionally substituted as defined above for aryl.

In another preferred embodiment, the present invention is concerned with compounds of Formula I wherein $R_5$ is —C(O)NR$_7$R$_8$.

In another preferred embodiment, the present invention is concerned with compounds of Formula I wherein $R_7$ is hydrogen and $R_8$ is aryl.

In another preferred embodiment, the present invention is concerned with compounds of Formula I wherein $R_7$ is hydrogen and $R_8$ is $C_1$–$C_6$alkylaryl.

In another preferred embodiment, the present invention is concerned with compounds of Formula I wherein $R_6$ is —C(O)NR$_7$R$_8$.

In another preferred embodiment, the present invention is concerned with compounds of Formula I wherein $R_7$ is hydrogen and $R_8$ is aryl.

In another preferred embodiment, the present invention is concerned with compounds of Formula I wherein $R_7$ is hydrogen and $R_8$ is $C_1$–$C_6$alkylaryl.

In another preferred embodiment, the present invention is concerned with compounds of Formula I wherein the ring system is pyrrolo[3,4-c]pyridine-1,3-dione.

In another preferred embodiment, the present invention is concerned with compounds of Formula I wherein the ring system is pyrrolo[3,4-b]pyridine-5,7-dione.

In another preferred embodiment, the present invention is concerned with compounds of Formula I wherein the ring system is pyrrolo[3,4-b]pyrazine-5,7-dione.

In another preferred embodiment, the present invention is concerned with compounds of Formula I wherein the ring system is pyrrolo[3,4-c]pyridine-1,3-dione.

In another preferred embodiment, the present invention is concerned with compounds of Formula I wherein $R_6$ is arylaminocarbonylamino$C_1$–$C_6$alkyl.

In another preferred embodiment, the present invention is concerned with compounds of Formula I wherein the aryl group is phenyl optionally substituted as defined above for aryl.

In another preferred embodiment, the present invention is concerned with compounds of Formula I wherein $R_6$ is aryloxy$C_1$–$C_6$alkyl.

In another preferred embodiment, the present invention is concerned with compounds of Formula I wherein the aryl group is 1,1-dioxo-benzo[d]isothiazol-3-yl.

In another preferred embodiment, the present invention is concerned with compounds of Formula I wherein the aryl group is 1,1-dioxo-5-phenyl-isothiazol-3-yl.

In another preferred embodiment, the present invention is concerned with compounds of Formula I wherein the ring system is 6-chloro-1,1,3-trioxo-2,3-dihydro-4H-thieno[3,2-e]-1,2,4-thiadiazin-2-yl.

In another preferred embodiment, the present invention is concerned with compounds of Formula I wherein the aryl group is 6-chloro-1,1-dioxo-2,3-dihydro-4H-thieno[3,2-e]-1,2,4-thiadiazin-3-yl.

In another preferred embodiment, the present invention is concerned with compounds of Formula I wherein $R_5$ is aryloxy$C_1$–$C_6$alkyl.

In another preferred embodiment, the present invention is concerned with compounds of Formula I wherein the aryl group is 1,1-dioxo-5-phenyl-isothiazol-3-yl.

In another preferred embodiment, the present invention is concerned with compounds of Formula I wherein the ring system is 1,1,3-trioxo-5-phenyl-isothiazol-2-yl.

In another preferred embodiment, the present invention is concerned with compounds of Formula I wherein the ring system is 5-benzyl-1,1-dioxo-[1,2,5]thiadiazolidin-2-yl.

In another preferred embodiment, the present invention is concerned with compounds of Formula I wherein the ring system is 5-ethyl-1,1-dioxo-[1,2,5]thiadiazolidin-2-yl.

In another preferred embodiment, the present invention is concerned with compounds of Formula I wherein $R_7$ is hydrogen and $R_8$ is aryl$C_1$–$C_6$alkyl; wherein the aryl and alkyl groups are optionally substituted as defined above for alkyl and aryl.

In another preferred embodiment, the present invention is concerned with compounds of Formula I wherein the aryl group is benzo[1,3]dioxol-5-yl.

In another preferred embodiment, the present invention is concerned with compounds of Formula I wherein the aryl group is 5-methoxy-2-methyl-1H-indol-3-yl.

The following compounds are preferred:

5-(4-Chloro-1,3-dioxo-1,3-dihydro-isoindol-2-ylmethyl)-2-(oxalyl-amino)-4,7-dihydro-5H-thieno[2,3-c]pyran-3-carboxylic acid;

5-(4,5,6,7-Tetrachloro-1,3-dioxo-1,3-dihydro-isoindol-2-yl-methyl)-2-(oxalyl-amino)-4,7-dihydro-5H-thieno[2,3-c]pyran-3-carboxylic acid;

5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Benzyloxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Fluoro-1,3-dioxo-1,3-dihydro-isoindol-2-ylmethyl)-2-(oxalyl-amino)-4,7-dihydro-5H-thieno[2,3-c]pyran-3-carboxylic acid;

5-(1,3-Dioxo-1,3-dihydro-benzo[f]Isoindol-2-ylmethyl)-2-(oxalyl-amino)-4,7-dihydro-5H-thieno[2,3-c]pyran-3-carboxylic acid;

5-(5-Acetylamino-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Acetylamino-1,3-dioxo-1,3-dihydro-isoindol-2-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-b]pyrazin-6-ylmethyl)-2-(oxalyl-amino)-4,7-dihydro-5H-thieno[2,3-c]pyran-3-carboxylic acid;

7-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-c]pyridin-6-ylmethyl)-2-(oxalyl-amino)-4,7-dihydro-5H-thieno[2,3-c]pyran-3-carboxylic acid;

5-(5-Nitro-1,3-dioxo-1,3-dihydro-isoindol-2-ylmethyl)-2-(oxalyl-amino)-4,7-dihydro-5H-thieno[2,3-c]pyran-3-carboxylic acid;

5-(5-Hydroxy-1,3-dioxo-1,3-dihydro-isoindol-2-ylmethyl)-2-(oxalyl-amino)-4,7-dihydro-5H-thieno[2,3-c]pyran-3-carboxylic acid, 5-(4-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Nitro-1,3-dioxo-1,3-dihydro-isoindol-2-ylmethyl)-2-(oxalyl-amino)-4,7-dihydro-5H-thieno[2,3-c]pyran-3-carboxylic acid;

5-(4-(4-Chloro-phenylsulfanyl)-6-methyl-1,3-dioxo-1,3-dihydro-pyrrolo[3,4-c]pyridin-2-ylmethyl)-2-(oxalyl-amino)-4,7-dihydro-5H-thieno[2,3-c]pyran-3-carboxylic acid;

5-(3-imidazol-1-yl-2,5-dioxo-pyrrolidin-1-ylmethyl)-2-(oxalyl-amino)-4,7-dihydro-5H-thieno[2,3-c]pyran-3-carboxylic acid;

Oxalic acid 3-carboxy-2-(oxalyl-amino)-4,7-dihydro-5H-thieno[2,3-c]pyran-5-ylmethyl ester methyl;

Oxalic acid (3-carboxy-2-(oxalyl-amino)-4,7-dihydro-5H-thieno[2,3-c]pyran-5-ylmethyl) ester;

7-Hydroxymethyl-2-(oxalyl-amino)-4,7-dihydro-5H-thieno[2,3-c]pyran-3-carboxylic acid;

7-(2,4-Dioxo-thiazolidin-3-ylmethyl)-2-(oxalyl-amino)-4,7-dihydro-5H-thieno[2,3-c]pyran-3-carboxylic acid;

7-(1,3-Dioxo-1,3-di hydro-isoindol-2-yloxymethyl)-2-(oxalyl-amino)-4,7-dihydro-5H-thieno[2,3-c]pyran-3-carboxylic acid;

7-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

7-(5,7-Dioxo-5,7-dihydro-[1,3]dioxolo[4,5-f]isoindol-6-ylmethyl-2-(oxalyl-amino)-4,7-dihydro-5H-thieno[2,3-c]pyran-3-carboxylic acid;

7-(((Benzo[1,3]dioxole-5-carbonyl)amino)methyl)-2-(oxalyl-amino)-7-dihydro-5H-thieno[2,3-c]pyran-3-carboxylic acid;

7-(3-(2,4-Dimethoxy-phenyl)ureidomethyl)-2-(oxalyl-amino)-4,7-dihydro-5H-thieno[2,3-c]pyran-3-carboxylic acid;

2-(Oxalyl-amino)-5-phenylcarbamoyl-4,7-dihydro-5H-thieno[2,3-c]pyran-3-carboxylic acid;

5-Benzylcarbamoyl-2-(oxalyl-amino)-4,7-dihydro-5H-thieno[2,3-c]pyran-3-carboxylic acid;

2-(Oxalyl-amino)-4,7-dihydro-5H-thieno[2,3-c]pyran-3,7-dicarboxylic acid 7-ethyl ester;

7-Benzylcarbamoyl-2-(oxalyl-amino)-4,7-dihydro-5H-thieno[2,3-c]pyran-3-carboxylic acid;

7-((2-(4-Methanesulfonyl-phenyl)-acetylamino)-methyl)-2-(oxalyl-amino)-4,7-dihydro-5H-thieno[2,3-c]pyran-3-carboxylic acid;

2-((3-Carboxy-2-(oxalyl-amino)-4,7-dihydro-5H-thieno[2,3-c]pyran-5-ylmethyl)carbamoyl)nicotinic acid;

7-(2,4-Dioxo-5-pyridin-2-ylmethylene-thiazolidin-3-ylmethyl)-2-(oxalyl-amino)-4,7-dihydro-5H-thieno[2,3-c]pyran-3-carboxylic acid;

7-(2,4-Dioxo-5-pyridin-2-ylmethyl-thiazolidin-3-ylmethyl)-2-(oxalyl-amino)-4,7-dihydro-5H-thieno[2,3-c]pyran-3-carboxylic acid;

7-(5-(4-Methoxy-benzylidene)-2,4-dioxo-thiazolidin-3-ylmethyl)-2-(oxalyl-amino)-4,7-dihydro-5H-thieno[2,3-c]pyran-3-carboxylic acid;

7-(5-(4-Acetylamino-benzylidene)-2,4-dioxo-thiazolidin-3-ylmethyl)-2-(oxalyl-amino)-4,7-dihydro-5H-thieno[2,3-c]pyran-3-carboxylic acid;

7-(5-(3,5-Dimethoxy-benzylidene)-2,4-dioxo-thiazolidin-3-ylmethyl)-2-(oxalyl-amino)-4,7-dihydro-5H-thieno[2,3-c]pyran-3-carboxylic acid;

7-[5-(1H-imidazol-4(5)-ylmethylene)-2,4-dioxo-thiazolidin-3-ylmethyl]-2-(oxalyl-amino)-4,7-dihydro-5H-thieno[2,3-c]pyran-3-carboxylic acid;

5-(1,3-Dioxo-4,7-epoxido-1,3,4,5,6,7-hexahydro-isoindol-2-ylmethyl)-2-(oxalyl-amino)-4,7-dihydro-5H-thieno[2,3-c]pyran-3-carboxylic acid;

7-(((2R)-2-Amino-3-phenyl-propionylamino)methyl)-2-(oxalyl-amino)-4,7-dihydro-5H-thieno[2,3-c]pyran-3-carboxylic acid;

7-((2-Acetylamino-3-(4-hydroxy-phenyl)-propionylamino)methyl)-2-(oxalyl-amino)-4,7-dihydro-5H-thieno[2,3-c]pyran-3-carboxylic acid;

7-((2-Acetylamino-3-methyl-butyrylamino)methyl)-2-(oxalyl-amino)-4,7-dihydro-5H-thieno[2,3-c]pyran-3-carboxylic acid;

2-(Oxalyl-amino)-7-(1,1,3-trioxo-1,3-dihydro-1H-benzo[d]isothiazol-2-ylmethyl)-4,7-dihydro-5H-thieno[2,3-c]pyran-3-carboxylic acid;

or a pharmaceutically acceptable salt thereof.

The following compounds are also preferred:

2-(Oxalyl-amino)-7-(1,1,3-trioxo-1H-benzo[d]isothiazol-3-yloxomethyl)-4,7-dihydro-5H-thieno[2,3-c]pyran-3-carboxylic acid;

2-(Oxalyl-amino)-7-(3-oxo-3H-benzo[d]isoxazol-2-ylmethyl)-4,7-dihydro-5H-thieno[2,3-c]pyran-3-carboxylic acid;

2-(Oxalyl-amino)-7-(1,1,3-trioxo-5-phenyl-1,3-dihydro-isothiazol-2-ylmethyl)-4,7-dihydro-5H-thieno[2,3-c]pyran-3-carboxylic acid;

7-(1,1-Dioxo-5-phenyl-1H-isothiazol-3-yloxymethyl)-2-(oxalyl-amino)-4,7-dihydro-5H-thieno[2,3-c]pyran-3-carboxylic acid;

2-(Oxalyl-amino)-5-(1,1,3-trioxo-5-phenyl-1,3-dihydro-isothiazol-2-ylmethyl)-4,7-dihydro-5H-thieno[2,3-c]pyran-3-carboxylic acid;

5-(1,1-Dioxo-5-phenyl-1H-isothiazol-3-yloxymethyl)-2-(oxalyl-amino)-4,7-dihydro-5H-thieno[2,3-c]pyran-3-carboxylic acid;

5-(6-Chloro-1,1,3-trioxo-2,3-dihydro-4H-thieno[3,2-e]-1,2,4-thiadiazin-2-ylmethyl)-2-(oxalyl-amino)-4,7-dihydro-5H-thieno[2,3-c]pyran-3-carboxylic acid;

5-(6-Chloro-1,1-dioxo-4H-thieno[3,2-e]-1,2,4-thiadiazine-3-yloxymethyl)-2-(oxalyl-amino)-4,7-dihydro-5H-thieno[2,3-c]pyran-3-carboxylic acid;

7-(1,3-Dioxo-1,3-dihydro-benzo[d]isothiazol-2-ylmethyl)-2-(oxalyl-amino)-4,7-dihydro-5H-thieno[2,3-c]pyran-3-carboxylic acid;

5-(1,3-Dioxo-1,3-dihydro-benzo[d]isothiazol-2-ylmethyl)-2-(oxalyl-amino)-4,7-dihydro-5H-thieno[2,3-c]pyran-3-carboxylic acid;

5-(5-Benzyl-1,1-dioxo-[1,2,5]thiadiazolidin-2-ylmethyl)-2-(oxalyl-amino)-4,7-dihydro-5H-thieno[2,3-c]pyran-3-carboxylic acid;

5-(5-Ethyl-1,1-dioxo-[1,2,5]thiadiazolidin-2-ylmethyl)-2-(oxalyl-amino)-4,7-dihydro-5H-thieno[2,3-c]pyran-3-carboxylic acid;

2-(Oxalyl-amino)-7-(1-oxo-1,3-dihydro-isoindol-2-ylmethyl)-4,7-dihydro-5H-thieno[2,3-c]pyran-3-carboxylic acid;

2-(Oxalyl-amino)-5-(2,2,2-trifluoro-acetoxymethyl)-4,7-dihydro-5H-thieno[2,3-c]pyran-3-carboxylic acid;

5-(((Benzo[1,3]dioxol-5-ylmethyl)-amino)methyl)-2-(oxalyl-amino)-4,7-dihydro-5H-thieno[2,3-c]pyran-3-carboxylic acid;

5-((2-Methoxy-benzylamino)methyl)-2-(oxalyl-amino)-4,7-dihydro-5H-thieno[2,3-c]pyran-3-carboxylic acid;

5-((2-Benzo[1,3]dioxol-5-yl-acetylamino)methyl)-2-(oxalyl-amino)-4,7-dihydro-5H-thieno[2,3-c]pyran-3-carboxylic acid;

5-(((5-Methoxy-2-methyl-1H-indol-3-carbonyl)amino)methyl)-2-(oxalyl-amino)-4,7-dihydro-5H-thieno[2,3-c]pyran-3-carboxylic acid;

5-(1,3-Dioxo-5-propylcarbamoyl-1,3-dihydro-isoindol-2-ylmethyl)-2-(oxalyl-amino)-4,7-dihydro-5H-thieno[2,3-c]pyran-3-carboxylic acid;

or a salt thereof with a pharmaceutically acceptable acid or base, or any optical isomer or mixture of optical isomers, including a racemic mixture, or any tautomeric form, or prodrug thereof.

Pharmacological Methods

The compounds are evaluated for biological activity with a truncated form of PTP1 B (corresponding to the first 321 amino acids), which was expressed in *E. coli* and purified to apparent homogeneity using published procedures well-known to those skilled in the art. The enzyme reactions are carried out using standard conditions essentially as described by Burke et al. (*Biochemistry* 35; 15989–15996 (1996)). The assay conditions are as follows. Appropriate concentrations of the compounds of the invention are added to the reaction mixtures containing different concentrations of the substrate, p-nitrophenyl phosphate (range: 0.16 to 10 mM—final assay concentration). The buffer used was 50 mM HEPES pH 7.0, 100 mM sodium chloride, 0.1% (w/v) bovine serum albumin, 5 mM glutathione, and 1 mM EDTA.). The reaction was started by addition of the enzyme and carried out in microtiter plates at 250 C for 60 minutes. The reactions are stopped by addition of NaOH. The enzyme activity was determined by measurement of the absorbance at 405 nm with appropriate corrections for absorbance at 405 nm of the compounds and p-nitrophenyl phosphate. The data are analyzed using nonlinear regression fit to classical Michaelis Menten enzyme kinetic models. Inhibition is expressed as $K_i$ values in μM. The results of representative experiments are shown in Table 1

TABLE 1

Inhibition of classical PTP1B by compounds of the invention

| Example no. | PTP1B $K_I$ values (μM) |
|---|---|
| 4 | 1.5 |
| 23 | 9.7 |
| 25 | 7.0 |
| 26 | 1.2 |
| 27 | 3.6 |
| 28 | 8.2 |
| 39 | 7.5 |
| 41 | 1.5 |
| 46 | 2.3 |
| 47 | 0.8 |
| 49 | 1.4 |
| 50 | 3.0 |
| 55 | 1.3 |

Analysis for Blood Glucose Lowering Effects

The compounds of the invention are tested for blood glucose lowering effects in diabetic, obese female ob/ob mice. The mice are of similar age and body weights and they are randomized into groups of ten mice. They have free access to food and water during the experiment. The compounds are administered by either by gavage, subcutaneous, intravenous or intraperitoneal injections. The control group receives the same volume of vehicle as the mice that receive the compounds. Non-limiting examples of dose-range: 0.1, 0.3, 1.0, 3.0, 10, 30, 100 mg per kg body weight. The blood glucose levels are measured two times before administration of the compounds of the invention and vehicle (to the control group). After administration of the compound, the blood glucose levels are measured at the following time points: 1, 2, 4, 6, and 8 hours. A positive response is defined either as (i) a more than 25 percent reduction in blood glucose levels in the group receiving the compound of the invention compared to the group receiving the vehicle at any time point or (ii) statistically significant (i.e. p<0.05) reduction in the area under the blood glucose curve during the whole period (i.e. 8 hrs) in the group treated with the compounds of the invention compared to the group receiving the vehicle.

Compounds that show positive response can be used as development candidates and used for treatment of human diseases such as diabetes and obesity.

The Synthesis of the Compounds

In accordance with one aspect of the invention, the compounds of the invention are prepared as illustrated in the following reaction scheme:

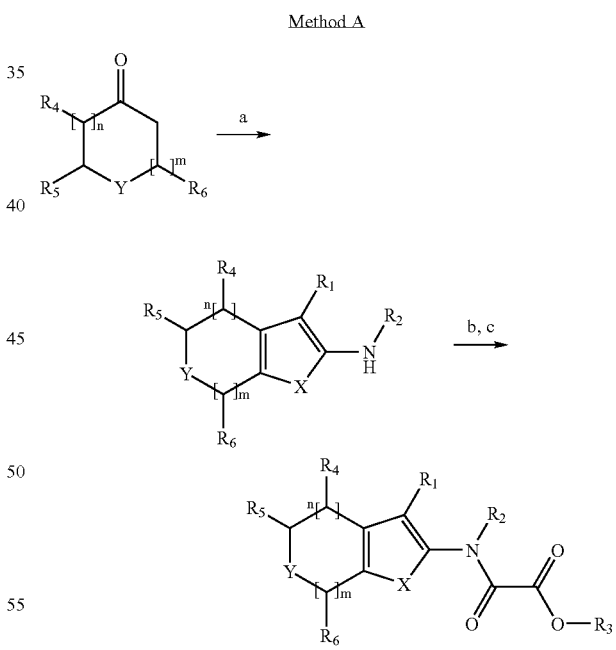

Method A a) $NCCH_2COOR_3$, sulphur, morpholine or triethylamine, EtOH; b) $R_3OCOCOimidazole$, THF; c) 25% $TFA/CH_2Cl_2$; wherein n, m, X, Y, $R_1$, $R_2$, $R_3$, $R_4$, $R_5$, and $R_6$ are defined above;

When $R_4$ is hydrogen the reaction step a) in Method A gives a mixture of regioisomers which can be separated by use of column chromatography known to thus skilled in the art.

Method B

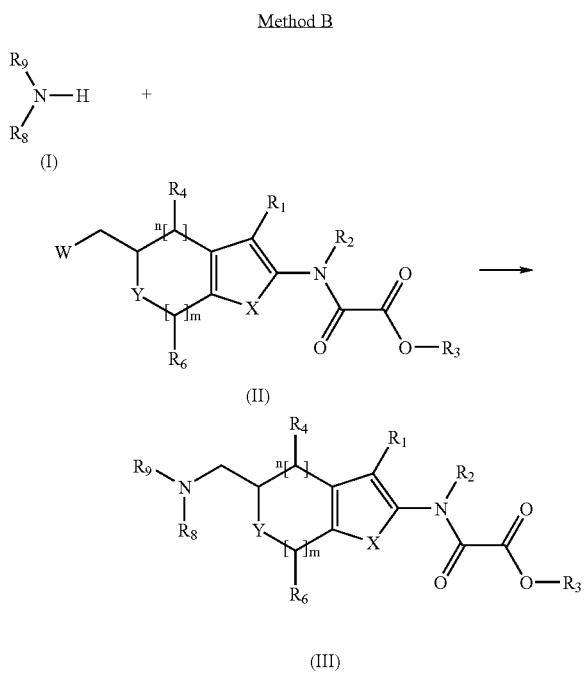

By allowing an amine (I) and a substituted oxalylamide (II) to react under basic conditions (e.g. K$_2$CO$_3$, in N,N-dimethylformamide or methylethylketone) or under Mitsunobu conditions (Oyo Mitsunobu, *Synthesis*, (1981) 1–28) to yield (III) wherein W is OH, OSO$_2$Me or halo, and n, m, X, Y, R$_1$, R$_2$, R$_3$, R$_4$, R$_6$, R$_8$ and R$_9$ are defined above.

Method C

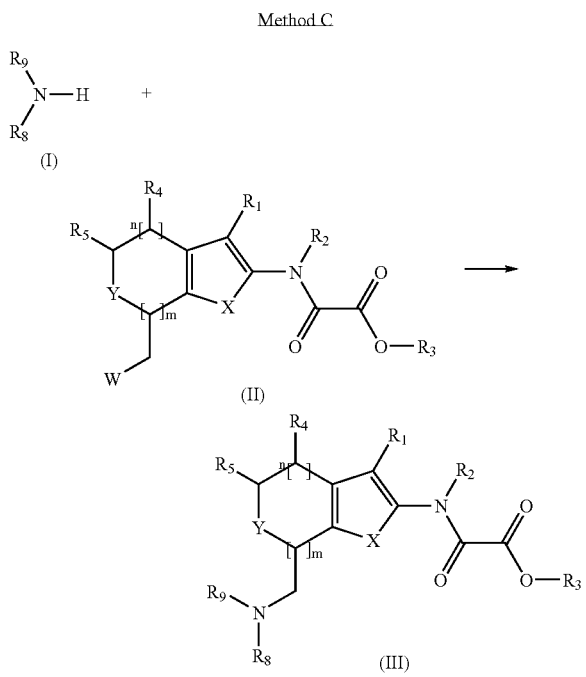

By allowing an amine (I) and a substituted oxalylamide (II) to react under basic conditions (e.g. K$_2$CO$_3$, in N,N-dimethylformamide or methylethylketone) or under Mitsunobu conditions (Oyo Mitsunobu, *Synthesis*, (1981) 1–28) to yield (III) wherein W is OH, OSO$_2$Me or halo, and n, m, X, Y, R$_1$, R$_2$, R$_3$, R$_4$, R$_5$, R$_8$ and R$_9$ are defined above.

Pharmacological Preparations

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator activated receptor) modulators, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is Incorporated herein by reference as well as orally active hypoglycaemic agents.

The orally active hypoglycaemic agents preferably comprise sulphonylureas, biguanides, meglitinides, oxadiazolidinediones, thiazolidinediones, glucosidase inhibitors, glucagon antagonists such as those disclosed in WO 99/01423 to Novo Nordisk A/S and Agouron Pharmaceuticals, inc., GLP-1 agonists, potassium channel openers such as those disclosed in WO 97/26265 and WO 99/03861 to Novo Nordisk A/S which are incorporated herein by reference, insulin sesitizers, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, PPAR and RXR agonists and agents acting on the ATP-dependent potassium channel of the β-cells. In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. metformin.

In yet another embodiment the present compounds are administered in combination with a meglitinide eg. repaglinide.

In still another embodiment the present compounds are administered in combination with a thiazolidinedione eg. troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl] thiazolidine-2,4-dione or a pharmaceutically acceptable salt thereof, preferably the potassium salt.

Furthermore, the present compounds may be administered in combination with the insulin sensitizers disclosed in WO 99/19313 such as (−) 3-[4-[2-Phenoxazin-10-yl)ethoxy]phenyl]-2-ethoxypropanoic acid or a pharmaceutically acceptable salts thereof, preferably the arginine salt.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. In combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

For the above indications the dosage will vary depending on the compound of the invention employed, on the mode of administration and on the therapy desired. However, in general, satisfactory results are obtained with a dosage of from about 0.5 mg to about 1000 mg, preferably from about 1 mg to about 500 mg of compounds of the invention, conveniently given from 1 to 5 times daily, optionally in sustained release form. Usually, dosage forms suitable for oral administration comprise from about 0.5 mg to about 1000 mg, preferably from about 1 mg to about 500 mg of the compounds of the invention admixed with a pharmaceutical carrier or diluent.

The compounds of the invention may be administered in a pharmaceutically acceptable acid addition salt form or where possible as a metal or a $C_{1-6}$-alkylammonium salt. Such salt forms exhibit approximately the same order of activity as the free acid forms.

This invention also relates to pharmaceutical compositions comprising a compound of the invention or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or nonaqueous liquid suspension or solution.

Generally, the compounds of this invention are dispensed in unit dosage form comprising 10–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet that may be prepared by conventional tabletting techniques contains

| Core: | | |
|---|---|---|
| Active compound (as free compound or salt thereof) | | 100 mg |
| Colloidal silicon dioxide (Areosil ®) | | 1.5 mg |
| Cellulose, microcryst. (Avicel ®) | | 70 mg |
| Modified cellulose gum (Ac-Di-Sol ®) | | 7.5 mg |
| Magnesium stearate | | |
| Coating: | | |
| HPMC | approx. | 9 mg |
| *Mywacett ® 9-40 T | approx. | 0.9 mg |

*Acylated monoglyceride used as plasticiser for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of Formula 1 and preparations containing them is further illustrated in the following examples, which, however, are not to be construed as limiting. Hereinafter, TLC is thin layer chromatography, CDCl$_3$ is deuterio chloroform, CD$_3$OD is tetradeuterio methanol and DMSO-d$_6$ is hexadeuterio dimethylsulfoxide. The structures of the compounds were confirmed by either elemental analysis or NMR, where peaks assigned to characteristic protons in the title compounds are presented where appropriate. $^1$H NMR shifts ($\delta_H$) are given in parts per million (ppm) down field from tetramethylsilane as internal reference standard. M.p.: is melting point and is given in ° C. and is not corrected. Column chromatography was carried out using the technique described by W. C. Still et al., *J. Org. Chem.* 43: 2923 (1978) on Merck silica gel 60 (Art. 9385). HPLC analyses are performed using 5 µm C18 4×250 mm column eluted with various mixtures of water and acetonitrile, flow=1 ml/min, as described in the experimental section.

Compounds used as starting material are either known compounds or compounds, which can readily be prepared by methods known per se.

Example 1

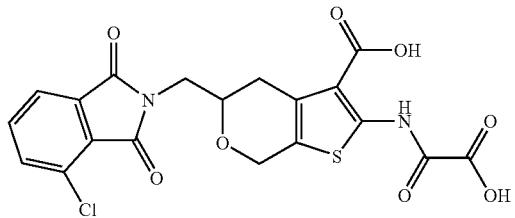

5-(4-Chloro-1,3-dioxo-1,3-dihydro-isoindol-2-ylmethyl)-2-(oxalyl-amino)-4,7-dihydro-5H-thieno[2,3-c]pyran-3-carboxylic acid To a mixture of benzyloxyacetaldehyde (8.3 g, 0.06 mol) in benzene (80 mL) was added 1-methoxy-3-trimethylsilyloxy-1,3-butadiene (10.6 g, 0.06 mol). The reaction mixture was stirred under nitrogen for 15 min., cooled to 0° C. and a solution of 0.5 M zinc chloride (55 ml, 0.03 mol) was added dropwise. The reaction mixture was allowed to warm to room temperature over 16 h and evaporated in vacuo. The resultant oil was diluted with ethyl acetate (100 ml), washed with 1N hydrochloric acid (3×50 ml), saturated sodium bicarbonate (3×50 ml), brine (3×50 ml), dried (MgSO$_4$) and evaporated in vacuo. The resulting oil was subjected to flash chromatography using a mixture of ethyl acetate/hexanes (1:2) as eluent. Pure fractions were collected affording after evaporation in vacuo 7.1 g (60%) of benzyloxy-methyl-2,3 30 dihydro-pyran-4-one as an oil.

$^1$H-NMR (400 MHz, CDCl$_3$) δ 7.39–7.31 (m, 6H), 5.42 (dd, 1H, J=6.1 Hz), 4.61 (d, 1H, J=3 Hz), 4.57 (m, 1H), 3.70 (m, 2H), 2.74 (dd, 1H, J=17 Hz and J=14 Hz), 2.41 (ddd, 1H, J=17 Hz, J=2 Hz and J=1 Hz).

The above 2,3-dihydro-pyran-4-one (7.1 g, 0.032 mol) and 10% palladium on carbon (0.4 g) in ethyl acetate (50 ml) were placed in a Parr bomb shaker and hydrogenated at 30 psi. The reaction mixture was shaken for 2 h, at which time TLC analysis (methanol/dichloromethane 1:9) Indicated the reaction was complete. The reaction mixture was filtered through a pad of Celite and the volatiles evaporated in vacuo. The residue was subjected to flash column chromatography using ethyl acetate as eluent. Pure fractions were collected affording after evaporation in vacuo 3.0 g (75%) of 2-hydroxymethyl-tetrahydro-pyran-4-one as an oil.

$^1$H-NMR (400 MHz, CDCl$_3$) δ 4.36–4.29 (m, 1H), 3.77–3.66 (m, 3H), 3.61–3.54 (m, 1H), 2.65–2.43 (m, 2H), 2.34–2.27 (m, 2H), 2.04 (bs, 1H, CH$_2$OH).

The above tetrahydro-pyran-4-one (1.90 g, 0.015 mol), tert-butyl cyanoacetate (2.7 g, 0.019 mol), sulfur (0.51 g, 0.016 mol) and morpholine (2.55 ml, 0.03 mol) were dissolved in absolute ethanol (20 ml), and heated to 50° C. for 16 hours. The reaction mixture was cooled, filtered and the filtrate evaporated in vacuo. The resultant oil was dissolved in ethyl acetate (50 ml), washed with water (2×50 ml), brine (2×50 m) and dried (MgSO$_4$). The solvent was evaporated in vacuo and the residue was subjected to flash column chromatography using ethyl acetate/hexanes (1:1) as eluent. Pure fractions were collected affording after evaporation of the solvent in vacuo 3.7 g (90%) of 2-amino-5-hydroxymethyl-4,7-dihydro-5H-thieno[2,3-c]pyran-3-carboxylic acid tert-butyl ester as a solid.

$^1$H-NMR (400 MHz, CDCl$_3$) δ 4.64 (s, 2H), 3.80–3.67 (m, 3H), 2.77–2.72 (m, 1H), 2.57–2.53 (m, 1H), 1.54 (s, 9H).

The above carboxylic acid tert-butyl ester (1.0 g, 3.5 mmol), 4-chloro-1,3-dioxo-1,3-dihydro-isoindol (0.67 g, 3.7 mmol) and triphenylphosphine (1.01 g, 3.9 mmol) were dissolved in dry tetrahydrofuran (30 ml) and cooled to 0° C. under a nitrogen atmosphere. Diisopropyl azodicarboxylate (DIAD) (0.62 ml, 3.9 mmol) was added dropwise at 0° C. and the solution allowed to stir overnight, slowly warming to room temperature. The volatiles were evaporated in vacuo and the resultant solid dissolved in ethyl acetate (50 ml). The organic phase was washed with brine (3×50 ml), dried (Na$_2$SO$_4$), filtered and evaporated in vacuo. The residue was subjected to flash column chromatography (300 ml silicagel) using a mixture of ethyl acetate/hexanes (1:3) as eluent. Semi pure fractions were collected affording after evaporation in vacuo 0.7 g, which was trituated with diethyl ether. The solid was filtered off and washed with diethyl ether and dried in vacuo affording 0.13 g (27%) of 2-amino-5-(4-chloro-1,3-dioxo-1,3-dihydro-isoindol-2-ylmethyl)-4,7-dihydro-5H-thieno[2,3-c]pyran-3-carboxylic acid tert-butyl ester as a solid. The filtrate was evaporated in vacuo. The residue (0.48 g) was subjected to flash column chromatography (300 ml silicagel) using a mixture of ethyl acetate/hexanes (1:3) as eluent. Pure fractions were collected affording after evaporation in vacuo an additional 0.36 g (23%) of 2-amino-5-(4-chloro-1,3-dioxo-1,3-dihydro-isoindol-2-ylmethyl)-4,7-dihydro-5H-thieno[2,3-c]pyran-3-carboxylic acid tert-butyl ester as a solid.

To the above 4,7-dihydro-5H-thieno[2,3-c]pyran-3-carboxylic acid tert butyl ester (0.36 g, 0.8 mmol) dissolved in tetrahydrofuran (20 ml) was added a mixture of imidazol-1-yl-oxo-acetic acid tert butyl ester (0.31 g, 1.6 mmol) in tetrahydrofuran (3.4 ml) under nitrogen. The reaction mixture was allowed to stir at room temperature for 18 hours. An additional portion of imidazol-1-yl-oxo-acetic acid tert butyl ester (0.3 g, 1.6 mmol) in tetrahydrofuran (2 ml) was added. The reaction mixture was allowed to stir at room temperature for an additional 60 hours. The reaction mixture was poured into water (50 ml) and extracted with ethyl acetate (3×50 ml). The combined organic phases were washed with brine (3×50 ml) dried ($Na_2SO_4$), filtered and the organic phase evaporated in vacuo. The residue (0.5 g) was purified by column chromatography (300 ml silicagel) using a mixture of ethyl acetate/heptane (1:2) as eluent. Pure fractions were collected and the solvent evaporated in vacuo affording 0.36 g (80%) of 2-(tert-butoxyoxalyl-amino)-5-(4-chloro-1,3-dioxo-1,3-dihydro-isoindol-2-ylmethyl)-4,7-dihydro-5H-thieno[2,3-c]pyran-3-carboxylic acid tert-butyl ester as a solid.

The above di-tert-butyl ester (0.3 g, 0.52 mmol) was dissolved in dichloromethane (1.2 ml) and trifluoroacetic acid (0.5 ml) was added. The reaction was stirred at room temperature for 18 hours. The volatiles were evaporated in vacuo and the residue triturated with a mixture of diethyl ether and heptane (1:1) (5 ml). The precipitate was filtered off, washed with heptane and diethyl ether, dried in vacuo at 50° C. for 18 hours which afforded 200 mg (69%) of the title compound as a solid.

M.p.: >250° C.

Calculated for $C_{19}H_{13}N_2ClO_8S$; C, 49.09%; H, 2.82%; N, 6.03%. Found: C, 48.79%; H, 2.79%; N, 5.89%.

Example 2

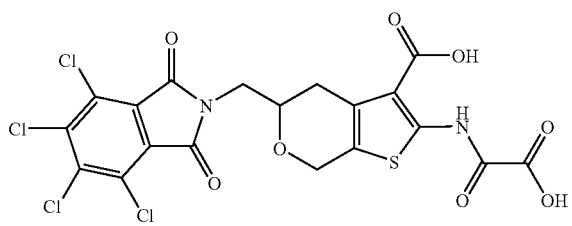

5-(4,5,6,7-Tetrachloro-1,3-dioxo-1,3-dihydro-isoindol-2-ylmethyl)-2-(oxalyl-amino)-4,7-dihydro-5H-thieno[2,3-c]pyran-3-carboxylic acid In a 4 ml scintillating vial, a solution of tetrachloro phthalimide (148 mg, 0.52 mmol) in N,N-dimethylformamide (2.0 ml) was heated to 100° C. for 10 minutes and treated with potassium hydride (55 mg, 0.48 mmol, 35% w/w dispersion in mineral oil). The resulting mixture was stirred until gas generation ended, 2-(tert-butoxyoxalyl-amino)-5-(4-nitro-benzenesulfonyl-oxymethyl)-4,7-dihydro-5H-thieno[2,3-c]pyran-3-carboxylic acid tert-butyl ester (151 mg, 0.25 mmol) and 18-crown-6 ether (31 mg, 0.12 mmol) were added. The solution was flushed with nitrogen gas before being stirred at 80° C. for 25 hours. The volatiles were evaporated in vacuo and the residue purified by silica gel chromatography using a mixture of hexanes/ethyl acetate (5:1) as eluent. Pure fractions were collected and the solvent evaporated in vacuo affording 39 mg (23%) of 2-(tert-butoxyoxalyl-amino)-5-(4,5,6,7-tetrachloro-1,3-dioxo-1,3-dihydro-isoindol-2-ylmethyl)-4,7-dihydro-5H-thieno[2,3-c]pyran-3-carboxylic acid tert-butyl ester as a solid.

$^1$H-NMR (300 MHz, $CDCl_3$) □ 12.50 (s, 1H), 4.80 (d, 1H, J=16 Hz), 4.67 (d, 1H, J=14 Hz), 4.14–3.99 (m, 2H), 3.84 (d, 1H, J=9 Hz), 2.99 (d, 1H, J=17 Hz), 2.70 (dd, 1H, J=17 Hz and J=5 Hz), 1.60 (s, 9H), 1.56 (s, 9H).

HPLC (254.4 nm) $R_t$=5.80 min,

In a 25 ml round bottom flask, 2-(tert-butoxyoxalyl-amino)-5-(4,5,6,7-tetrachloro-1,3-dioxo-1,3-dihydro-isoindol-2-ylmethyl)-4,7-dihydro-5H-thieno[2,3-c]pyran-3-carboxylic acid tert-butyl ester (39 mg, 0.06 mmol) was dissolved in 20% trifluoroaceetic acid in dichloromethane (4 ml). The solution was left open to the atmosphere without stirring for 24 hours. A precipitate was filtered off and washed with diethyl ether, affording after drying 29 mg (90%) of the title compound as a solid.

$^1$H-NMR (300 MHz, DMSO-$d_6$) δ 12.32 (s, 1H), 4.76 (d, 1H, J=16 Hz), 4.59 (d, 1H, J=14 Hz), 4.0–3.6 (m partially obscured by water, 3H), 3.1 (d partially obscured by water, 1H, J=17), 2.61 (dd partially obscured by DMSO, 1H, J=20 Hz and J=11 Hz).

HPLC (254.4 nm) $R_t$=4.15 min,

Example 3

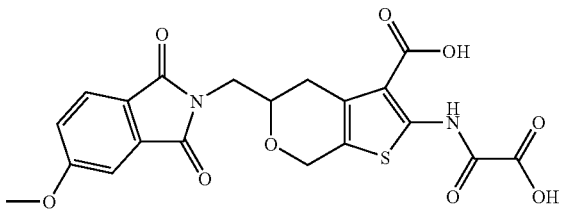

5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid To a solution of 4-hydroxyphthalic acid (0.25 g, 1.37 mmol) in anhydrous N,N-dimethylformamide (3 ml) under nitrogen was added sodium hydride (0.22 g, 5.48 mmol). The solution was stirred for 5 minutes and then methyl iodide (0.68 ml) was added and continued stirring for 3 hours. Several drops of water were added to quench the reaction and the mixture was concentrated in vacuo. The crude material was partitioned between ethyl acetate (40 ml) and water (10 ml). The layers were separated and the organic layer washed with brine (2×10 ml), dried ($Na_2SO_4$), filtered and the solvent evaporated in vacuo. The resulting oil was dissolved in methanol (8 ml) and 1N sodium hydroxide (4 ml) was added. The reaction was stirred at ambient temperature for 24 hours, after which LC-MS indicated only partial hydrolysis. The material was reconstituted in methanol (5 ml) and treated with of sodium hydroxide (0.12 g, 3.0 mmol) dissolved in water (1 ml). The reaction mixture was stirred for 48 hours, at which time a precipitate had formed. The mixture was acidified with 6 N hydrochloric acid until pH=1, causing the solution to become homogeneous. The reaction was concentrated in vacuo and the residue partitioned between ethyl acetate (30 ml) and 0.5N hydrochloric acid (10 ml). The layers were separated and the organic layer concentrated in vacuo to give 100 mg (51%) of 4-methoxy-phthalic acid as a solid.

$^1$H-NMR (300 MHz, $CD_3OD$) δ 7.83 (d, 1H, J=8 Hz), 7.10–7.06 (m, 2H), 3.87 (s, 3H).

LC-MS: $R_t$=1.45 min, m/z: 197 [M+H]$^+$

A solution of 4-methoxy-phthalic acid (0.10 g, 0.51 mmol), 1-hydroxy-benzotriazole (0.15 g, 1.1 mmol), 1-(3-dimethylaminopropyl)-3-ethyl-carbodiimide hydrochloride (0.22 g, 1.1 mmol), and triethylamine (0.35 ml, 2.5 mmol) was prepared in distilled acetonitrile (4 ml) under nitrogen. 2-Amino-5-aminomethyl-4,7-dihydro-5H-thieno-[2,3-c]pyran-3-carboxylic acid tert-butyl ester (0.11 g, 0.39 mmol) was added in small portions and the reaction was stirred at ambient temperature for 18 hours and then concentrated in vacuo. The crude mixture was diluted in ethyl acetate (30 ml) and washed with 1% hydrochloric acid (5 ml), saturated sodium bicarbonate (5 ml), and brine (5 ml). The organic layer was dried ($Na_2SO_4$), filtered, and the solvent evaporated in vacuo. The crude material was purified by silica gel chromatography using a 10% mixture of ethyl acetate/dichloromethane as eluent. Pure fractions were collected and the solvent evaporated in vacuo to give 54 mg (31%) of 2-amino-5-(5-methoxy-1,3-dioxo-1,3-dihydro-isoindol-2-ylmethyl)-4,7-dihydro-5H-thieno-[2,3-c]pyran-3-carboxylic acid tert-butyl ester.

$^1$H-NMR (300 MHz, $CDCl_3$) δ 7.76 (d, 1H, J=8 Hz), 7.32 (s, 1H), 7.14 (d, 1H, J=8 Hz), 4.62–4.48 (m, 2H), 4.00–3.72 (m, 3H), 3.91 (s, 3H), 2.86 (d, 1H, J=17 Hz), 2.55 (dd, 1H, J=17 Hz and J=10 Hz), 1.49 (s, 9H).

To a solution of the above 2-amino-5-(5-methoxy-1,3-dioxo-1,3-dihydro-isoindol-2-ylmethyl)-4,7-dihydro-5H-thieno-[2,3-c]pyran-3-carboxylic acid tert-butyl ester (54 mg, 0.12 mmol) in distilled dichloromethane (3 ml) under nitrogen was added midazol-1-yl-oxo-acetic acid tert-butyl ester (0.25 g, 0.36 mmol) and triethylamine (50 μl, 0.36 mmol). The reaction was stirred for 4 hours concentrated in vacuo and the residue reconstituted in ethyl acetate (20 ml). The organic layer was washed with 1% hydrochloric acid (2×5 ml), saturated sodium bicarbonate (5 ml), and brine (5 ml). The organic phase was dried ($Na_2SO_4$), filtered, and the solvent evaporated in vacuo. The crude material was purified by silica gel chromatography using a 5% mixture of ethyl acetate/dichloromethane as eluent. Pure fractions were collected and the solvent evaporated in vacuo to give 56 mg (81%) of 2-(tert-butoxyoxalyl-amino)-5-(5-methoxy-1,3-dioxo-1,3-dihydro-isoindol-2-ylmethyl)-4,7-dihydro-5H thieno-[2,3-c]pyran-3-carboxylic acid tert-butyl ester.

$^1$H-NMR (300 MHz, $CDCl_3$) δ 12.48 (s, 1H), 7.75 (d, 1H, J=8 Hz), 7.32 (d, 1H, J=2 Hz), 7.15 (dd, 1H, J=8 Hz and J=2 Hz), 4.78 (d, 1H, J=15 Hz), 4.65 (d, 1H, J=15 Hz), 4.03 –3.75 (m, 3H), 3.91 (s, 3H), 2.95 (d, 1H, J=17 Hz), 2.66 (dd, 1H, J=17 Hz and J=9 Hz), 1.58 (s, 9H), 1.54 (s, 9H).

APCI-MS: m/z: 574 [M+H]+

The above 2-(tert-butoxyoxalyl-amino)-5-(5-methoxy-1,3-dioxo-1,3-dihydro-isoindol-2-ylmethyl)-4,7-dihydro-5H-thieno-[2,3-c]pyran-3-carboxylic acid tert-butyl ester (55 mg, 0.096 mmol) was dissolved in a solution of 50% trifluoroacetic acid/dichloromethane (4 ml). The reaction was stirred at ambient temperature for 7 hours concentrated in vacuo and evaporated in vacuo from dichloromethane (3×10 ml). The resulting precipitate was washed with dichloromethane and dried in vacuo to give 17 mg (40%) of the title compound as a solid.

$^1$H-NMR (300 MHz, DMSO-$d_6$) δ 12.32 (s, 1H), 7.81 (d, 1H, J=8 Hz), 7.40 (d, 1H, J=2 Hz), 7.31 (dd, 1H, J=8 Hz and J=2 Hz), 4.75 (d, 1H, J=15 Hz), 4.56 (d, 1H, J=15 Hz), 3.92 (s, 3H), 3.91–3.69 (m, 3H), 2.98 (d, 1H, J=17 Hz), 2.57 (dd, 1H, J=17 Hz and J=9 Hz).

APCI-MS: m/z: 459 [M–H]$^-$

HPLC (254.4 nm): $R_t$=3.36 min,

Example 4

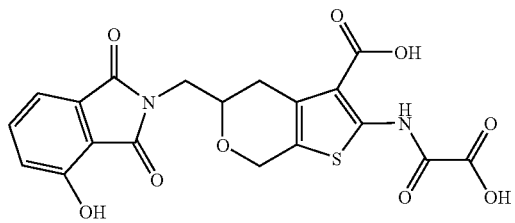

5-(4-Hydroxy-1,3-dioxo-1,3-dihydro-isoindol-2-ylmethyl)-2-(oxalyl-amino)-4,7-dihydro-5-H-thieno [2,3-c]pyran-3-carboxylic acid 5-(4-Benzyloxy-1,3-dioxo-1,3-dihydro-isoindol-2-ylmethyl)-2-(tert-butoxyoxalyl-amino)-4,7-dihydro-5H-thieno [2,3-c]pyran-3-carboxylic acid tert-butyl ester was prepared in a similar way as described in Example 1.

To a solution of the above benzylether (0.7 g, 1.08 mmol) in ethyl acetate (50 ml) was added 10% palladium on carbon (0.2 g). The mixture was hydrogenated at 1 atm. for 5 hours, filtered and the volatiles evaporated in vacuo. The residue (0.6 g) was purified by column chromatography (500 ml silicagel) using a mixture of ethyl acetate/heptane (1:1) as eluent. Pure fractions were collected and the solvent evaporated in vacuo affording 0.4 g (67%) of 2-(tert-butoxyoxalyl-amino)-5-(4-hydroxy-1,3-dioxo-1,3-dihydro-isoindol-2-yl-methyl)-4,7-dihydro-5H-thieno[2,3-c]pyran-3-carboxylic acid tert-butyl ester as an oil.

TLC: $R_f$=0.2 (ethyl acetate/heptane 1:1)

The above di-tert-butyl ester (0.4 g, 0.72 mmol) was dissolved in 25% trifluoroacetic acid in dichloromethane (25 ml). The reaction was stirred at room temperature for 18 hours. The volatiles were evaporated in vacuo and the residue triturated with diethyl ether (5 ml). The precipitate was filtered off, washed with heptane and diethyl ether, dried in vacuo at 50° C. for 18 hours which afforded 230 mg (72%) of the title compound as a solid.

M.p.: >250° C.;

Calculated for $C_{19}H_{14}N_2O_9S$, 0.5×$H_2O$; C, 50.11%; H, 3.32%; N, 6.15%. Found: C, 50.06%; H, 3.17%; N, 5.98%.

Example 5

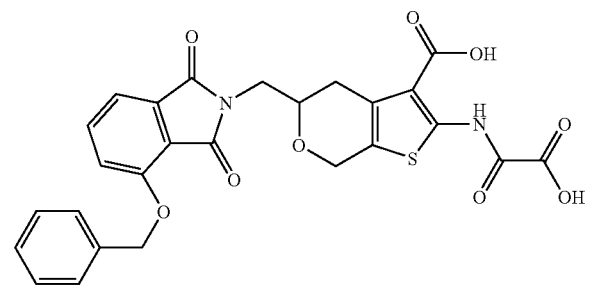

5-(4-Benzyloxy-1,3-dioxo-1,3-dihydro-isoindol-2-ylmethyl)-2-(oxalyl-amino)-4,7-dihydro-5H-thieno [2,3-c]pyran-3-carboxylic acid 5-(4-Benzyloxy-1,3-dioxo-1,3-dihydro-isoindol-2-ylmethyl)-2-(tert-butoxyoxalyl-amino)-4,7-dihydro-5H-thieno[2,3-c]pyran-3-carboxylic acid tert-butyl ester (0.7 g, 1.08 mmol) (prepared in a similar way as described in Example 1) was dissolved in 25% trifluoroacetic acid in dichloromethane (25 ml). The reaction was stirred at room temperature for 18 hours. The volatiles were evaporated in vacuo and the residue trituated with diethyl ether (25 ml). The precipitate was filtered off, washed with diethyl ether and dried in vacuo at 50° C. for 3 hours which afforded 400 mg (69%) of the title compound as a solid.

M.p.: 194–196° C.;

Calculated for $C_{26}H_{20}N_2O_9S$, $1 \times H_2O$, $0.6 \times CF_3COOH$; C, 52.44%, H, 3.66%; N, 4.50%. Found: C, 52.33%; H, 3.65%; N, 4.62%.

Example 6

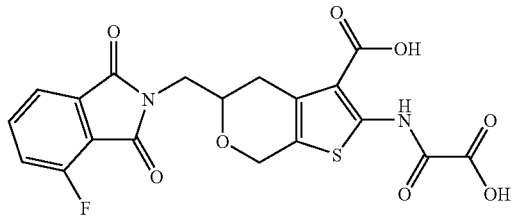

5-(4-Fluoro-1,3-dioxo-1,3-dihydro-isoindol-2-ylmethyl)-2-(oxalyl-amino)-4,7-dihydro-5H-thieno[2,3-c]pyran-3-carboxylic acid Prepared in a similar way as described in Example 1.

M.p.: >250° C.;

Calculated for $C_{19}H_{13}FN_2O_8S$, $1 \times H_2O$; C, 48.93%; H, 3.24%; N, 6.01%. Found: C, 48.90%; H, 3.15%; N, 5.86%.

Example 7

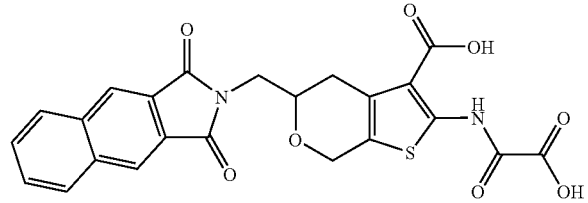

5-(1,3-Dioxo-1,3-dihydro-benzo[f]isoindol-2-ylmethyl)-2-(oxalyl-amino)-4,7-dihydro-5H-thieno[2,3]pyran-3-carboxylic acid In a 4 ml scintillating vial, a solution of benzo[f]Isoindole-1,3-dione (145 mg, 0.74 mmol) In N,N-dimethylformamide (2.0 ml) was treated with potassium hydride (55 mg, 0.48 mmol, 35% w/w dispersion in mineral oil). The resulting mixture was stirred until gas generation ended and the resulting precipitate was filtered off and washed with dichloromethane which afforded 121 mg (69%) of benzo[f]Isoindole-1,3-dione potassium salt as a solid.

$^1$H-NMR (300 MHz, $D_2O$) δ 8.00–7.87 (m, 4H), 7.62 (s, 2H).

In a 4 ml scintillating vial, the above potassium salt (121 mg, 0.5 mmol) in N,N-dimethylformamide (1.5 ml) was treated with 18-crown 6 ether (34 mg, 0.13 mmol) and 2-(tert-butoxyoxalyl-amino)-5-(4-nitro-benzene-sulfonyloxymethyl)-4,7-dihydro-5H-thieno[2,3-c]pyran-3-carboxylic acid tert-butyl ester (148 mg, 0.25 mmol). The solution was flushed with nitrogen gas before being stirred at 80° C. for 7 hours. The volatiles were evaporated in vacuo and the residue purified by silica gel chromatography using a mixture of ethyl acetate/dichloromethane (1:49) as eluent. Pure fractions were collected and the solvent evaporated in vacuo affording 85 mg (57%) of 2-(tert-butoxyoxalyl-amino)-5-(1,3-dioxo-1,3-dihydro-benzo[f]isoindole-2-ylmethyl)-4,7-dihydro-5H-thieno[2,3-c]pyran-3-carboxylic acid tert-butyl ester as a solid.

$^1$H-NMR (300 MHz, $CDCl_3$) δ 12.52 (s, 1H), 8.37 (s, 2H), 8.08 (m, 2H), 7.72 (m, 2H), 4.84–4.65 (m, 2H), 4.16–3.90 (m, 3H), 3.02 (d, 1H, J=17 Hz), 2.73 (dd, 1H, J=17 Hz and J=10 Hz), 1.61 (s, 9H), 1.58 (s, 9H).

In a 25 ml round bottom flask the above 2-(tert-butoxyoxalyl-amino)-5-(1,3-dioxo-1,3-dihydrobenzo[isoindole-2-ylmethyl)-4,7-dihydro-5H-thieno[2,3-c]pyran-3-carboxylic acid tert-butyl ester (85 mg, 0.14 mmol) was dissolved in 20% trifluoroacetic acid in dichloromethane (4 ml). The solution was left open to the atmosphere without stirring for 24 hours. The precipitate was filtered off and washed with diethyl ether, affording after drying 62 mg (90%) of the title compound as a solid.

$^1$H-NMR (300 MHz, DMSO-$d_6$) δ 12.32 (s, 1H), 9.02 (s, 2), 4.81–4.59 (m, 2H), 3.97–3.81 (m partially obscured by water, 3H), 3.08 (d, 1H, J=18 Hz), 2.74–2.53 (m partially obscured by DMSO, 1H).

Example 8

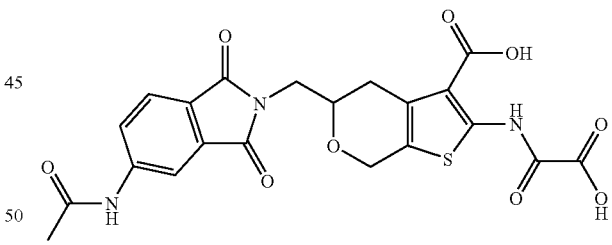

5-(5-Acetylamino-1,3-dioxo-1,3-dihydro-isoindol-2-ylmethyl)-2-(oxalyl-amino)-4,7-dihydro-5H-thieno[2,3-c]pyran-3-carboxylic acid To a solution of N-(1,3-dioxo-2,3-dihydro-1H-isoindol-5-yl)-acetamide (51 mg, 0.25 mmol) In N,N-dimethylformamide (1.5 ml) under nitrogen at room temperature was added potassium hydride (35 wt. % dispension in mineral oil, 29 mg, 0.25 mmol). The solution was stirred at room temperature for 3 hours. A solid precipitated during this period. 2-(tert-Butoxyoxalyl-acid tert-butyl ester (100 mg, 0.17 mmol) was added to the suspension and the solution was stirred at 80° C. for 12 hours. The solvent was evaporated in vacuo and the resulting residue was purified by silica gel chromatography using a gradient of ethyl acetate/hexane (10–25 %) as eluent. Pure fractions were collected and the solvent evaporated in vacuo affording 50 mg (50%) of 5-(5-acetylamino-1,3-dioxo-1,3-dihydro-isoindol-2-ylmethyl)-2-(tert-butoxyoxalyl-amino)-4,7-dihydro-5H-thieno[2,3-c]pyran-3-carboxylic acid tert-butyl ester as a solid.

$^1$H-NMR (CDCl$_3$): δ 12.53 (s, 1H), 8.03 (d, 1H, J=1.5 Hz), 7.91 (dd, 1H, J=7.8 and J=1.8 Hz) 7.83 (d, 1H, J=8.1 Hz), 7.45 (s, 1H), 4.80 (d, 1H, J=16 Hz), 4.66 (d, 1H, J=16 Hz), 4.03 (m, 2H), 3.83 (q, 1H, J=15 Hz), 2.98 (d, 1H, J=9 Hz), 2.64–2.78 (m, 1H), 2.27 (s, 3H), 1.62 (s, 9H), 1.57 (s, 9H).

To a mixture of trifluoroacetic acid/dichloromethane (2 ml, 1:1) at room temperature was added the above 5-(5-acetylamino-1,3-dioxo-1,3-dihydro-isoindol-2-ylmethyl)-2-(tertbutoxyoxalyl-amino)-4,7-dihydro-5H-thieno[2,3-c]pyran-3-carboxylic acid tert-butyl ester (40 mg, 0.067 mmol). The solution was stirred for 5 hours at which time the solvent was removed in vacuo. The residue was washed with dichloromethane, filtered off, and dried in vacuo, which afforded 23 mg (70%) of the title compound as a solid.

$^1$H-NMR (DMSO-d$_6$): 612.32 (s, 1H), 10.58 (s, 1H), 8.21 (s, 1H) 7.84 (s, 2H), 4.76 (d, 1H, J=15 Hz), 4.58 (d, 1H, J=15 Hz), 3.80–4.00 (m, 3H), 3.00 (d, 1H, J=17 Hz), 2.58–2.73 (m, 1H), 2.13 (s, 3H).

MS: m/z: 488 [M+H]$^+$.

Example 9

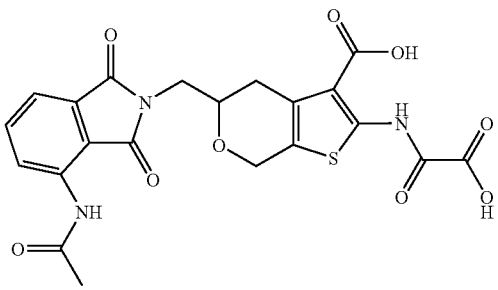

5-(4-Acetylamino-1,3-dioxo-1,3-dihydro-isoindol-2-ylmethyl)-2-(oxalyl-amino)-4,7-dihydro-5H-thieno[2,3-c]pyran-3-carboxylic acid The title compound was prepared in a similar way as described in Example 8.

$^1$H-NMR (DMSO-d$_6$): δ 12.32 (s, 1H), 9.76 (s, 1H), 8.45 (d, 1H, J=8.4 Hz) 7.79 (t, 1H, J=8.4 Hz), 7.58 (d, 1H, J=8.4 Hz), 4.77 (d, 1H, J=15 Hz), 4.58 (d, 1H, J=15 Hz), 3.68–3.94 (m, 3H), 3.02 (d, 1H, J=16 Hz), 2.55–2.78 (m, 1H), 2.20 (s, 3H).

MS: m/z: 488 [M+H]$^+$.

Example 10

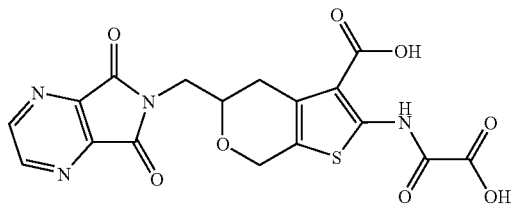

5-(5,7-Dioxo-5,7-dihydro-pyrrolo[3,4-b]pyrazin-6-ylmethyl)-2-(oxalyl-amino)-4,7-dihydro-5H-thieno[2,3-c]pyran-3-carboxylic acid In a 4-ml scintillating vial, a solution of 2-amino-5-aminomethyl-4,7-dihydro-5H-thieno[2,3-c]pyran-3-carboxylic acid tert-butyl ester (148 mg, 0.5 mmol) in tetrahydrofuran (1.0 ml) was treated with a solution of pyrazine phthtalic acid anhydride (85 mg, 0.56 mmol) in tetrahydrofuran (1.0 ml) and N,N-dimethylformamide (0.5 ml). The reaction mixture was allowed to stir at room temperature for 1 hour. N,N-Diisopropylethylamine (220 μl, 0.13 mmol) and 1-(3-dimethylaminopropyl)-3-ethylcarbodiimide hydrochloride (121 mg, 0.6 mmol) were added. The reaction mixture was shaken vigorously for 10 seconds before being stirred at room temperature for 14 hours. The volatiles were evaporated in vacuo and the residue purified by silica gel chromatography using a mixture of dichloromethane/ethyl acetate (3:1) as eluent. Pure fractions were collected and the solvent evaporated in vacuo affording 25 mg (12%) of the 2-amino-5-(5,7-dioxo-5,7-dihydro-pyrrolo[3,4-b]pyrazin-6-ylmethyl)-4,7-dihydro-5H-thieno[2,3-c]pyran-3-carboxylic acid tert-butyl ester as a solid.

$^1$H-NMR (300 MHz, CDCl$_3$) δ 8.97 (s, 2H), 4.62–4.49 (m, 2H), 4.21–4.04 (m, 2H), 3.94 (dd, 1H, J=14 Hz and J=4 Hz), 2.91 (d, 1H, J=17 Hz), 2.63 (dd, 1H, J=17 Hz and J=10 Hz), 1.68 (s, 9H).

In a 4 ml scintillating vial a solution of the above 2-amino-5-(5,7-dioxo-5,7-dihydro-pyrrolo[3,4-b]pyrazin-6-ylmethyl)-4,7-dihydro-5H-thieno[2,3-c]pyran-3-carboxylic acid tert-butyl ester (25 mg, 0.06 mmol) in tetrahydrofuran (3 ml) was treated with midazol-1-yl-oxo-acetic acid tert-butyl ester (0.36 mmol). After stirring for 3 hours at room temperature the reaction solution was concentrated to dryness in vacuo. The residue was purified by silica gel chromatography using a mixture of hexanes/ethyl acetate (3:1) as eluent. Pure fractions were collected and the solvent evaporated in vacuo affording 31 mg (95%) of 2-(tert-butoxyoxalyl-amino)-5-(5,7-dioxo-5,7-dihydro-pyrrolo[3,4-b]pyrazin-6-ylmethyl)-4,7-dihydro-5H-thieno[2,3-c]pyran-3-carboxylic acid tert-butyl ester as a solid.

$^1$H-NMR (300 MHz, CDCl$_3$) δ 12.49 (s, 1H), 8.96 (s, 2H), 4.80–4.61 (m, 2H), 4.21–4.04 (m, 2H), 3.96 (dd, 1H, J=14 Hz and J=4 Hz), 3.03 (d, 1H, J=16 Hz), 2.70 (dd, 1H, J=17 Hz and J=10 Hz), 1.60 (s, 9H), 1.59 (s, 9H).

In a 25 ml round bottom flask the above 2-(tert-butoxyoxalyl-amino)-5-(5,7-dioxo-5,7-dihydro-pyrrolo[3,4-b]pyrazin-6-ylmethyl)-4,7-dihydro-5H-thieno[2,3-c]pyran-3- carboxylic acid tert-butyl ester, (31 mg, 0.06 mmol) was dissolved in 20% trifluoroacetic acid in dichloromethane (4 ml). The solution was left open to the atmosphere without stirring for 24 hours. A precipitate was filtered off and washed with diethyl ether, affording after drying 22 mg (90%) of the title compound as a solid.

$^1$H-NMR (300 MHz, DMSO-d$_6$) δ 12.31 (s, 1H), 9.02 (s, 2), 4.81–4.59 (m, 2H), 3.97–3.81 (m partially obscured by water, 3H), 3.08 (d, 1H, J=18 Hz,), 2.74–2.53 (m partially obscured by DMSO, 1H).

HPLC (254.4 nm) R$_t$=2.97 min,

MS (APCI$^-$): m/z: 432 [M–H]$^-$

Example 11

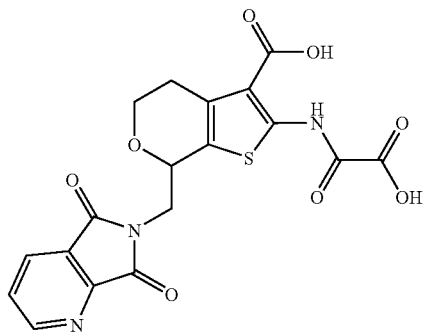

7-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid A solution of furo[3,4-b]pyridine-5,7-dione (86.1 mg, 0.58 mmol) and of 2-(tert-butoxyoxalyl-amino)-7-aminomethyl-4,7-dihydro-5H-thieno[2,3-c]pyran-3-carboxylic acid tert-butyl ester (194 mg, 0.47 mmol) in acetonitrile (2.0 ml) was stirred for 10 min. at room temperature. 1-(3-dimethylaminopropyl)-3-ethylcarbodiimide hydrochloride (89.2 mg, 0.564 mmol) and triethylamine (198 μl, 1.41 mmol) were added and the mixture was stirred at room temperature for 20 hours. The volatiles were removed in vacuo and the crude product dissolved in dichloromethane (60 ml) and washed with water (3×30 ml). The organic layer was dried (MgSO$_4$), filtered and the solvent removal in vacuo. The residue (338 mg) was purified by column chromatography on silica gel utilizing a mixture of hexane/ethyl acetate (90/10 to 50/50) as gradient which afforded after evaporation of the solvent in vacuo 85 mg (33%) of 2-(tert-butoxyoxalyl-amino)-7-(5, 7-dioxo-5,7-dihydro-pyrrolo[3,4-b]pyridin-6-ylmethyl)-4, 7-dihyd-5H-thieno[2,3-c]pyran-3-carboxylic acid tert-butyl ester as an oil.

$^1$H-NMR (300 MHz, CDCl$_3$), δ 9.00 (d, 1H, J=4.8 Hz), 8.21 (d, 1H, J=7.5 Hz), 7.64 (dd, 1H, J=4.8 Hz and J=6.8 Hz), 5.12 (d, 1H, J=7.2 Hz), 4.24–4.1 (m, 2H), 3.97–3.91 (m, 1H), 3.75 (m, 1H), 2.90 (m, 1H), 1.29 (s, 9H), 1.27 (s, 9H).

MS: m/z: 544 [M+H]$^+$.

The above 2-(tert-butoxyoxalyl-amino)-7-(5,7-dioxo-5,7-dihydro-pyrrolo[3,4-b]pyridin-6-ylmethyl)-4,7-dihyd-5H-thieno[2,3-c]pyran-3-carboxylic acid tert-butyl ester (47.4 mg, 0.087 mmol) was stirred in 50% trifluoroacetic acid in dichloromethane (2 ml) at room temperature for 5 hours. The solvent was removed in vacuo and the residue was washed with diethyl ether (4×3.0 ml) and dried which afforded 26.5 mg (70%) of the title compound as a solid.

$^1$H-NMR (400 MHz, CD$_3$OD): δ 8.96 (d, 1H, J=5 Hz), 8.30 (d, 1H, J=7.6 Hz), 7.79 (dd, 1H, J=5.2 Hz and J=5.2 Hz), 5.10 (d, 1H, J=6.4 Hz), 4.16 (m, 2H), 3.96 (dd, 1H, J=3.2 Hz and J=3.6 Hz), 3.78 (m, 1H), 2.95 (m, 2H).

MS: m/z: 432 [M+H]$^+$.

Example 12

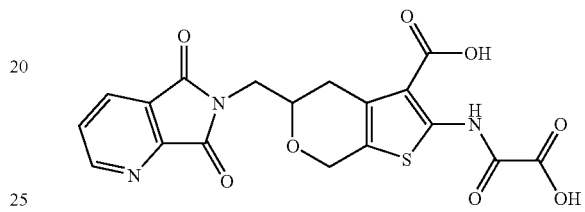

5-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid Pyrrolo[3,4-b]pyridine-5,7-dione (74.2 mg, 0.5 mmol) was stirred with sodium hydride (60% dispersion in mineral oil, 20.04 mg, 0.5 mmol) in N,N-dimethylformamide (4.0 ml) at room temperature under inert atmosphere. 2-(tert-Butoxyoxalyl-amino)-5-(4-nitro-benzene-sulfonyloxymethyl)-4,7-dihydro-5H-thieno[2,3-c]pyran-3-carboxylic acid tert-butyl ester (198 mg, 0.33 mmol) was added to the sodium salt formed and the reaction was stirred at 80° C. for 20 hours. The solvent was removed in vacuo and the crude product was purified by preparative TLC (hexane:ethyl acetate 50:50) which afforded 58 mg (21%) of 2-(tert-butoxyoxalyl-amino)-5-(5,7-dioxo-5,7-dihydro-pyrrolo[3, 4-b]pyridin-6-ylmethyl)-4,7-dihydro-5H-thieno[2,3-c]pyran-3-carboxylic acid tert-butyl ester as a solid.

$^1$H-NMR (300 MHz, CDCl$_3$): δ 9.00 (d, 1H, J=5 Hz), 8.20 (d, 1H, J=7.5 Hz), 7.65 (dd, 1H, J=5 Hz and J=5 Hz), 4.80 (d, 1H, J=14.7 Hz), 4.66 (d, 1H, J=14.7 Hz), 4.10 (m, 2H), 3.91 (d, 1H, J=13.2 Hz), 3.02 (d, 1H, J=16.5 Hz), 2.70 (m, 1H), 1.61 (s, 9H), 1.58 (s, 9H).

MS: m/z: 544 [M+H]$^+$.

The above 2-(tert-butoxyoxalyl-amino)-5-(5,7-dioxo-5,7-dihydro-pyrrolo[3,4-b]pyridin-6-ylmethyl)-4,7-dihydro-5H-thieno[2,3-c]pyran-3-carboxylic acid tert-butyl ester (46.4 mg, 0.09 mmol) was stirred in 20% trifluoroacetic acid in dichloromethane (3.0 ml) at room temperature for 2 hours. The volatiles were removed in vacuo and the residue was washed with diethyl ether (5×3 ml) affording 37 mg (99%) of the title compound as a solid.

$^1$H-NMR (300 MHz, CDCl$_3$): δ 8.96 (d, 1H, J=5.4 Hz), 8.20 (d, 1H, J=7.7 Hz), 7.64 (m, 1H), 4.77 (d, 1H, J=14.7 Hz), 4.61 (d, 1H, J=14.7 Hz), 4.07 (m, 2H), 3.86 (d, 1H, J=10.5 Hz), 3.12 (d, 1H, J=17.4 Hz), 2.77–2.68 (m, 2H).

MS: m/z: 432 [M+H]$^+$.

Example 13

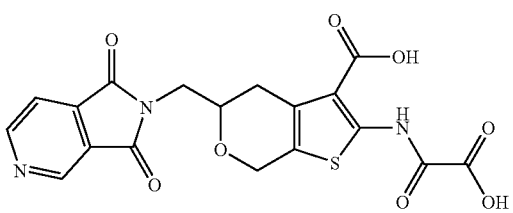

5-(5,7-Dioxo-5,7-dihydro-pyrrolo[3,4-c]pyridin-6-ylmethyl)-2-(oxalyl-amino)-4,7-dihydro-5H-thieno[2,3-c]pyran-3-carboxylic acid To a solution of pyrrolo[3,4-c]pyridine-1,3-dione (74 mg, 0.50 mmol) in N,N-dimethylformamide (1 ml) under nitrogen at room temperature was added potassium hydride (35 wt. % dispersion in mineral oil, 57 mg, 0.50 mmol). The solution was stirred at room temperature for 3 hours. A solid precipitated during this period. 18-Crown-6 (33 mg, 0.13 mmol) and 2-(tert-butoxyoxalyl-amino)-5-(4-nitro-benzenesulfonyloxymethyl)-4,7-dihydro-5H-thieno[2,3-c]pyran-3-carboxylic acid tert-butyl ester (150 mg, 0.25 mmol) were then added. The solution was stirred at 80° C. for 12 hours and the solvent evaporated in vacuo. The residue was purified by silica gel chromatography using a gradient of ethyl acetate/hexane (10–25%) as eluent. Pure fractions were collected and the solvent evaporated in vacuo affording 93 mg (68%) of 2-(tert-butoxyoxalyl-amino)-5-(1,3-dioxo-1,3-dihydro-pyrrolo[3,4-c]pyridin-2-ylmethyl)-4,7-dihydro-5H-thieno[2,3-c]pyran-3-carboxylic acid tert-butyl ester as a solid.

$^1$H-NMR (CDCl$_3$): δ 12.49 (s, 1H), 9.20 (s, 1H), 9.11 (d, 2H, J=4.8 Hz) 7.80 (d, 2H, J=4.8 Hz), 4.80 (d, 1H, J=16 Hz), 4.66 (d, 1H, J=16 Hz), 4.00–4.18 (m, 2H), 3.70–3.95 (m, 1H), 3.01 (d, 1H, J=17 Hz), 2.64–2.78 (m, 1H), 1.60 (s, 9H), 1.59 (s, 9H).

To a mixture of trifluoroacetic acid/dichloromethane (1 ml, 1:1) at room temperature was added the above 2-(tert-butoxyoxalyl-amino)-5-(1,3-dioxo-1,3-dihydro-pyrrolo[3,4-c]pyridin-2-ylmethyl)-4,7-dihydro-5H-thieno[2,3-c]pyran-3-carboxylic acid tert-butyl ester (29 mg, 0.053 mmol). The solution was stirred for 5 hours and the solvent evaporated in vacuo. The residue was washed with dichloromethane afford after drying in vacuo 22 mg (96%) of the title compound as a solid.

$^1$H-NMR (DMSO-d$_6$): δ 12.32 (s, 1H), 9.15 (s, 1H), 9.11 (d, 2H, J=4.8 Hz) 7.92 (d, 2H, J=4.8 Hz), 4.76 (d, 1H, J=15 Hz), 4.58 (d, 1H, J=16 Hz), 3.75–4.00 (m, 4H), 3.04 (d, 1H, J=17 Hz).

MS: m/z: 432 (M+H)$^+$.

Example 14

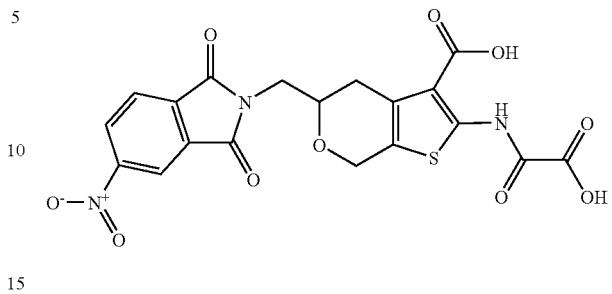

5-(5-Nitro-1,3-dioxo-1,3-dihydro-isoindol-2-ylmethyl)-2-(oxalyl-amino)-4,7-dihydro-5H-thieno[2,3-c]pyran-3-carboxylic acid In a 4-ml scintillating vial, a solution of 2-amino-5-aminomethyl-4,7-dihydro-5H-thieno[2,3-c]pyran-3-carboxylic acid tert-butyl ester (58 mg, 0.2 mmol) in tetrahydrofuran (2.0 ml) was treated with 4-nitrophthalic acid (63 mg, 0.3 mmol), diisopropylethylamine (190 μl, 1.1 mmol), and 1,3-diisopropylcarbodiimide (120 μl, 0.77 mmol). The reaction mixture was shaken vigorously for 10 seconds before being stirred at 50° C. for 43 hours and at room temperature for 20 hours. The solution was diluted with ethyl acetate (25 ml), washed with 0.5N aqueous hydrochloric acid (25 ml), saturated aqueous sodium bicarbonate (25 ml), and the brine (25 ml). The organic layer was dried (MgSO$_4$), filtered and the solvent evaporated in vacuo. Crude 2-amino-5-(5-nitro-1,3-dioxo-1,3-dihydro-isoindol-2-ylmethyl)-4,7-dihydro-5H-thieno[2,3-c]pyran-3-carboxylic acid tert-butyl ester was obtained as a solid and used immediately in the next step.

In a 4 ml scintillating vial a solution of the above crude 2-amino-5-(5-nitro-1,3-dioxo-1,3-dihydro-isoindol-2-ylmethyl)-4,7-dihydro-5H-thieno[2,3-c]pyran-3-carboxylic acid tert-butyl ester in dichloromethane (3 ml) was treated with midazol-1-yl-oxo-acetic acid tert-butyl ester (147 mg, 0.75 mmol). After stirring for 2 hours at room temperature the reaction mixture was concentrated to dryness in vacuo. The residue was purified by silica gel chromatography using a mixture of hexanes/ethyl acetate (3:1) as eluent. Pure fractions were collected and the solvent evaporated in vacuo which afforded 30 mg (26%) of 2-(tert-butoxyoxalyl-amino)-5-(5-nitro-1,3-dioxo-1,3-dihydro-isoindol-2-ylmethyl)-4,7-dihydro-5H-thieno[2,3-c]pyran-3-carboxylic acid tert-butyl ester as a solid.

$^1$H-NMR (300 MHz, CDCl$_3$) δ 12.47 (s, 1H), 8.71 (s, 1H), 8.64 (d, 1H, J=8 Hz), 8.08 (d, 1H, J=9 Hz), 4.79 (d, 1H, J=14 Hz), 4.65 (d, 1H, J=14 Hz), 4.21–3.97 (m, 2H), 3.89 (d, 1H, J=12 Hz), 3.01 (d, 1H, J=16 Hz), 2.83–2.61 (m, 1H), 1.63 (ds, 18H).

In a 25 ml round bottom flask, the above 2-(tert-butoxyoxalyl-amino)-5-(5-nitro-1,3-dioxo-1,3-dihydro-isoindol-2-ylmethyl)-4,7-dihydro-5H-thieno[2,3-c]pyran-3-carboxylic acid tert-butyl ester (30 mg, 0.05 mmol) was dissolved in a mixture of 20% trifluoroacetic acid in dichloromethane (4 ml). The solution was left open to the atmosphere without stirring of 24 hours. A precipitate was filtered off and washed with diethyl ether, affording after drying 22 mg (90%) of the title compound as a solid.

$^1$H-NMR (300 MHz, DMSO-d$_6$) δ 12.31 (s, 1H), 8.63 (d, 1H, J=8 Hz), 8.15 (d, 1H, J=8 Hz), 4.76 (d, 1H, J=16 Hz), 4.57 (d, 1H, J=16 Hz), 4.42–3.74 (m partially obscured by water, 3H), 3.04 (d partially obscured by water, 1H, J=16 Hz), 2.61 (m partially obscured by DMSO, 1H).

HPLC (254.4 nm) R$_t$=3.40 min,
MS (APCI$^+$): m/z: 407 [M+H]$^+$

Example 15

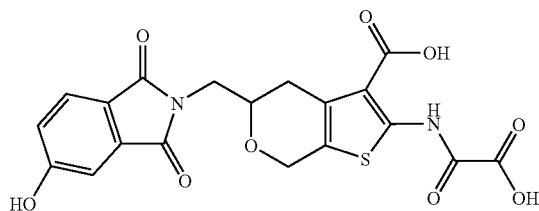

5-(5-Hydroxy-1,3-dioxo-1,3-dihydro-isoindol-2-ylmethyl)-2-(oxalyl-amino)-4,7-dihydro-5H-thieno[2,3-c]pyran-3-carboxylic acid To a solution of 4-hydroxyphthalic acid (0.45 g, 2.47 mmol) in anhydrous N,N-dimethylformamide (5 ml) under nitrogen was added chloromethyl methyl ether (1.13 ml, 14.8 mmol) and diisopropylethylamine (2.6 ml, 14.8 mmol). The reaction was stirred at ambient temperature for 18 hours and then concentrated in vacuo. The crude material was partitioned between ethyl acetate (50 ml) and water (15 ml). The layers were separated, the organic layer washed with water (3×10 ml), brine (2×10 ml), dried (Na$_2$ SO$_4$), filtered and the solvent evaporated in vacuo. The resulting oil was dissolved in ethanol (5 ml) and sodium hydroxide (0.12 g, 7.4 mmol) dissolved in water (1 ml) was added to the reaction. The solution was stirred at ambient temperature for 48 hours and then concentrated in vacuo affording 4-methoxymethoxy-phthalic acid di-sodium salt, which was used without purification.

$^1$H-NMR (300 MHz, CD$_3$OD) δ 7.59 (d, 1H, J=8 Hz), 7.06 (d, 1H, J=3 Hz), 6.89 (dd, 1H, J=8 Hz and J=3 Hz), 5.18 (s, 2H), 3.42 (s, 3H).

A solution of 4-methoxymethoxy-phthalic acid di-sodium salt (0.19 g, 0.70 mmol), 1-hydroxybenzotriazole (0.2 g, 3.6 equiv.), 1-(3-dimethylamino-propyl)-3-ethylcarbodiimide hydrochloride (0.28 g, 3.6 equiv.), and triethylamine (0.33 ml, 6 equiv.) was prepared in distilled acetonitrile (5 ml) under nitrogen. The mixture was stirred for 5 minutes before 2-amino-5-aminomethyl-4,7-dihydro-5H-thieno[2,3-c]pyran-3-carboxylic acid tert-butyl ester (115 mg, 0.40 mmol) was added in small portions. The reaction was stirred at ambient temperature for 18 hours and concentrated in vacuo. The crude mixture was diluted with ethyl acetate (30 ml) and washed with 1% hydrochloric acid (5 ml), saturated sodium bicarbonate (5 ml), and brine (5 ml). The organic layer was dried (Na$_2$SO$_4$), filtered, and the solvent evaporated in vacuo. The crude material was purified by silica gel chromatography using a gradient of ethyl acetate/dichloromethane (5 to 10% gradient) as eluent. Pure fractions were collected and the solvent evaporated in vacuo to give 44 mg (23%) of 2-amino-5-(5-methoxy-methoxy-1,3-dioxo-1,3-dihydro-isoindol-2-ylmethyl)-4,7-dihydro-5H-thieno[2,3-c]pyran-3-carboxylic acid tert-butyl ester.

$^1$H-NMR (300 MHz, CDCl$_3$) δ 7.75 (d, 1H, J=8 Hz), 7.48 (d, 1H, J=2 Hz), 7.27 (dd, 1H, J=8 Hz and J=2 Hz), 5.26 (s, 2H), 4.60–4.46 (m, 2H), 3.99–3.71 (m, 3H), 3.47 (s, 3H), 2.85 (d, 1H, J=17 Hz), 2.55 (dd, 1H, J=17 Hz and J=9 Hz), 1.48 (s, 9H).

To a solution of the above 2-amino-5-(5-methoxy-methoxy-1,3-dioxo-1,3-dihydro-isoindol-2-ylmethyl)-4,7-dihydro-5H-thieno[2,3-c]pyran-3-carboxylic acid tert-butyl ester (44 mg, 0.095 mmol) in distilled dichloromethane (3 ml) under nitrogen was added midazol-1-yl-oxo-acetic acid tert-butyl ester (56 mg, 0.29 mmol) and triethylamine (26 μl, 0.19 mmol). The reaction was stirred for 4 hours, concentrated in vacuo and reconstituted in ethyl acetate (20 ml). The organic layer was washed with 1% hydrochloric acid (2×5 ml), saturated sodium bicarbonate (5 ml), and brine (5 ml). The resulting solution was dried (Na$_2$SO$_4$), filtered, and the solvent evaporated in vacuo. The crude material was purified by silica gel chromatography using a 5% mixture of ethyl acetate/dichloromethane as eluent. Pure fractions were collected and the solvent evaporated in vacuo to give 35 mg (63%) of 2-(tert-butoxyoxalyl-amino)-5-(5-methoxymethoxy-1,3-dioxo-1,3-dihydro-isoindol-2-ylmethyl)-4,7-dihydro-5H-thieno[2,3-c]pyran-3-carboxylic acid tert-butyl ester.

$^1$H-NMR (300 MHz, CDCl$_3$) δ 12.50 (s, 1H), 7.75 (d, 1H, J=8 Hz), 7.49 (d, 1H, J=2 Hz), 7.28 (dd, 1H, J=8 Hz and J=2 Hz), 5.26 (s, 2H), 4.77 (d, 1H, J=15 Hz), 4.64 (d, 1H, J= 15 Hz), 4.03–3.74 (m, 3H), 3.47 (s, 3H), 2.95 (d, 1H, J=17 Hz), 2.65 (dd, 1H, J=17 Hz and J=9 Hz), 1.58 (s, 9H), 1.54 (s, 9H).

APCI-MS: m/z: 604 [M+H]$^+$

The above 2-(tert-butoxyoxalyl-amino)-5-(5-methoxymethoxy-1,3-dioxo-1,3-dihydro-5 isoindol-2-ylmethyl)-4,7-dihydro-5H-thieno[2,3-c]pyran-3-carboxylic acid tert-butyl ester (35 mg, 0.058 mmol) was dissolved in a mixture of 50% trifluoroacetic acid/dichloromethane (2.5 ml). The reaction was stirred at ambient temperature for 7 hours, concentrated in vacuo and the residue evaporated in vacuo from dichloromethane (3×10 ml). The resulting precipitate was washed with dichloromethane and dried in vacuo to give 20 mg (77%) of the title compound as a solid.

$^1$H-NMR (300 MHz, DMSO-d$_6$) δ 12.31 (s, 1H), 10.97 (s, 1H), 7.72 (d, 1H, J=8 Hz), 7.18 (s, 1H), 7.10 (d, 1H, J=8 Hz), 4.74 (d, 1H, J=15 Hz), 4.58 (d, 1H, J=15 Hz), 3.96–3.62 (m, 3H), 2.99 (d, 1H, J=17 Hz), 2.60–2.50 (m, 1H, partially obscured by DMSO).

APCI-MS: m/z: 445 [M−H]$^-$
HPLC (254.4 nm): R$_t$=2.92 min,

Example 16

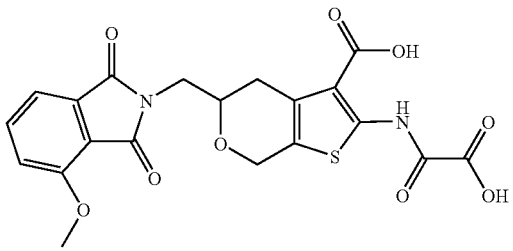

5-(4-Methoxy-1,3-dioxo-1,3-dihydro-isoindol-2-ylmethyl)-2-(oxalyl-amino)-4,7-dihydro-5H-thieno[2,3-c]pyran-3-carboxylic acid To a solution of 4-hydroxy-isobenzofuran-1,3-dione (195 mg, 1.2 mmol) in anhydrous N,N-dimethylformamide (4 ml) under nitrogen was added sodium hydride (61 mg, 1.56 mmol). The solution was stirred for 15 minutes and then methyl iodide (0.37 ml, 6.0 mmol) was added. The reaction was stirred for 48 hours and then quenched with saturated ammonium chloride. The mixture was concentrated in vacuo, diluted in ethyl acetate (20 ml) and the organic phase washed with 1N hydrochloric acid (5 ml) and brine (3×5 ml). The organic layer was dried ($MgSO_4$) and concentrated in vacuo. To the crude solid was added methanol causing a precipitate to form. The flask was cooled in an ice bath for 2 hours and the solid filtered off, washed with methanol and dried in vacuo which afforded 0.1 g (47%) of 4-methoxy-isobenzofuran-1,3-dione as a solid.

$^1$H-NMR (300 MHz, DMSO-$d_6$) δ 7.95 (t, 1H, J=8 Hz), 7.61 (d, 1H, J=8 Hz), 7.58 (d, 1H, J=8 Hz), 3.99 (s, 3H).

APCI-MS: m/z: 179 [M+H]$^+$

A solution of 2-amino-5-aminomethyl-4,7-dihydro-5H-thieno[2,3-c]pyran-3-carboxylic acid tert-butyl ester (122 mg, 0.43 mmol, prepared as described in Example 17) and 4-methoxy-isobenzofuran-1,3-dione (92 mg, 0.52 mmol) was prepared in distilled tetrahydrofuran (4 ml) under nitrogen. 1-Hydroxybenzotriazole (87 mg, 0.65 mmol), 1-(3-dimethylaminopropyl)-3-ethylcarbodiimide hydrochloride (123 mg, 0.65 mmol), and triethylamine (0.29 ml, 2.15 mmol) were added. The reaction was stirred at ambient temperature for 18 hours and concentrated in vacuo. The crude mixture was diluted with ethyl acetate (25 ml) and washed with 1N hydrochloric acid (5 ml), saturated sodium bicarbonate (5 ml), and brine (5 ml). The organic layer was dried ($Na_2SO_4$), filtered, and the solvent evaporated in vacuo to give 0.18 g (94%) of 2-amino-5-(4-methoxy-1,3-dioxo-1,3-dihydro-isoindol-2-ylmethyl)-4,7-dihydro-5H-thieno[2,3-c]pyran-3-carboxylic acid tert-butyl ester.

$^1$H-NMR (300 MHz, CDCl$_3$) δ 7.66 (t, 1H, J=7 Hz), 7.43 (d, 1H, J=7 Hz), 7.19 (d, 1H, J=7 Hz), 4.59–4.46 (m, 2H), 4.06–3.72 (m, 3H), 4.00 (s, 3H), 2.87–2.81 (m, 1H), 2.60–2.51 (m, 1H), 1.48 (s, 9H).

To a solution of the above 2-amino-5-(4-methoxy-1,3-dioxo-1,3-dihydro-isoindol-2-ylmethyl)-4,7-dihydro-5H-thieno[2,3-c]pyran-3-carboxylic acid tert-butyl ester (0.18 g, 0.42 mmol) in distilled dichloromethane (5 ml) under nitrogen was added imidazol-1-yl-oxo-acetic acid tert-butyl ester (0.25 g, 1.26 mmol) and triethylamine (0.23 ml, 1.68 mmol). The reaction was stirred for 12 hours, concentrated in vacuo and reconstituted in ethyl acetate (25 ml). The organic layer was washed with 1N hydrochloric acid (2×5 ml), saturated sodium bicarbonate (5 ml), and brine (5 ml). The resulting solution was dried ($Na_2SO_4$), filtered, and the solvent evaporated in vacuo. The crude material was purified by silica gel chromatography using a gradient of ethyl acetate/dichloromethane (0 to 10% gradient). Pure fractions were collected and the solvent evaporated in vacuo to give 195 mg (81%) of 2-(tert-butoxyoxalyl-amino)-5-(4-methoxy-1,3-dioxo-1,3-dihydro-isoindol-2-ylmethyl)-4,7-dihydro-5H-thieno[2,3-c]pyran-3-carboxylic acid tert-butyl ester as an oil.

$^1$H-NMR (300 MHz, CDCl$_3$) δ 12.48 (s, 1H), 7.65 (t, 1H, J=7 Hz), 7.43 (d, 1H, J=7 Hz), 7.19 (d, 1H, J=7 Hz), 4.77 (d, 1H, J=15 Hz), 4.63 (d, 1H, J=15 Hz), 4.04–3.75 (m, 3H), 4.00 (s, H), 2.94 (d, 1H, J=17 Hz), 2.65 (dd, 1H, J=17 Hz and J=10 Hz), 1.58 (s, 9H), 1.53 (s, 9H).

LC-MS: R$_t$=4.17 min, m/z: 573 [M+H]$^+$

The above 2-(tert-butoxyoxalyl-amino)-5-(4-methoxy-1,3-dioxo-1,3-dihydro-isoindol-2-ylmethyl)-4,7-dihydro-5H-thieno[2,3-c]pyran-3-carboxylic acid tert-butyl ester (0.15 g, 0.26 mmol) was dissolved in a mixture of 50% trifluoroacetic acid/dichloromethane (5 ml). The reaction was stirred at ambient temperature for 7 hours, concentrated in vacuo and the residue evaporated in vacuo from dichloromethane (3×10 ml). The resulting precipitate was washed with dichloromethane and dried in vacuo to give 100 mg (83%) of the title compound as a solid.

$^1$H-NMR (300 MHz, DMSO-$d_6$) δ 12.31 (s, 1H), 7.79 (t, 1H, J=8 Hz), 7.48 (d, 1H, J=8 Hz), 7.42 (d, 1H, J=8 Hz), 4.74 (d, 1H, J=15 Hz), 4.56 (d, 1H, J=15 Hz), 3.95 (s, 3H), 3.91–3.79 (m, 2H), 3.69–3.63 (m, 1H), 2.98 (d, 1H, J=17 Hz), 2.57 (dd, 1H, J=17 Hz and J=10 Hz).

LC-MS: R$_t$=1.26 min, m/z: 461 [M+H]$^+$

HPLC (254.4 nm): R$_t$=3.10 min,

Example 17

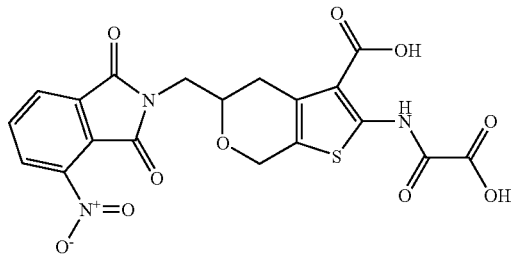

5-(4-Nitro-1,3-dioxo-1,3-dihydro-isoindol-2-ylmethyl)-2-(oxalyl-amino)-4,7-dihydro-5H$_2$O thieno[2,3-c]pyran-3-carboxylic acid In a 50-ml round-bottom flask, a suspension of 2-amino-5-(1,3-dioxo-1,3-dihydro-isoindol-2-ylmethyl)-4,7-dihydro-5H-thieno[2,3-c]pyran-3-carboxylic acid tert-butyl ester (2.00 g, 4.8 mmol) in absolute ethanol (20 ml) was flushed with nitrogen and sealed with a rubber septum. Hydrazine (0.5 ml, 15.9 mmol) was added, followed by an additional portion of absolute ethanol (20 ml) at room temperature. The reaction mixture was heated to 80° C. for 3.5 hours and then allowed to stir at room temperature for 14 hours. The precipitate was filtered off and washed with absolute ethanol. The filtrate was concentrated in vacuo leaving an oil, which was dissolved in dichloromethane (30 ml) and refiltered. The solvent was evaporated in vacuo affording 1.2 g (86%) of 2-amino-5-aminomethyl-4,7-dihydro-5H-thieno[2,3-c]pyran-3-carboxylic acid tert-butyl ester as a solid.

$^1$H-NMR (300 MHz, CDCl$_3$) δ 5.92 (s, 2H), 4.64 (s, 2H), 3.68–3.60 (m, 1H), 2.98–2.74 (m, 3H), 2.56–2.44 (m, 1H), 1.54 (s, 9H).

MS (APCI$^+$): m/z: 285.3 [M+H]$^+$

In a 4-ml scintillating vial, a solution of the above 2-amino-5-aminomethyl-4,75 dihydro-5H-thieno[2,3-c]pyran-3-carboxylic acid tert-butyl ester (63 mg, 0.2 mmol) in tetrahydrofuran (2.0 ml) was treated with 3-nitro-phthalic acid (66 mg, 0.3 mmol), N,N-diisopropylethylamine (190 µl, 1.1 mmol), and 1,3-diisopropyl-carbodiimide (120 µl, 0.77 mmol). The reaction mixture was shaken vigorously for 10 seconds before being stirred at 50° C. for 43 hours and at room temperature for 20 hours. The reaction mixture was diluted with ethyl acetate (25 ml) and washed with 0.5 N aqueous hydrochloric acid (25 ml), saturated sodium bicarbonate (25 ml), and brine (25 ml). The organic layer was dried (MgSO$_4$), filtered and the solvent evaporated in vacuo affording crude 2-amino-5-(4-nitro-1,3-dioxo-1,3-dihydro-isoindol-2-ylmethyl)-4,7-dihydro-5H-thieno[2,3-c]pyran-3-carboxylic acid tert-butyl ester as a solid.

In a 4 ml scintillating vial a solution of the above crude 2-amino-5-(4-nitro-1,3-dioxo-1,3-dihydro-isoindol-2-ylmethyl)-4,7-dihydro-5H-thieno[2,3-c]pyran-3-carboxylic acid tert-butyl ester in dichloromethane (3 ml) was treated with midazol-1-yl-oxo-acetic acid tert-butyl ester (147 mg, 0.75 mmol). After stirring for 2 hours at room temperature the reaction solution was concentrated to dryness in vacuo. The residue was purified by silica gel chromatography using a mixture of hexanes/ethyl acetate (3:1) as eluent. Pure fractions were collected and the solvent evaporated in vacuo affording 30 mg (26%) of 2-(tert-butoxyoxalyl-amino)-5-(4-nitro-1,3-dioxo-1,3-dihydro-isoindol-2-ylmethyl)-4,7-dihydro-5H-thieno[2,3-c]pyran-3-carboxylic acid tert-butyl ester as a solid.

$^1$H-NMR (300 MHz, CDCl$_3$) δ 8.17 (d, 1H, J=5 Hz), 8.11 (d, 1H, J=6 Hz), 7.94 (t, 1H, J=8 Hz), 4.80 (d, 1H, J=14 Hz), 4.67 (d, 1H, J=15 Hz), 4.16–3.97 (m, 3H), 3.88 (d, 1H, J=10 Hz), 3.01 (d, 1H, J=16 Hz), 2.70 (dd, 1H, J=16 Hz and J=10 Hz), 1.62 (s, 9H), 1.59 (s, 9H).

In a 25 ml round bottom flask, the above 2-(tert-butoxyoxalyl-amino)-5-(4-nitro-1,3-dioxo-1,3-dihydro-isoindol-2-ylmethyl)-4,7-dihydro-5H-thieno[2,3-c]pyran-3-carboxylic acid tert-butyl ester (30 mg, 0.05 mmol) was dissolved in a mixture of 20% trifluoroacetic acid in dichloromethane (4 ml). The solution was left open to the atmosphere without stirring. After standing for 24 hours a precipitate was filtered off and washed with diethyl ether, affording after drying 22 mg (90%) of the title compound as a solid.

$^1$H-NMR (300 MHz, DMSO-d$_6$) δ 12.33 (s, 1H), 8.32 (d, 1H, J=9 Hz), 8.20 (d, 1H, J=9 Hz), 8.07 (t, 1H, J=9 Hz), 4.77 (d, 1H, J=14 Hz), 4.59 (d, 1H, J=16 Hz), 4.00–3.65 (m partially obscured by water, 3H), 3.04 (d partially obscured by water, 1H, J=16 Hz), 2.63 (dd partially obscured by DMSO, 1H, J=17 Hz and J=13 Hz).

HPLC (254.4 nm) R$_t$=3.33 min, 100%.

MS (APCI$^+$): m/z: 392 [M+H]$^+$

Example 18

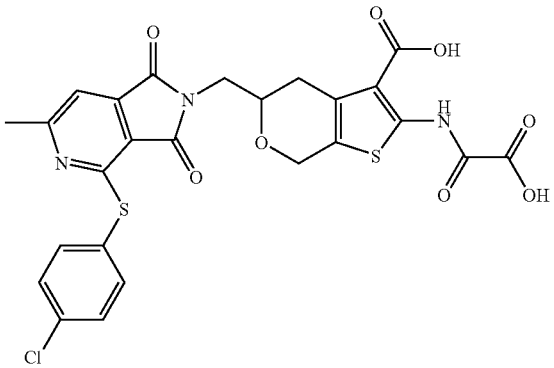

5-(4-(4-Chloro-phenylsulfanyl)-6-methyl-1,3-dioxo-1,3-dihydro-pyrrolo[3,4-c]pyridin-2-ylmethyl)-2-(oxalyl-amino)-4,7-dihydro-5H-thieno[2,3-c]pyran-3-carboxylic acid Under a nitrogen atmosphere, 4-(4-chloro-phenylsulfanyl)-6-methyl-pyrrolo[3,4-c]-1,3-dione (914 mg, 3.0 mmol), tributylphosphine (1.66 ml, 4.5 mmol) and 2-amino-5-hydroxymethyl-4,7-dihydro-5H-thieno[2,3-c]pyran-3-carboxylic acid tert-butyl ester (855 mg, 3.0 mmol) were successively dissolved in dry benzene (90 ml). Solid azodicarboxylic dipiperidine (1.13 g, 4.5 mmol) was added under stirring at 0° C. to the solution. After stirring for 10 min, the reaction mixture was brought to room temperature and the stirring continued for 4 hours. The mixture was cooled on ice, and additional portions of tributylphosphine (1.66 ml, 4.5 mmol) and azodicarboxylic dipiperidine (1.13 g, 4.5 mmol) were added. After stirring for 10 min, the reaction mixture was brought to room temperature and the stirring continued for 18 hours. Heptane (30 ml) was added to the reaction and the precipitate filtered off (discard). After evaporation of the solvent the product was purified by flash chromatography to give 1.3 g (76%) of 2-amino-5-(4-(4-chloro-phenylsulfanyl)-6-methyl-1,3-dioxo-1,3-dihydro-pyrrolo[3,4-c]pyridin-2-ylmethyl)-4,7-dihydro-5H-thieno[2,3-c]pyran-3-carboxylic acid tert-butyl ester as an oil.

Mp: 118–119° C.;

$^1$H-NMR (CDCl$_3$) δ 1.55 (s, 9H), 2.50 (s, 3H), 2.50–2.65 (m, 1H), 2.85–2.95 (m, 1H), 3.75–3.85 (m, 1H), 3.95–4.05, (m, 2H), 4.50–4.15 (m, 2H), 5.95 (bs, 2H), 7.30 (s, 1H), 7.40 (d, 2H), 7.55 (d, 2H).

To a ice cooled solution of 2-amino-5-(4-(4-chloro-phenylsulfanyl)-6-methyl-1,3-dioxo-1,3-dihydro-pyrrolo[3,4-c]pyridin-2-ylmethyl)-4,7-dihydro-5H-thieno[2,3-c]pyran-3-carboxylic acid tert-butyl ester (572 mg, 1 mmol) and dry triethylamine (2 ml) in dry tetrahydrofuran (10 ml) was added imidazol-1-yl-oxo-acetic acid tert-butyl ester (588 mg, 3 mmol). After 10 min, the reaction mixture was brought to room temperature and the stirring continued for 18 hours. The mixture was concentrated in vacuo and submitted to flash chromatography using a mixture of toluene/ethyl acetate (30:1) as eluent. Pure fraction were collected and the solvent evaporated in vacuo to give 360 mg (51%) of 2-(tert-butoxyoxalyl-amino)-5-(4-(4-chloro-phenylsulfanyl)-6-methyl-1,3-dioxo-1,3-dihydro-pyrrolo[3,4-c]pyridin-2-ylmethyl)-4,7-dihydro 5H-thieno[2,3-c]pyran-3-carboxylic acid tert-butyl ester as a solid.

Mp.: 134–136° C.;

¹H-NMR (CDCl₃) δ 1.60 (s, 9H), 1.63 (s, 9H), 2.50 (s, 3H), 2.65–2.75 (m, 1H), 2.95–3.05 (m, 1H), 3.75–3.90 (m, 1H), 4.00–4.10, (m, 2H), 4.60–4.85 (m, 2H), 7.30 (s, 1H), 7.40 (d, 2H), 7.55 (d, 2H), 12.50 (s, 1H).

To 2-(tert-butoxyoxalyl-amino)-5-(4-(4-chloro-phenylsulfanyl)-6-methyl-1,3-dioxo-1,3-dihydro-pyrrolo[3,4-c]pyridin-2-ylmethyl)-4,7-dihydro-5H-thieno[2,3-c]pyran-3-carboxylic acid tert-butyl ester (324 g, 0.46 mmol) was added a mixture of trifluoroacetic acid (2.5 ml) and dichloromethane (7.5 ml). The mixture was stirred for 5 hours, and added petroleum ether/ethyl acetate. The precipitate was isolated off and re-suspended in ethyl acetate. The title compound 136 mg (50%) was isolated by filtration.

Mp: 239–240° C.

Calculated for C₂₅H₁₈ClN₃O₈S₂, 0.75×H₂O; C, 49.92%; H, 3.27%; N, 6.99%. Found: C, 49.83%; H, 3.16%; N, 6.85%.

¹H-NMR (CDCl₃) δ 2.48 (s, 3H), 2.65–2.75 (m, 1H), 2.95–3.05 (m, 1H), 3.50–4.00 (m, 3H), 4.50–4.90 (m, 2H), 7.50–7.68 (m, 5H), 12.30 (s, 1H).

Example 19

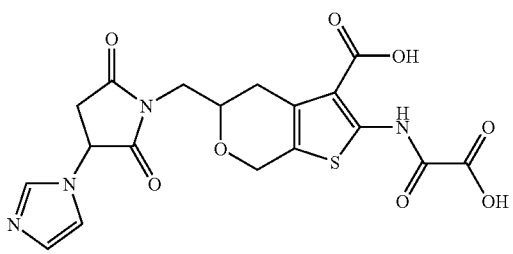

5-(3-imidazol-1-yl-2,5-dioxo-pyrrolidin-1-ylmethyl)-2-(oxalyl-amino)-4,7-dihydro-5H-thieno[2,3-c]pyran-3-carboxylic acid To a solution of 2-amino-5-aminomethyl-4,7-dihydro-5H-thieno[2,3-c]pyran-3-carboxylic acid tert-butyl ester (0.53 g, 1.86 mmol, prepared as described in Example 17) in tetrahydrofuran (10 ml) was added, maleic acid (0.24 g, 2.05 mmol) and diisopropylcarbodiimide (0.58 ml, 3.72 mmol). The reaction mixture was heated to reflux for 3 h. and then allowed to cool to room temperature over an 18 hours period. The solvent was stripped off in vacuo and the residue diluted into ethyl acetate (50 ml). The organic phase was washed with saturated sodium bicarbonate (2×50 ml), 1% hydrochloric acid (2×20 ml), brine (3×50 ml), dried (MgSO₄), filtered, and the solvent evaporated in vacuo affording an oil which was subjected to flash chromatography using a mixture of ethyl acetate/hexanes (6:4) as eluent. Pure fractions (R_f=0.25) were collected and the solvent evaporated in vacuo to give 0.60 g (90%) of 2-amino-5-(2,5-dioxo-2,5-dihydro-pyrrol-1-ylmethyl)-4,7-dihydro-5H-thieno[2,3-c]pyran-3-carboxylic acid tert-butyl ester as an oil.

¹H-NMR (300 MHz, CDCl₃) δ 7.31 (d, 1H, J=5.7 Hz), 6.63 (d, 1H, J=5.4 Hz), 5.94 (bs, 2H), 4.67 (s, 2H), 3.93 (m, 1H), 3.82 (m, 2H), 2.89–2.83 (m, 1H), 2.69–2.60 (m, 1H), 1.54 (s, 9H).

MS: APCI (+): m/z: 365.2 [M+H];

To a solution of the above 2-amino-5-(2,5-dioxo-2,5-dihydro-pyrrol-1-ylmethyl)-4,7-dihydro-5H-thieno[2,3-c]pyran-3-carboxylic acid tert-butyl ester (60 mg, 1.64 mmol) in tetrahydrofuran (2 ml) was added midazol-1-yl-oxoacetic acid tert-butyl ester (50 mg, 2.46 mmol). The solution was stirred at room temperature for 48 hours. The solvent was stripped off in vacuo and the resultant oil diluted in ethyl acetate (20 ml), washed with brine (3×25 ml), dried (MgSO₄), filtered and the solvent evaporated in vacuo. The residue was subjected preparative thin layer chromatography using a mixture of methanol/dichloromethane (1:9) as eluent which afforded 25 mg (28%) of 2-(tert-butoxyoxalylamino)-5-(3-imidazol-1-yl-2,5-dioxo-pyrrolidin-1-ylmethyl)-4,7-dihydro-5H-thieno[2,3-c]pyran-3-carboxylic acid tert-butyl ester as a mixture of diastereoisomers.

¹H-NMR (300 MHz, CDCl₃) δ 7.65 (s, 1H), 6.94 (s, 1H), 5.92 (m, 1H), 5.22 (m, 1H), 4.68–4.53 (m, 2H), 4.00 (m, 3H), 3.71 (m, 1H), 3.47–3.38 (m, 1H), 3.03–2.87 (m, 1H), 2.61 (m, 1H), 1.60 (s, 9H), 1.54 (s, 9H). MS: APCI (+): m/z: 561.2 (M+H).

To the above 2-(tert-butoxyoxalyl-amino)-5-(3-imidazol-1-yl-2,5-dioxo-pyrrolidin-1-ylmethyl)-4,7-dihydro-5H-thieno[2,3-c]pyran-3-carboxylic acid tert-butyl ester (25 mg, 0.05 mmol) was added a mixture of 20% trifluoroacetic acid in dichloromethane (2 ml). The reaction mixture was allowed to stir at room temperature for 2 hours, at which time the mixture was concentrated in vacuo. The resultant solid was triturated with diethyl ether (2×), which afforded 13 mg (65%) of the title compound as a solid.

¹H-NMR (300 MHz, CD₃OD) δ 9.15 (s, 1H), 7.78 (s, 1H), 7.63 (m, 1H), 5.75 (m, 1H), 4.69 (m, 2H), 4.46 (m, 1H), 3.85 (m, 2H), 3.66 (m, 1H), 3.02 (m, 1H), 2.83 (m, 1H), 2.64 (m, 1H), 2.46 (m, 1H).

MS: ESI (−): m/z: 447.4 [M−H].

Example 20

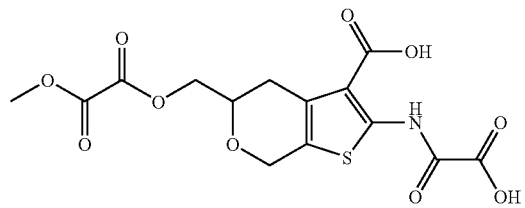

Oxalic acid 3-carboxy-2-(oxalyl-amino)-4,7-dihydro-5H-thieno[2,3-c]pyran-5-ylmethyl ester methyl To a solution of 2-amino-5-hydroxymethyl-4,7-dihydro-5H-thieno[2,3-c]pyran-3-carboxylic acid tert-butyl ester (8.0 g, 28 mmol) in dry tetrahydrofuran (50 ml) was added midazol-1-yl-oxo-acetic acid tert-butyl ester (27.51 g, 0.14 mol) and triethylamine (3.93 ml, 0.14 mol). The reaction mixture was stirred at room temperature for 20 hours. The volatiles were removed in vacuo and the crude product was dissolved in ethyl acetate (300 ml) and washed with a saturated solution of sodium bicarbonate (3×100 ml), dilute hydrochloric acid (3×100 ml), water (3×100 ml) and brine (100 ml). The organic layer was dried (MgSO₄), filtered and the solvent removed in vacuo. The residue (16 g) was purified on column chromatography on silica gel using a gradient of hexane/ethyl acetate (90:10 to 50:50 gradient) as eluent. Pure fractions were collected and the solvent evaporated in vacuo which afforded 11 g (91%) of oxalic acid 2-amino-3-tert-butoxycarbonyl-4,7-dihydro-5H— thieno[2,3-c]pyran-5-ylmethyl ester tert-butyl ester as a solid.

$^1$H-NMR (300 MHz, CDCl$_3$): δ 5.94 (s, 2H), 4.86 (d, 1H, J=14.7 Hz), 4.77 (d, 1H, J=14.4 Hz), 4.64 (m, 1H), 3.82–3.71 (m, 2H), 2.85 (d, 1H, J=16.8 Hz), 2.68 (d, 1H, J=10.5 Hz), 1.62 (s, 9H), 1.61 (s, 9H).

MS: m/z: 414 [M+H]$^+$.

A solution of the above oxalic acid 2-amino-3-tert-butoxycarbonyl-4,7-dihydro-5H-thieno[2,3-c]pyran-5-ylmethyl ester tert-butyl ester (8.3 g, 20.1 mmol) and potassium carbonate (1.7 g, 12.3 mmol) was stirred in methanol (80 ml) in presence of water (3 ml) at room temperature for 10 min., at which time TLC indicated reaction complete. Methanol was removed in vacuo and the crude product was dissolved in dichloromethane (300 ml) and washed with water (3×150 ml). The organic phase was dried (MgSO$_4$), filtered and the solvent evaporated in vacuo. The residue was purified on flash chromatography on silica gel using a gradient of hexane/ethyl acetate (90:10 to 50:50 gradient) as eluent. Pure fractions were collected and the solvent evaporated in vacuo affording 0.65 g (9%) of oxalic acid 2-amino-3-tert-butoxycarbonyl-4,7-dihydro-5H-thieno[2,3-c]pyran-5-ylmethyl ester methyl ester as a solid.

$^1$H-NMR (300 MHz, CDCl$_3$): δ 4.86 (d, 1H, J=15 Hz), 4.78 (d, 1H, J=15 Hz), 4.00 (s, 3H), 3.82–3.70 (m, 3H), 2.86 (d, 1H, J=17 Hz), 2.66 (dd, 1H, J=10.2 Hz and J=10.5 Hz), 1.62 (s, 9H).

MS: m/z: 316 (M-55).

To a solution of the above oxalic acid 2-amino-3-tert-butoxycarbonyl-4,7-dihydro-5H-thieno[2,3-c]pyran-5-ylmethyl ester methyl ester (160 mg, 0.43 mmol) in dry tetrahydrofuran (3.0 ml) was added midazol-1-yl-oxo-acetic acid tert-butyl ester (420.4 mg, 2.15 mmol) and triethylamine (120 μl, 0.86 mmol). The resulting mixture was stirred at room temperature for 20 hours. The solvent was evaporated in vacuo and the crude product was purified by flash chromatography on silica gel using a gradient of hexane/ethyl acetate (95:5 to 80:20 gradient) as eluent. Pure fractions were collected and the solvent evaporated in vacuo affording 173 mg (81%) of oxalic acid 2-amino-3-tert-butoxycarbonyl-2-(tert-butoxyoxalyl-amino)-4,7-dihydro-5H-thieno[2,3-c]pyran-5-ylmethyl ester methyl ester as a solid.

$^1$H-NMR (300 MHz, CDCl$_3$): δ 4.81 (dd, 2H, J=14.7 Hz and J=14.2 Hz), 4.40 (m, 2H), 4.00 (s, 3H), 2.96 (d, 1H, J=15.3 Hz), 2.69 (dd, 1H, J=10.8 Hz and J=10.8 Hz), 1.61 (s, 9H), 1.57 (s, 9H).

MS: m/z: 388.3 (M-11).

The above oxalic acid 2-amino-3-tert-butoxycarbonyl-2-(tert-butoxyoxalyl-amino)-4,7-dihydro-5H-thieno[2,3-c]pyran-5-ylmethyl ester methyl ester (93.8 mg, 0.19 mmol) was stirred in 20% trifluoroacetic acid in dichloromethane (2 ml) for 20 h. at room temperature. The solvent was removal in vacuo which afforded 73 mg (95%) of the title compound as a solid.

$^1$H-NMR (300 MHz, CD$_3$OD): δ 4.76 (d, 2H, J=5.7 Hz), 4.18 (d, 2H, J=4.8 Hz), 3.97 (s, 3H), 2.99 (d, 2H, J=16.2 Hz), 2.65 (d, 1H, J=10.8 Hz).

MS: m/z: 386 [M–H]$^-$.

Example 21

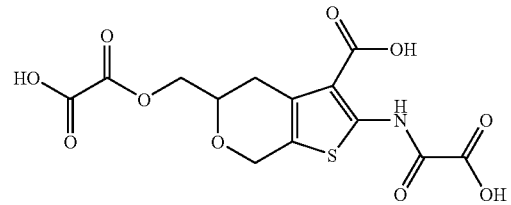

Oxalic acid (3-carboxy-2-(oxalyl-amino)-4,7-dihydro-5H-thieno[2,3-c]pyran-5-ylmethyl) ester To a solution of a mixture of 2-amino-5-hydroxymethyl-4,7-dihydro-5H-thieno[2,3-c]pyran-3-carboxylic acid tert-butyl ester and 2-amino-7-hydroxymethyl-4,7-dihydro-5H-thieno[2,3-c]pyran-3-carboxylic acid tert-butyl ester (1:4 estimated based on $^1$H-NMR) (200 mg, 0.70 mmol) and diisopropylethylamine (0.25 ml, 1.4 mmol) in dichloromethane (6.0 ml) cooled to 0° C. under nitrogen was added triethylchlorosilane (0.18 ml, 1.1 mmol). The solution was stirred at 0° C. for 5 min. and then stirred at room temperature for 15 min. The solution was washed with saturated sodium bicarbonate and brine, dried (MgSO$_4$), filtered and the solvent evaporated in vacuo. The residue was purified by silica gel chromatography using a 5% mixture of ethyl acetate/hexane as eluent. Pure fractions were collected and the solvent evaporated in vacuo affording 42 mg (16%) of 2-amino-5-triethylsilanyloxymethy-4,7-dihydro-5H-thieno[2,3-c]pyran-3-carboxylic acid tert-butyl ester (1) and 193 mg (69%) of 2-amino-7-triethylsilanyloxy-methyl-4,7-dihydro-5H-thieno[2,3-c]pyran-3-carboxylic acid tert-butyl ester (2).

(1) $^1$H-NMR (CDCl$_3$): δ 4.58 (m, 1H), 4.18–4.07 (m, 1H), 3.84 (dd, 1H, J=9.6 Hz and J=6.0 Hz), 3.80–3.70 (m, 1H), 3.60 (dd, 1H, J=9.6 and J=7.8 Hz), 2.92–2.70 (m, 2H), 1.58 (s, 9H), 0.98 (t, 9H, J=7.8 Hz), 0.64 (q, 6H, J=7.8 Hz);

(2) $^1$H-NMR (CDCl$_3$): δ 4.62 (s, 2H), 3.85–3.64 (m, 3H), 2.82 (dm, 1H, J=15 Hz), 2.49 (dd, 1H, J=15 Hz and J=11 Hz), 1.58 (s, 9H), 0.98 (t, 9H, J=7.8 Hz), 0.64 (q, 6H, J=7.8 Hz).

To a solution of 2-amino-7-triethylsilanyloxymethy-4,7-dihydro-5H-thieno[2,3-c]pyran-3-carboxylic acid tert-butyl ester (6.0 g, 15 mmol) in dichloromethane (10 ml) cooled to 0° C. under the nitrogen was added a solution of imidazol-1-yl-oxo-acetic acid tert-butyl ester (4.5 g, 18 mmol) in dichloromethane. The solution was stirred at 0° C. for 10 min. The reaction was quenched with water (1.0 ml). The solution was washed with brine and dried (MgSO$_4$), filtered and the solvent evaporated in vacuo. The residue was purified by silica gel chromatography using a 10% mixture of ethyl acetate/hexane as eluent. Pure fractions of two compounds were collected and the solvent evaporated in vacuo affording 4.5 g (56%) of 2-(tert-butoxyoxalyl-amino)-7-triethylsilanyloxymethyl-4,7-dihydro-5H-thieno[2,3-c]pyran-3-carboxylic acid tert-butyl ester (A) as a solid and 50 mg of oxalic acid 3-(tert-butoxycarbonyl-2-(tert-butoxyoxalyl-amino)-4,7-dihydro-5H-thieno[2,3-c]pyran-3-carboxylic acid tert-butyl ester (B) as a solid.

(A) $^1$H-NMR (CDCl$_3$): 612.53 (s, 1H), 4.85 (d, 1H, J=12 Hz), 4.65 (d, 1H, J=12 Hz), 3.90–3.60 (m, 3H), 2.94 (d, 1H, J=15 Hz), 2.63 (dd, 1H, J=15, 11 Hz), 1.63 (s, 9H), 1.61 (s, 9H), 0.98 (t, 9H, J=7.8 Hz), 0.64 (q, 6H, J=7.8 Hz).

(B) $^1$H-NMR (CDCl$_3$): 612.47 (s, 1H), 4.82 (q, 2H, J=14 Hz), 4.43 (m, 2H), 4.01 (m, 1H), 2.97 (d, 1H, J=14 Hz), 2.69 (dd, 1H, J=19.9 Hz), 1.63 (s, 9H), 1.61 (s, 9H), 1.58 (s, 9H).

To a solution of the above 2-(tert-butoxyoxalyl-amino)-7-triethylsilanyl-oxymethyl-4,7-dihydro-5H-thieno[2,3-c]pyran-3-carboxylic acid tert-butyl ester (4.5 g, 8.5 mmol) In tetrahydrofuran (10 ml) at room temperature was added 0.5 N hydrochloric acid (2.0 ml). The solution was stirred at room temperature for 0.5 hour. Ethyl acetate (100 ml) was added and the resulting solution was washed with saturated sodium bicarbonate, brine, dried (MgSO$_4$), filtered and the solvent evaporated in vacuo. The residue was purified by silica gel chromatography using a 10% mixture of ethyl acetate/hexane as eluent. Pure fractions were collected and the solvent evaporated in vacuo affording 3.0 g (84%) of 2-(tert-butoxyoxalyl-amino)-7-hydroxymethyl-4,7-dihydro-5H-thieno[2,3-c]pyran-3-carboxylic acid tert-butyl ester as a solid.

$^1$H-NMR (CDCl$_3$): δ 12.53 (s, 1H), 4.86 (d, 1H, J=12 Hz), 4.60 (d, 1H, J=12 Hz), 3.85–3.65 (m, 3H), 2.85 (d, 1H, J=15 Hz), 2.65 (dd, 1H, J=15 Hz and J=11 Hz), 1.63 (s, 9H), 1.61 (s, 9H).

To a solution of the above 2-(tert-butoxyoxalyl-amino)-7-hydroxy-methyl-4,7-dihydro-5H-thieno[2,3-c]pyran-3-carboxylic acid tert-butyl ester (3.0 g, 7.1 mmol) in dichloromethane (10 ml) at room temperature was added pyridine (2.5 ml, 28.5 mmol) and 4-nitro-benzenesulfonyl chloride (4.7 g, 21.4 mmol). The solution was heated to 50° C. and stirred for 4.5 hours. The solution was cooled to room temperature and washed with 0.5 N hydrochloric acid, saturated sodium bicarbonate, brine, dried (MgSO$_4$), filtered and the solvent evaporated in vacuo. The residue was purified by silica gel chromatography using a gradient of ethyl acetate/hexane (0–100%) as eluent. Pure fractions were collected and the solvent evaporated in vacuo affording 3.6 g (84%) of 2-(tert-butoxyoxalyl-amino)-7-(4-nitro-benzenesulfonyloxymethyl)-4,7-dihydro-5H thieno[2,3-c]pyran-3-carboxylic acid tert-butyl ester as a solid.

$^1$H-NMR (CDCl$_3$): δ 12.40 (s, 1H), 8.43 (d, 2H, J=9.0 Hz), 8.17 (d, 2H, J=9.0 Hz), 4.72 (d, 1H, J=14 Hz), 4.64 (d, 1H, J=14 Hz), 4.38–4.24 (m, 2H), 3.98–3.86 (m, 1H), 2.92 (d, 1H, J=17 Hz), 2.65 (dd, 1H, J=17 and J=12 Hz), 1.63 (s, 9H), 1.61 (s, 9H).

MS: m/z: 598 [M–H]$^-$.

To a solution of 50% trifluoroacetic acid/dichloromethane (1 ml) at room temperature was added oxalic acid 3-(tert-butoxycarbonyl-2-(tert-butoxyoxalyl-amino)-4,7-dihydro-5H-thieno[2,3-c]pyran-3-carboxylic acid tert-butyl ester (50 mg, 0.092 mmol). The solution was stirred for 3 hours. The solvent was removed in vacuo. The residue was washed with dichloromethane affording after filtration 25 mg (73%) of the title compound as a solid.

$^1$H-NMR (DMSO-d$_6$): δ 12.32 (s, 1H), 4.82 (d, 1H, J=15 Hz), 4.68 (d, 1H, J=15 Hz), 4.37 (s, 1H), 3.92 (m, 1H), 2.93 (d, 1H, J=16 Hz), 2.60 (dd, 1H, J=30 Hz and J=10 Hz).

MS: m/z: 372 [M–H]$^-$.

Example 22

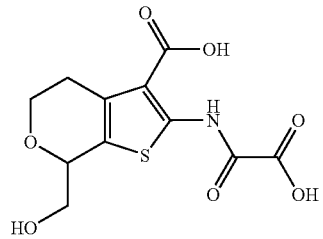

7-Hydroxymethyl-2-(oxalyl-amino)-4,7-dihydro-5H-thieno[2,3-c]pyran-3-carboxylic acid To a mixture of 2-hydroxymethyl-tetrahydro-pyran-4-one (35 g, 0.27 mol), tert-butyl cyanoacetate (58.68 ml g, 0.4 mol), and sulphur (9.47 g, 0.3 mol) in absolute ethanol (400 ml) was added morpholin (47 ml, 0.54 mol), and the resulting mixture was heated to 45° C. for 16 hours. The reaction mixture was cooled, filtered and the filtrate evaporated in vacuo. The resultant oil was dissolved in ethyl acetate (600 ml), washed with water (3×200 ml), brine (200 m), dried (Na$_2$SO$_4$), filtered and the solvent evaporated in vacuo. The residue was crystallised from diethyl ether (100 ml) followed by addition of a mixture of diethyl ether and heptane (100 ml, 1:1). The precipitate was filtered off, washed with a mixture of diethyl ether and heptane (90 ml, 1:1) and dried in vacuo at 50° C. for 52 hours affording 44.51 g of a mixture of 5 and 7 regioisomers according to NMR. The mixture of regioisomers (44.51 g) was suspended in diethyl ether (500 ml) and stirred at room temperature for 96 hours and at reflux temperature for 2 hours. After cooling to room temperature the precipitate was filtered off and washed with a mixture of diethyl ether and heptane (100 ml, 1:1) which afforded after drying in vacuo at 50° C., 22.12 g (29%) of 2-amino-5-hydroxymethyl-4,7-dihydro-5H-thieno[2,3-c]pyran-3-carboxylic acid tert-butyl ester as a solid.

All filtrates were pooled and evaporated in vacuo affording 55 g of a mixture of regioisomers. To 40.16 g (0.141 mol) of this regioisomer mixture dissolved in dichloromethane (450 ml) was added diisopropyl-ethylamine (49.5 ml, 0.28 mol) and the mixture was cooled to 0° C. Chlorothiethylsilane (38.2 ml, 0.23 mol) was added dropwise and the mixture was stirred for 10 minutes and for 15 minutes at room temperature. The reaction mixture was washed with saturated aqueous sodium carbonate (3×150 ml), brine (3×150 ml), dried (Na$_2$SO$_4$), filtered and the solvent evaporated in vacuo. The residue (70.4 g) was partitioned into two portions, which were subjected to flash chromatography (2l silicagel) using a mixture of ethyl acetate/hexane (1:20) as eluent. Pure fractions of 2-amino-5-triethylsilanyloxymethyl-4,7-dihydro-5H-thieno[2,3-c]pyran-3-carboxylic acid tert-butyl ester and 2-amino-7-triethylsilanyl-hydroxymethyl-4,7-dihydro-5H-thieno[2,3-c]pyran-3-carboxylic acid tert-butyl ester were collected. A fraction containing both isomers (18.84 g) was re-subjected to flash chromatography (2 I silicagel) using a mixture of ethyl acetate/hexane (1:20) as eluent. A total of 28.1 g (50%) of 2-amino-5-triethylsilanylhydroxymethyl-4,720 dihydro-5H-thieno[2,3-c]pyran-3-carboxylic acid tert-butyl ester was obtained. A total of 18.2 g (32%) of 2-amino-7-triethylsilanylhydroxymethyl-4,7-dihydro-5H-thieno[2,3-c]pyran-3-carboxylic acid tert-butyl ester was obtained.

To the above 2-amino-7-triethylsilanylhydroxymethyl-4,7-dihydro-5H-thieno[2,3-c]pyran-3-carboxylic acid tert-butyl ester (18.2 g, 0.046 mol) dissolved in dichloromethane (200 ml) was added a mixture of imidazol-1-yl-oxo-acetic acid tert butyl ester (17.9 g, 0.091 mol) in dichloromethane (30 ml) under nitrogen. The reaction mixture was allowed to stir at room temperature for 18 hours. The reaction mixture was evaporated in vacuo and the residue was dissolved in ethyl acetate (100 ml) and washed with 1N hydrochloric acid (3×50 ml), brine (3×75 ml), dried (Na$_2$SO$_4$), filtered and the organic phase evaporated in vacuo affording in quantitative yield 2-(tert-butoxyoxalyl-amino)-7-triethylsilanyloxymethyl-4,7-dihydro-5H-thieno[2,3-c]pyran-3-carboxylic acid tert-butyl ester ester as a oil.

To a mixture of the above 7-triethylsilanyl ether (24.0 g, 0.046 mol) in tetrahydrofuran (100 ml) was added 1 N hydrochloric acid (18 ml) and the reaction mixture was stirred at room temperature for 1.5 hour. Ethyl acetate (150 ml) was added and the reaction mixture was washed with saturated aqueous sodium carbonate (3×100 ml), brine (3×100 ml), dried (Na$_2$SO$_4$), filtered and the solvent evaporated in vacuo. The residue was trituated with a mixture of diethyl ether and heptane (1:5) and the precipitate was filtered off, washed with heptane and dried in vacuo at 50° C. for 16 hours affording 13.55 g (57%) of 2-(tert-butoxyoxalyl-amino)-7-hydroxymethyl-4,7-dihydro-5H-thieno[2,3-c]pyran-3-carboxylic acid tert-butyl ester as a solid.

The above 2-(tert-butoxyoxalyl-amino)-7-hydroxymethyl-4,7-dihydro-5H-thieno[2,3-c]pyran-3-carboxylic acid tert-butyl ester (16 mg, 0.033 mmol) was dissolved in 50% trifluoroacetic acid in dichloromethane (1 ml). The reaction was stirred at room temperature for 3 hours. The volatiles were evaporated in vacuo and the residue washed with dichloromethane, which afforded 7 mg (73%) of the title compound as a solid.

$^1$H NMR (DMSO-d$_6$): δ 12.32 (s, 1H), 4.62 (s, 1H), 4.12 (m, 1H), 3.62–3.78 (m, 2H), 3.40–3.52 (m, 1H), 2.83 (m, 2H).

MS: m/z: 300 [M–H]$^-$.

Example 23

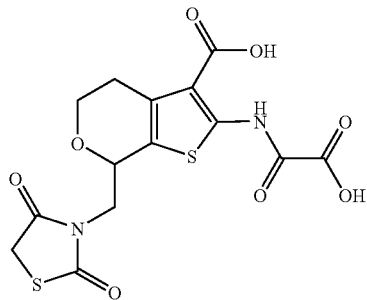

7-(2,4-Dioxo-Thiazolidin-3-ylmethyl)-2-(oxalyl-amino)-4,7-dihydro-5H-thieno[2,3-c]pyran-3-carboxylic acid To a solution of 2-amino-7-hydroxymethyl-4,7-dihydro-5H-thieno[2,3-c]pyran-3-carboxylic acid tert-butyl ester (0.13 g, 0.46 mmol) in tetrahydrofuran (3 ml) was added triphenylphosphine (0.13 g, 0.51 mmol), and thiazolidin-2,4-dione (60 mg, 0.51 mmol). The reaction mixture was cooled to 0° C. and diisopropylazodicarboxylate (99 µl, 0.51 mmol) was added via syringe. The resultant mixture was stirred for 18 hours, gradually warming to room temperature. The volatiles were evaporated in vacuo and the resulting oil was diluted in ethyl acetate (50 ml). The organic phase was washed with saturated sodium bicarbonate (3×50 ml), brine (3×50 ml), dried (MgSO$_4$), filtered and the solvent evaporated in vacuo. The residue was subjected to flash chromatography using a mixture of dichloromethane/methanol (9:1) as eluent. Pure fractions were collected (R$_f$=0.70) and the solvent evaporated in vacuo which afforded 89 mg (51%) of 2-amino- 7-(2,4-dioxo-thiazolidin-3-ylmethyl)-4,7-dihydro-5H-thieno[2,3-c]pyran-3-carboxylic acid tert-butyl ester as an oil.

$^1$H-NMR (300 MHz, CDCl$_3$) δ 6.02 (s, 2H), 4.82 (dm, 1H), 4.13–4.02 (bm, 2H), 3.99 (s, 2H), 3.75–3.67 (m, 1H), 3.60 (dd, 1H, J=14 Hz and J=3.3 Hz), 2.81–2.74 (m, 2H), 1.54 (s, 9H).

MS: APCI (+): m/z: 385.6 [M+H],

To a solution of the above of 2-amino-7-(2,4-dioxo-thiazolidin-3-ylmethyl)-4,7-dihydro-5H-thieno[2,3-c]pyran-3-carboxylic acid tert-butyl ester (89 mg) in tetrahydrofuran (5 ml) was added midazol-1-yl-oxo-acetic acid tert-butyl ester (79 mg, 0.31 mmol) and the mixture allowed to stir overnight at room temperature. The volatiles were evaporated in vacuo, the residue diluted with ethyl acetate and subjected to preparative chromatography using a mixture of dichloromethane/methanol (9:1) as eluent. Material eluting with R$_f$ 0.72 was collected and the solvent evaporated in vacuo affording 40 mg (25%) of 2-(tert-butoxyoxalyl-amino)-7-(2,4-dioxo-thiazolidin-3-ylmethyl)-4,7-dihydro-5H-thieno[2,3-c]pyran-3-carboxylic acid tert-butyl ester as an oil.

$^1$H-NMR (300 MHz, CDCl$_3$) δ 12.53 (s, 1H), 5.03 (dm, 1H), 4.12–4.04 (m, 2H), 4.01 (s, 2H), 3.79–3.71 (m, 2H), 2.88 (m, 2H), 1.62 (s, 9H), 1.59 (s, 9H).

MS: APCI (+): m/z: 513.3 [M+H].

The above 2-(tert-butoxyoxalyl-amino)-7-(2,4-dioxo-thiazolidin-3-ylmethyl)-4,7-dihydro-5H-thieno[2,3-c]pyran-3-carboxylic acid tert-butyl ester (40 mg) was dissolved in 50% trifluoroacetic acid in dichloromethane (1 ml) and stirred at room temperature for 3 hours. The mixture was concentrated in vacuo, the residue triturated with dichloromethane and methanol, which afforded after drying in vacuo 18 mg (87%) of the title compound as a solid.

$^1$H-NMR (300 MHz, DMSO-d$_6$+CD$_3$OD) δ 4.98 (dm, 1H), 4.16 (s, 2H), 4.14–4.02 (m, 2H), 3.78–3.72 (m, 2H), 2.91 (m, 2H).

APCI (–): m/z: 399 [M–H];

LC-MS: s, 99%.

Example 24

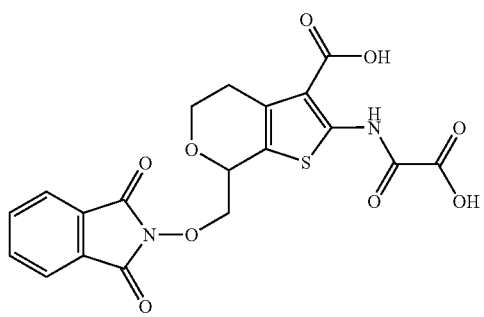

7-(1,3-Dioxo-1,3-dihydro-isoindol-2-yloxymethyl)-2-(oxalyl-amino)-4,7-dihydro-5H-thieno[2,3-c]pyran-3-carboxylic acid To a mixture of 2-(tert-butoxyoxalyl-amino)-7-hydroxymethyl-4,7-dihydro-5H-thieno[2,3-c]pyran-3-carboxylic acid tert-butyl ester (0.5 g, 1.2 mmol), 2-hydroxy-isoindole-1,3-dione (0.21 g, 1.3 mmol) and triphenylphosphine (0.35 g, 1.33 mmol) in dry tetrahydrofuran (20 ml) cooled to 0° C. under a nitrogen atmosphere was added diethyl azodicarboxylate (DEAD) (205 μl, 1.33 mmol). The reaction mixture was allowed to stir overnight, slowly warming to room temperature. The volatiles were evaporated in vacuo and the resultant solid dissolved in ethyl acetate (50 ml). The organic phase was washed with saturated aqueous sodium hydrogencarbonate (3×30 ml), water (3×50 ml), dried ($Na_2SO_4$), filtered and evaporated in vacuo. The residue (1.02 g) was subjected to flash column chromatography (300 ml silicagel) using a mixture of ethyl acetate/hexane (1:2) as eluent. Pure fractions were collected affording after evaporation in vacuo 0.37 g (54%) of 2-(tert-butoxyoxalyl-amino)-7-(1,3-dioxo-1,3-dihydro-isoindol-2-yloxymethyl)-4,7-dihydro-5H-thieno[2,3-c]pyran-3-carboxylic acid tert-butyl ester as an oil.

The above di-tert-butyl ester (0.33 g, 0.59 mmol) was dissolved in 25% trifluoroacetic acid in dichloromethane (2 ml). The reaction was stirred at room temperature for 6.5 h. The volatiles were evaporated in vacuo and the residue triturated with a mixture of diethyl ether and heptane (5 ml, 1:1). The precipitate was filtered off, washed with heptane and diethyl ether, dried in vacuo at 50° C. for 18 hours which afforded 200 mg (77%) of the title compound as a solid.

M.p.: 251.5–254° C.;

Calculated for $C_{19}H_{14}N_2O_9S$; C, 51.12%; H, 3.16%; N, 6.28%. Found: C, 51.46%; H, 3.71%; N, 5.87%.

Example 25

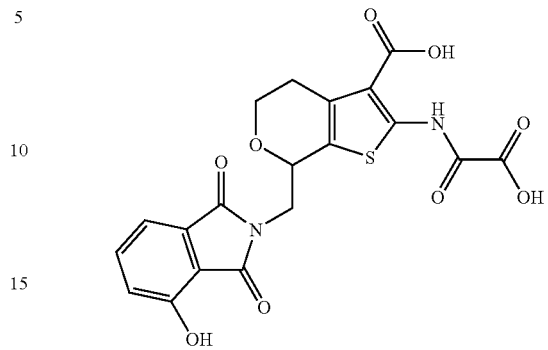

7-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid To a solution of 4-hydroxy-isobenzofuran-1,3-dione (0.5 g, 3.03 mmol) in anhydrous N,N-dimethylformamide (6 ml) under nitrogen was added N,N-diisopropylethylamine (1.05 ml, 6.06 mmol). The solution was stirred with cooling in an ice bath and chloromethyl methyl ether (0.46 ml, 6.06 mmol) was added. The reaction was allowed to slowly warm to ambient temperature and then stirred for an additional 7 hours. The mixture was concentrated in vacuo to a small volume and diluted with ethyl acetate (75 ml). The organic layer was washed with water (2×40 ml), brine (20 ml), dried ($Na_2SO_4$), filtered, and the solvent evaporated in vacuo to give 0.6 g (95%) of 4-methoxymethoxy-isobenzofuran-1,3-dione as a solid.

$^1$H-NMR (400 MHz, $CDCl_3$) δ 7.81 (t, 1H, J=8 Hz), 7.62 (d, 1H, J=8 Hz), 7.59 (d, 1H, J=8 Hz), 5.43 (s, 2H), 3.55 (s, 3H).

A mixture of 2-amino-7-aminomethyl-4,7-dihydro-5H-thieno[2,3-c]pyran-3-carboxylic acid tert-butyl ester (0.15 g, 0.53 mmol) and 4-methoxy-methoxy-isobenzofuran-1,3-dione (135 mg, 0.64 mmol) was dissolved in distilled acetonitrile (7 ml) under nitrogen. The flask was cooled in an ice bath with stirring and 1-(3-dimethylaminopropyl)-3-ethylcarbodiimide hydrochloride (0.12 g, 0.64 mmol), and triethylamine (0.22 ml, 1.59 mmol) were added. The reaction was warmed to ambient temperature and stirred for 18 hours. The solution was concentrated in vacuo and the residue dissolved in ethyl acetate (40 ml). The organic layer was washed with 1% hydrochloric acid (2×10 ml), saturated sodium bicarbonate (10 ml), and brine (10 ml). The resulting solution was dried ($Na_2SO_4$), filtered, and the solvent evaporated in vacuo which afforded 0.18 g of a crude 2-amino-7-(4-methoxymethoxy-1,3-dioxo-1,3-dihydro-isoindol-2-ylmethyl)-4,7-dihydro-5H-thieno[2,3-c]pyran-3-carboxylic acid tert-butyl ester which was used without further purification.

$^1$H-NMR (400 MHz, $CDCl_3$) δ 7.65–7.58 (m, 2H), 7.51 (d, 1H, J=8 Hz), 6.00–5.86 (2s, 2H), 5.39 (s, 2H), 4.94–4.89 (m, 1H), 4.18–4.02 (m, 2H), 3.86–3.65 (m, 1H), 3.54 (s, 3H), 2.85–2.73 (m, 2H), 1.55 (s, 9H).

APCI-MS: m/z: 475.4 [M+H]$^+$

To a solution of crude 2-amino-7-(4-methoxymethoxy-1,3-dioxo-1,3-dihydro-isoindol-2-ylmethyl)-4,7-dihydro-5H-thieno[2,3-c]pyran-3-carboxylic acid tert-butyl ester (0.18 g) in distilled dichloromethane (4 ml) under nitrogen was added midazol-1-yl-oxo-acetic acid tert-butyl ester (0.23 g, 1.2 mmol). The reaction was stirred for 3 hours, concentrated in vacuo and reconstituted in ethyl acetate (30 ml). The organic layer was washed with 1% hydrochloric acid (2×5 ml), saturated sodium bicarbonate (5 ml), and brine (5 ml). The resulting solution was dried ($Na_2SO_4$), filtered, and the solvent evaporated in vacuo. The crude material was purified by silica gel chromatography using a gradient of ethyl acetate/dichloromethane (0 to 5% gradient) as eluent. Pure fractions were collected and the solvent evaporated in vacuo to give 90 mg (28% in two steps) of 2-(tert-butoxy-oxalyl-amino)-7-(4-methoxy-methoxy-1,3-dioxo-1,3-dihydro-isoindol-2-ylmethyl)-4,7-dihydro-5H-thieno[2,3-c]pyran-3-carboxylic acid tert-butyl ester as an oil.

$^1$H-NMR (400 MHz, $CDCl_3$) 612.54 (s, 1H), 7.64 (t, 1H, J=8 Hz), 7.51 (d, 1H, J=8 Hz), 7.46 (d, 1H, J=8 Hz), 5.40 (s, 2H), 5.11–5.07 (m, 1H), 4.16–4.08 (m, 2H), 3.84–3.72 (m, 2H), 3.55 (s, 3H), 2.95–2.81 (m, 2H), 1.62 (s, 9H), 1.59 (s, 9H).

APCI-MS: m/z: 603.8 [M+H]$^+$

The above 2-(tert-butoxyoxalyl-amino)-7-(4-methoxymethoxy-1,3-dioxo-1,3-dihydro-isoindol-2-ylmethyl)-4,7-dihydro-5H-thieno[2,3-c]pyran-3-carboxylic acid tert-butyl ester (86 mg, 0.143 mmol) was dissolved in a solution of 50% trifluoroacetic acid/dichloromethane (4 ml). The reaction was stirred at ambient temperature for 7 hours, concentrated in vacuo and evaporated in vacuo from dichloromethane (3×10 ml). The resulting precipitate was washed with dichloromethane and dried in vacuo to give 55 mg (86%) of the title compound as a solid.

$^1$H-NMR (400 MHz, DMSO-$d_6$) 612.34 (s, 1H), 11.10 (s, 1H), 7.63 (t, 1H, J=8 Hz), 7.31 (d, 1H, J=8 Hz), 7.22 (d, 1H, J=8 Hz), 4.99–4.95 (m, 1H), 4.05–4.00 (m, 1H), 3.91–3.86 (m, 1H), 3.76–3.66 (m, 2H), 2.88–2.80 (m, 2H).

APCI-MS: m/z: 447.4 [M+H]$^+$

HPLC (254.4 nm): $R_t$=2.92 min

Example 26

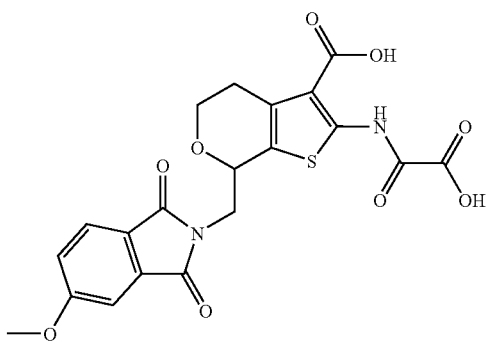

5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid The title compound was prepared in a similar way as described in Example 25.

M.p.: 234–236° C.;

Calculated for $C_{20}H_{16}N_2O_9S$, 0.25×$H_2O$; C, 51.67%; H, 3.58%; N, 6.03%. Found: C, 51.95%; H, 3.92%; N, 6.06%.

Example 27

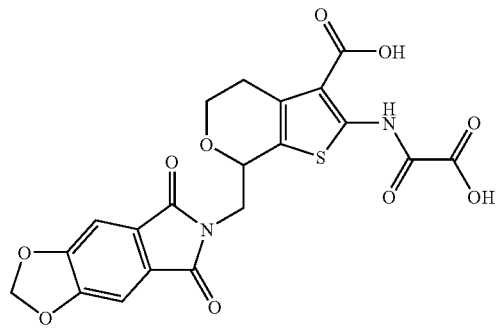

7-(5,7-Dioxo-5,7-dihydro-[1,3]dioxolo[4,5-f]isoindol-6-ylmethyl-2-(oxalyl-amino)-4,7-dihydro-5H-thieno[2,3-c]pyran-3-carboxylic acid The title compound was prepared in a similar way as described in Example 25.

M.p.: 239.5–242.5° C.;

Calculated for $C_{20}H_{14}N_2O_{10}S$, 0.1×$H_2O$; C, 50.45%; H, 3.01%; N, 5.88%. Found: C, 51.06%; H, 3.43%; N, 5.93%.

Example 28

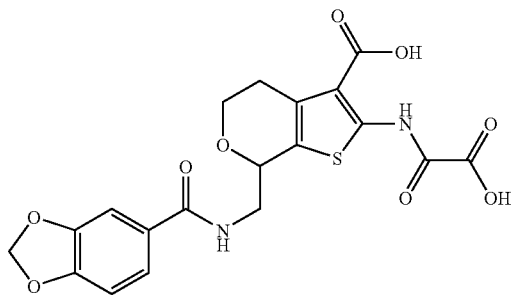

7-(((Benzo[1,3]dioxole-5-carbonyl)amino)methyl)-2-(oxalyl-amino)-4,7-dihydro-5H-thieno[2,3-c]pyran-3-carboxylic acid Phthalimidoacetaldehyde diethyl acetal (100 g, 0.38 mol) and 1 N hydrochloric acid (600 ml) was mixture was stirred at reflux temperature for 5 min. or until a homogeneous solution is obtained. The reaction mixture was cooled and the precipitate was filtered off and dried in vacuo at 50° C. for 16 hours, which afforded 63.3 g (88%) of phthalimidoacetaldehyde as a solid.

$^1$H-NMR (300 MHz, $CDCl_3$) δ 4.58 (s, 2H), 7.76–7.78 (m, 2H), 7.90–7.92 (m, 2H), 9.67 (s, 1H).

To a mixture of phthalimidoacetaldehyde (64 g, 0.34 mol) and trans-1-methoxy-3-(trimethylsilyloxy)-1,3-butadiene (81.5 g, 0.38 mol) in benzene (600 ml) stirred for 15 min. under nitrogen was added dropwise a 45% solution of zinc chloride diethyl ether complex in dichloromethane (55.5 ml, 0.17 mol) at 0° C. The reaction was allowed warm up to room temperature overnight. To the reaction mixture was added water (500 ml) and the resulting mixture was extracted with ethyl acetate (200 ml). The organic extract was washed successively with 1.0 N hydrochloric acid (2×200 ml) and brine (200 ml). The organic phase was dried (Na$_2$SO$_4$), filtered and the solvent evaporated in vacuo which afforded a slowly crystallising oil (98 g). To the solid was added a mixture of ethyl acetate and diethyl ether (400 ml, 1:1) and the resulting precipitate was filtered off, washed with a small portion of diethyl ether and dried at 50° C. for 1 hour affording 59.8 g (69%) of 2-(4-oxo-3,4-dihydro-2H-pyran-2-ylmethyl)-isoindole-1,3-dione as a solid. The filtrate was evaporated in vacuo and the residue purified by column chromatography on silica gel (1 L) using a mixture of ethyl acetate and heptane (1:2) as eluent. Pure fractions were collected and the solvent evaporated in vacuo to almost dryness, the solid was filtered off and dried in vacuo at 50° C. for 16 h affording an additional 15 g (17%) of 2-(4-oxo-3,4-dihydro-2H-pyran-2-ylmethyl)-isoindole-1,3-dione as a solid.

1H-NMR (300 MHz, CDCl$_3$) δ2.61 (d, 2H), 3.85 (dd, 1H), 4.18 (dd, 1H), 4.76 (m, 1H), 5.43 (d, 1H), 7.28 (d, 1H), 7.69–7.77 (m, 2H), 7.84–7.88 (m, 2H).

2-(4-Oxo-3,4-dihydro-2H-pyran-2-ylmethyl)-isoindole-1,3-dione (13 g, 0.051 mol) was dissolved in ethyl acetate (250 ml) and placed in a Parr bottle. 10% Pd/C (1.5 g) was carefully added and the mixture was shaken under a pressure of 30 psi of hydrogen for 6.5 hours (Parr apparatus). Filtration followed by evaporation of the ethyl acetate in vacuo afforded a crude 11.5 g of 2-(4-oxo-tetrahydro-pyran-2-ylmethyl)-isoindole-1,3-dione pure enough for the next step. Analytical pure compound could be obtained by purification of a small sample (250 mg) by column chromatography on silica gel, utilising a mixture of hexane/ethyl acetate as a gradient (from 100/0 to 50/50). Pure fractions were collected and the solvent evaporated in vacuo affording 142 mg (55%) of 2-(4-oxo-tetrahydro-pyran-2-ylmethyl)-isoindole-1,3-dione as a solid.

$^1$H-NMR (400 MHz, CDCl$_3$) δ 2.30–2.68 (m, 4H), 3.62 (m, 1H), 3.74 (m, 1H), 4.00 (m, 2H), 7.75 (m, 2H), 7.88 (m, 2H).

To a mixture of 2-(4-oxo-tetrahydro-pyran-2-ylmethyl)-isoindole-1,3-dione (11.5 g, 44 mmol), tert-butyl cyanoacetate (6.9 g, 49 mmol) and elemental sulfur (1.6 g, 49 mmol) in ethanol (250 ml) was added morpholin (15 ml) and the resulting mixture was stirred at 50° C. for 16 hours. The cooled reaction mixture was filtered and the precipitate filtered off and washed with diethyl ether and dried in vacuo affording 6.5 g (35%) of 2-amino-5-(1,3-dioxo-1,3-dihydro-isoindol-2-ylmethyl)-4,7-dihydro-5H-thieno[2,3-c]pyran-3-carboxylic acid tert-butyl ester as a solid.

The filtrate was evaporated in vacuo and the residue was dissolved in ethyl acetate (200 ml) washed with water (2×100 ml), brine (100 ml), dried (Na$_2$SO$_4$), filtered and the solvent evaporated in vacuo affording 6.0 g (33%) of almost regioisomer pure 2-amino-7-(1,3-dioxo-1,3-dihydro-isoindol-2-ylmethyl)-4,7-dihydro-5H-thieno[2,3-c]pyran-3-carboxylic acid tert-butyl ester as a solid.

2-Amino-5-(1,3-dioxo-1,3-dihydro-isoindol-2-ylmethyl)-4,7-dihydro-5H-thieno[2,3-c]pyran-3-carboxylic acid tert-butyl ester $^1$H-NMR (300 MHz, CDCl$_3$) δ 1.50 (s, 9H), 2.54–2.63 (m, 1H), 2.84–2.90 (m, 1H), 3.79 (q, 1H), 3.96–4.04 (m, 2H), 4.48–4.62 (m, 1H), 5.91 (bs, 2H, NH$_2$), 7.70 (m, 2H), 7.84 (m, 2H).

2-Amino-7-(1,3-dioxo-1,3-dihydro-isoindol-2-ylmethyl)-4,7-dihydro-5H-thieno[2,3-c]pyran-3-carboxylic acid tert-butyl ester $^1$H-NMR (300 MHz, CDCl$_3$) δ 1.50 (s, 9H), 2.71–2.90 (m, 2H), 3.67–3.77 (m, 2H), 4.02–4.15 (m, 2H), 4.90 (m, 1H), 6.04 (bs, 2H, NH$_2$), 7.70 (m, 2H), 7.84 (m, 2H).

To a solution of 2-amino-7-(1,3-dioxo-1,3-dihydro-isoindol-2-ylmethyl)-4,7-dihydro-5H-thieno[2,3-c]pyran-3-carboxylic acid tert-butyl ester (6.0 g, 0.014 mol) in ethanol (100 ml) was added hydrazine-hydrate (1.4 ml, 0.029 mol). The mixture was stirred at reflux temperature for 1 hour. The cooled reaction mixture was filtered and the solvent evaporated in vacuo. The residue was dissolved in diethyl ether (200 ml) and washed with water (100 ml), brine (100 ml), dried (Na$_2$SO$_4$), filtered and the solvent evaporated in vacuo affording 2.9 g (71%) of 2-amino-7-aminomethyl-4,7-dihydro-5H-thieno[2,3-c]pyran-3-carboxylic acid tert-butyl ester as an oil.

To a ice cooled mixture of 2-amino-7-aminomethyl-4,7-dihydro-5H-thieno[2,3-c]pyran-3-carboxylic acid tert-butyl ester (1.4 g, 4.92 mmol), triethylamine (2 ml) in dichloromethane (100 ml) was added dropwise a solution of benzo[1,3]dioxole-5-carbonyl chloride (1.0 g, 5.41 mmol) in dichloromethane (25 ml) during 1.5 hour. The ice cooled reaction mixture was stirred for an additional 0.5 hour. The volatiles were evaporated in vacuo and the residue was dissolved in ethyl acetate (200 ml) and washed with water (2×100 ml), brine (100 ml), dried (Na$_2$SO$_4$), filtered and the solvent evaporated in vacuo. The residue (2 g) was subjected to flash column chromatography (1 l silicagel) using a mixture of ethyl acetate/hexane (1:2) as eluent. Pure fractions were collected affording after evaporation in vacuo 0.3 g (14%) of 2-amino-7-(((benzo[1,3]dioxole-5-carbonyl)amino)-methyl)-4,7-dihydro-5H-thieno[2,3-c]pyran-3-carboxylic acid tert-butyl ester as an oil.

TLC: R$_f$=0.44 (ethyl acetate/heptane 1:1).

A mixture of the above 2-amino-7-(((benzo[1,3]dioxole-5-carbonyl)-amino)methyl)-4,7-dihydro-5H-thieno[2,3-c]pyran-3-carboxylic acid tert-butyl ester (0.3 g, 0.69 mmol), imidazol-1-yl-oxo-acetic acid tert-butyl ester (0.16 g, 0.83 mmol) in dry tetrahydrofuran (50 ml) was stirred at room temperature for 16 hours. The volatiles were evaporated in vacuo and the residue was dissolved in ethyl acetate (100 ml) and washed with water (2×50 ml), brine (50 ml), dried (Na$_2$SO$_4$), filtered and the solvent evaporated in vacuo. The residue (0.35 g) was subjected to flash column chromatography (500 ml silicagel) using a mixture of ethyl acetate/hexane (1:1) as eluent. Pure fractions were collected and the solvent evaporated in vacuo. The residue was triturated with diethyl ether (5 ml), filtered off and dried in vacuo at 50° C. for 5 hours which afforded 0.17 g (44%) of 7-(((benzo[1,3]dioxole-5-carbonyl)amino)methyl)-2-(tert-butoxyoxalyl-amino)-4,7-dihydro-5H-thieno[2,3-c]pyran-3-carboxylic acid tert-butyl ester as a solid.

TLC: R$_f$=0.37 (ethyl acetate/heptane 1.1).

The above di-tert-butyl ester (0.17 g, 0.30 mmol) was dissolved in 25% trifluoroacetic acid in dichloromethane (20 ml). The reaction was stirred at room temperature for 5.5 hours. The volatiles were evaporated in vacuo and the residue triturated with diethyl ether (10 ml). The precipitate was filtered off, washed with diethyl ether, dried in vacuo at 50° C. for 72 hours which afforded 100 mg (74%) of the title compound as a solid.

M.p.: 227–230° C.;

Calculated for C$_{19}$H$_{16}$N$_2$O$_9$S, 0.5×H$_2$O; C, 49.89%; H, 3.75%; N, 6.12%. Found: C, 50.02%; H, 3.68%; N, 5.98%.

Example 29

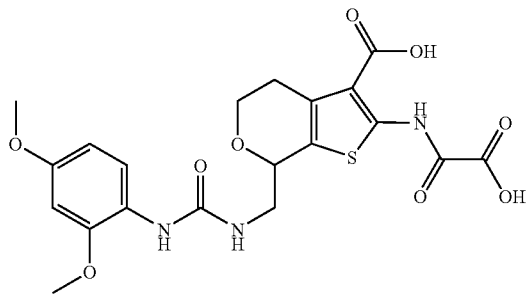

7-(3-(2,4-Dimethoxy-phenyl)ureidomethyl)-2-(oxalyl-amino)-4,7-dihydro-5H-thieno[2,3-c]pyran-3-carboxylic acid To a solution of 2-amino-7-aminomethyl-4,7-dihydro-5H-thieno[2,3-c]pyran-3-carboxylic acid tert-butyl ester (64 mg, 0.22 mmol) in dichloromethane (1 ml) was added 2,4-dimethoxyphenylisocyanate (40 mg, 0.22 mmol). The reaction mixture was stirred at room temperature for 18 hours. The reaction mixture was concentrated in vacuo, diluted with ethyl acetate (30 ml), washed with saturated sodium carbonate (3×25 ml), brine (3×25 ml), dried (MgSO$_4$), filtered and the solvent evaporated in vacuo. The residue was subjected to preparative thin layer chromatography (100% dichloromethane). $R_f$=0.8 was isolated and the solvent evaporated in vacuo which afforded 55 mg (53%) of 2-amino-7-(3-(2,4-dimethoxy-phenyl)ureidomethyl)-4,7-dihydro-5H-thieno[2,3-c]pyran-3-carboxylic acid tert-butyl ester as an oil.

$^1$H-NMR (300 MHz, CDCl$_3$) δ 7.75 (d, 1H, J=9.6 Hz), 7.62 (d, 1H, J=8.1 Hz), 6.45 (m, 3H), 5.00 (bs, 2H), 4.68 (m, 1H), 4.12 (m, 2H), 3.80 (s, 3H), 3.76 (s, 3H), 3.76–3.67 (m, 1H), 3.30 (dd, 1H, J=14 Hz and J=6.9 Hz), 2.76 (m, 2H), 1.55 (s, 9H).

MS: APCI (+): m/z 464.3 [M+H].

To a solution of the above 2-amino-7-(3-(2,4-dimethoxy-phenyl)ureidomethyl)-4,7-dihydro-5H-thieno[2,3-c]pyran-3-carboxylic acid tert-butyl ester (47 mg, 0.11 mmol) in dichloromethane (1 ml) was added triethylamine (28 μl, 0.22 mmol) and midazol-1-yl-oxo-acetic acid tert-butyl ester (40 mg, 0.22 mmol). The mixture was stirred at room temperature for 18 hours. The volatiles were evaporated in vacuo and the residue diluted with ethyl acetate (35 ml). The organic phase was washed with saturated sodium carbonate (3×25 ml), brine (3×25 ml), dried (MgSO$_4$), filtered, and the solvent evaporated in vacuo. The resultant oil was subjected to preparative thin layer chromatography (60% ethyl acetate/40% hexanes). Pure 2-(tert-butoxyoxalyl-amino)-7-(3-(2,4-dimethoxy-phenyl)ureidomethyl)-4,7-dihydro-5H-thieno[2,3-c]pyran-3-carboxylic acid tert-butyl ester 34 mg (58%) was isolated as an oil.

$^1$H-NMR (300 MHz, CDCl$_3$) δ 12.49 (s, 1H), 7.70 (d, 1H, J=9.6 Hz), 6.62 (bs, 1H), 6.47 (m, 3H), 5.02 (bs, 1H), 4.84 (m, 1H), 4.19 (dm, 1H), 3.82 (s, 3H), 3.79 (s, 3H), 3.75–3.70 (m, 1H), 3.36 (dd, 1H, J=13.5 Hz and J=7.5 Hz), 2.87 (m, 2H), 1.61 (s, 9H), 1.60 (s, 9H).

MS: APCI (+): m/z: 592.4 [M+H].

The above 2-(tert-butoxyoxalyl-amino)-7-(3-(2,4-dimethoxy-phenyl)ureidomethyl)-4,7-dihydro-5H-thieno[2,3-c]pyran-3-carboxylic acid tert-butyl ester (34 mg) was dissolved in 20% trifluoroacetic acid in dichloromethane (2 ml) and stirred at room temperature for 3 hours. The volatiles were evaporated in vacuo and the residue was titurated with diethyl ether (2×), filtered off and washed with a small amount of dichloromethane, which afforded after drying in vacuo 16 mg (89%) of the title compound as a solid.

$^1$H-NMR (300 MHz, CD$_3$OD) δ 7.66 (d, 1H, J=9 Hz), 6.53 (d, 1H, J=2.7 Hz), 6.44 (dd, 2H, J=9 Hz and J=2.7 Hz), 4.82 (m, 1H), 4.2 (m, 2H), 3.82 (s, 3H), 3.76 (s, 3H), 3.67 (dd, 2H, J=13 Hz and J=4.5 Hz), 2.94 (m, 2H).

MS: APCI (+): m/z: 480.3 [M+H];

Example 30

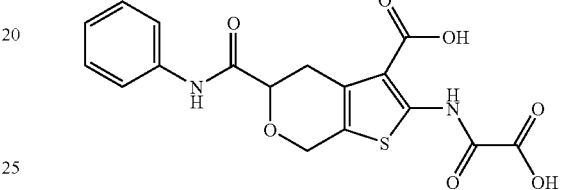

2-(Oxalyl-amino)-5-phenylcarbonyl-4,7-dihydro-5H-thieno[2,3-c]pyran-3-carboxylic acid A solution of glyoxylic acid ethyl ester, polymer form (2.02 g, 8.9 mmol) and (3-methoxy-1 methylene-allyloxy) trimethylsilane (1.9 ml, 8.9 mmol, Danishefsky's diene) in benzene (12 ml) was placed under nitrogen. Zinc chloride (0.5 N in tetrahydrofuran, 8.9 ml, 4.45 mmol) was added and the reaction stirred at ambient temperature for 72 hours. The mixture was concentrated in vacuo, diluted with ethyl acetate (100 ml) and washed with 1 N hydrochloric acid (20 ml), saturated sodium bicarbonate (20 ml), and brine (20 ml). The organic layer was dried (Na$_2$SO$_4$), filtered, and the solvent evaporated in vacuo. The residue was purified by silica gel chromatography using a mixture of ethyl acetate/hexane (1:2) as eluent. Pure fractions were collected and the solvent evaporated in vacuo which afforded 1.2 g (75%) of 4-oxo-3,4-dihydro-2H-pyran-2-carboxylic acid ethyl ester as an oil.

$^1$H-NMR (400 MHz, CDCl$_3$) δ 7.40 (d, 1H, J=6 Hz), 5.48 (d, 1H, J=6 Hz), 5.01 (t, 3H, J=8 Hz), 4.28 (q, 2H, J=7 Hz), 2.85 (d, 2H, J=8 Hz), 1.29 (t, 3H, J=7 Hz).

To a solution of the above of 4-oxo-3,4-dihydro-2H-pyran-2-carboxylic acid ethyl ester (1.0 g, 5.9 mmol) in ethyl acetate (12 ml) was added 10% palladium on activated carbon (0.15 g). The reaction was shaken on a Parr hydrogenator under a hydrogen atmosphere (30 psi) for 1.5 hour. The mixture was filtered through celite and concentrated in vacuo. The residue was purified by silica gel chromatography using diethyl ether as eluent. Pure fractions were collected and the solvent evaporated in vacuo which affording 0.6 g (60%) of 4-oxo-tetrahydro-2H-pyran-2-carboxylic acid ethyl as an oil.

$^1$H-NMR (300 MHz, CDCl$_3$) δ 4.41–4.35 (m, 1H), 4.26 (q, 2H, J=7 Hz), 3.81–3.70 (m, 1H), 2.73–2.58 (m, 3H), 2.44–2.36 (m, 1H), 1.29 (t, 3H, J=7 Hz).

To a solution of 4-oxo-tetrahydro-2H-pyran-2-carboxylic acid ethyl (0.6 g, 3.5 mmol) in absolute ethanol (6 ml) was added sulfur (0.12 g, 3.85 mmol) and tert-butyl cyanoacetate (0.64 g, 4.55 mmol). The solution was stirred under nitrogen in a 50° C. oil bath and morpholin (0.61 ml, 7.0 mmol) was added. The reaction was stirred for 18 hours and then cooled to ambient temperature and excess sulfur removed by filtration. The filtrate was concentrated in vacuo and reconstituted in ethyl acetate (50 ml). The organic phase was washed with brine (2×10 ml), dried ($Na_2SO_4$), filtered, and the solvent evaporated in vacuo. The residue was purified by silica gel chromatography using a gradient of ethyl acetate/hexane (20 to 25% gradient) as eluent. Pure fraction of the two isomers were collected and the solvent evaporated in vacuo which afforded 0.47 g of 2-amino-4,7-dihydro-5H-thieno[2,3-c]pyran-3,5-dicarboxylic acid 3-tert-butyl ester 5-ethyl ester (A) and 0.3 g of 2-amino-4,7-dihydro-5H-thieno[2,3-c]pyran-3,7-dicarboxylic acid 3-tert-butyl ester 7-ethyl ester (B) in 62% combined yield.

(A)
$^1$H-NMR (300 MHz, $CDCl_3$) δ 5.96 (bs, 2H), 4.77–4.61 (m, 2H), 4.32–4.18 (m, 3H), 3.19–3.12 (m, 1H), 2.90–2.80 (m, 1H), 1.52 (s, 9H), 1.29 (t, 3H, J=7 Hz).

(B)
$^1$H-NMR (300 MHz, $CDCl_3$) δ 5.10 (s, 1H), 4.28–4.13 (m, 3H), 3.98–3.91 (m, 1H), 2.82–2.76 (m, 2H), 1.51 (s, 9H), 1.31 (t, 3H, J=7 Hz).

The above 2-amino-4,7-dihydro-5H-thieno[2,3-c]pyran-3,5-dicarboxylic acid 3-tert-butyl ester 5-ethyl ester (275 mg, 0.84 mmol) was dissolved in a mixture of ethanol (4 ml) and tetrahydrofuran (1 ml). Sodium hydroxide (1N, 1.6 ml, 1.68 mmol) was added and the reaction stirred at ambient temperature for 5 hours after which TLC analysis indicated that the reaction was complete. The reaction was monitored with a pH meter and neutralized with 1N hydrochloric acid until pH=6.9. The solution was concentrated in vacuo to give 2-amino-4,7-dihydro-5H-thieno[2,3-c]pyran-3,5-dicarboxylic acid 3-tert-butyl ester as a solid. Sodium chloride remained as an impurity.

$^1$H-NMR (300 MHz, $CD_3OD$) δ4.67–4.54 (m, 2H), 4.00–3.95 (m, 1H), 3.20–3.12 (m, 1H), 2.74–2.63 (m, 1H), 1.54 (s, 9H).

APCI-MS: m/z: 300 [M+H]+

To a solution of the above 2-amino-4,7-dihydro-5H-thieno[2,3-c]pyran-3,5-dicarboxylic acid 3-tert-butyl ester (94 mg, 0.31 mmol) and 1-(3-dimethylaminopropyl)-3-ethylcarbodiimide hydrochloride (72 mg, 0.37 mmol) in distilled dichloromethane (4 ml) under nitrogen was added aniline (321 µl, 0.34 mmol) followed by 2,6-lutidine (0.11 ml, 0.93 mmol). The reaction was stirred for 72 hours, concentrated in vacuo and reconstituted in ethyl acetate (30 ml). The organic layer was washed with 1% hydrochloric acid (10 ml), saturated sodium bicarbonate (10 ml), brine (10 ml), dried ($Na_2SO_4$), filtered, and the solvent evaporated in vacuo to give 51 mg (45%) of 2-amino-5-phenylcarbamoyl-4,7-dihydro-5H-thieno[2,3-c]pyran-3-carboxylic acid tert-butyl ester as a solid.

$^1$H-NMR (400 MHz, $CDCl_3$) δ 8.40 (s, 1H), 7.60 (d, 1H, J=7 Hz), 7.49 (d, 1H, J=8 Hz), 7.34 (t, 1H, J=8 Hz), 7.32 (t, 1H, J=8 Hz), 7.13 (t, 1H, J=7 Hz), 6.03 (s, 2H), 4.82–4.73 (m, 2H), 4.25–4.22 (m, 1H), 3.43–3.38 (m, 1H), 2.79–2.72 (m, 1H), 1.54 (s, 9H).

APCI-MS: m/z: 375.5 [M+H]+

To a solution of the above 2-amino-5-phenylcarbamoyl-4,7-dihydro-5H-thieno[2,3-c]pyran-3-carboxylic acid tert-butyl ester (51 mg, 0.14 mmol) in distilled dichloromethane (3 ml) under nitrogen was added midazol-1-yl-oxo-acetic acid tert-butyl ester (80 mg, 0.42 mmol) and triethylamine (38 µl, 0.28 mmol). The reaction was stirred for 4 hours, concentrated in vacuo and reconstituted in ethyl acetate (25 ml). The organic layer was washed with 1% hydrochloric acid (2×5 ml), saturated sodium bicarbonate (5 ml), brine (5 ml), dried ($Na_2SO_4$), filtered, and the solvent evaporated in vacuo. The crude material was purified by silica gel chromatography using a 4% mixture of ethyl acetate/dichloromethane as eluent. Pure fractions were collected and the solvent evaporated in vacuo to give 41 mg (26% over two steps) of 2-(tert-butoxyoxalyl-amino)-5-phenylcarbamoyl-4,7-dihydro-5H-thieno[2,3-c]pyran-3-carboxylic acid tert-butyl ester.

$^1$H-NMR (300 MHz, $CDCl_3$) δ 12.56 (s, 1H), 8.40 (s, 1H), 7.59 (d, 2H, J=8 Hz), 7.33 (t, 2H, J=8 Hz), 7.12 (t, 1H, J=7 Hz), 5.01–4.85 (m, 2H), 4.27–4.22 (m, 1H), 3.54–3.47 (m, 1H), 3.89–2.79 (m, 1H), 1.60 (s, 9H), 1.58 (s, 9H).

APCI-MS: m/z: 503.2 [M+H]+

The above 2-(tert-butoxyoxalyl-amino)-5-phenylcarbamoyl-4,7-dihydro-5H-thieno[2,3-c]pyran-3-carboxylic acid tert-butyl ester (37 mg, 0.074 mmol) was dissolved in a solution of 50% trifluoroacetic acid/dichloromethane (3 ml). The reaction was stirred at ambient temperature for 7 hours, concentrated in vacuo and evaporated in vacuo from dichloromethane (3×10 ml). The resulting precipitate was washed with ethyl ether and dried in vacuo to give 18 mg (62%) of the title compound.

$^1$H-NMR (400 MHz, DMSO-$d_6$) δ 12.32 (s, 1H), 9.85 (s, 1H), 7.69 (d, 2H, J=8 Hz), 7.31 (t, 2H, J=8 Hz), 7.07 (t, 1H, J=7 Hz), 4.98 (d, 1H, J=15 Hz), 4.83 (d, 1H, J=15 Hz), 4.35–4.31 (m, 1H), 3.23 (d, 1H, J=17 Hz), 2.84 (dd, 1H, J=17 Hz and J 10 Hz).

APCI-MS: m/z: 391.3 [M+H]+
HPLC (254.4 nm): $R_t$=3.22 min,

Example 31

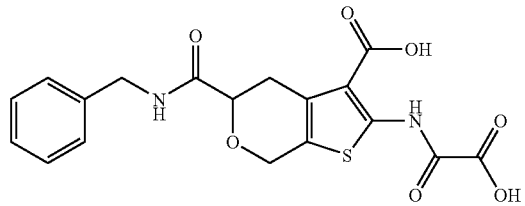

5-Benzylcarbamoyl-2-(oxalyl-amino)-4,7-dihydro-5H-thieno[2,3-c]pyran-3-carboxylic acid To a solution of 2-amino-4,7-dihydro-5H-thieno[2,3-c]pyran-3-carboxylic acid ester (101 mg, 0.34 mmol, prepared in Example 31) and 1-(3-dimethylaminopropyl)-3-ethylcarbodiimide hydrochloride (78 mg, 0.41 mmol) in distilled dichloromethane (4 ml) under nitrogen was added benzylamine (40 µl, 0.37 mmol) followed by 2,6-lutidine (0.12 ml, 1.02 mmol). The reaction was stirred for 72 hours, concentrated in vacuo and reconstituted in ethyl acetate (30 ml). The organic layer was washed with 1% hydrochloric acid (10 ml), saturated sodium bicarbonate (10 ml), brine (10 ml), dried ($Na_{2\ SO4}$) over sodium sulfate, filtered, and the solvent evaporated in vacuo to give 72 mg (56%) of 2-amino-5-benzylcarbamoyl-4,7-dihydro-5H-thieno[2,3-c]pyran-3-carboxylic acid tert-butyl ester.

$^1$H-NMR (400 MHz, $CDCl_3$) δ 7.36–7.28 (m, 5H), 4.66 (s, 2H), 4.44 (d, 2H, J=5 Hz), 4.17–4.13 (m, 1H), 3.40–3.33 (m, 1H), 2.75–2.66 (m, 1H), 1.54 (s, 9H).

APCI-MS: m/z: 389.5 [M+H]+

To a solution of the above 2-amino-5-benzylcarbamoyl-4,7-dihydro-5H-thieno[2,3-c]pyran-3,carboxylic acid tert-butyl ester (72 mg, 0.19 mmol) in distilled dichloromethane (4 ml) under nitrogen was added midazol-1-yl-oxo-acetic acid tert-butyl ester (0.11 g, 0.57 mmol) and triethylamine (51 μl, 0.38 mmol). The reaction was stirred for 4 hours, concentrated in vacuo and reconstituted in ethyl acetate (25 ml). The organic layer was washed with 1% hydrochloric acid (2×5 ml), saturated sodium bicarbonate (5 ml), brine (5 ml), dried ($Na_2SO_4$), filtered, and the solvent evaporated in vacuo. The crude material was purified by silica gel chromatography using a gradient of ethyl acetate/dichloromethane (5 to 10% gradient) as eluent. Pure fractions were collected and the solvent evaporated in vacuo to give 42 mg (24% over two steps) of 5-benzylcarbamoyl-2-(tert-butoxyoxalyl-amino)-4,7-dihydro-5H-thieno[2,3-c]pyran-3, carboxylic acid tert-butyl ester as an oil.

$^1$H-NMR (400 MHz, $CDCl_3$) δ 12.56 (s, 1H), 7.37–7.29 (m, 5H), 6.97 (t, 1H, J=6 Hz), 4.89–4.77 (m, 2H), 4.58–4.46 (m, 2H), 4.20–4.16 (m, 1H), 3.50–3.44 (m, 1H), 2.84–2.76 (m, 1H), 1.61 (s, 9H), 1.60 (s, 9H).

APCI-MS: m/z: 517.3 [M+H]$^+$

The above 5-benzylcarbamoyl-2-(tert-butoxyoxalyl-amino)-4,7-dihydro-5H-thieno[2,3-c]pyran-3,carboxylic acid tert-butyl ester (36 mg, 0.07 mmol) was dissolved in a solution of 50% trifluoroacetic acid/dichloromethane (3 ml). The reaction was stirred at ambient temperature for 7 hours, concentrated in vacuo and evaporated in vacuo from dichloromethane (3×10 ml). The resulting precipitate was washed with dichloromethane and dried in vacuo to give 14 mg (50%) of the title compound as a solid.

$^1$H-NMR (400 MHz, DMSO-$d_6$) δ 12.31 (s, 1H), 8.48 (t, 1H, J=6 Hz), 7.31–7.20 (m, 5H), 4.91 (d, 1H, J=15 Hz), 4.76 (d, 1H, J=15 Hz), 4.32–4.29 (m, 2H), 4.20–4.16 (m, 1H), 3.22 (m, 1H, partially obscured by water), 2.70–2.63 (m, 1H).

APCI-MS: m/z: 405.2 [M+H]$^+$

HPLC (254.4 nm): $R_t$=3.06 min.

Example 32

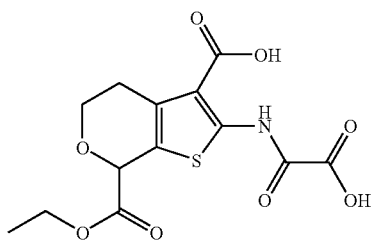

2-(Oxalyl-amino)-4,7-dihydro-5H-thieno[2,3-c]pyran-3,7-dicarboxylic acid 7-ethyl ester To a solution of 2-amino-4,7-dihydro-5H-thieno[2,3-c]pyran-3,7-dicarboxylic acid 3-tert-butyl ester 7-ethyl ester (60 mg, 0.18 mmol) in distilled dichloromethane (3 ml) under nitrogen was added midazol-1-yl-oxo-acetic acid tert-butyl ester (0.11 g, 0.54 mmol) and triethylamine (50 μl, 0.36 mmol). The reaction was stirred for 4 hours, concentrated in vacuo and reconstituted in ethyl acetate (20 ml). The organic layer was washed with 1% hydrochloric acid (2×5 ml), saturated sodium bicarbonate (5 ml), brine (5 ml), dried ($Na_2SO_4$), filtered, and the solvent evaporated in vacuo. The crude material was purified by silica gel chromatography using a 6% mixture of ethyl acetate/dichloromethane as eluent. Pure fractions were collected and the solvent evaporated in vacuo affording 78 mg (95%) of 2-(tert-butoxyoxalyl-amino)-4,7-dihydro-5H-thieno[2,3-c]pyran-3,7-dicarboxylic acid 3-tert-butyl ester 7-ethyl ester as an oil.

$^1$H-NMR (300 MHz, $CDCl_3$) δ 12.54 (s, 1H), 5.28 (s, 1H), 4.27 (q, 2H, J=7 Hz), 4.25–4.18 (m, 1H), 4.04–3.96 (m, 1H), 2.96–2.80 (m, 2H), 1.60 (s, 9H), 1.57 (s, 9H).

LC-MS: $R_t$=3.97 min., 456.3 [M+H]$^+$

The above 2-(tert-butoxyoxalyl-amino)-4,7-dihydro-5H-thieno[2,3-c]pyran-3,7-dicarboxylic acid 3-tert-butyl ester 7-ethyl ester (72 mg, 0.16 mmol) was dissolved in a solution of 50% trifluoroacetic acid/dichloromethane (4 ml). The reaction was stirred at ambient temperature for 7 hours, concentrated in vacuo and the residue evaporated in vacuo from dichloromethane (3×10 ml). The resulting precipitate was washed with dichloromethane and dried in vacuo to give 48 mg (88%) of the title compound as a solid.

$^1$H-NMR (400 MHz, DMSO-$d_6$) δ 12.34 (s, 1H), 5.47 (s, 1H), 4.19 (q, 2H, J=7 Hz), 3.98–3.94 (m, 2H), 2.90–2.78 (m, 2H), 1.23 (t, 3H, J=7 Hz).

APCI-MS: m/z: 344.2 [M+H]$^+$

HPLC (254.4 nm): $R_t$=2.82 min,

Example 33

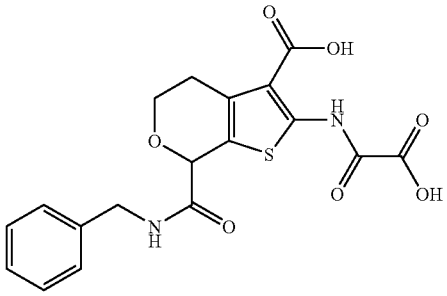

7-Benzylcarbamoyl-2-(oxalyl-amino)-4,7-dihydro-5H-thieno[2,3-c]pyran-3-carboxylic acid To a solution of 2-amino-4,7-dihydro-5H-thieno[2,3-c]pyran-3,7-dicarboxylic acid 3-tert-butyl ester 7-ethyl ester (0.12 g, 0.37 mmol) in ethanol (3 ml) was added potassium hydroxide (56 mg, 1.0 mmol) dissolved in a minimum amount of water. The mixture was stirred for 24 hours, then 1N hydrochloric acid was added until pH=7. The solution was concentrated in vacuo and the residue partitioned between ethyl acetate (35 ml) and water (10 ml). The layers were separated and 1% hydrochloric acid (1 ml) was added to the aqueous layer. The aqueous layer was then extracted further with ethyl acetate (3×15 ml) and the combined organic extracts were washed with brine, dried ($Na_2SO_4$) and filtered. Triethylamine (3 drops) was added to the solution to stabilize the acid-sensitive compound. The solution was concentrated in vacuo affording 2-amino-4,7-dihydro-5H-thieno[2,3-c]pyran-3,7-dicarboxylic acid 3-tert-butyl ester triethylamine salt (approximately 0.13 g) as a solid.

$^1$H-NMR (400 MHz, $CDCl_3$) δ 5.01 (s, 1H), 4.28–4.23 (m, 1H), 3.90–3.85 (m, 1H), 2.88–2.71 (m, 3H), 1.56 (s, 9H).

A solution of the above 2-amino-4,7-dihydro-5H-thieno[2,3-c]pyran-3,7-dicarboxylic acid 3-tert-butyl ester triethylamine salt (0.12 g, 0.30 mmol) and 1-(3-dimethylaminopropyl)-3-ethylcarbodiimide hydrochloride (71 mg, 0.36 mmol) was prepared in distilled acetonitrile under nitrogen. Benzylamine (36 μl, 0.33 mmol) was added followed by 2,6-lutidine (70 μl, 0.60 mmol). The reaction was stirred at ambient temperature for 18 hours, then concentrated in vacuo and reconstituted in ethyl acetate (30 ml). The organic layer was washed with 1% hydrochloric acid (2×5 ml), saturated sodium bicarbonate (2×5 ml), and brine (10 ml), dried ($Na_2SO_4$), filtered, and the solvent evaporated in vacuo which afforded crude 2-amino-7-benzylcarbamoyl-4,7-dihydro-5H-thieno[2,3-c]pyran-3-carboxylic acid tert-butyl ester which was used without purification.

To a solution of the above crude 2-amino-7-benzylcarbamoyl-4,7-dihydro-5H-thieno[2,3-c]pyran-3-carboxylic acid tert-butyl ester (77 mg, 0.2 mmol) in distilled dichloromethane (3 ml) under nitrogen was added midazol-1-yl-oxoacetic acid tert-butyl ester (0.11 g, 0.6 mmol) and triethylamine (55 μl, 0.4 mmol). The reaction was stirred for 5 hours, concentrated in vacuo and reconstituted in ethyl acetate (20 ml). The organic layer was washed with 1% hydrochloric acid (2×5 ml), saturated sodium bicarbonate (5 ml), brine (5 ml), dried ($Na_2SO_4$), filtered, and the solvent evaporated in vacuo. The crude material was purified by silica gel chromatography using a 5% mixture of ethyl acetate/dichloromethane as eluent. Pure fractions were collected and the solvent evaporated in vacuo affording 29 mg (19% over two steps) of 7-benzylcarbamoyl-2-(tert-butoxyoxalyl-amino)-4,7-dihydro-5H-thieno[2,3-c]pyran-3-carboxylic acid tert-butyl ester as an oil.

$^1$H-NMR (400 MHz, $CDCl_3$) δ 12.49 (s, 1H), 7.35–7.26 (m, 5H), 6.96 (t, 1H, J=6 Hz), 5.20 (s, 1H), 4.55–4.41 (m, 2H), 4.22–4.17 (m, 1H), 3.87–3.81 (m, 1H), 2.97–2.84 (m, 2H), 1.61 (s, 9H), 1.59 (s, 9H).

APCI-MS: m/z: [M−H]⁻

The above 7-benzylcarbamoyl-2-(tert-butoxyoxalyl-amino)-4,7-dihydro-5H-thieno[2,3-c]pyran-3-carboxylic acid tert-butyl ester (29 mg, 0.06 mmol) was dissolved in a solution of 50% trifluoroacetic acid/dichloromethane (2 ml). The reaction was stirred at ambient temperature for 7 hours, concentrated in vacuo and the residue evaporated in vacuo from dichloromethane (3×10 ml). The resulting precipitate was washed with dichloromethane and dried in vacuo to give 18 mg (80%) of the title compound as an solid.

$^1$H-NMR (400 MHz, DMSO-$d_6$) δ 12.33 (s, 1H), 8.67 (t, 1H, J=6 Hz), 7.30–7.21 (m, 5H), 5.23 (s, 1H), 4.31–4.28 (m, 2H), 4.13–4.10 (m, 1H), 3.88–3.85 (m, 1H), 2.86 (bs, 2H).

APCI-MS: m/z: 405 [M+H]⁺

HPLC (254.4 nm): $R_t$=3.12 min,

Example 34

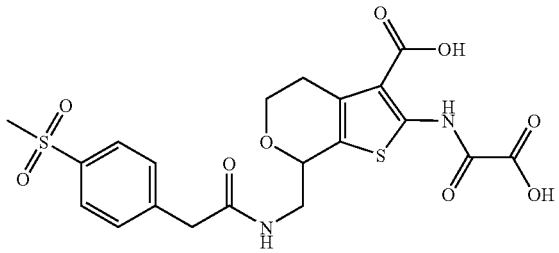

7-((2-(4-Methanesulfonyl-phenyl)-acetylamino)-methyl)-2-(oxalyl-amino)-4,7-dihydro-5H-thieno[2,3-c]pyran-3-carboxylic acid To a solution of (4-methanesulfonyl-phenyl)-acetic acid (90.4 mg, 0.42 mmol) in a mixture of dichloromethane (3 ml) and N,N-dimethylformamide (1 ml) cooled at 0° C. was added diisopropyl-ethylamine (306 μl, 1.76 mmol), diisopropylazodicarboxylate (72 μl, 0.45 mmol) and 1-hydroxybenzotriazole (56.6 mg, 0.42 mmol). After being stirred for 20 minutes, 2-amino-7-aminomethyl-4,7-dihydro-5H-thieno[2,3-c]pyran-3-carboxylic acid tert-butyl ester (100 mg, 0.35 mmol) dissolved in dichloromethane (1 ml) was added via syringe. The reaction mixture was stirred for 18 hours while slowly warming to room temperature. The volatiles were evaporated in vacuo and the residue diluted with ethyl acetate (50 ml). The organic phase was washed with saturated sodium bicarbonate (3×50 ml), 1% hydrochloric acid (3×50 ml), brine (3×50 ml), dried ($MgSO_4$), filtered, and the solvent evaporated in vacuo. The resultant oil was subjected to preparative thin layer chromatography using a mixture of methanol/dichloromethane (1:9) as eluent. Fraction with $R_f$=0.5 was isolated which afforded after evaporating the solvent in vacuo 115 mg (69%) of 2-amino-7-((2-(4-methanesulfonyl-phenyl)acetylamino)-methyl)-4,7-dihydro-5H-thieno[2,3-c]pyran-3-carboxylic acid tert-butyl ester as an oil.

$^1$H-NMR (300 MHz, $CDCl_3$) δ 7.87 (d, 2H, J=8.7 Hz), 7.39 (d, 2H, J=7.5 Hz), 5.91 (bs, 2H), 4.65 (m, 1H), 4.09 (dt, 1H, J=7.8 Hz and J=3.3 Hz), 3.85–3.65 (m, 2H), 3.61 (s, 2H), 3.45–3.38 (m, 2H), 3.05 (s, 3H), 2.75 (m, 2H), 1.56 (s, 9H).

MS: APCI (+): m/z: 481 [M+H].

To a solution of the above 2-amino-7-((2-(4-methanesulfonyl-phenyl)acetylamino)-methyl)-4,7-dihydro-5H-thieno[2,3-c]pyran-3-carboxylic acid tert-butyl ester (110 mg, 0.23 mmol) in dichloromethane (3 ml) was added triethylamine (96 μl, 0.69 mmol) and midazol-1-yl-oxoacetic acid tert-butyl ester (134 mg, 0.69 mmol). The reaction was stirred at room temperature for 18 hours. The reaction mixture was concentrated in vacuo, diluted in ethyl acetate (50 ml), washed with saturated sodium carbonate (3×50 ml), brine (3×50 ml), dried ($MgSO_4$), filtered and the solvent evaporated in vacuo. The resultant oil was subjected to preparative thin layer chromatography using a mixture of methanol/dichloromethane (1:9). Fraction with $R_f$=0.5 was collected and the solvent evaporated in vacuo affording 70 mg (50%) of 2-(tert-butoxyoxalyl-amino)-7-((2-(4-methanesulfonyl-phenyl)acetylamino)-methyl)-4,7-dihydro-5H-thieno[2,3-c]pyran-3-carboxylic acid tert-butyl ester as an oil.

¹H-NMR (300 MHz, CDCl₃) δ 12.49 (s, 1H), 7.88 (d, 2H, J=8.1 Hz), 7.46 (d, 2H, J=8.1 Hz), 5.88 (bs, 1H), 4.78 (m, 1H), 4.15 (dt, 1H, J=12 Hz and J=4 Hz), 3.86–3.71 (m, 2H), 3.64 (s, 2H), 3.42–3.34 (m, 2H), 3.04 (s, 3H), 2.85 (m, 2H), 1.62 (s, 9H), 1.61 (s, 9H).

MS: APCI (+): m/z: 609 (M+H)[minor], m/z: 497 (–2 tert butyls)[major];

The above 2-(tert-butoxyoxalyl-amino)-7-((2-(4-methanesulfonyl-phenyl)acetylamino)-methyl)-4,7-dihydro-5H-thieno[2,3-c]pyran-3-carboxylic acid tert-butyl ester (60 mg, 0.098 mmol) was dissolved in 50% trifluoroacetic acid in dichloromethane (2 ml) and allowed to stir at room temperature for 3 hours. The reaction mixture was concentrated in vacuo, the residue titurated with diethyl ether (3×), and dried in vacuo which afforded 45 mg (92%) of the title compound as a solid.

¹H-NMR (300 MHz, DMSO-d₆) δ 12.34 (s, 1H), 8.47 (m, 1H), 7.82 (d, 2H, J=7.8 Hz), 7.50 (d, 2H, J=7.8 Hz), 4.75 (bs, 1H), 4.10 (m, 1H), 3.69 (m, 1H), 3.60 (d, 2H, J=3.6 Hz), 3.52 (m, 1H), 3.35 (m, 2H), 3.18 (s, 3H), 2.83 (m, 2H).

MS: APCI (–): m/z: 495 [M–H];

Example 35

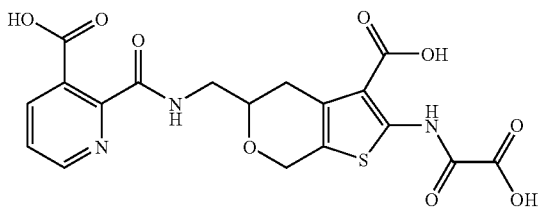

2-((3-Carboxy-2-(oxalyl-amino)-4,7-dihydro-5H-thieno[2,3-c]pyran-5-ylmethyl)carbamoyl)nicotinic acid 2-(tert-Butoxyoxalyl-amino)-5-aminomethyl-4,7-dihydro-5H-thieno[2,3-c]pyran-3-carboxylic acid tert-butyl ester (164 mg, 0.58 mmol) was stirred for 20 hours at 80° C. with furo[3,4-b]pyridine-5,7-dione (86.1 mg, 0.58 mmol) in a mixture of tetrahydrofuran (1.0 ml) and N,N-dimethylformamide (0.25 ml). The volatiles were removed in vacuo and the residue was dissolved in ethyl acetate (50 ml) and washed with water (3×30 ml). The organic layer was dried (MgSO₄), filtered, and the solvent evaporated in vacuo. The residue (78 mg) was purified by preparative TLC (hexane/ethyl acetate, 50:50) which afforded 2 products: 2-((2-amino-3-tert-butoxycarbonyl-4,7-dihydro-5H-thieno[2,3-c]pyran-5-ylmethyl)carbamoyl)nicotinic acid (A) (27.9 mg, 11%) and 2-amino-5-(5,7-dioxo-5,7-dihydro-pyrrolo-[3,4-b]pyridin-6-ylmethyl)-4,7-dihydro-5H-thieno[2,3-c]pyran-3-carboxylic acid tert-butyl ester (B) (21.3 mg, 9%).

(A)
1H-NMR (300 MHz, CDCl₃): δ 9.02 (s, 1H), 8.74 (d, 1H, J=3.3 Hz), 8.14 (d, 1H, J=7.5 Hz), 7.40 (dd, 1H, J=4.8 Hz and J=5.1 Hz), 6.71 (m, 1H), 5.98 (s, 2H), 4.63 (s, 2H), 4.00 (m, 1H), 3.42 (m, 1H), 2.90 (dd, 1H, J=3.3 Hz and J=3.6 Hz), 2.59 (dd, 1H, J=11 Hz and J=11 Hz), 1.48 (s, 9H).
MS m/z: 434 [M+H]⁺;

(B)
¹H-NMR (300 MHz, CDCl₃) δ 8.99 (d, 1H, J=5.1 Hz), 8.20 (d, 1H, J=9 Hz), 7.64 (dd, 1H, J=5.7 Hz and J=4.8 Hz), 5.94 (s, 2H), 4.60 (d, 1H, J=14 Hz), 4.51 (d, 1H, J=14 Hz), 4.05 (m, 2H), 3.87 (d, 1H, J=12.5 Hz), 2.92 (d, 1H, J=17 Hz), 2.61 (m, 1H), 1.53 (s, 9H).
MS: APCI (+): m/z: 416 [M+1][minor], 360 (M-tert-butyl) [major].

To a solution of the above 2-((2-amino-3-tert-butoxycarbonyl-4,7-dihydro-5H-thieno[2,3-c]pyran-5-ylmethyl)carbamoyl)nicotinic acid (27.9 mg, 0.064 mmol) in tetrahydrofuran (2 ml) was added midazol-1-yl-oxo-acetic acid tert-butyl ester (38 mg, 0.193 mmol) and triethylamine (9 µl, 0.064 mmol). The resulting mixture was stirred at room temperature for 20 hours. The solvent was removed in vacuo and the residue was dissolved in dichloromethane (20 ml) and washed with water (3×10 ml). The extracts were dried (MgSO₄), filtered and the solvent evaporated in vacuo. The residue was purified by preparative TLC (0.5 mm, hexane/ethyl acetate, 1/1 to 2/3 gradient). After evaporation of the solvent in vacuo 917 mg (46%) of 2-(3-tert-butoxycarbonyl-2-(tert-butoxyoxalyl-amino)-4,7-dihydro-5H-thieno[2,3-c]pyran-5-ylmethyl)carbamoyl)nicotinic acid was isolated as a solid.

¹H-NMR (300 MHz, CDCl₃): δ 9.04 (s, 1H), 8.75 (s, 1H), 8.15 (d, 1H, J=7.5 Hz), 7.42 (dd, 1H, J=6.9 Hz and J=5.1 Hz), 6.73 (m, 1H), 4.81 (dd, 2H, J=15.3 Hz and J=14.4 Hz), 4.03 (m, 1H), 3.83 (m, 1H), 3.47 (m, 1H), 2.99 (d, 1H, J=17.1 Hz), 2.59 (dd, 1H, J=11.1 Hz and J=10.8 Hz), 1.61 (s, 9H), 1.48 (s, 9H).

MS: m/z: 506 [M–55].

The above 2-(3-tert-butoxycarbonyl-2-(tert-butoxyoxalyl-amino)-4,7-dihydro-5H-thieno[2,3-c]pyran-5-ylmethyl)carbamoyl)nicotinic acid (13.1 mg, 0.023 mmol) was stirred in 50% trifluoroacetic acid in dichloromethane (2 ml) at room temperature for 7 hours. The solvent was evaporated in vacuo which afforded 10 mg (96%) of the title compound as a solid.

¹H-NMR (300 MHz, DMSO-d₆): δ 9.04 (s, 1H), 8.77 (d, 1H, J=7.7 Hz), 8.16 (d, 1H, J=7.5 Hz), 7.60 (d, 1H, J=7.8 Hz), 4.88 (d, 1H, J=9 Hz), 4.76 (d, 1H, J=9 Hz), 3.96 (m, 1H), 3.02 (m, 1H), 2.78 (m, 1H).

MS: m/z: 481 [M+33].

Example 36

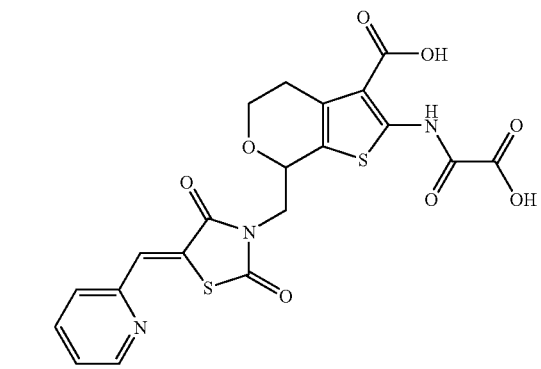

7-(2,4-Dioxo-5-pyridin-2-ylmethylene-thiazolidin-3-ylmethyl)-2-(oxalyl-amino)-4,7-dihydro-5H-thieno[2,3-c]pyran-3-carboxylic acid To a mixture of 2-(tert-butoxyoxalyl-amino)-7-hydroxymethyl-4,7-dihydro-5H-thieno[2,3-c]pyran-3-carboxylic acid tert-butyl ester (1.0 g, 2.42 mmol), 5-pyridin-2-ylmethylene-thiazolidine-2,4-dione (0.55 g, 2.66 mmol, prepared in a similar way as described in *J. Med. Chem.* 41 (10), 1619–1630 (1998)) and triphenylphosphine (0.7 g, 2.66 mmol) in dry tetrahydrofuran (75 ml) cooled to 0° C. under a nitrogen atmosphere was added diethyl azodicarboxylate (DEAD) (420 µl ml, 2.66 mmol). The reaction mixture was allowed to stir overnight, slowly warming to room temperature. The volatiles were evaporated in vacuo, the resultant solid was washed with diethyl ether, filtered off and dried in vacuo at 50° C., which affording 1.4 g (96%) of 2-(tert-butoxyoxalyl-amino)-7-(2,4-dioxo-5-pyridin-2-ylmethylene-thiazolidin-3-ylmethyl)-4,7-dihydro-5H-thieno[2,3-c]pyran-3-carboxylic acid tert-butyl ester as a solid.

TLC: $R_f$=0.46 (ethyl acetate/heptane 1:1).

The above di-tert-butyl ester (1.0 g, 1.66 mmol) was dissolved in 25% trifluoroacetic acid in dichloromethane (30 ml). The reaction was stirred at room temperature for 16 hours. The volatiles were evaporated in vacuo and the residue triturated with diethyl ether (50 ml). The precipitate was filtered off, washed with diethyl ether, dried in vacuo at 50° C. for 16 hours, which afforded 0.8 g of semi pure title compound. The title compound (0.8 g) was suspended in ethyl acetate (25 ml) and heated at reflux temperature for 0.5 hour. Isopropanol (5 ml) was added and the mixture was cooled to room temperature the precipitate filtered off and dried in vacuo at 50° C. for 16 hours, which afforded 0.37 g (37%) of the title compound as a solid.

Calculated for $C_{20}H_{15}N_3O_8S_2$, 0.5×$H_2O$, 0.75×isopropanol; C, 49.17%; H, 4.08%; N, 7.73%. Found: C, 48.97%; H, 4.03%; N, 7.45%.

Example 37

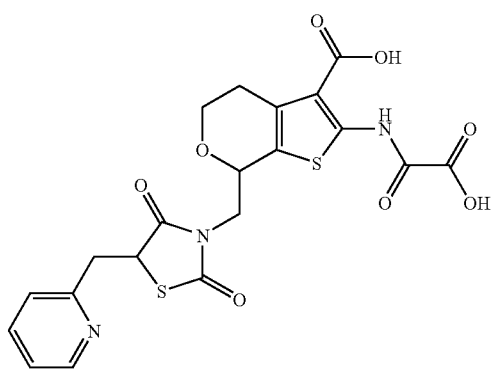

7-(2,4-Dioxo-5-pyridin-2-ylmethyl-thiazolidin-3-ylmethyl)-2-(oxalyl-amino)-4,7-dihydro-5H-thieno[2,3-c]pyran-3-carboxylic acid To a solution of 5-pyridin-2-ylmethylene-thiazolidine-2,4-dione (5.0 g, 0.024 mol, prepared in a similar way as described in *J. Med. Chem.* 41 (10), 1619–1630 (1998)) in tetrahydrofuran (300 ml) was added 10% palladium on carbon (1 g) and the resulting mixture was hydrogenated. After 50 ml of hydrogen was consumed and additional portion of 10% palladium on carbon (5 g) was added and the hydrogenation was continued at 50 psi for 16 hours. The mixture was filtered and the filtrate evaporated in vacuo. The residue was subjected to flash column chromatography (1 l silicagel) using a mixture of ethyl acetate/hexane (1:1) as eluent. Semi pure fractions were collected and the solvent evaporated in vacuo affording 0.8 g (16%) of 5-pyridin-2-ylmethyl-thiazolidine-2,4-dione as a solid.

To a mixture of 2-(tert-butoxyoxalyl-amino)-7-hydroxymethyl-4,7-dihydro-5H-thieno[2,3-c]pyran-3-carboxylic acid tert-butyl ester (0.7 g, 1.69 mmol), 5-pyridin-2-ylmethyl-thiazolidine-2,4-dione (0.36 g, 1.86 mmol) and triphenylphosphine (0.49 g, 1.86 mmol) in dry tetrahydrofuran (40 ml) cooled to 0° C. under a nitrogen atmosphere was added diethyl azodicarboxylate (DEAD) (290 µl ml, 1.86 mmol). The reaction mixture was allowed to stir overnight, slowly warming to room temperature. The volatiles were evaporated in vacuo, the resultant residue was subjected to flash column chromatography (0.5 l silicagel) using a mixture of ethyl acetate/hexane (1:2) as eluent. Pure fractions were collected and the solvent evaporated in vacuo affording 0.6 g (59%) of 2-(tert-butoxyoxalyl-amino)-7-(2,4-dioxo-5-pyridin-2-ylmethyl-thiazolidin-3-ylmethyl)-4,7-dihydro-5H-thieno[2,3-c]pyran-3-carboxylic acid tert-butyl ester as a solid.

TLC: $R_f$=0.43 (ethyl acetate/heptane 1:1).

The above di-tert-butyl ester (0.5 g, 0.83 mmol) was dissolved in 25% trifluoroacetic acid in dichloromethane (25 ml). The reaction was stirred at room temperature for 16 hours. The volatiles were evaporated in vacuo and the residue triturated with diethyl ether (20 ml). The precipitate was filtered off, washed with diethyl ether, dried in vacuo at 50° C. for 1 hour, which afforded 0.3 g of semi pure title compound. The title compound (0.3 g) was suspended in isopropanol (15 ml) and heated at reflux temperature for 5 min., cooled to room temperature and the precipitate filtered off and dried in vacuo at 50° C. for 16 hours, which afforded 0.2 g (49%) of the title compound as a solid.

M.p.: >250° C.;

Calculated for $C_{20}H_{17}N_3O_8S_2$, 0.25×$H_2O$; C, 48.43%; H, 3.56%; N, 8.47%. Found: C, 48.41%; H, 3.57%; N, 8.10%.

Example 38

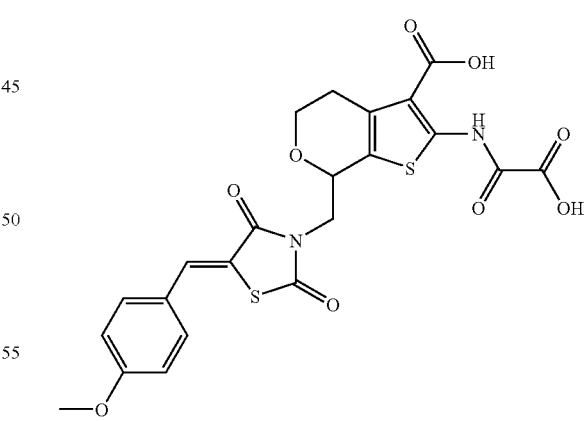

7-(5-(4-Methoxy-benzylidene)-2,4-dioxo-thiazolidin-3-ylmethyl)-2-(oxalyl-amino)-4,7-dihydro-5H-thieno[2,3-c]pyran-3-carboxylic acid The title compound was prepared in a similar way as described in Example 37.

M.p.: 236–238° C.;

Calculated for C$_{22}$H$_{18}$N$_3$O$_9$S$_2$, 0.5×H$_2$O; C, 50.09%; H, 3.63%; N, 5.31%. Found: C, 49.92%; H, 3.59%; N, 5.18%.

Example 39

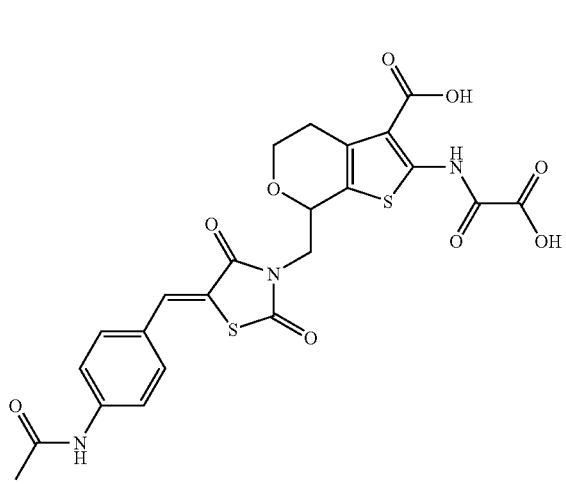

7-(5-(4-Acetylamino-benzylidene)-2,4-dioxo-thiazolidin-3-ylmethyl)-2-(oxalyl-amino)-4,7-dihydro-5H-thieno[2,3-c]pyran-3-carboxylic acid The title compound was prepared in a similar way as described in Example 37.
M.P.: >250° C.;
Calculated for C$_{23}$H$_{19}$N$_3$O$_9$S$_2$, 2×H$_2$O; C, 47.50%; H, 3.99%; N, 7.23%. Found: C, 47.60%; H, 3.45%; N, 6.80%.

Example 40

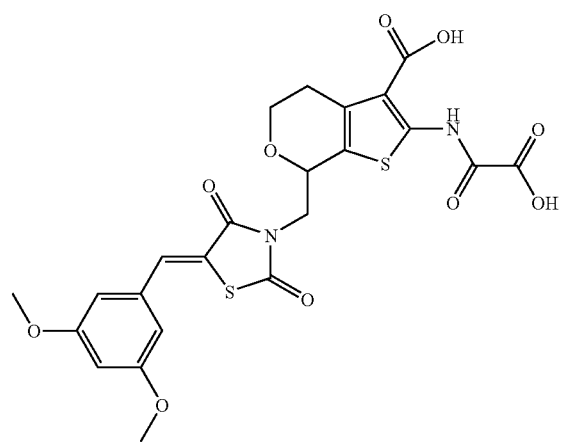

7-(5-(3,5-Dimethoxy-benzylidene)-2,4-dioxo-thiazolidin-3-ylmethyl)-2-(oxalyl-amino)-4,7-dihydro-5H-thieno[2,3-c]pyran-3-carboxylic acid The title compound was prepared in a similar way as described in Example 37.
$^1$H-NMR (300 MHz, DMSO-d$_6$) δ 12.37 (s, 1H), 7.92 (s, 1H), 6.80 (d, 2H, J=1.8 Hz), 6.66 (t, 1H, J=2.1 Hz), 5.00 (m, 1H), 4.06 (bm, 2H), 3.81 (s, 6H), 3.71 (dd, 2H, J=6.6 Hz and J=6 Hz), 2.83 (m, 2H).
MS: APCI (+): m/z: 549 [M+H];

Example 41

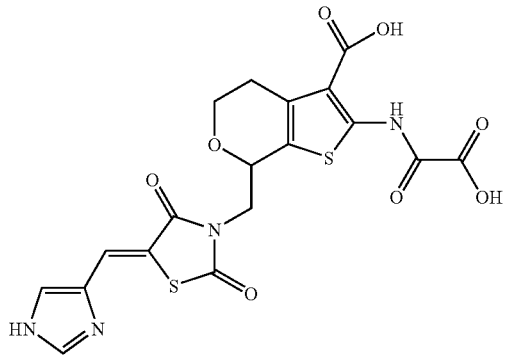

7-(5-(1H-imidazol-4(5)-ylmethylene)-2,4-dioxo-thiazolidin-3-ylmethyl)-2-(oxalyl-amino)-4,7-dihydro-5H-thieno[2,3-c]pyran-3-carboxylic acid The title compound was prepared in a similar way as described in Example 37.
M.P.: >250° C.;
Calculated for C$_{18}$H$_{14}$N$_4$O$_8$S$_2$; C, 40.65%; H, 2.56%; N, 9.17 Found: C, 40.54%; H, 2.55%; N, 9.46%

Example 42

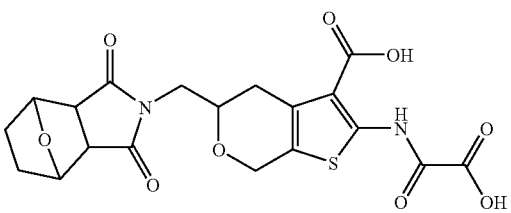

5-(1,3-Dioxo-4,7-epoxido-13,4,5,6,7-hexahydro-isoindol-2-ylmethyl)-2-(oxalyl-amino)-4,7-dihydro-5H-thieno[2,3-c]pyran-3-carboxylic acid To a solution of 2-(tert-butoxyoxalyl-amino)-5-hydroxymethyl-4,7-dihydro-5H-thieno[2,3-c]pyran-3-carboxylic acid tert-butyl ester (0.20 g, 0.48 mmol) in tetrahydrofuran (5 ml) was added 10-oxa-4-aza-tricyclo(5,2,1,0,2,6)decane-3,5-dione (81 mg, 0.48 mmol) and triphenylphosphine (126 mg, 0.48 mmol). The mixture was cooled to 0° C. and diisopropylazodicarboxylate (94.5 μl, 0.48 mmol) was added via syringe. The reaction was stirred for 18 hours while slowly warming to room temperature. The volatiles were evaporated in vacuo, and the residue diluted into ethyl acetate (50 ml), washed with saturated sodium bicarbonate (3×50 ml), brine (3×50 ml), dried (MgSO$_4$), filtered and the solvent evaporated in vacuo. The semi-solid residue was subjected to preparative thin layer chromatography using a mixture of ethyl acetate/hexanes (4:1) as eluent. Fraction with R$_f$=0.68 was isolated which afforded 64 mg (24%) of 2-(tert-butoxyoxalyl-amino)-5-(1,3-dioxo-4,7-epoxido-1,3,4,5,6,7-hexahydro-isoindol-2-ylmethyl)-4,7-dihydro-5H-thieno[2,3-c]pyran-3-carboxylic acid tert-butyl ester as a solid.

¹H-NMR (300 MHz, CDCl₃) δ 12.47 (s, 1H), 4.89 (m, 2H), 4.80–4.61 (m, 2H), 3.93–3.86 (m, 1H), 3.83–3.79 (m, 1H), 3.62–3.57 (dd, 1H, J=12.6 Hz and J=3.6 Hz), 2.92 (q, 6.9, 2H), 2.60 (dd, 2H, J=17.1 Hz and J=10.5 Hz), 1.85 (m, 2H), 1.60 (s, 18H).

MS: APCI (–): m/z: 561 [M–H].

The above 2-(tert-butoxyoxalyl-amino)-5-(1,3-dioxo-4,7-epoxido-1,3,4,5,6,7-hexahydro-isoindol-2-ylmethyl)-4,7-dihydro-5H-thieno[2,3-c]pyran-3-carboxylic acid tert-butyl ester (51 mg) was dissolved in 50% trifluoroacetic acid in dichloromethane (5 ml) and stirred at room temperature for 2 hours. The reaction mixture was evaporated in vacuo and the residue titurated with diethyl ether (3×10 ml). The solid was filtered of and dried affording 30 mg (71%) of the title compound as a solid.

¹H-NMR (300 MHz, DMSO-d₆) δ 12.31 (s, 1H), 7.68 (bs, 1H), 4.69 (s, 2H), 4.67 (d, 1H, J=15 Hz), 4.56 (d, 1H, J=15 Hz), 3.63 (bm, 1H), 3.50 (d, 1H, J=5 Hz), 3.46 (d, 1H, J=5 Hz), 3.08 (d, 2H, J=15 Hz,), 2.94 (d, 1H, J=2.4 Hz), 2.89 (m, 1H), 1.64 (s, 4H).

MS: APCI (–): m/z: 449 [M–H];

Example 43

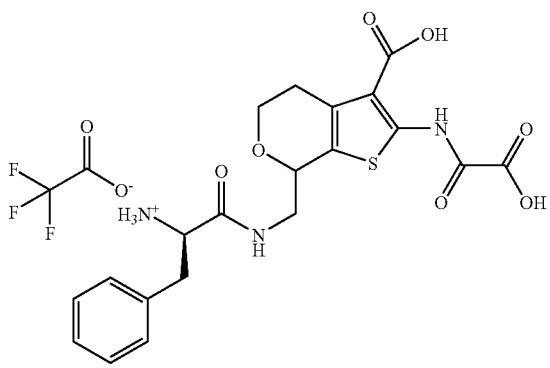

7-((2-(R)-Amino-3-phenyl-propionylamino)methyl)-2-(oxalyl-amino)-4,7-dihydro-5H-thieno[2,3-c]pyran-3-carboxylic acid, trifluoroacetic acid salt To a stirred solution of a mixture of 2-amino-7-aminomethyl-4,7-dihydro-5H-thieno[2,3-c]pyran-3-carboxylic acid tert-butyl ester and 2-amino-5-aminomethyl-4,7-dihydro-5H-thieno[2,3-c]pyran-3-carboxylic acid tert-butyl ester (4.7 g, 16 mmol) was added diisopropylethylamine (2.8 ml, 16 mmol) and succinimidyl-2,2,2-trichloroethylcarbonate (4.8 g, 16 mmol) portion wise. The reaction mixture was stirred at room temperature for 18 hours, washed with saturated sodium hydrogen carbonate, dried (MgSO₄), filtered and the solvent evaporated in vacuo. The residue was chromatographyed on sillica (90 g) using a mixture of ethyl acetate/heptane (1:1) as eluent. Pure fraction were collected and the solvent evaporated in vacuo affording 6.78 g of crude product which was dissolved in dichloromethane (5 ml) followed by heptane (30 ml) which was added as a top layer. After crystallisation and filtration 5.44 g (74%) of 2-amino-7-((2,2,2-trichloro-ethoxycarbonyl-amino)methyl)-4,7-dihydro-5H-thieno[2,3]pyran-3-carboxylic acid tert-butyl ester was obtained as an oil.

¹H-NMR (CDCl₃) □ 1.55 (s, 9H), 2.78 (m, 2H), 3.32 (m, 1H), 3.62 (m, 1H), 3.72 (m, 1H), 4.15 (m, 1H), 4,68 (m, 1H), 4.71 (s, 2H), 6.00 (s, 2H).

The above 2-amino-7-((2,2,2-trichloro-ethoxycarbony-lamino)methyl)-4,7-dihydro-5H-thieno[2,3-c]pyran-3-carboxylic acid tert-butyl ester (4.0 g, 8.0 mmol) was dissolved in a mixture of tetrahydrofuran (15 ml) and a aqueous phosphate buffer (pH 3; 5 ml) followed by addition of zinc (16 g, 0.244 mol). The reaction mixture was stirred for 6 hours at room temperature at which time the solvent was removed in vacuo. To the residue was added diethyl ether (20 ml) and water (40 ml). Sodium carbonate was added to the aqueous phase until pH=8 and the aqueous phase extracted with dichloromethane (3×). The combined organic phases were dried (MgSO₄), filtered and the solvent removed in vacuo. The residue was purified by flash chromatography on sillicagel (90 g) using a mixture of dichloromethane/ethanol/25% ammonia in water 100:10:0.7 as eluent. Pure fractions were collected and the solvent evaporated in vacuo affording 1.52 g (61%) of 2-amino-7-aminomethyl-4,7-dihydro-5H-thieno[2,3-c]pyran-3-carboxylic acid tert-butyl ester.

¹H-NMR (CDCl₃) δ 1.45 (s, 9H), 2.69 (dt, 2H).

Calculated for C₁₃H₂₀N₃O₃S; C, 54.91%; H, 7.09%; N, 9.85%. Found: C, 54.53%; H, 7.19%; N, 9.61%.

LC-MS: m/z: 285,2, R_f=4.14 min

To a solution of Boc-D-phe-OH (0.28 g, 1.05 mmol) in dichloromethane (10 ml) was added 1-hydroxy benzotriazole (0.14 g, 1.05 mmol) and 1-ethyl-3-(3-dimethylaminopropyl) car-bodiimid hydrochloride (0.18 g, 1.054 mmol). The reaction mixture was stirred for 15 min at room temperature. 2-Amino-7-aminomethyl-4,7-dihydro-5H-thieno[2,3-c]pyran-3-carboxylic acid tert-butyl ester (0.30 g, 1.054 mmol) dissolved in dichloromethane (15 ml) was added. Ethyl diisopropylamine (0.18 ml, 1.05 mmol) was added and the reaction mixture was stirred over night at room temperature. The reaction was washed with 10% aqueous citric acid (15 ml), saturated aqueous sodium hydrogencarbonate, dried (MgSO₄), filtered and the solvent removed in vacuo affording 594 mg (100%) of 2-amino-7-(((1R)-2-tert-butoxycarbonylamino-3-phenyl-propionylamino)-methyl)-4,7-dihydro-5H-thieno[2,3-c]pyran-3-carboxylic acid tert-butyl ester.

¹H-NMR(CDCl₃) δ 1.42 (s, 9H), 1.55 (s, 9H), 2.73 (m, 2H), 3.05 (m, 2H), 3.16 (m, 1H), 4.06 (m, 1H), 4.32 (m, 1H), 5.05 (s, 1H), 6.01 (s, 2H), 6.10 (s, 1H), 7.20 (m, 5H).

LC-MS: m/z: 532.2, R_f=7.11 min

2-Amino-7-((2-(R)-tert-butoxycarbonylamino-3-phenyl-propionylamino)-methyl)-4,7-dihydro-5H-thieno[2,3-c]pyran-3-carboxylic acid tert-butyl ester (0.58 g, 1.09 mmol) was dissolved in dichloromethane (15 ml). Triethylamine (0.3 ml, 2.18 mmol) was added and the reaction mixture was cooled in an ice bath. Imidazol-1-yl-oxo-acetic acid tert-butyl ester (0.43 g, 2.18 mmol) dissolved in dichloromethane (5 ml) was added to the reaction mixture. The reaction mixture was stirred overnight at room temperature diluted with dichloromethane (20 ml), washed with 1 N hydrochloric acid (15 ml), saturated sodium hydrogencarbonate (15 ml), dried (MgSO₄), filtered and the solvent removed in vacuo. The residue was purified by flash chromatography sillicagel (40 g) using a mixture of ethyl acetate/heptane 1:1 as eluent. Pure fractions were collected and the solvent evaporated in vacuo affording 512 mg (69%) of 7-((2-(R)-tert-butoxycarbonylamino-3-phenyl-propionylamino)methyl)-2-(tert-butoxy-oxalylamino)-4,7-dihydro-5H-thieno[2,3-c]pyran-3-carboxylic acid tert-butyl ester as an oil.

¹H-NMR (CDCl₃) δ1.42 (s, 9H), 1.59 (s, 9H), 1.61 (s, 9H), 2.86 (m, 2H), 3.02 (m, 2H), 3.15 (m, 1H), 3.64 (m, 1H), 3.87 (m, 1H), 4.09 (m, 1H), 4.28 (m, 1H), 4.51 (m, 1H), 4.67 (m, 1H), 5.10 (s, 1H), 6.00 (s, 1H), 7.20 (m, 5H), 12.5 (s, 1H).

7-((2-(R)-tert-Butoxycarbonylamino-3-phenyl-propionylamino)methyl)-2-(tert-butoxyoxalyl-amino)-4,7-dihydro-5H-thieno[2,3-c]pyrran-3-carboxylic acid tert-butyl ester (0.51 g, 0.76 mmol) was dissolved in dichloromethane (5 ml). Trifluoroacetic acid (5 ml) was added and the reaction mixture was stirred for 2 hours at room temperature. The solvent was removed in vacuo (stripped 3 times with dichloromethane) which afforded 314 mg (92%) of the title compound.

Calculated for C₂₀H₂₁N₃O₇S; 1×CF₃COOH, 1×H₂O; C, 45.60%; H, 4.17%; N, 7.25%. Found: C, 45.78%; H, 4.20%; N, 7.05%.

LC-MS: R$_t$=3.61 min, and R$_t$=3.77 min, m/z: 448.2

Example 44

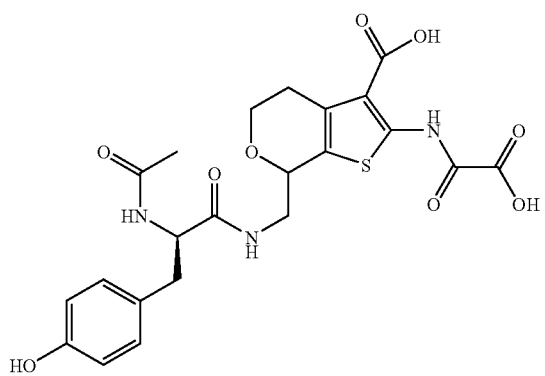

7-((2-(R)-Acetylamino-3-(4-hydroxy-phenyl)-propionylamino)methyl)-2-(oxalyl-amino)-4,7-dihydro-5H-thieno[2,3-c]pyran-3-carboxylic acid To a mixture of Ac-D-Tyr-OH (235 mg, 1.05 mmol) dissolved in dichloromethane (10 ml) was added 1-hydroxybenzotriazole (0.14 g, 1.05 mmol), 1-ethyl-3-(3-dimethylamino propyl)carbodiimide hydrochloride (0.20 g, 1.05 mmol) and the reaction mixture was stirred for 15 min at room temperature. 2-Amino-7-aminomethyl-4,7-dihydro-5H-thieno[2,3-c]pyran-3-carboxylic acid tert-butyl ester (0.3 g, 1.05 mmol) dissolved in dichloromethane (10 ml) was added followed by N,N-diisopropyl-ethylamine (0.18 ml, 1.05 mmol). The resulting reaction mixture was stirred for 18 hours at room temperature, diluted with dichloromethane (15 ml) was washed with 10% aqueous citric acid (25 ml), saturated sodium hydrogencarbonate, dried (MgSO₄), filtered and the solvent removed in vacuo. The residue was purified by flash chromatography on sillicagel (40 g) using ethyl acetate as eluent. Pure fractions were collected and the solvent evaporated in vacuo affording 304 mg (59%) of 7-((2-(R)-acetyl-amino- 3-(4-hydroxy-phenyl) propionylamino)methyl)-2-amino-4,7-dihydro-5H-thieno[2,3-c]pyran-3-carboxylic acid tert-butyl ester as an oil.

¹H-NMR (CDCl₃) double set of peaks from diastereomers; selected peaks: δ 1.55 (s, 9H), 1.95 (s, 3H), 2.74 (m, 2H), 2.92 (m, 2H), 3.23 (m, 1H), 3.63 (m, 2H), 6.05 (s, 2H).

LC-MS: R$_t$=5.17 min, m/z: 490.4 [M+H]⁺

7-((2-(R)-Acetylamino-3-(4-hydroxy-phenyl)propionylamino)methyl)-2-amino-4,7-dihydro-5H-thieno[2,3-c]pyran-3-carboxylic acid tert-butyl ester (0.3 g, 0.61 mmol) was dissolved in dichloromethane (15 ml). Triethylamine (0.17 ml, 1.22 mmol) was added and the reaction mixture was cooled to 0° C. Imidazol-1-yl-oxo-acetic acid tert-butyl ester (0.24, 1.22 mmol) dissolved in dichloromethane (10 ml) was added dropwise. The resulting reaction mixture was stirred at room temperature for 18 hours.

Dichloromethane (20 ml) was added and the mixture was washed with 1 N hydrochloric acid (15 ml), saturated sodium hydrogencarbonate (20 ml), dried (MgSO₄), filtered and the solvent removed in vacuo. The residue was purified by flash chromatography on sillicagel (40 g) using ethyl acetate as eluent. Pure fractions were collected and the solvent evaporated in vacuo affording 208 mg (55%) of 7-((2-(R)-acetylamino-3-(4-hydroxy-phenyl)-propionylamino)methyl)-2-(tert-butoxyoxalyl-amino)-4,7-dihydro-5H-thieno[2,3-c]pyran-3-carboxylic acid tert-butyl ester as an oil.

LC-MS: m/z: 618.4 [M+H]⁺, R$_t$=6.97 min.

7-((2-(R)-Acetylamino-3-(4-hydroxy-phenyl)-propionylamino)methyl)-2-(tert-butoxyoxalyl-amino)-4,7-dihydro-5H-thieno[2,3-c]pyran-3-carboxylic acid tert-butyl ester (0.2 g, 0.32 mmol) was dissolved in dichloromethane (8 ml) and trifluoroacetic acid (4 ml) was added. The reaction mixture was stirred 7 hours at room temperature. The solvent was evaporated in vacuo (stripped 3 times with dichloromethane) which afforded 200 mg (100%) of the title compound.

Calculated for C₂₂H₂₃N₃O₉S, 3×H₂O; C, 47.22%; H, 5.22%; N, 7.51%. Found: C, 47.05%; H, 4.88%; N, 7.39%.

LC-MS: R$_t$=3.64 min, m/z: 506.4 [M+H]⁺

Example 45

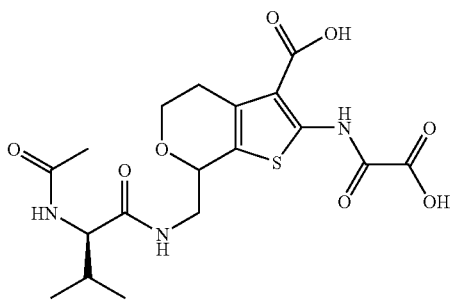

7-((2-(R)-Acetylamino-3-methyl-butyrylamino)methyl)-2-(oxalyl-amino)-4,7-dihydro-5H-thieno[2,3-c]pyran-3-carboxylic acid

89

To a solution of Ac-D-Val-OH (0.17 g, 1.09 mmol) dissolved in dichloromethane (15 ml) was added N,N-dimethylformamide (1 ml), 1-hydroxybenzotriazole (0.15 g, 1.09 mmol) and 1-ethyl-3-(3-dimethylamino-propyl)carbodiimide hydrochloride (0.21 g, 1.09 mmol). The reaction mixture was stirred for 15 min. at room temperature at which time a solution of 2-amino-7-aminomethyl-4,7-dihydro-5H-thieno[2,3-c]pyran-3-carboxylic acid tert-butyl ester (0.31 g, 1.09 mmol) in dichloromethane (10 ml) was added followed by N,N-diisopropylethylamine (0.186 ml, 1.09 mmol). The resulting mixture was stirred over night at room temperature diluted with dichloromethane (10 ml) washed with 10% aqueous citric acid (20 ml), sodium hydrogencarbonate, dried (MgSO$_4$), filtered and the solvent was evaporated in vacuo affording 415 mg (90%) of 7-((2-(R)-acetylamino-3-methyl-butyrylamino)methyl)-2-amino-4,7-dihydro-5H-thieno[2,3-c]pyran-3-carboxylic acid tert-butyl ester as an oil.

$^1$H-NMR (CDCl$_3$) δ 0.88 (t, 3H), 0.98 (t, 2H), 1.55 (s, 9H), 2.02 (d, 1H), 2.77 m, (2H), 3.40 (m, 1H), 4.14 (m, 1H).

LC-MS: R$_t$=5.17 min., m/z: 426.4 [M+H]$^+$

To a mixture of 7-((2-(R)-acetylamino-3-methyl-butyrylamino)methyl)-2-amino-4,7-dihydro-5H-thieno[2,3-c]pyran-3-carboxylic acid tert-butyl ester (0.4 g, 0.94 mmol) dissolved in dichloromethane (10 ml) and triethylamine (0.26 g, 1.87 mmol) cooled to 0° C. was added a solution of imidazol-1-yl-oxo-acetic acid tert-butyl ester (0.37 g, 1.87 mmol) in dichloro-methane (10 ml). The resulting mixture was stirred for 18 hours at room temperature diluted with dichloromethane (20 ml) washed with 1N hydrochloric acid (15 ml), saturated sodium hydrogencarbonate, dried (MgSO$_4$), filtered and the solvent evaporated in vacuo which afforded 515 mg (97%) of 7-((2-(R)-acetylamino-3-methyl-butyrylamino)methyl)-2-(tert-butoxyoxalyl-amino)-4,7-dihydro-5H-thieno[2,3-c]pyran-3-carboxylic acid tert-butyl ester as an oil.

LC-MS: R$_t$=7.11, m/z: 554.4 [M+H]$^+$.

HPLC: R$_t$=34.16, Area (%) 100%.

To a solution of the above 7-((2-(R)-acetylamino-3-methyl-butyrylamino)-methyl)-2-(tert-butoxyoxalyl-amino)-4,7-dihydro-5H-thieno[2,3-c]pyran-3-carboxylic acid tert-butyl ester (0.5 g, 0.90 mmol) dissolved in dichloromethane (3 ml) was added trifluoroacetic acid (1 ml) and the reaction mixture was stirred for 18 hours at room temperature. Trifluoroacetic acid (4 ml) was added and the mixture was stirred for an additional 3 hours at room temperature. The volatiles were evaporated in vacuo (and stripped 3 times with dichloromethane) affording 282 mg (71%) of the title compound.

Calculated for C$_{18}$H$_{23}$N$_3$O$_8$S, 2×H$_2$O; C, 45.28%; H, 5.70%; N, 8.80%. Found: C, 45.20%; H, 5.50%; N, 8.80%.

LC-MS: R$_t$=3.60 min, m/z: 442.2 [M+H]$^+$

90

Example 46

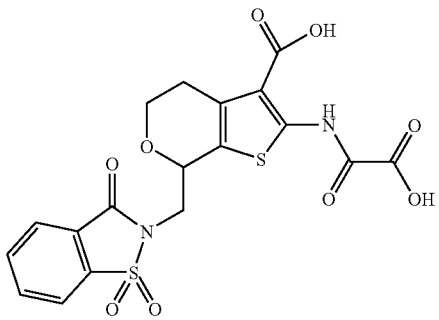

2-(Oxalyl-amino)-7-(1,1,3-trioxo-1,3-dihydro-1H-benzo[d]isothiazol-2-ylmethyl)-4,7-dihydro-5H-thieno[2,3-c]pyran-3-carboxylic acid The title compound was prepared in a similar way as described in Example 23 using 2-amino-7-hydroxymethyl-4,7-dihydro-5H-thieno[2,3-c]pyran-3-carboxylic acid tert-butyl ester and saccharine as starting material. O- and N-alkylated products were separated by column chromatography.

M.p.: 210–212° C.;

Calculated for C$_{18}$H$_{14}$N$_2$O$_9$S$_2$, 0.5×H$_2$O, 0.75×Ethyl acetate; C, 44.49%; H, 3.83%; N, 5.32%. Found: C, 44.70%; H, 3.61%; N, 4.90%

Example 47

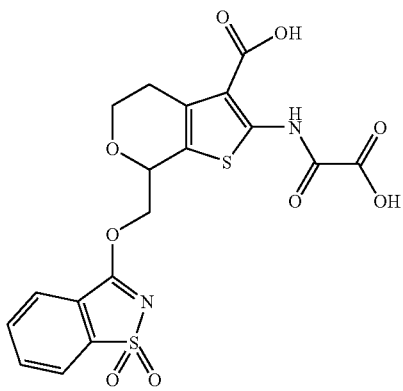

2-(Oxalyl-amino)-7-(1,1,3-trioxo-1H-benzo[disothiazol-3-yloxomethyl)-4,7-dihydro-5H-thieno[2,3-c]pyran-3-carboxylic acid The title compound was prepared in a similar way as described in Example 23 using 2-amino-7-hydroxymethyl- 4,7-dihydro-5H-thieno[2,3-c]pyran-3-carboxylic acid tert-butyl ester and saccharine as starting material. O- and N-alkylated products were separated by column chromatography.

M.p.: 234–236° C.;

Calculated for $C_{18}H_{14}N_2O_9S_2$, $0.6 \times CH_3COOEt$; C, 47.18%; H, 3.65%; N, 5.39%. Found: C, 46.93%; H, 3.76%; N, 5.29%.

Example 48

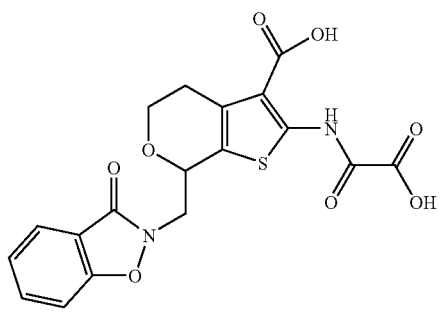

2-(Oxalyl-amino)-7-(3-oxo-3H-benzo[d]isoxazol-2-ylmethyl)-4,7-dihydro-5H-thieno[2,3-c]pyran-3-carboxylic acid The title compound was prepared in a similar way as described in Example 23 using 2-amino-7-hydroxymethyl-4,7-dihydro-5H-thieno[2,3-c]pyran-3-carboxylic acid tert-butyl ester and benzo[d]isoxazol-3-one as starting material.

M.p.: 236–237° C.;

Calculated for $C_{18}H_{14}N_2O_8S$, $0.3 \times H_2O$; C, 51.02%; H, 3.47%; N, 6.61%. Found: C, 51.16%; H, 3.47%; N, 6.31%.

Example 49

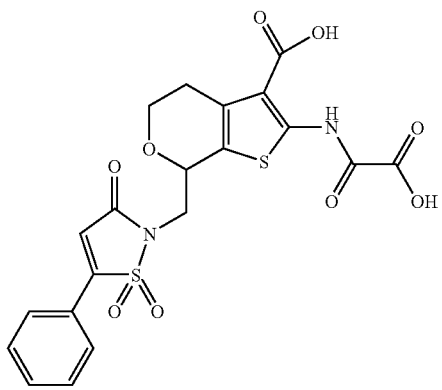

2-(Oxalyl-amino)-7-(1,1,3-trioxo-5-phenyl-1,3-dihydro-isothiazol-2-ylmethyl)-4,7-dihydro-5H-thieno[2,3-c]pyran-3-carboxylic acid The title compound was prepared in a similar way as described in Example 23 using 2-amino-7-hydroxymethyl-4,7-dihydro-5H-thieno[2,3-c]pyran-3-carboxylic acid tert-butyl ester and 1,1-dioxo-5-phenyl-1,2-dihydro-1H-isothiazol-3-one as starting material. O- and N-alkylated products were separated by column chromatography.

$^1$H-NMR (DMSO-$d_6$) δ 2.85 (bs, 2H), 3.75 (m, 1H), 3.92 (dd, 1H), 4.10 (m, 2H), 5.08 (m, 1H), 7.64 (m, 3H), 7.69 (s, 1H), 7.92 (m, 2H), 12.35 (s, 1H, NHCO).

LC-MS: $R_t$=4.90 min, m/z: 493 [M+H]$^+$

Example 50

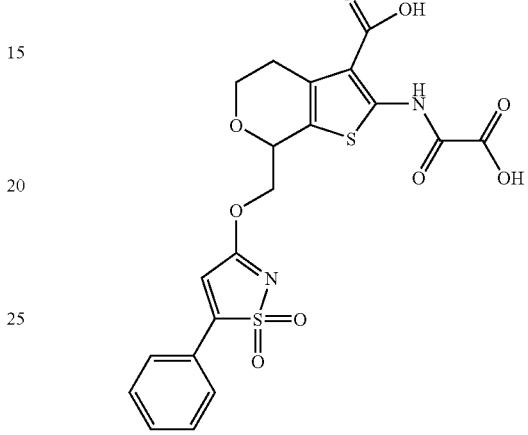

7-(1,1-Dioxo-5-phenyl-1H-isothiazol-3-yloxymethyl)-2-(oxalyl-amino)-4,7-dihydro-5H-thieno[2,3-c]pyran-3-carboxylic acid The title compound was prepared in a similar way as described in Example 23 using 2-amino-7-hydroxymethyl-4,7-dihydro-5H-thieno[2,3-c]pyran-3-carboxylic acid tert-butyl ester and 1,1-dioxo-5-phenyl-1,2-dihydro-1H-isothiazol-3-one as starting material. O— and N-alkylated products were separated by column chromatography.

$^1$H-NMR (DMSO-$d_6$) δ 2.86 (bs, 2H), 3.79 (m, 1H), 4.13 (m, 1H), 4.75 (m, 2H), 5.17 (bs, 1H), 7.60 (m, 3H), 7.70 (s, 1H), 7.88 (m, 2H), 12.35 (s, 1H, NHCO).

LC-MS: $R_t$=4.78 min, m/z: 493 [M+H]$^+$

Example 51

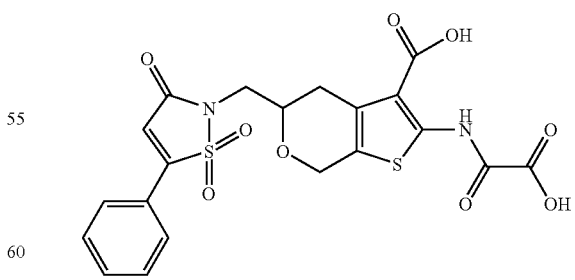

2-(Oxalyl-amino)-5-(1,1,3-trioxo-5-phenyl-1,3-dihydro-isothiazol-2-ylmethyl)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1,1-dioxo-5-phenyl-1,2-dihydro-1H-isothiazol-3-one as starting material. O- and N-alkylated products were separated by column chromatography.

$^1$H-NMR (DMSO-d$_6$) δ 2.62 (dd, 1H), 3.05 (d, 1H), 3.88 (m, 2H), 3.98 (m, 1H), 4.60–4.86 (dd, 2H), 7.66 (m, 4H), 7.93 (m, 2H), 12.3 (s, 1H, NHCO).

Example 52

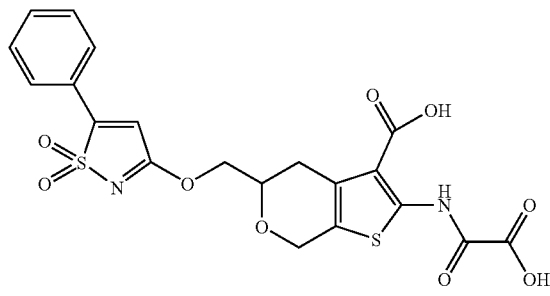

5-(1,1-Dioxo-5-phenyl-1H-isothiazol-3-yloxymethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1,1-dioxo-5-phenyl-1,2-dihydro-1H-isothiazol-3-one as starting material. O- and N-alkylated products were separated by column chromatography.

Mp.: 230–232° C.;

Calculated for C$_{20}$H$_{16}$N$_2$O$_9$S$_2$, 1×H$_2$O; C, 47.06%; H, 3.55%; N, 5.49%. Found: C, 46.88%; H, 3.44%; N, 5.45%.

Example 53

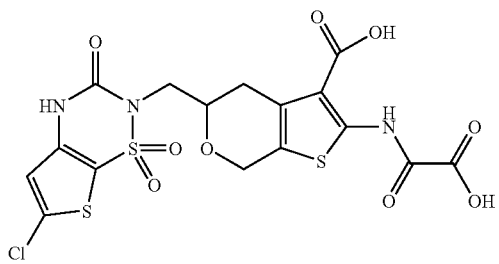

5-(6-Chloro-1,1,3-trioxo-2,3-dihydro-4H-thieno[3,2-el-1,2,4-thiadiazin-2-ylmethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1,1-dioxide-6-chloro-2,3-dihydro-4H-thieno[3,2-e]-1,2,4-thiadiazine-3-one as starting material. O- and N-alkylated products were separated by column chromatography.

$^1$H-NMR (DMSO-d$_6$) δ 2.60 (dd, 1H), 2.98 (d, 1H), 3.87–3.96 (m, 2H), 4.04 (m, 1H), 4.56–4.82 (dd, 2H), 7.0 (s, 1H), 11.95 (s, 1H, NHCO), 12.3 (s, 1H, NHCO).

Example 54

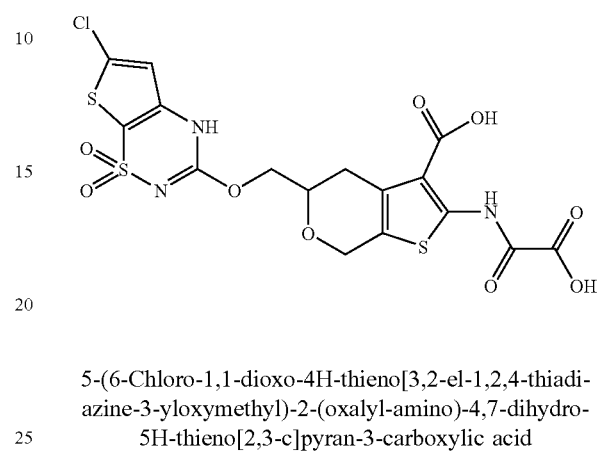

5-(6-Chloro-1,1-dioxo-4H-thieno[3,2-el-1,2,4-thiadiazine-3-yloxymethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1,1-dioxide-6-chloro-2,3-dihydro-4H-thieno[3,2-e]-1,2,4-thiadiazine-3-one as starting material. O- and N-alkylated products were separated by column chromatography.

Mp.: >250° C.;

Calculated for C$_{16}$H$_{12}$ClN$_3$O$_9$S$_3$, 0.75×H$_2$O; C, 35.89%; H, 2.54%; N, 7.85%. Found: C, 35.84%; H, 2.36%; N, 7.74%.

Example 55

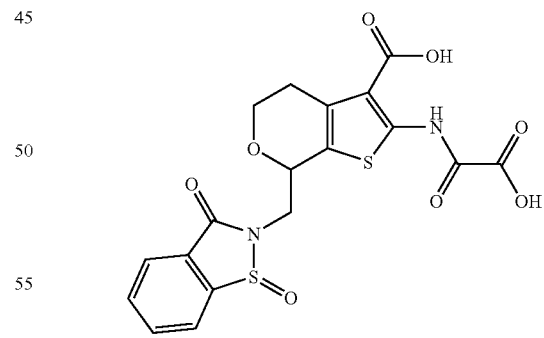

7-(1,3-Dioxo-1,3-dihydro-benzo[d]isothiazol-2-ylmethyl)-2-(oxalyl-amino)-4,7-dihydro-5H-thieno[2,3-c]pyran-3-carboxylic acid The title compound was prepared in a similar way as described in Example 23 using 2-amino-7-hydroxymethyl-4,7-dihydro-5H-thieno[2,3-c]pyran-3-carboxylic acid tert-

Example 56

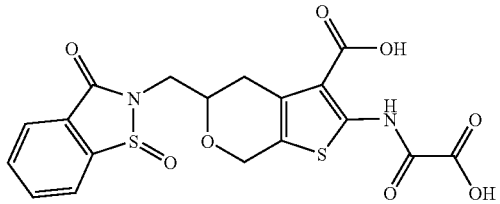

5-(1,3-Dioxo-1,3-dihydro-benzo[d]isothiazol-2-ylmethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1-oxo-1,2-dihydro-1H-benzo[d]isothiazol-3-one as starting material. O- and N-alkylated products were separated by column chromatography.

Mp.: 230–231° C.;

Calculated for $C_{18}H_{14}N_2O_8S_2$, $0.5 \times H_2O$; C, 47.06%; H, 3.29%; N, 6.10%. Found: C, 46.94%; H, 3.42%; N, 6.26%.

Example 57

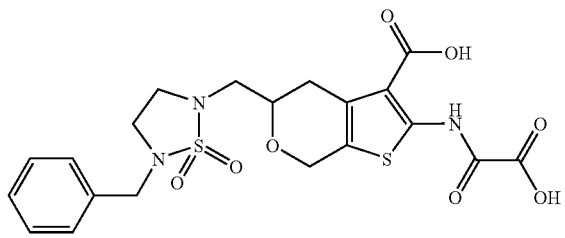

5-(5-Benzyl-1,1-dioxo-[1,2,5]thiadiazolidin-2-ylmethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 2-benzyl-[1,2,5]thiadiazolidine 1,1-dioxide as starting material.

Mp.: 188–192° C.;

LC-MS: $R_t$=5.00 min, m/z: 496 [M+H]$^+$

Example 58

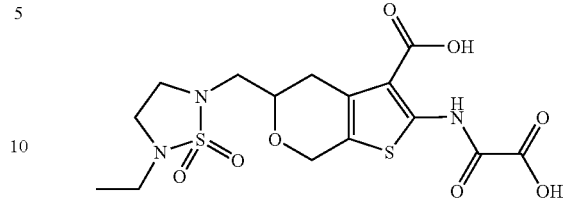

5-(5-Ethyl-1,1-dioxo-[1,2,5-thiadiazolidin-2-ylmethyl)-2-(oxalyl-amino)-4,7-dihydro-5H— _thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 2-ethyl-[1,2,5]thiadiazolidine 1,1-dioxide as starting material.

LC-MS: $R_t$=4.18 min, m/z: 434 [M+H]$^+$

Example 59

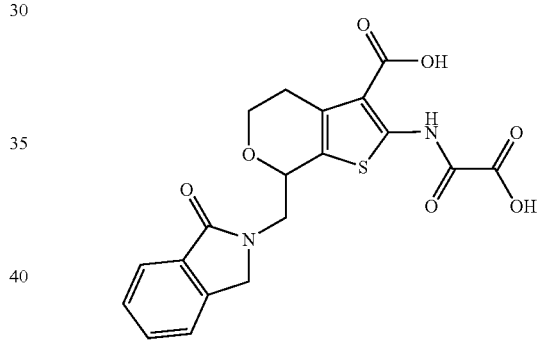

2-(Oxalyl-amino)-7-(1-oxo-1,3-dihydro-isoindol-2-ylmethyl)-4,7-dihydro-5H-thieno[2,3-c]pyran-3-carboxylic acid To a solution of 2-amino-7-aminomethyl-4,7-dihydro-5H-thieno[2,3-c]pyran-3-carboxylic acid tert-butyl ester (100 mg, 0.38 mmol) and N,N-diisopropylethylamine (72 μL, 0.41 mmol) in acetonitrile (6 ml) at 0° C. was added 2-bromomethyl-benzoic acid methyl ester (43 mg, 0.19 mmol). The reaction mixture was stirred for 16 hours and the solvent evaporated in vacuo. The residue was diluted in ethyl acetate (50 ml), washed with 1N hydrochloric acid, saturated sodium bicarbonate, brine, dried (MgSO$_4$), filtered and the solvent evaporated in vacuo, which afforded 50 mg (68%) of 2-amino-7-(1-oxo-1,3-dihydro-isoindol-2-ylmethyl)-4,7-dihydro-5H-thieno[2,3-c]pyran-3-carboxylic acid tert-butyl ester as an oil.

$^1$H-NMR (CDCl$_3$) δ 7.86 (d, 1H, J=8 Hz), 7.55 (t, 1H, J=8 Hz), 7.45 (t, 2H, J=8 Hz), 4.88 (dt, 1H, J=6, 2 Hz), 4.68 (d, 1H, J=17 Hz), 4.48 (d, 1H, J=17 Hz), 4.25–4.10 (m, 1H), 4.03 (dd, 1H, J=17 and J=3 Hz), 3.80–3.75 (m, 2H), 2.92–2.70 (m, 2H), 1.54 (s, 9H).

--- butyl ester and 1-oxo-1,2-dihydro-1H-benzo[d]isothiazol-3-one as starting material. O- and N-alkylated products were separated by column chromatography.

LC-MS: $R_t$=3.82 min, m/z: 451 [M+H]$^+$

To a solution of 2-amino-7-(1-oxo-1,3-dihydro-isoindol-2-ylmethyl)-4,7-dihydro-5H-thieno[2,3-c]pyran-3-carboxylic acid tert-butyl ester (50 mg, 0.13 mmol) in tetrahydrofuran (1 ml) was added imidazol-1-yl-oxo-acetic acid tert-butyl ester (100 mg, 0.51 mmol). The mixture was stirred at room temperature for 24 hours. The solvent was removed in vacuo. The residue was taken into ethyl acetate (50 ml), washed with saturated sodium bicarbonate and brine, dried (Na$_2$SO$_4$) and filtered. The solvent was removed in vacuo and the residue was chromatographed using a mixture of 10% ethyl acetate/dichloromethane as eluent, which afforded 55 mg (83%) of 2-(tert-butoxyoxalyl-amino)-7-(1-oxo-1,3-dihydro-isoindol-2-ylmethyl)-4,7-dihydro-5H-thieno[2,3-c]pyran-3-carboxylic acid tert-butyl ester as an oil.

$^1$H-NMR (CDCl$_3$) δ 12.59 (s, 1H), 7.88 (d, 1H, J=7 Hz), 7.54 (t, 1H, J=7 Hz), 7.46 (t, 2H, J=7 Hz), 5.04 (dd, 1H, J=6 Hz and J=2 Hz), 4.69 (d, 1H, J=17 Hz), 4.46 (d, 1H, J=17 Hz), 4.26–4.10 (m, 2H), 3.77 (dd, 1H, J=9 Hz and J=3 Hz), 3.70 (dd, 1H, J=15 Hz and J=9 Hz), 3.02–2.80 (m, 2H), 1.55 (s, 18H).

A solution of 2-(tert-butoxyoxalyl-amino)-7-(1-oxo-1,3-dihydro-isoindol-2-ylmethyl)-4,7-dihydro-5H-thieno[2,3-c]pyran-3-carboxylic acid tert-butyl ester (55 mg, 0.11 mmol) in 50% trifluoroacetic acid/dichloromethane (2 ml) was stirred for 16 hours. The volatiles were removed in vacuo and the residue was washed with dichloromethane and dried, which afforded 29 mg (50%) of the title compound as a solid trifluoroacetate.

$^1$H-NMR (DMSO-d$_6$) δ12.35 (s, 1H), 7.70 (d, 1H, J=8 Hz), 7.61 (d, 1H, J=3 Hz), 7.52–7.47 (m, 2H), 5.04 (s, 1H), 4.59 (d, 1H, J=18 Hz), 4.58 (d, 1H, J=18 Hz), 4.19–4.08 (m, 1H), 3.88 (d, 1H, J=6 Hz), 3.78–3.66 (m, 1H), 3.38 (q, 1H, J=7 Hz), 2.85 (s, 2H);

LC-MS: R$_t$=2.12 min, m/z: 417 (M+H)$^+$.

Example 60

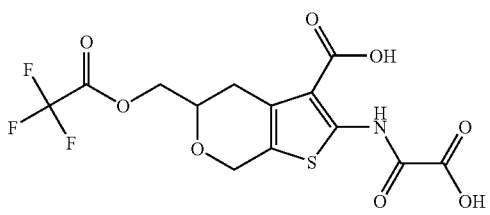

2-(Oxalyl-amino)-5-(2,2,2-trifluoro-acetoxymethyl)-4,7-dihydro-5H-thieno[2,3-c]pyran-3-carboxylic acid 2-(tert-Butoxyoxalyl-amino)-5-hydroxymethyl-4,7-dihydro-5H-thieno[2,3-c]pyran-3-carboxylic acid tert-butyl ester (0.5 g, 1.21 mmol) was dissolved in dichloromethane (9 ml) and trifluoroacetic acid (3 ml) was added. The reaction mixture was stirred 64 hours at room temperature. The precipitate was filtered off and washed with diethyl ether and dried in vacuo at 50° C. for 4 hours, which afforded 180 mg (50%) of the title compound as a solid.

Mp.: 231–233° C.;

Calculated for C$_{13}$H$_{10}$F$_3$NO$_8$S; C, 39.30%; H, 2.56%; N, 3.57%. Found: C, 39.30%; H, 2.54%; N, 3.53%.

Example 61

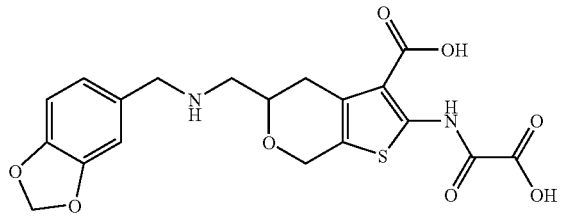

5-(((Benzo[1,3]dioxol-5-ylmethyl)-amino)-methyl)-2-(oxalyl-amino)-4,7-dihydro-5H-thieno[2,3-c]pyran-3-carboxylic acid To a solution of oxalyl chloride (1 ml, 11.13 mmol) in dichloromethane (40 ml) cooled to −78° C. under an atmosphere of nitrogen was added dropwise a solution of dimethylsulfoxide (1.6 ml, 21.78 mmol) in dichloromethane (16 ml) during 5 min. After stirring for 15 min at −78° C. a solution of 2-(tert-butoxyoxalyl-amino)-5-hydroxymethyl-4,7-dihydro-5H-thieno[2,3-c]pyran-3-carboxylic acid tert-butyl ester (2.0 g, 4.84 mmol) in dichloromethane (30 ml) was added dropwise and the resulting mixture was stirred for 0.5 hour at −78° C. N,N-Diisopropylethylamine (4.2 ml, 24.18 mmol) was added and the reaction mixture allowed reaching room temperature at which time heptane (700 ml) was added. The mixture was filtered through anhydrous sodium sulfate and the solvent evaporated in vacuo. The residue (2.71 g) was purified on column chromatography using a mixture of ethyl acetate/heptane (1:4) as eluent which afforded 0.93 g (47%) of 2-(tert-butoxyoxalyl-amino)-5-formyl-4,7-dihydro-5H-thieno[2,3-c]pyran-3-carboxylic acid tert-butyl ester as an oil. To a mixture of 2-(tert-butoxyoxalyl-amino)-5-formyl-4,7-dihydro-5H-thieno[2,3-c]pyran-3-carboxylic acid tert-butyl ester (0.46 g, 1.12 mmol) and piperonylamine (145 μl, 1.12 mmol) in 1,2-dichloroethane (25 ml) was added sodium triacetoxyborohydride (0.35 g, 1.57 mmol) and the resulting mixture was stirred at room temperature for 1 hour. The mixture was washed with saturated aqueous sodium hydrogencarbonate (2×30 ml) and dried (Na$_2$SO$_4$), filtered and the solvent evaporated in vacuo. The residue (0.56 g) was purified on column chromatography using a mixture of ethyl acetate/heptane (1:1) as eluent followed by a mixture of 10% triethylamine in ethyl acetate/heptane (1:1) as eluent. Semi pure fractions were collected and the solvent evaporated in vacuo. The residue (180 mg) was subjected to preparative TLC using a mixture of 10% triethylamine in ethyl acetate/ethanol (4:1) as eluent. The desired band was taken off and extracted with methanol (400 ml) for 0.5 hour, filtered and the solvent evaporated in vacuo, which afforded 250 mg (<100%, contains dichloromethane and silicagel) of 5-(((benzo[1,3]dioxol-5-ylmethyl)-amino)methyl)-2-(tert-butoxyoxalyl-amino)-4,7-dihydro-5H-thieno[2,3-c]pyran-3-carboxylic acid tert-butyl ester as an oil.

LC-MS: R$_t$=5.75 min, m/z: 547 [M+H]$^+$.

5-(((Benzo[1,3]dioxol-5-ylmethyl)-amino)methyl)-2-(tert-butoxyoxalyl-amino)-4,7-dihydro-5H-thieno[2,3-c]pyran-3-carboxylic acid tert-butyl ester (250 mg) was dissolved in dichloromethane (9 ml) and trifluoroacetic acid (3 ml) was added. The reaction mixture was stirred 16 hours at room temperature. The volatiles were evaporated in vacuo and the residue trituated with a small portion of diethyl ether. The solid precipitate was filtered off and washed with diethyl ether and dried in vacuo at 50° C. for 16 hours, which afforded 160 mg of the title compound as a solid.

Calculated for $C_{19}H_{18}N_2O_8S$, $2\times TFA$, $3\times H_2O$; C, 38.56%; H, 3.66%; N, 3.91%. Found: C, 38.61%; H, 3.90%; N, 4.22%.

Example 62

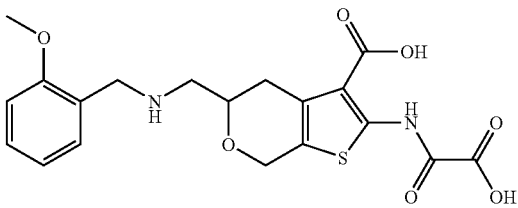

5-((2-Methoxy-benzylamino)methyl)-2-(oxalyl-amino)-4,7-dihydro-5H-thieno[2,3-c]pyran-3-carboxylic acid The title compound was prepared in a similar way as described in Example 60 using 2-(tert-butoxyoxalyl-amino)-5-formyl-4,7-dihydro-5H-thieno[2,3-c]pyran-3-carboxylic acid tert-butyl ester and 2-methoxy-benzylamine as starting material.

Calculated for $C_{19}H_{20}N_2O_7S$, $0.75\times TFA$; C, 48.67%; H, 4.13%; N, 5.54%. Found: C, 48.61%; H, 4.42%; N, 5.35%.

Example 63

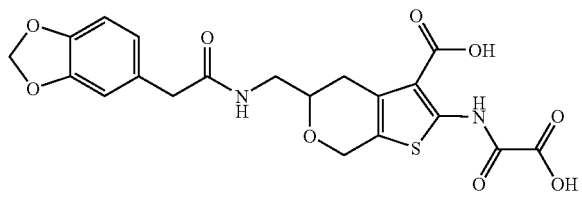

5-((2-Benzo[1,3]-dioxol-5-yl-acetylamino)methyl)-2-(oxalyl-amino)-4,7-dihydro-5H-thieno[2,3-c]pyran-3-carboxylic acid To a solution of 3,4-methylenedioxy phenylacetic acid (0.22 g, 1.09 mmol), 1-(3-dimethylaminopropyl)-3-ethylcarbodiimide, hydrochloride (0.27 g, 1.42 mmol) in acetonitrile (6 ml) was added triethylamine (0.46 ml, 3.27 mmol). The resultant mixture was allowed to stir at ambient temperature for 10 min. before 2-amino-5-aminomethyl-4,7-dihydro-5H-thieno[2,3-c]pyran-3-carboxylic acid tert-butyl ester (0.311 g, 1.09 mmol) was added. The reaction mixture was allowed to stir at ambient temperature for 18 hours and then concentrated in vacuo. To the residue ethyl acetate and water were added and the layers separated. The organic layer was washed with hydrochloric acid (0.5M, (v/v)), saturated sodium bicarbonate (2×25 ml) and brine (2×25 ml). The organic layer was dried (MgSO$_4$), filtered and the solvent evaporated in vacuo. The crude 2-amino-5-((2-benzo[1,3]dioxol-5-yl-acetylamino)-methyl]-4,7-dihydro-5H-thieno[2,3-c]pyran-3-carboxylic acid tert-butyl ester was used immediately in the next step.

$^1$H-NMR (CDCl$_3$) δ 6.78–6.69 (m, 3H), 5.97 (bs, 2H), 5.95 (s, 2H), 4.60–4.58 (m, 1H), 4.53 (s, 2H), 3.73 (ddd, 1H, J=14 Hz, J=7.6 Hz and J=3.2 Hz), 3.65–3.59 (m, 1H), 3.49 (s, 2H), 3.11 (ddd, 1H, J=12.4 Hz, J=4 Hz and J=4.4 Hz), 2.76 (dm, 1H), 2.44 (ddt, 1H, J=19.6 Hz, J=13.2 Hz and J=2.4 Hz), 1.51 (s, 9H).

To a solution of the above crude 2-amino-5-((2-benzo[1,3]dioxol-5-yl-acetylamino)-methyl]4,7-dihydro-5H-thieno[2,3-c]pyran-3-carboxylic acid tert-butyl ester (0.17 g, 0.38 mmol) in dichloromethane (5 ml) was added imidazol-1-yl-oxo-acetic acid tert-butyl ester (0.22 g, 1.14 mmol). The reaction mixture was stirred at room temperature for 18 hours, the volatiles evaporated in vacuo and the residue diluted with ethyl acetate. The organic layer was washed with hydrochloric acid (1% (v/v), 2×25 ml), saturated sodium bicarbonate (2×25 ml) and brine (2×25 ml). The organic layer was dried (MgSO$_4$), filtered, concentrated in vacuo and the residue subjected to flash chromatography using a mixture of ethyl acetate/hexanes (1:2) as eluent, which afforded 0.12 g (55%) of 2-(tert-butoxyoxalyl-amino)-5-((2-benzo[1,3]dioxol-5-yl-acetylamino)-methyl-4,7-dihydro-5H-thieno[2,3-c]pyran-3-carboxylic acid tert-butyl ester as an oil.

$^1$H-NMR (CDCl$_3$) δ12.51 (bs, 1H), 6.78 (d, 1H, J=8 Hz), 6.77 (d, 1H, J=1.6 Hz), 6.71 (dd, 1H, J=8.4 Hz and J=1.6 Hz), 5.96 (s, 2H), 4.70 (m, 2H, J=35 Hz, J=15.2 Hz), 3.67–3.62 (m, 1H) and J=2 Hz), 3.77 (ddd, 1H, J=10.8 Hz, J=7.6 Hz and J=3.2 Hz), 3.67–3.62 (m, 1H), 3.50 (s, 2H), 3.15 (ddd, 1H, J=12.8 Hz, J=8.4 Hz and J=4.4 Hz), 2.87 (dt, 1H, J=16 Hz and J=3 Hz), 2.57–2.50 (m, 1H), 1.61 (s, 9H), 1.57 (s, 9H);

LC-MS: m/z: 575.0 [M+H]$^+$ 2-(tert-Butoxyoxalyl-amino)-5-((2-benzo[1,3]dioxol-5-yl-acetylamino)-methyl]-4,7-dihydro-5H-thieno[2,3-c]pyran-3-carboxylic acid tert-butyl ester (0.12 g, 0.20 mmol) was dissolved in a 50% solution of trifluoroacetic acid/dichloromethane (2 ml). The reaction mixture was stirred at ambient temperature for 18 hours, concentrated in vacuo to ⅕ of the volume and the precipitate filtered off and washed with dichloromethane (2×) affording 50 mg (50%) of the title compound as a solid.

$^1$H-NMR (DMSO-d$_6$) δ 12.32 (bs, 1H), 8.20 (t, 1H, J=6.8 Hz), 6.81 (m, 2H), 6.70 (m, 1H), 5.95 (s, 2H), 4.80 (d, 1H, J=19.6 Hz), 4.63 (d, 1H, J=20 Hz), 3.65 (m, 1H), 3.34 (s, 2H), 3.30–3.20 (m, 3H), 2.87 (dm, 1H);

LC-MS: m/z: 463.0 [M+H]$^+$.

Example 64

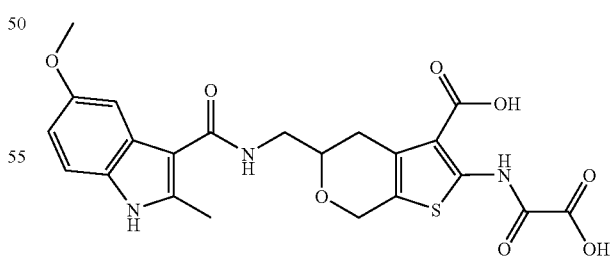

5-(((5-Methoxy-2-methyl-1H-indol-3-carbonyl)amino)methyl)-2-(oxalyl-amino)-4,7-dihydro-5H-thieno[2,3-c]pyran-3-carboxylic acid To a solution of 5-methoxy-2-methyl indole-3-acetic acid (0.26 g, 1.18 mmol), and 1-(3-dimethylaminopropyl)-3- ethylcarbodiimide, hydrochloride (0.27 g, 1.4 mmol) in acetonitrile (10 ml) was added triethylamine (0.46 ml, 3.2 mmol). The reaction mixture was allowed to stir for 10 min at room temperature before compound 2-amino-5-aminomethyl-4,7-dihydro-5H-thieno[2,3-c]pyran-3-carboxylic acid tert-butyl ester (0.307 g, 1.08 mmol) was added. The reaction mixture was allowed to stir for 18 hours and then concentrated in vacuo. Ethyl acetate and water were added and the layers separated. The organic layer was washed with hydrochloric acid (0.5M, (v/v)), saturated sodium bicarbonate (2×25 ml) and brine (2×25 ml). The organic layer was dried (MgSO$_4$), filtered and concentrated in vacuo. The crude 2-amino-5-(((5-methoxy-2-methyl-1H-indol-3-carbonyl)amino-methyl)-4,7-dihydro-5H-thieno[2,3-c]pyran-3-carboxylic acid tert-butyl ester was used immediately in the next step.

$^1$H-NMR (CDCl$_3$) δ 7.90 (bs, 1H), 7.19 (d, 1H, J=8.8 Hz), 6.87 (d, 1H, J=2.4 Hz), 6.79 (dd, 1H, J=8.8 Hz and J=2.4 Hz), 6.18 (m, 1H), 5.94 (s, 2H), 4.33 (m, 2H, J=25 Hz, J=14 Hz, J=2.8 Hz and J=1.6 Hz), 3.80 (s, 3H), 3.76 (ddd, 1H, J=14 Hz, J=8 Hz and J=2.8 Hz), 3.65 (s, 3H), 3.53 (m, 1H), 2.99 (ddd, 1H, J=13 Hz, J=5.6 Hz and J=4 Hz), 2.76 (dt, 1H, J=16.8 Hz, J=2.8 Hz), 2.42–2.40 (m, 1H), 2.38 (s, 3H), 1.51 (s, 9H).

To a solution of the crude 2-amino-5-(((5-methoxy-2-methyl-1H-indol-3-carbonyl)amino)methyl)-4,7-dihydro-5H-thieno[2,3-c]pyran-3-carboxylic acid tert-butyl ester (0.35 g, 0.72 mmol) in dichloromethane (5 ml) was added imidazol-1-yl-oxo-acetic acid tert-butyl ester (0.42 g, 2.1 mmol). The reaction mixture was stirred at room temperature for 18 hours. The reaction mixture was concentrated in vacuo and the residue diluted with ethyl acetate. The organic layer was washed with hydrochloric acid (1% (v/v), 2×25 ml), saturated sodium bicarbonate (2×25 ml) and brine (2×25 ml). The organic layer was dried (MgSO$_4$), filtered, concentrated in vacuo and the residue subjected to flash chromatography using a mixture of ethyl acetate/hexanes (1:1) as eluent, which afforded 0.24 (55%) of 2-(tert-butoxyoxalyl-amino)-5-(((5-methoxy-2-methyl-1H-indol-3-carbonyl)amino)methyl)-4,7-dihydro-5H-thieno[2,3-c]pyran-3-carboxylic acid tert-butyl ester as an oil.

$^1$H-NMR (CDCl$_3$) δ12.50 (bs, 1H), 7.92 (s, 1H), 7.20 (dd, 1H, J=8.4 Hz and J=0.4 Hz), 6.88 (d, 1H, J=2.4 Hz), 6.80 (dd, 1H, J=8.8 Hz and J=2.4 Hz), 6.21 (m, 1H), 4.56 (dd, 1H, J=14.8 Hz and J=2.8 Hz), 4.44 (dt, 1H, J=14.4 Hz and J=2.8 Hz), 4.11 (q, 1H, J=7.2 Hz), 3.81–3.75 (m, 1H), 3.79 (s, 3H), 3.66 (s, 2H), 3.58–3.54 (m, 1H), 3.01 (ddd, 1H, J=14 Hz, J=8.8 Hz and J=4.4 Hz), 2.85 (dt, 1H, J=16.8 Hz and J=6 Hz), 2.52–2.45 (m, 1H), 2.38 (s, 3H), 1.60 (s, 9H), 1.57 (s, 9H);

LC-MS: m/z: 614.1 [M+H]$^-$.

2-(tert-Butoxyoxalyl-amino)-5-(((5-methoxy-2-methyl-1H-indol-3-carbonyl)amino)methyl)-4,7-dihydro-5H-thieno[2,3-c]pyran-3-carboxylic acid tert-butyl ester (0.24 g, 0.39 mmol) was dissolved in a 50% solution of trifluoroacetic acid/dichloromethane (2 ml). The reaction mixture was stirred at ambient temperature for 18 hours, concentrated in vacuo to ⅕ of the volume and the precipitate filtered off. The filtrate was washed with dichloromethane (2×) and dried, which afforded 100 mg (50%) of the title compound as a solid.

$^1$H-NMR (DMSO-d$_6$) δ 12.31 (bs, 1H), 10.58 (s, 1H), 7.98 (t, 1H, J=6.8 Hz), 7.08 (d, 1H, J=11.2 Hz), 6.98 (d, 1H, J=2.4 Hz), 6.58 (dd, 1H, J=11.6 Hz and J=2.8 Hz), 5.75 (d, 1H, J=0.8 Hz), 4.77 (d, 1H, J=19.6 Hz), 4.58 (d, 1H, J=20 Hz), 3.69 (s, 3H), 3.64–3.62 (m, 1H), 3.43 (s, 2H)—, 3.31–3.20 (m, 1H), 20.92–2.84 (m, 1H), 2.52 (m, 1H-partially obscured by DMSO), 2.30 (s, 3H);

LC-MS: m/z: 500.1 [M–H]$^-$.

Example 65

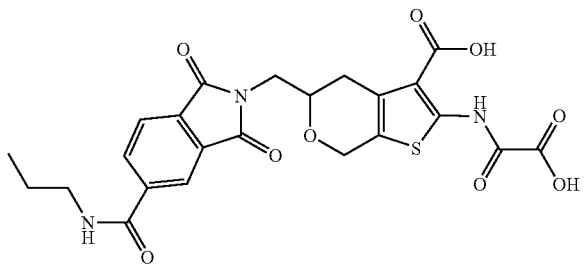

5-(1,3-Dioxo-5-propylcarbamoyl-1,3-dihydro-isoindol-2-ylmethyl)-2-(oxalyl-amino)-4,7-dihydro-5H-thieno[2,3-c]pyran-3-carboxylic acid In a 10-mL scintillating vial, a solution of 2-amino-5-aminomethyl-4,7-dihydro-5H-thieno[2,3-c]pyran-3-carboxylic acid tert-butyl ester (149 mg, 0.5 mmol) in N,N-dimethylformamide (4 mL) was treated with trimellitic anhydride (120 mg, 0.62 mmol) and stirred at 100° C. for 24 hours. The solution was then diluted with ethyl acetate (25 mL) and washed with 0.5N aqueous hydrogen chloride (25 mL) and brine (25 mL). The organic layer was dried (MgSO$_4$), filtered, and concentrated in vacuo affording 229 mg (100%) of 2-(2-amino-3-tert-butoxycarbonyl-4,7-dihydro-5H-thieno[2,3-c]pyran-5-ylmethyl)-1,3-dioxo-2,3-dihydro-1H-isoindole-5-carboxylic acid as a solid.

$^1$H-NMR (300 MHz, CDCl$_3$) δ 8.58 (s, 1H), 8.49 (d, 1H, J=9 Hz), 8.00 (d, 1H, J=10 Hz), 4.64–4.54 (m, 2H), 4.08–4.02 (m, 2H), 3.88–3.80 (m, 1H), 2.98–2.83 (m, 1H), 2.68–2.54 (m, 1H), 1.57 (s, 9H).

HPLC (254.4 nm) R$_t$=3.98 min.

In a 250 mL round bottom flask, a solution of 2-(2-amino-3-tert-butoxycarbonyl-4,7-dihydro-5H-thieno[2,3-c]pyran-5-ylmethyl)-1,3-dioxo-2,3-dihydro-1H-isoindole-5-carboxylic acid (500 mg, 1.1 mmol) in dichloromethane (7 mL) was treated with a solution of imidazol-1-yl-oxo-acetic acid tert-butyl ester (633 mg, 3.2 mmol) in dichloromethane (1.0 mL). After stirring for 4 hours at room temperature the reaction solution was dissolved in ethyl acetate (100 mL) and washed with distilled water (2×50 mL), 0.5 N aqueous hydrogen chloride (3×50 mL), and brine (50 mL). The organic layer was dried (MgSO$_4$), filtered, and concentrated in vacuo to yield 370 mg (58%) of 2-(2-(tert-butoxyoxalyl-amino)-3-tert-butoxycarbonyl-4,7-dihydro-5H-thieno[2,3-c]pyran-5-ylmethyl)-1,3-dioxo-2,3-dihydro-1H-isoindole-5-carboxylic acid as a solid.

$^1$H-NMR (300 MHz, CDCl$_3$) δ 12.49 (s, 1H), 8.58 (s, 1H), 8.50 (d, 1H, J=8 Hz), 8.00 (d, 1H, J==8 Hz), 4.84–4.65 (m, 2H), 4.17–4.00 (m, 2H), 3.92–3.84 (m, 1H), 3.08–2.94 (m, 1H), 2.78–2.64 (m, 1H), 1.61 (s, 9H), 1.57 (s, 9H).

In a 50 mL round bottom flask, a solution of 2-(2-(tert-butoxyoxalyl-amino)-3-tert-butoxycarbonyl-4,7-dihydro-5H-thieno[2,3-c]pyran-5-ylmethyl)-1,3-dioxo-2,3-dihydro-1H-isoindole-5-carboxylic acid (208 mg, 0.36 mmol) in dichloromethane (5.0 mL) was treated with N,N-diisopropyl ethylamine (200 μL, 1.1 mmol) and 1-(3-dimethylaminopropyl)-3-ethylcarbodiimide hydrochloride (84 mg, 0.44 mmol). The solution was allowed to stir for 50 minutes at room temperature before propylamine (30 μL, 0.36 mmol) was added dropwise. The solution was stirred for an additional 18 hours at room temperature. The volatiles were evaporated in vacuo and the residue was purified by silica gel chromatography using a mixture of hexane/ethyl acetate (9:1) as eluent, which afforded 51 mg (23%) of 2-(tert-butoxyoxalyl-amino)-5-(1,3-dioxo-5-propylcarbamoyl-1,3-dihydro-isoindol-2-ylmethyl)-4,7-dihydro-5H-thieno[2,3-c]pyran-3-carboxylic acid tert-butyl ester as a solid.

$^1$H-NMR (300 MHz, CDCl$_3$) δ 12.48 (s, 1H), 8.24–8.16 (m, 2H), 7.93 (d, 1H, J=8 Hz), 6.39 (t, 1H, J=6 Hz), 4.18–4.63 (m, 2H), 4.10–3.96 (m, 2H), 3.92–3.78 (m, 1H), 3.47 (q, 2H, J=7 Hz), 2.99 (d, 1H, J=17), 2.76–2.60 (m, 1H), 1.68 (q, 2H, J=7 Hz), 1.61 (s, 9H), 1.57 (s, 9H), 1.01 (t, 3H, J=7 Hz).

In a 25 mL round bottom flask 2-(tert-butoxyoxalyl-amino)-5-(1,3-dioxo-5-propylcarbamoyl-1,3-dihydro-isoindol-2-ylmethyl)-4,7-dihydro-5H-thieno[2,3-c]pyran-3-carboxylic acid tert-butyl ester (40 mg, 0.07 mmol) was dissolved in 20% trifluoroacetic acid in dichloromethane (4 mL). The solution was left open to the atmosphere without stirring. After 24 hours the precipitate was filtered off and washed with diethyl ether, affording 32 mg (90%) of the title compound as a solid.

$^1$H-NMR (300 MHz, DMSO-d$_6$) 612.32 (s, 1H), 8.81 (s, 1H), 8.58 (s, 1H), 8.00 (s, 1H), 4.90–4.48 (m partially obscured by water, 2H), 4.00–3.64 (m partially obscured by water, 3H), 3.36–3.16 (m partially obscured by water, 2H), 3.13–2.90 (d partially obscured by water, 1H), 2.69–2.53 (m partially obscured by DMSO, 1H), 1.69–1.38 (m, 2H), 1.00–0.74 (m, 3H).

HPLC (254.4 nm) R$_t$=3.09 min.

MS (APCI) m/z: 515.4 [M–H]$^-$.

What is claimed is:

1. A compound of Formula I

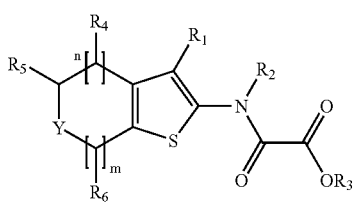

Formula 1 wherein
n is 1 or 2;
m is 1 or 2,
Y is O, SO or SO$_2$
R$_1$ is COOH, COOC$_1$–C$_6$alkyl, COOarylC$_1$–C$_6$alkyl, COOC$_1$–C$_6$alkylcarbonyloxyC$_1$–C$_6$alkyl, COOC$_1$–C$_6$alkylcarbonyloxyarylC$_1$–C$_6$alkyl;
R$_2$ is hydrogen;
R$_3$ is hydrogen, C$_1$–C$_6$alkyl, arylC$_1$–C$_6$alkyl, C$_1$–C$_6$alkylcarbonyloxyC$_1$–C$_6$alkyl or C$_1$–C$_6$alkylcarbonyloxyarylC$_1$–C$_6$alkyl;
R$_4$ is hydrogen, C$_1$–C$_6$alkyl, aryl, arylC$_1$–C$_6$alkyl, provided R$_4$ does not represent a heterocyclic ring; wherein the alkyl and aryl groups are optionally substituted as defined below;
R$_5$, is hydrogen, trihalomethyl, C$_1$–C$_6$alkyl, aryl, arylC$_1$–C$_6$alkyl, C$_1$–C$_6$alkyloxycarbonyl, aryloxycarbonyl, arylC$_1$–C$_6$alkyloxycarbonyl, C$_1$–C$_6$alkyloxy, C$_1$–C$_6$alkyloxyC$_1$–C$_6$alkyl, aryloxyC$_1$–C$_6$alkyl, arylC$_1$–C$_6$alkyloxyC$_1$–C$_6$-alkyl, NR$_7$R$_8$, C$_1$–C$_6$alkylaminoC$_1$–C$_6$alkyl, arylC$_1$–C$_6$alkylaminoC$_1$–C$_6$alkyl, di(arylC$_1$–C$_6$alkyl)aminoC$_1$–C$_6$alkyl, C$_1$–C$_6$alkylcarbonyl, C$_1$–C$_6$alkylcarbonylC$_1$–C$_6$alkyl, di(arylC$_1$–C$_6$alkyl)aminoC$_1$–C$_6$alkyl, C$_1$–C$_6$alkylcarbonylC$_1$–C$_6$alkyl, C$_1$–C$_6$alkylcarboxyC$_1$–C$_6$alkyl, arylcarboxyC$_1$–C$_6$alkyl, arylC$_1$–C$_6$alkylcarboxyC$_1$–C$_6$alkyl, C$_1$–C$_6$alkylcarbonylamino, C$_1$–C$_6$alkylcarbonylaminoC$_1$–C$_6$alkyl, -carbonylNR$_8$C$_1$–C$_6$alkylCOR$_{10}$, wherein R$_{10}$ is NR$_7$R$_8$ or C$_1$–C$_6$alkylNR$_7$R$_8$, arylC$_1$–C$_6$alkylcarbonylamino, arylC$_1$–C$_6$alkylcarbonylaminoC$_1$–C$_6$alkyl, CONR$_7$R$_8$, C$_1$–C$_6$alkylCONR$_7$R$_8$, or arylaminocarbonylaminoC$_1$–C$_6$alkyl, provided R$_6$ does not represent a heterocyclic ring; wherein the alkyl and aryl groups are optionally substituted as defined below;

R$_6$ is hydrogen, trihalomethyl, C$_1$–C$_6$alkyl, aryl, arylC$_1$–C$_6$alkyl, C$_1$–C$_6$alkyloxycarbonyl, aryloxycarbonyl, arylC$_1$–C$_6$alkyloxycarbonyl, C$_1$–C$_6$alkyloxy, C$_1$–C$_6$alkyloxyC$_1$–C$_6$alkyl, aryloxyC$_1$–C$_6$alkyl, arylC$_1$–C$_6$alkyloxyC$_1$–C$_6$-alkyl, NR$_7$R$_8$, C$_1$–C$_6$alkylaminoC$_1$–C$_6$alkyl, arylC$_1$–C$_6$alkylaminoC$_1$–C$_6$alkyl, di(arylC$_1$–C$_6$alkyl)aminoC$_1$–C$_6$alkyl, C$_1$–C$_6$alkylcarbonyl, C$_1$–C$_6$alkylcarbonylC$_1$–C$_6$alkyl, arylC$_1$–C$_6$alkylcarbonyl, arylC$_1$–C$_6$alkylcarbonylC$_1$–C$_6$alkyl, C$_1$–C$_6$alkylcarboxyC$_1$–C$_6$alkyl, arylcarboxyC$_1$–C$_6$alkyl, arylC$_1$–C$_6$alkylcarboxyC$_1$–C$_6$alkyl, C$_1$–C$_6$alkylcarbonylamino, -carbonylNR$_8$C$_1$–C$_6$alkylCOR$_{10}$, wherein R$_{10}$ is NR$_7$R$_8$, or C$_1$–C$_6$alkylNR$_7$R$_8$, arylC1–C$_6$alkylcarbonylamino, arylC$_1$–C$_6$alkylcarbonylaminoC$_1$–C$_6$alkyl, CONR$_7$R$_8$, or arylaminocarbonylaminoC$_1$–C$_6$alkyl; wherein the alkyl and aryl groups are optionally substituted as defined below;

R$_7$ and R$_9$ are are independently a saturated or partially saturated cyclic 5, 6 or 7 membered amine, imide or lactam or are independently selected from hydrogen, C$_1$–C$_6$alkyl, aryl, arylC$_1$–C$_6$alkyl, C$_1$–C$_6$alkylcarbonyl, C$_1$–C$_6$alkylcarboxy or arylC$_1$–C$_6$alkylcarboxy wherein the alkyl and aryl groups are optionally substituted as defined below; or R$_7$ and R$_8$ together with the nitrogen to which they are attached form a saturated, partially saturated or aromatic monocyclic, bicyclic or tricyclic ring system containing from 3 to 14 carbon atoms and from 0 to 3 additional heteroatoms selected from nitrogen, oxygen or sulphur, wherein the ring system is optionally substituted with at least one C$_1$–C$_6$alkyl, aryl, arylC$_1$–C$_6$alkyl, hydroxy, C$_1$–C$_6$alkyloxy, C$_1$–C$_6$-alkyloxyC$_1$–C$_6$alkyl, C$_1$–C$_6$alkyl-aminoC$_1$–C$_6$alkyl or NR$_{11}$R$_{12}$, wherein R$_{11}$ and R$_{12}$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy; wherein the alkyl and aryl groups are optionally substituted as defined below;

wherein the optionally substituted alkyl groups are substituted with one or more groups independently selected from halo, cyano, nitro, trihalomethyl, carbamoyl, hydroxy, oxo, COOR$_3$, C$_1$–C$_6$alkyl, C$_1$–C$_6$alkyloxy, aryloxy, arylC$_1$–C$_6$alkyloxy, C$_1$–C$_6$alkylamino arylamino, arylC$_1$–C$_6$alkylamino, di(arylC$_1$–C$_6$alkyl)amino, C$_1$–C$_6$alkylcarbonyl, arylC$_1$–C$_6$alkylcarbonyl, C$_1$–C$_6$alkylcarboxy, arylcarboxy, arylC$_1$–C$_6$alkylcarbonyl, C$_1$–C$_6$alkylcarbonylamino, —C$_1$–C$_6$alkylaminoCOR$_{13}$, wherein R$_{13}$ is C$_1$–C$_6$alkyl, aryl, arylC$_1$–C$_6$alkyl, C$_1$–C$_6$alkyloxy, aryloxy, arylC$_1$–C$_6$alkyloxy; arylC$_1$–C$_6$alkylcarbonylamino tetrahydrofuranyl, morpholinyl piperazinyl, or a saturated or partially saturated cyclic 5, 6 or 7 membered amine, imide or lactam, and wherein the optionally substituted aryl groups are substituted with a group selected from halo, nitro, cyano, trihalomethyl, C$_1$–C$_6$alkyl, aryl, arylC$_1$–C$_6$alkyl, hydroxy, C$_1$–C$_6$alkyloxy, C$_1$–C$_6$alkyloxyC$_1$–C$_6$alkyl, aryloxy, arylC$_1$–C$_6$alkyloxy, arylC$_1$–C$_6$alkyloxyC$_1$–C$_6$alkyl, C$_1$–C$_6$alkylamino, C$_1$–C$_6$alkylaminoC$_1$–C$_6$alkyl, arylamino, arylC$_1$–C$_6$alkylamino, arylC$_1$–C$_6$alkylaminoC$_1$–C$_6$alkyl, di(arylC$_1$–C$_6$alkyl)aminoC$_1$–C$_6$alkyl, C$_1$–C$_6$alkylamino, arylC$_1$–C$_6$alkylcarbonylC$_1$–C$_6$alkyl, arylC$_1$–C$_6$alkylcarbonyl, arylC$_1$–C$_6$alkylcarbonylC$_1$–C$_6$alkyl, C$_1$–C$_6$alkylcarboxy, C$_1$–C$_6$alkylcarboxyC$_1$–C$_6$alkyl, arylC$_1$–C$_6$alkylcarboxy, arylC$_1$–C$_6$alkylcarboxyC$_1$–C$_6$alkyl, C$_1$–C$_6$alkylcarbonylamino, C$_1$–C$_6$alkylcarbonylaminoC$_1$–C$_6$alkyl, arylC$_1$–C$_6$alkylcarbonylamino, or arylC$_1$–C$_6$-alkylcarbonylaminoC$_1$–C$_6$alkyl;

or a salt thereof with a pharmaceutically acceptable acid or base, or any optical isomer or mixture of optical isomers, a racemic mixture, or any tautomeric form, or prodrug thereof.

2. The compound according to claim 1, wherein R$_1$ is COOH, COOC$_1$–C$_6$alkyl, COOarylC$_1$–C$_6$-alkyl, COOC$_1$–C$_6$alkylcarbonyloxyC$_1$–C$_6$alkyl or COOC$_1$–C$_6$alkylcarbonyloxyarylC$_1$–C$_6$alkyl.

3. The compound according to claim 1, wherein n and m are 1.

4. The compound according to claim 1, wherein Y is oxygen.

5. The compound according to claim 1, wherein R$_4$ and R$_6$ are hydrogen.

6. The compound according to claim 1, wherein R$_6$ is C$_1$–C$_6$alkylNR$_7$R$_8$.

7. The compound according to claim 6, wherein R$_7$ is hydrogen and R$_8$ is arylC$_1$–C$_6$alkyl.

8. The compound according to claim 7, wherein the aryl group is pyridyl.

9. The compound according to claim 7, wherein the aryl group is phenyl optionally substituted with methoxy or CH$_3$(CO).

10. The compound according to claim 1, wherein R$_6$ is arylaminocarbonylaminoC$_1$–C$_6$alkyl.

11. The compound according to claim 1, wherein R$_6$ is aryloxyC$_1$–C$_6$alkyl.

12. The compound according to claim 11, wherein the aryl group is 1,1-dioxo-benzo[d]isothiazol-3-yl.

13. The compound according to claim 11, wherein the aryl group is 1,1-dioxo-5-phenyl-isothiazol-3-yl.

14. The compound according to claim 11, wherein the aryl group is benzo[1,3]dioxol-5-yl.

15. The compound according to claim 11, wherein the aryl group is 5-methoxy-2-methyl-1H-indol-3-yl.

16. A composition comprising an effective amount of a compound of claim 1, together with one or more pharmaceutically acceptable carriers or diluents and an insulin sensitizer.

17. A composition comprising an effective amount of a compound of claim 1, together with one or more pharmaceutically acceptable carriers or diluents and an agent stimulating insulin release from β cells.

18. A composition comprising a compound of claim 1, together with one or more pharmaceutically acceptable carriers or diluents and an antiobesity agent.

19. A composition according to claim 16, wherein the insulin sensitizer is a thiazolidinedione or a pharmaceutically acceptable salt thereof.

20. A composition according to claim 16, wherein the insulin sensitizer is selected from troglitazone, ciglitazone, pioglitazone, rosiglitazone, 5-[4-[3-Methyl-oxo-3,4-dihydro-2-quinazolinyl]methoxy]phenyl-methyl]thiazolidine-2, 4-dione and 3-[4-[2-Phenoxazin-10-yl)ethoxy]phenyl]-2-ethoxypropanoic acid or a pharmaceutically acceptable salt thereof.

21. A composition according to claim 16, wherein the insulin sensitizer is (–) 3-[4-[2-Phenoxazin-10-yl)ethoxy]phenyl]-2-ethoxypropanoic acid or a pharmaceutically acceptable salt thereof.

22. A composition according to claim 17, wherein the agent stimulating insulin release from P cells is repaglinide.

23. A composition according to claim 18, wherein the antiobesity agent is orlistat.

24. A compound of Formula 1

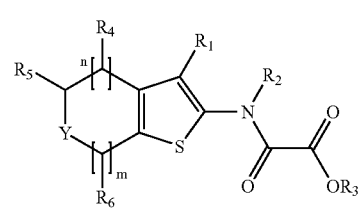

Formula 1 wherein
n is 1 or 2;
m is 1 or 2;
Y is O, S, SO or SO$_2$;
R$_1$ is COOH, COOC$_1$–C$_6$alkyl, COOarylC$_1$–C$_6$alkyl, COOC$_1$–C$_6$alkylcarbonyloxyC$_1$–C$_6$alkyl, COOC$_1$–C$_6$alkylcarbonyloxyarylC$_1$–C$_6$alkyl;
R$_2$ is hydrogen;
R$_3$ is hydrogen, C$_1$–C$_6$alkyl, arylC$_1$–C$_6$alkyl, C$_1$–C$_6$alkylcarbonyloxyC$_1$–C$_6$alkyl or C$_1$–C$_6$alkylcarbonyloxyarylC$_1$–C$_6$alkyl;
R$_4$ is hydrogen, C$_1$–C$_6$alkyl, aryl, arylC$_1$–C$_6$alkyl, provided R$_4$ does not represent a heterocyclic ring; wherein the alkyl and aryl groups are optionally substituted as defined below;
R$_5$ is C$_6$alkylNR$_7$R$_8$ wherein R$_7$ and R$_8$ together with the nitrogen to which they are attached form a saturated, partially saturated or aromatic monocyclic, bicyclic or tricyclic ring system selected from the group consisting of pyrrolopyrazine, pyrrolopyridine, benzo[d]isoxazole, 1,1-dioxo-1,3-dihydro-benzo[d]isothiazole, pyrrolidine and 1,3-dihydro-benzo[d]isothiazole substituted with two oxo groups at the atom positions adjacent to the nitrogen atom, wherein the ring system is optionally be substituted with at least one $C_1$–$C_6$alkyl, aryl, arylC$_1$–C$_6$alkyl, COOR$_3$, hydroxy, nitro, oxo, C$_1$–C$_6$alkyloxy, arylC$_1$–C$_6$alkyloxy, C$_1$–C$_6$alkyloxyC$_1$–C$_6$alkyl, C$_1$–C$_6$alkylaminoC$_1$–C$_6$alkyl or NR$_9$R$_{10}$, wherein R$_9$ and R$_{10}$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy; wherein the alkyl and aryl groups are optionally substituted as defined below;

wherein the optionally substituted alkyl groups are substituted with one or more groups independently selected from halo, cyano, nitro, trihalomethyl, carbamoyl, hydroxy, oxo, C$_1$–C$_6$alkyl, C$_1$–C$_6$alkyloxy, aryloxy, arylC$_1$–C$_6$alkyloxy, C$_1$–C$_6$alkylamino, arylamino, arylC$_1$–C$_6$alkylamino, di(arylC$_1$–C$_6$alkyl)amino, C$_1$–C$_6$alkylcarbonyl, arylC$_1$–C$_6$alkylcarbonyl, C$_1$–C$_6$alkylcarboxy, arylcarboxy, arylC$_1$–C$_6$alkylcarboxy, C$_1$–C$_6$alkylcarbonylamino, —C$_1$–C$_6$alkylaminoCOR$_{13}$, wherein R$_{13}$ is C$_1$–C$_6$alkyl, aryl, arylC$_1$–C$_6$alkyl, C$_1$–C$_6$alkyloxy, aryloxy, arylC$_1$–C$_6$alkyloxy; arylC$_1$–C$_6$alkylcarbonylamino, tetrahydrofuranyl, morpholinyl, piperazinyl, or a saturated or partially saturated cyclic 5, 6, or 7 membered amine, imide or lactam, and wherein the optionally substituted aryl group is substituted with a group selected from halo, nitro, cyano, trihalomethyl, C$_1$–C$_6$alkyl, aryl, arylC$_1$–C$_6$alkyl, hydroxy, COOR$_3$, C$_1$–C$_6$alkyloxy, C$_1$–C$_6$alkyloxyC$_1$–C$_6$alkyl, aryloxy, arylC$_1$–C$_6$alkyloxy, arylC$_1$–C$_6$alkyloxyC$_1$– C$_6$alkyl, C$_1$–C$_6$alkylamino, C$_1$–C$_6$alkylaminoC$_1$–C$_6$alkyl, arylamino, arylC$_1$–C$_6$alkylamino, arylC$_1$–C$_6$alkylaminoC$_1$–C$_6$alkyl, di(arylC$_1$–C$_6$alkyl)aminoC$_1$–C$_6$alkyl, C$_1$–C$_6$alkylcarbonyl, C$_1$–C$_6$alkylcarbonylC$_1$–C$_6$alkyl, arylC$_1$–C$_6$alkylcarbonyl, arylC$_1$–C$_6$alkylcarbonylC$_1$–C$_6$alkyl, C$_1$–C$_6$alkylcarboxy, C$_1$–C$_6$alkylcarboxyC$_1$–C$_6$alkyl, arylC$_1$–C$_6$alkylcarboxy, arylC$_1$–C$_6$alkylcarboxyC$_1$–C$_6$alkyl, carboxyC$_1$–C$_6$alkyloxy, C$_1$–C$_6$alkylcarbonylamino, C$_6$alkylaminoCOR$_{13}$, wherein R$_{13}$ is C$_1$–C$_6$alkyl, aryl, arylC$_1$–C$_6$alkyl, C$_1$–C$_6$alkyloxy, aryloxy, arylC$_1$–C$_6$alkyloxy; arylC$_1$–C$_6$alkylcarbonylamino or, arylC$_1$–C$_6$alkylcarbonylaminoC$_1$–C$_6$alkyl;

R$_6$ is hydrogen;

or a salt thereof with a pharmaceutically acceptable acid or base, or any optical isomer or mixture of optical isomers, a racemic mixture, or any tautomeric form, or prodrug thereof.

25. The compound according to claim 24, wherein the ring system is 1,3-dihydro-benzo[d]isothiazolyl, substituted with 2 oxo groups at the atom positions adjacent to the nitrogen atom.

26. The compound according to claim 24, wherein the ring system is thiazolidin-2,4-dione.

27. The compound according to claim 24, wherein the ring system is 5-(aryl-methyl)-thiazolidin-2,4-dione.

28. The compound according to claim 24, wherein the ring system is pyrrolo[3,4-b]pyridine-5,7-dione.

29. The compound according to claim 24, wherein the ring system is pyrrolo[3,4-b]pyridine-1,3-dione.

30. The compound according to claim 24, wherein the ring system is pyrrolo[3,4-b]pyrazine-5,7-dione.

31. A composition comprising an effective amount of a compound of claim 24, together with one or more pharmaceutically acceptable carriers or diluents and an insulin sensitizer.

32. A composition comprising an effective amount of a compound of claim 24, together with one or more pharmaceutically acceptable carriers or diluents and an agent stimulating insulin release from β cells.

33. A composition comprising a compound of claim 24, together with one or more pharmaceutically acceptable carriers or diluents and an antiobesity agent.

34. A composition according to claim 31, wherein the insulin sensitizer is a thiazolidinedione or a pharmaceutically acceptable salt thereof.

35. A composition according to claim 31, wherein the insulin sensitizer is selected from troglitazone, ciglitazone, pioglitazone, rosiglitazone, 5-[4-[3-Methyl-4-oxo-3,4-dihydro-2-quinazolinyl]methoxy]phenyl-methyl]thiazolidine-2, 4-dione and 3-[4-[2-Phenoxazin-10-yl)ethoxy]phenyl]-2-ethoxypropanoic acid or a pharmaceutically acceptable salt thereof.

36. A composition according to claim 31, wherein the insulin sensitizer is (−) 3-[4-[2-Phenoxazin-10-yl)ethoxy] phenyl]-2-ethoxypropanoic acid or a pharmaceutically acceptable salt thereof.

37. A composition according to claim 32, wherein the agent stimulating insulin release from β cells is repaglinide.

38. A composition according to claim 33, wherein the antiobesity agent is orlistat.

39. A compound of Formula 1

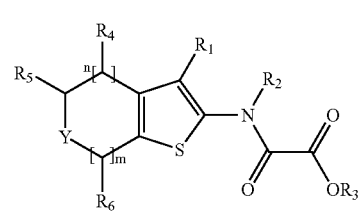

Formula 1 wherein n is 1 or 2;

m is 1 or 2;

Y is O, S, SO or SO$_2$;

R$_1$ is COOH, COOC$_1$–C$_6$alkyl, COOarylC$_1$–C$_6$alkyl, COOC$_1$–C$_6$alkylcarbonylC$_1$–C$_6$alkyl, COOC$_1$–C$_6$alkylcarbonyloxyarylC$_1$–C$_6$alkyl;

R$_2$ is hydrogen;

R$_3$ is hydrogen, C$_1$–C$_6$alkyl, arylC$_1$–C$_6$alkyl, C$_1$–C$_6$alkylcarbonyloxyC$_1$–C$_6$alkyl or C$_1$–C$_6$alkylcarbonyloxyarylC$_1$–C$_6$alkyl;

R$_4$ is hydrogen, C$_1$–C$_6$alkyl, aryl, aryl C$_1$–C$_6$alkyl, provided R$_1$ does not represent a heterocyclic group; wherein the alkyl and aryl groups are optionally substituted as defined below;

R$_5$ is C$_1$–C$_6$alkylNR$_7$R$_8$ wherein R$_7$ and R$_8$ together with the nitrogen to which they are attached form isoindol wherein the ring system is optionally be substituted with at least one C$_1$–C$_6$alkyl, aryl, arylC$_1$–C$_6$alkyl, fluoro, hydroxy, oxo, C$_1$–C$_6$alkyloxy, arylC$_1$–C$_6$alkyloxy, C$_1$–C$_6$-alkyloxyC$_1$–C$_6$alkyl, C$_1$–C$_6$alkylamino-C$_1$–C$_6$alkyl or NR$_9$R$_{10}$, wherein R$_9$ and R$_{10}$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy; wherein the alkyl and aryl groups are optionally substituted as defined below or optionally substituted with one chloro or six chloros;

wherein the optionally substituted alkyl groups are substituted with one or more groups independently selected from halo, cyano, nitro, trihalomethyl, carbamoyl, hydroxy, oxo, COOR$_3$, C$_1$–C$_6$alkyl, C$_1$–C$_6$alkyloxy, aryloxy, arylC$_1$–C$_6$alkyloxy, C$_1$–C$_6$alkylamino, arylamino arylC$_1$–C$_6$alkylamino, di(arylC$_1$–C$_6$alkyl)amino, C$_1$–C$_6$alkylcarbonyl, arylC$_1$–C$_6$-alkylcarbonyl, C$_1$–C$_6$alkylcarboxy, arylcarboxy, arylC$_1$–C$_6$alkylcarboxy, C$_1$–C$_6$alkylcarbonylamino, C$_1$–C$_6$alkylaminoCOR$_{12}$C$_6$alkylaminoCOR$_{13}$, wherein R$_{13}$ is C$_1$–C$_6$alkyl, aryl, arylC$_1$–C$_6$alkyl, C$_1$–C$_6$alkyloxy, aryloxy, arylC$_1$–C$_6$alkyloxy; arylC$_1$–C$_6$alkylcarbonylamino, tetrahydrofuranyl, morpholinyl, piperazinyl, or a saturated or partially saturated cyclic 5, 6 or 7 membered amine, imide or lactam, and wherein the optionally substituted aryl group is substituted with a group selected from halo, nitro, cyano, trihalomethyl, C$_1$–C$_6$alkyl, aryl, arylC$_1$–C$_6$alkyl, hydroxy, COOR$_3$, C$_1$–C$_6$alkyloxy, C$_1$–C$_6$alkyloxyC$_1$–C$_6$alkyl, aryloxy, arylC$_1$–C$_6$alkyloxy, arylC$_1$–C$_6$alkyloxyC$_1$–C$_6$alkyl, C$_1$–C$_6$alkylthio, arylC$_1$–C$_6$alkylthio, NR$_7$R$_8$, C$_1$–C$_6$alkylamino, C$_1$–C$_6$alkylaminoC$_1$–C$_6$alkyl, arylamino, arylC$_1$–C$_6$alkylamino, arylC$_1$–C$_6$alkylaminoC$_1$–C$_6$alkyl, di(arylC$_1$–C$_6$alkyl)aminoC$_1$–C$_6$alkyl, C$_1$–C$_6$alkylcarbonyl, C$_1$–C$_6$alkylcarbonylC$_1$–C$_6$alkyl, arylC$_1$–C$_6$alkylcarbonyl, arylC$_1$–C$_6$alkylcarbonylC$_1$–C$_6$alkyl, C$_1$–C$_6$alkylcarboxy, C$_1$–C$_6$alkylcarboxyC$_1$–C$_6$alkyl, arylC$_1$–C$_6$alkylcarboxy, arylC$_1$–C$_6$alkylcarboxyC$_1$–C$_6$alkyl, carboxyC$_1$–C$_6$-alkyloxy, C$_1$–C$_6$alkylcarbonylamino, C$_1$–C$_6$alkylcarbonylaminoC$_1$–C$_6$alkyl, -carbonylNR$_7$C$_1$–C$_6$alkylCOR$_{11}$, wherein R$_{11}$ is C$_1$–C$_6$alkyl, aryl, arylC$_1$–C$_6$alkyl, C$_1$–C$_6$alkyloxy, aryloxy, arylC$_1$–C$_6$alkyloxy; arylC$_1$–C$_6$alkylcarbonylamino, arylC$_1$–C$_6$-alkylcarbonylaminoC$_1$–C$_6$alkyl;

R$_6$ is hydrogen;

or a salt thereof with a pharmaceutically acceptable acid or base, or any optical isomer or mixture of optical isomers, a racemic mixture, or any tautomeric form, or prodrug thereof.

40. The compound of claim 39, wherein the ring system is optionally substituted with hydroxy, nitro, methoxy, benzyloxy, fluoro, chloro CH$_3$CH$_2$CH$_2$NHC(O)- or CH$_3$C(O)NH.

41. A composition comprising an effective amount of a compound of claim 39, together with one or more pharmaceutically acceptable carriers or diluents and an insulin sensitizer.

42. A composition comprising an effective amount of a compound of claim 39, together with one or more pharmaceutically acceptable carriers or diluents and an agent stimulating insulin release from β cells.

43. A composition comprising a compound of claim 39, together with one or more pharmaceutically acceptable carriers or diluents and an antiobesity agent.

44. A composition according to claim 41, wherein the insulin sensitizer is a thiazolidinedione or a pharmaceutically acceptable salt thereof.

45. A composition according to claim 41, wherein the insulin sensitizer is selected from troglitazone, ciglitazone, pioglitazone, rosiglitazone, 5-[4-[3-Methyl-4-oxo-3,4-dihydro-2-quinazolinyl]methoxy]phenyl-methyl]thiazolidine-2,4-dione and 3-[4-[2-Phenoxazin-10-yl)ethoxy]phenyl]-2-ethoxypropanoic acid or a pharmaceutically acceptable salt thereof.

46. A composition according to claim 41, where the insulin sensitizer is (−) 3-[4-[2-Phenoxazin-10-yl)-ethoxy] phenyl]-2-ethoxypropanoic acid or a pharmaceutically acceptable salt thereof.

47. A composition according to claim 42, wherein the agent stimulating insulin release from βcells is repaglinide.

48. A composition according to claim 43, wherein the antiobesity agent is orlistat.

49. A compound of Formula I

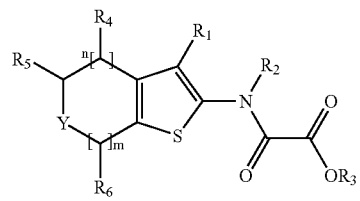

Formula 1 wherein n is 1 or 2;

m is 1 or 2;

Y is O, S, SO or SO$_2$;

R$_1$ is COOH, COOC$_1$–C$_6$alkyl, COOarylC$_1$–C$_6$alkyl, COOC$_1$–C$_6$alkylcarbonyloxyC$_1$–C$_6$alkyl, COOC$_1$–C$_6$alkylcarbonyloxyarylC$_1$–C$_6$alkyl;

R$_2$ is hydrogen;

R$_3$ is hydrogen, C$_1$–C$_6$alkyl, arylC$_1$–C$_6$alkyl, C$_1$–C$_6$alkylcarbonyloxyC$_1$–C$_6$alkyl or C$_1$–C$_6$alkylcarbonyloxyarylC$_1$–C$_6$alkyl;

R$_4$ is hydrogen, C$_1$–C$_6$alkyl, aryl, arylC$_1$–C$_6$alkyl, provided R$_4$ does not represent a heterocycle ring; wherein the alkyl and aryl groups are optionally substituted as defined below;

R$_5$ is C$_1$–C$_6$alkylNR$_7$R$_8$ or arylC$_1$–C$_6$alkylcarbonylaminoC$_1$–C$_6$alkyl, wherein the alkyl and aryl groups are optionally substituted as defined below;

R$_6$ is hydrogen, trihalomethyl, C$_1$–C$_6$alkyl, aryl, arylC$_1$–C$_6$alkyl, hydroxy, oxo, carboxy, carboxyC$_1$–C$_6$alkyl, C$_1$–C$_6$alkyloxycarbonyl, aryloxycarbonyl, arylC$_1$–C$_6$alkyloxycarbonyl, C$_1$–C$_6$alkyloxyC$_1$–C$_6$alkyl, aryloxyC$_1$–C$_6$alkyl, arylC$_1$–C$_6$alkyloxyC$_1$–C$_6$alkyl, NR$_7$R$_8$, C$_1$–C$_6$alkylaminoC$_1$–C$_6$alkyl, arylC$_1$–C$_6$alkylaminoC$_1$–C$_6$alkyl, di(arylC$_1$–C$_6$alkyl)aminoC$_1$–C$_6$alkyl, C$_1$–C$_6$alkylcarbonyl, C$_1$–C$_6$alkylcarbonyl, C$_6$alkyl, arylC$_1$–C$_6$alkylcarbonyl, arylC$_1$–C$_6$-alkylcarbonylC$_1$–C$_6$alkyl, C$_1$–C$_6$alkylcarboxyC$_1$–C$_6$alkyl, arylcarbonylC$_1$–C$_6$alkyl, arylC$_1$–C$_6$alkylcarboxyC$_1$–C$_6$alkyl, C$_1$–C$_6$alkylcarbonylamino, C$_1$–C$_6$alkylcarbonylaminoC$_1$–C$_6$alkyl, carbonylNR$_8$C$_1$–C$_6$alkylCOR$_{13}$, wherein R$_{13}$ is NR$_7$R$_8$, or C$_1$–C$_6$alkylNR$_7$R$_8$, arylC$_1$–C$_6$alkylcarbonylamino, arylC$_1$–C$_6$alkylcarbonylaminoC$_1$–C$_6$alkyl, CONR$_7$R$_8$, C$_1$–C$_6$alkylCONR$_7$R$_8$ or arylaminocarbonylaminoC$_1$–C$_6$alkyl; wherein the alkyl and aryl groups are optionally substituted as defined below;

111

R₇ and R₈ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein the alkyl and aryl groups are optionally substituted as defined below; or R₇ and R₈ are independently a saturated or partially saturated cyclic 5, 6 or 7 membered amine, imide or lactam;

wherein the optionally substituted alkyl groups are substituted with one or more groups independently selected from halo, cyano, nitro, trihalomethyl, carbamoyl, hydroxy, oxo, COOR₃, $C_1$–$C_6$alkyloxy, aryloxy, aryl$C_1$–$C_6$alkyloxy, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$alkylcarbonyl, $C_1$–$C_6$alkyl-carboxy, arylcarboxy, aryl$C_1$–$C_6$alkylcarboxy, $C_1$–$C_6$alkylcarbonylamino, —$C_1$–$C_6$alkylaminoCOR₁₃, wherein R₁₃ is $C_1$–$C_6$alkyl, aryl, aryl$C_1$–$C_6$alkyl, $C_1$–$C_6$alkyloxy, aryloxy, aryl$C_1$–$C_6$alkyloxy, aryl$C_1$–$C_6$alkylcarbonylamino, tetrahydrofuranyl, morpholinyl, piperazinyl, or a saturated or partially saturated cyclic 5, 6, or 7 membered amine, imide or lactam; and wherein the optionally substituted aryl group is substituted with a group selected from halo, nitro cyano, trihalomethyl, $C_1$–$C_6$alkyl, aryl, aryl$C_1$–$C_6$alkyl, hydroxy, COOR₃, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, $C_1$–$C_6$alkylthio, arylthio, aryl$C_1$–$C_6$alkylthio, $C_1$–$C_6$-alkylamino, $C_1$–$C_6$alkylamino$C_1$–$C_6$alkyl, arylamino, aryl$C_1$–$C_6$alkylamino, aryl$C_1$–$C_6$-alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, aryl$C_1$–$C_6$alkylcarboxy, $C_1$–$C_6$alkylcarbonylamino, $C_1$–$C_6$alkylcarbonylamino$C_1$–$C_6$alkyl, aryl$C_1$–$C_6$alkylcarbonylamino, aryl$C_1$–$C_6$-alkylcarbonylamino$C_1$–$C_6$alkyl;

or a salt thereof with a pharmaceutically acceptable acid or base, or any optical isomer or mixture of optical isomers, a racemic mixture, or any tautomeric form, or prodrug thereof.

50. The compound according to claim 40, wherein R₁ is COOH, COOC₁–C₆alkyl, COOarylC₁–C₆alkyl, COOC₁–C₆alkylcarbonyloxyC₁–C₆alkyl, COOC₁–C₆alkylcarbonyloxyarylC₁–C₆alkyl.

51. The compound according to claim 49, wherein n and m are 1.

52. The compound according to claim 49, wherein Y is oxygen.

53. The compound according to claim 49, wherein R₄ and R₆ are hydrogen.

54. The compound according to claim 49, wherein 16 is C₁–C₆alkylNR₇R₈.

55. The compound according to claim 54, wherein R₇ is hydrogen and R₅ is arylC₁–C₆alkyl.

56. The compound according to claim 55, wherein the aryl group is pyridyl.

57. The compound according to claim 55, wherein the aryl group is phenyl optionally substituted with methoxy or CH₃C(O).

58. The compound according to claim 49, wherein R₆ is arylaminocarbonylaminoC₁–C₆alkyl.

59. The compound according to claim 49, wherein R₆ is aryloxyC₁–C₆alkyl.

60. The compound according to claim 59, wherein the aryl group is 1,1-dioxo-benzo[d]isothiazol-3-yl.

61. The compound according to claim 59, wherein the aryl group is 1,1-dioxo-5-phenyl-isothiazol-3-yl.

62. The compound according to claim 59, wherein the aryl group is benzo[1,3]dioxol-5-yl.

63. The compound according to claim 59, wherein the aryl group is 5-methoxy-2-methyl-1H-indol-3-yl.

64. A composition comprising an effective amount of a compound of claim 49, together with one or more pharmaceutically acceptable carriers or diluents and an insulin sensitizer.

65. A composition comprising an effective amount of a compound of claim 49, together with one or more pharmaceutically acceptable carriers or diluents and an agent stimulating insulin release from β cells.

66. A composition comprising a compound of claim 49, together with one or more pharmaceutically acceptable carriers or diluents and an antiobesity agent.

67. A composition according to claim 64, wherein the insulin sensitizer is a thiazolidinedione or a pharmaceutically acceptable salt thereof.

68. A composition according to claim 64, wherein the insulin sensitizer is selected from troglitazone, ciglitazone, pioglitazone, rosiglitazone, 5-[[4-[3-Methyl-4-oxo-3,4-dihydro-2-quinazolinyl]methoxy]phenyl-methyl]thiazolidine-2,4-dione and 3-[4-[2-Phenoxazin-10-yl)ethoxy]phenyl]-2-ethoxypropanoic acid or a pharmaceutically acceptable salt thereof.

69. A composition according to claim 64, wherein the insulin sensitizer is (–) 3-[4-[2-Phenoxazin-10-yl)ethoxy]phenyl]-2-ethoxypropanoic acid or a pharmaceutically acceptable salt thereof.

70. A composition according to claim 65, wherein the agent stimulating insulin release from β cells is repaglinide.

71. A composition according to claim 66, wherein the antiobesity agent is orlistat.

72. A compound which acts as an inhibitor of Protein Tyrosine Phosphatases selected from the group consisting of
2-(Oxalyl-amino)(1,1,3-trioxo-1,3-dihydro-1H-benzo[d]isothiazol-2-ylmethyl)-4,7-dihydro-5H-thieno[2,3-c]pyran carboxylic acid;
5-(4-Chloro-1, 3-dioxo-1,3-dihydro-isoindol-2-yl-methyl)-2-(oxalyl-amino)-4,7-dihydro-5H-thieno[2,3-c]pyran-3-carboxylic acid;
5-(4,5,6,7-Tetrachloro-1,3-dioxo-1,3-dihydro-isoindol-2-ylmethyl)-2-(oxalyl-amino)-4,7-dihydro-5H-thieno[2,3-c]pyran-3-carboxylic acid;
5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;
5-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;
5-(4-Benzyloxy-1,3-dioxo-1,3-dihydro-isoindol-2-ylmethyl)-2-(oxalyl-amino)-4,7-dihydro-5H-thieno[2,3-c]pyran-3-carboxylic acid;
5-(4-Fluoro-1,3-dioxo-1,3-dihydro-isoindol-2-ylmethyl)-2-(oxalyl-amino)-4,7-dihydro-5H-thieno[2,3-c]pyran-3-carboxylic acid;
5-(1,3-Dioxo-1,3-dihydro-benzo[f]isoindol-2-ylmethyl)-2-(oxalyl-amino)-4,7-dihydro-5H-thieno[2,3-c]pyran-3-carboxylic acid;
5-(5-Acetylamino-1,3-dioxo-1,3-dihydro-isoindol-2-ylmethyl)-2-(oxalyl-amino)-4,7-dihydro-5H-thieno[2,3-c]pyran-3-carboxylic acid;
5-(4-Acetylamino-1,3-dioxo-1,3-dihydro-isoindol-2-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-b]pyrazin-6-ylmethyl)-2-(oxalyl-amino)-4,7-dihydro-5H-thieno[2,3-c]pyran-3-carboxylic acid;

7-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid;

5-(5-Nitro-1,3-dioxo-1,3-dihydro-isoindol-2-ylmethyl)-2-(oxalyl-amino)-4,7-dihydro-5H-thieno[2,3-c]pyran-3-carboxylic acid;

5-(5-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Methoxy-1,3-dioxo-1,3-dihydro-isoindol-2-ylmethyl)(oxalyl-amino)-4,7-dihydro-5H-thieno[2,3-c]pyran-3-carboxylic acid;

5-(4-Nitro-1,3-dioxo-1,3-dihydro-isoindol-2-ylmethyl)-2-(oxalyl-amino)-4,7-dihydro-5H-thieno[2,3-c]pyran-3-carboxylic acid;

5-(4-(4-Chloro-phenylsulfanyl)-6-methyl-1,3-dioxo-1,3-dihydro-pyrrolo[3,4-c]pyridin-2-ylmethyl)-2-(oxalyl-amino)-4,7-dihydro-5H-thieno[2,3-c]pyran-3-carboxylic acid;

5-(3-imidazol-1-yl-2,5-dioxo-pyrrolidin-1-ylmethyl)-2-(oxalyl-amino)-4,7-dihydro-5H-thieno[2,3-c]pyran-3-carboxylic acid;

Oxalic acid 3-carboxy-2-(oxalyl-amino)-4,7-dihydro-5H-thieno[2,3-c]pyran-5-ylmethyl ester methyl;

Oxalic acid (3-carboxy-2-(oxalyl-amino)-4,7-dihydro-5H-thieno[2,3-c] 5-ylmethyl) ester, 7-Hydroxymethyl-2-(oxalyl-amino)-4,7-dihydro-5H-thieno[2,3-c]pyran-3-carboxylic acid;

7-(2,4-Dioxo-thiazolidin-3-ylmethyl)-2-(oxalyl-amino)-4,7-dihydro-5H-thieno[2,3-c]pyran-3 carboxylic acid;

7-(1,3-Dioxo-1,3-dihydro-isoindol-2-yloxymethyl)-2-oxalyl-amino)-4,7-dihydro-5H-thieno[2,3-c]pyran-3-carboxylic acid;

7-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

5-(5-Methoxy-1,3-dioxo-1,3-dihydro-isoindol-2-ylmethyl)-2-(oxalyl-amino)-4,7-dihydro-5H-thieno[2,3-c]pyran-3 carboxylic acid;

7-(5,7-Dioxo-5,7-dihydro-[1,3]dioxolo[4,5-f]isoindol-6-ylmethyl)-2-oxalyl-amino)-4,7-dihydro-5H-thieno[2,3-c]pyran-3-carboxylic acid;

7-(((Benzo[1,3]dioxole carbonyl)amino)ethyl oxalyl-amino)-4,7-dihydro-5H-thieno[2,3-c]pyran-3-carboxylic acid;

7-(3-(2,4-Dimethoxy-phenyl)ureidomethyl)-2-(oxalyl-amino)-4,7-dihydro-5H-thieno[2,3-c]pyran-3-carboxylic acid;

2-(Oxalyl-amino)-5-phenylcarbamoyl-4,7-dihydro-5H-thieno[2,3-c]pyran-3-carboxylic acid;

5-Benzylcarbamoyl-2-(oxalyl-amino)-4,7-dihydro-5H-thieno[2,3-c]pyran-3-carboxylic acid;

2-(Oxalyl-amino)-4,7-dihydro-5H-thieno[2,3-c]pyran-3,7-dicarboxylic acid 7-ethyl ester;

7-Benzylcarbamoyl-2-(oxalyl-amino)-4,7-dihydro-5H-thieno[2,3-c]pyran-3-carboxylic acid;

7-((2-(4-Methanesulfonyl-phenyl)-acetylamino)-methyl)-2-(Oxalyl-amino)-4,7-dihydro-5H-thieno[2,3-c]pyran-3-carboxylic acid;

2-(3-Carboxy-2-(oxalyl-amino)-4,7-dihydro-5H-thieno[2,3-c]pyran-5-ylmethyl)-carbamoyl)nicotinic acid;

7-(2,4-Dioxo-5-pyridin-2-ylmethylene-thiazolidin-3-yl-methyl)-2-oxalyl amino)-4,7-dihydro-5H-thieno[2,3-c]pyran-3-carboxylic acid;

7-(2,4-Dioxo-5-pyridin-2-ylmethylene-thiazolidin-3-yl-methyl)-2-(oxalyl-amino)-4,7-dihydro-5H-thieno[2,3-c]pyridin-3-carboxylic acid;

7-(5-(4-Methoxy-benzylidene)-2,4-dioxo-thiazolidin-3-ylmethyl)-2-(oxalyl-amino)-4,7-dihydro-5H-thieno[2,3-c]pyran-3-carboxylic acid;

7-(5-(4-Acetylamino-benzylidene)-2,4-dioxo-thiazolidin-3-ylmethyl)-2-(oxalyl-amino)-4,7-dihydro-5H-thieno[2,3-c]pyran-3-carboxylic acid;

7-(5-(3,5-Dimethoxy-benzylidene)-2,4-dioxo-thiazolidin-3-ylmethyl)-2-(oxalyl-amino)-4,7-dihydro-5H-thieno[2,3-c]pyran-3-carboxylic acid;

7-[5-(1H-Imidazol-4(5)-ylmethylene)-2,4-dioxo-thiazolidin-3-ylmethyl]-2-(oxalyl-amino)-4,7-dihydro-5H-thieno[2,3-c]pyran-3-carboxylic acid;

5-(1,3-Dioxo-4,7-epoxido-1,3,4,5,6,7-hexahydro-isoindol-2-ylmethyl)-2-(oxalyl-amino)-4,7-dihydro-5H-thieno[2,3-c]pyran-3-carboxylic acid;

7-(((2R) Amino-3-phenyl-propionylamino)methyl)-2-(oxalyl-amino)-4,7-dihydro-5H-thieno[2,3-c]pyran-3-carboxylic acid;

7-((2-Acetylamino-3-(4-hydroxy-phenyl)-propionylamino)methyl)-2-(oxalyl-amino)-4,7-dihydro-5H-thieno[2,3-c]pyran-3-carboxylic acid;

7-((2-Acetylamino-3-methyl-butyrylamino)methyl)-3-(oxalyl-amino)-4,7-dihydro-5H-thieno[2,3-c]pyran-3-carboxylic acid;

2-(Oxalyl-amino)-7-(1,1,3-trioxo-1,3-dihydro-1H-benzo[d]isothiazol-2-ylmethyl)-4,7-dihydro-5H-thieno[2,3-c]pyran-3-carboxylic acid;

2-(Oxalyl-amino)-7-(1,1,3-trioxo-1,3-dihydro-1H-benzo[d]isothiazol-3-yloxomethyl)-4,7-dihydro-5H-thieno[2,3-c]pyran-3-carboxylic acid;

2-(Oxalyl-amino)-7-(3-oxo-3H-benzo[d]isoxazol-2-ylmethyl)-4,7-dihydro-5H-thieno[2,3-c]pyran-3-carboxylic acid;

2-(Oxalyl-amino)-7-(1,1,3-trioxo-5-phenyl-1,3-dihydro-isothiazol-2-ylmethyl)-4,7-dihydro-5H-thieno[2,3-c]pyran-3-carboxylic acid;

7-(1,1-Dioxo-5-phenyl-1H-isothiazol-3-yloxymethyl)-2-(oxalyl-amino)-4,7-dihydro-5H-thieno[2,3-c]pyran-3-carboxylic acid;

2-(Oxalyl-amino)-5-(1,1,3-trioxo-5-phenyl-1,3-dihydro-isothiazol-2-ylmethyl)-4,7-dihydro-5H-thieno[2,3-c]pyran-3-carboxylic acid;

5-(1,1-Dioxo-5-phenyl-1H-isothiazol-3-yloxymethyl)-2-(oxalyl-amino)-4,7-dihydro-5H-thieno[2,3-c]pyran-3-carboxylic acid;

5-(6-Chloro-1,1,3-trioxo-2,3-dihydro-4H-thieno[3,2-e]-1,2,4-thiadiazin-2-ylmethyl)-2-(oxalyl-amino)-4,7-dihydro-5H-thieno[3,2-c]pyran-3-carboxylic acid;

5-(6-Chloro-1,1-dioxo-4H-thieno[3,2-e]-1,2,4-thiadiazine-3-yloxymethyl)-2-(oxalyl-amino)-4,7-dihydro-5H-thieno[2,3-c]pyran carboxylic acid;

7-(1,3-Dioxo-1,3-dihydro-benzo[d]isothiazol-2-ylmethyl)-2-(oxalyl-amino)-4,7-dihydro-5H-thieno[2,3-c]pyran carboxylic acid;

5-(1,3-Dioxo-1,3-dihydro-benzo[d]isothiazol-2-ylmethyl)-2-(oxalyl-amino)-4,7-dihydro-5H-thieno[2,3-c]pyran-3-carboxylic acid;

5-(5-Benzyl-1,1-dioxo-[1,2,5]thiadiazolidin-2-ylmethyl)-2-(oxalyl-amino)-4,7-dihydro-5H-thieno[2,3-c]pyran-3-carboxylic acid;

5-(5-Ethyl-1,1-dioxo-[1,2,5]thiadiazolidin-2-ylmethyl)-2-(oxalyl-amino)-4,7-dihydro-5H-thieno[2,3-c]pyran-3-carboxylic acid;

2-(Oxalyl-amino)-7-(1-oxo-1,3-dihydro-isoindol-2-ylmethyl)-4,7-dihydro-5H-thieno[2,3-c]pyran-3-carboxylic acid;

2-(Oxalyl-amino)-5-(2,2,2-trifluoro-acetoxymethyl)-4,7-dihydro-5H-thieno[2,3-c]pyran-3-carboxylic acid;

5-(((Benzo[1,3]dioxol-5-ylmethyl)-amino)methyl)-2-(oxalyl-amino)-4,7-dihydro-5H-thieno[2,3-c]pyran-3-carboxylic acid;

5-((2-Methoxy-benzylamino)methyl)-2-(oxalyl-amino)-4,7-dihydro-5H-thieno[2,3-c]pyran-3-carboxylic acid;

5-((2-Benzo[1 3]dioxol yl-acetylamino)methyl)-2-(oxalyl-amino)-4,7-dihydro-5H-thieno[2,3-c]pyran-3-carboxylic acid;

5-(((5-Methoxy-2-methyl-1H-indol-3-carbonyl)amino)methyl)-2-(oxalyl-amino)-4,7-dihydro-5H-thieno[2,3-c]pyran-3-carboxylic acid;

5-(1,3-Dioxo-5-propylcarbamoyl-1,3-dihydro-isoindol-2-ylmethyl)-2-(oxalyl-amino)-4,7-dihydro-5H-thieno[2,3-c]pyran-3-carboxylic acid;

or a salt thereof with a pharmaceutically acceptable acid or base, or any optical isomer or mixture of optical isomers, including a racemic mixture, or any tautomeric form, or prodrug thereof.

73. A compound of Formula I

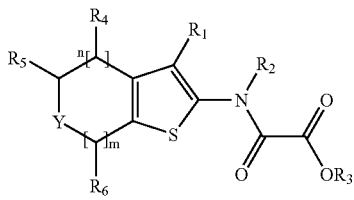

Formula 1 wherein
n is 1 or 2;
m is 1 or 2;
Y is O, S, SO or $SO_2$;
$R_1$ is COOH, $COOC_1$–$C_6$alkyl, $COOC_1$–$C_6$alkylcarbonyloxyC_1$–$C_6$alkyl, $COOC_1$–$C_6$alkylcarbonyloxyarylC_1$–$C_6$alkyl;

$R_2$ is hydrogen;

$R_3$ is hydrogen, $C_1$–$C_6$alkyl, arylC_1$–$C_6$alkyl, $C_1$–$C_6$alkylcarbonyloxyC_1$–$C_6$alkyl or $C_1$–$C_6$alkylcarbonyloxyarylC_1$–$C_6$alkyl;

$R_4$ is hydrogen, $C_1$–$C_6$alkyl, aryl, arylC_1$–$C_6$alkyl, provided $R_4$ does not represent a heterocyclic ring; wherein the alkyl and aryl groups are optionally substituted as defined below;

$R_5$, is hydrogen, trihalomethyl, $C_1$–$C_6$alkyl, aryl, arylC_1$–$C_6$alkyl, $C_1$–$C_6$alkyloxycarbonyl, aryloxycarbonyl, arylC_1$–$C_6$alkyloxycarbonyl, $C_1$–$C_6$alkyloxy, $C_1$–$C_6$alkyloxyC_1$–$C_6$alkyl, aryloxyC_1$–$C_6$alkyl, arylC_1$–$C_6$alkyloxyC_1$–$C_6$-alkyl, $NR_7R_8$, $C_1$–$C_6$alkylaminoC_1$–$C_6$alkyl, arylC_1$–$C_6$alkylaminoC_1$–$C_6$alkyl, di(arylC_1$–$C_6$alkyl)aminoC_1$–$C_6$alkyl, $C_1$–$C_6$alkylcarbonyl, $C_1$–$C_6$alkylcarbonylC_1$–$C_6$alkyl, arylC_1$–$C_6$alkylcarbonyl, arylC_1$–$C_6$alkylcarbonylC_1$–$C_6$alkyl, $C_1$–$C_6$alkylcarboxyC_1$–$C_6$alkyl, arylcarboxyC_1$–$C_6$alkyl, arylC_1$–$C_6$alkylcarboxyC_1$–$C_6$alkyl, $C_1$–$C_6$alkylcarbonylamino, $C_1$–$C_6$alkylcarbonylaminoC_1$–$C_6$alkyl, -carbonylNR_8C_1$–$C_6$alkylCOR_{10}$, wherein $R_{10}$ is $NR_7R_8$, or $C_1$–$C_6$alkylNR_7R_8$, arylC_1$–$C_6$alkylcarbonylamino, arylC_1$–$C_6$alkylcarbonylaminoC_1$–$C_6$alkyl, $CONR_7R_8$, $C_1$–$C_6$alkylCONR_7R_8$ or arylaminocarbonylaminoC_1$–$C_6$alkyl, provided $R_5$ does not represent a heterocylic ring; wherein the alkyl and aryl groups are optionally substituted as defined below and;

$R_6$ is trihalomethyl, $C_1$–$C_6$alkyl, aryl, arylC_1$–$C_6$alkyl, $C_1$–$C_6$alkyloxycarbonyl, aryloxycarbonyl, arylC_1$–$C_6$alkyloxycarbonyl, $C_1$–$C_6$alkyloxy, $C_1$–$C_6$alkyloxyC_1$–$C_6$alkyl, aryloxyC_1$–$C_6$alkyl, arylC_1$–$C_6$alkyloxyC_1$–$C_6$-alkyl, $NR_7R_8$, $C_1$–$C_6$alkylaminoC_1$–$C_6$alkyl, arylC_1$–$C_6$alkylaminoC_1$–$C_6$alkyl, di(arylC_1$–$C_6$alkyl)aminoC_1$–$C_6$alkyl, $C_1$–$C_6$alkylcarbonyl, $C_1$–$C_6$alkylcarbonylC_1$–$C_6$alkyl, arylC_1$–$C_6$alkylcarbonyl, arylC_1$–$C_6$alkylcarbonylC_1$–$C_6$alkyl, $C_1$–$C_6$alkylcarboxyC_1$–$C_6$alkyl, arylcarboxyC_1$–$C_6$alkyl, arylC_1$–$C_6$alkylcarboxyC_1$–$C_6$alkyl, $C_1$–$C_6$alkylcarbonylamino, carbonylNR_8C_1$–$C_6$alkylCOR_{10}$, wherein $R_{10}$ is $NR_7R_8$, or $C_1$–$C_6$alkylNR_7R_8$, arylC_1$–$C_6$alkylcarbonylamino, arylC_1$–$C_6$alkylcarbonylaminoC_1$–$C_6$alkyl, $CONR_7R_8$, or arylaminocarbonylaminoC_1$–$C_6$alkyl; wherein the alkyl and aryl groups are optionally substituted as defined below and;

$R_7$ and $R_8$ are independently selected from hydrogen, $C_1$–$C_6$alkyl, aryl, arylC_1$–$C_6$alkyl, $C_1$–$C_6$alkylcarbonyl, $C_1$–$C_6$alkylcarboxy or arylC_1$–$C_6$alkylcarboxy, a saturated or partially saturated cyclic 5, 6 or 7 membered amine, imide or lactam, or $R_7$ and $R_8$ together with the nitrogen to which they are attached form a saturated, partially saturated or aromatic monocyclic, bicyclic or tricyclic ring system containing from 3 to 14 carbon atoms and from 0 to 3 additional heteroatoms selected from nitrogen, oxygen or sulphur, wherein the ring system is optionally substituted with at least one $C_1$–$C_6$alkyl, aryl, arylC_1$–$C_6$alkyl, hydroxy, $C_1$–$C_6$alkyloxy, $C_1$–$C_6$-alkyloxyC_1$–$C_6$alkyl, $C_1$–$C_6$alkyl-aminoC_1$–$C_6$alkyl or $NR_{11}R_{12}$, wherein $R_{11}$ and $R_{12}$ are independently selected from hydrogen, $C_1$–$C_6$alkyl, aryl, arylC_1$–$C_6$alkyl, $C_1$–$C_6$alkylcarbonyl, arylcarbonyl, arylC_1$–$C_6$alkylcarbonyl, $C_1$–$C_6$alkylcarboxy or arylC_1$–$C_6$alkylcarboxy; wherein the alkyl and aryl groups are optionally substituted as defined below, wherein the optionally substituted alkyl groups are substituted with one or more groups independently selected from halo, cyano, nitro, trihalomethyl, carbamoyl, hydroxy, oxo, $COOR_3$, $C_1$–$C_6$alkyl, $C_1$–$C_6$alkyloxy, aryloxy, arylC_1$–$C_6$alkyloxy, $C_1$–$C_6$alkylamino, arylamino, arylC_1$–$C_6$alkylamino, di(arylC_1$–$C_6$alkyl)amino, $C_1$–$C_6$alkylcarbonyl, arylC_1$–$C_6$alkylcarbonyl, $C_1$–$C_6$alkylcarboxy, arylcarboxy, arylC_1$–$C_6$alkylcarboxy, $C_1$–$C_6$alkylcarbonylamino, —$C_1$–$C_6$alkylaminoCOR_{13}$, wherein $R_{13}$ is $C_1$–$C_6$alkyl, aryl, arylC_1$–$C_6$alkyl, $C_1$–$C_6$alkyloxy, aryloxy, arylC_1$–$C_6$alkyloxy, arylC_1$–$C_6$alkylcarbonylamino, tetrahydrofuranyl, morpholinyl, piperazinyl, or a saturated or partially saturated cyclic 5, 6 or 7 membered amine, imide or lactam;
and wherein the optionally substituted aryl group is substituted with a group selected from halo, nitro, cyano, trihalomethyl, $C_1$–$C_6$alkyl, aryl, aryl$C_1$–$C_6$alkyl, hydroxy, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, $C_1$–$C_6$alkylamino, $C_1$–$C_6$alkylamino$C_1$–$C_6$alkyl, arylamino, aryl$C_1$–$C_6$alkylamino, aryl$C_1$–$C_6$alkylamino$C_1$–$C_6$alkyl, di(aryl$C_1$–$C_6$alkylcarbonyl, aryl$C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$alkyl, aryl$C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, aryl$C_1$–$C_6$alkylcarbonylamino, aryl$C_1$–$C_6$alkylcarbonylamino$C_1$–$C_6$alkyl;

or a salt thereof with a pharmaceutically acceptable acid or base, or any optical isomer or mixture of optical isomers, a racemic mixture, or any tautomeric form, or prodrug thereof.

74. A compound of Formula I

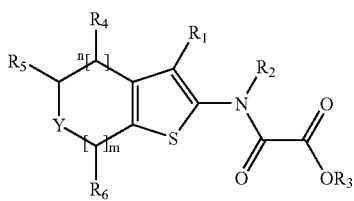

Formula 1 wherein
n is 1 or 2;
m is 1 or 2;
Y is O, S, SO or $SO_2$;
$R_1$ is COOH, COO$C_1$–$C_6$alkyl, COOaryl$C_1$–$C_6$alkyl, COO$C_1$–$C_6$alkylcarbonyloxy$C_1$–$C_6$alkyl, COO$C_1$–$C_6$alkylcarbonyloxyaryl$C_1$–$C_6$alkyl;
$R_2$ is hydrogen;
$R_3$ is hydrogen, $C_1$–$C_6$alkyl, aryl$C_1$–$C_6$alkyl, $C_1$–$C_6$alkylcarbonyloxy$C_1$–$C_6$alkyl or $C_1$–$C_6$alkylcarbonyloxyaryl$C_1$–$C_6$alkyl;
$R_4$ is hydrogen, $C_1$–$C_6$alkyl, aryl, aryl$C_1$–$C_6$alkyl, provided $R_4$ does not represent a heterocyclic ring; wherein the alkyl and aryl groups are optionally substituted as defined below;
$R_5$, is trihalomethyl, $C_1$–$C_6$alkyl, aryl, aryl$C_1$–$C_6$alkyl, $C_1$–$C_6$alkyloxycarbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy$C_1$–$C_6$alkyl, aryl$C_1$–$C_6$alkyloxy$C_1$–$C_6$-alkyl, $NR_7R_8$, $C_1$–$C_6$alkylamino$C_1$–$C_6$alkyl, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy$C_1$–$C_6$alkyl, arylcarboxy$C_1$–$C_6$alkyl, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, -carbonyl$NR_8C_1$–$C_6$alkylCOR$_{10}$, wherein $R_{10}$ is $NR_7R_8$, or $C_1$–$C_6$alkyl$NR_7R_8$, aryl$C_1$–$C_6$alkylcarbonylamino, aryl$C_1$–$C_6$alkylcarbonylamino$C_1$–$C_6$alkyl, $CONR_7R_8$, $C_1$–$C_6$alkyl$CONR_7R_8$ or arylaminocarbonylamino$C_1$–$C_6$alkyl, provided $R_5$ does not represent a heterocyclic ring; wherein the alkyl and aryl groups are optionally substituted as defined below and;
$R_6$ is hydrogen, trihalomethyl, $C_1$–$C_6$alkyl, aryl, aryl$C_1$–$C_6$alkyl, $C_1$–$C_6$alkyloxycarbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy$C_1$–$C_6$alkyl, aryl$C_1$–$C_6$alkyloxy$C_1$–$C_6$-alkyl, $NR_7R_8$, $C_1$–$C_6$alkylamino$C_1$–$C_6$alkyl, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy$C_1$–$C_6$alkyl, arylcarboxy$C_1$–$C_6$alkyl, aryl$C_1$–$C_6$alkylcarboxy$C_1$–$C_6$alkyl, $C_1$–$C_6$alkylcarbonylamino, carbonyl$NR_8C_1$–$C_6$alkylCOR$_{10}$, wherein $R_{10}$ is $NR_7R_8$, or $C_1$–$C_6$alkyl$NR_7R_8$, aryl$C_1$–$C_6$alkylcarbonylamino, aryl$C_1$–$C_6$alkylcarbonylamino$C_1$–$C_6$alkyl, $CONR_7R_8$, or arylaminocarbonylamino$C_1$–$C_6$alkyl; wherein the alkyl and aryl groups are optionally substituted as defined below and;
$R_7$ and $R_8$ are independently selected from hydrogen, $C_1$–$C_6$alkyl, aryl, aryl$C_1$–$C_6$alkyl, $C_1$–$C_6$alkylcarbonyl, $C_1$–$C_6$alkylcarboxy or aryl$C_1$–$C_6$alkylcarboxy, a saturated or partially saturated cyclic 5, 6 or 7 membered amine, imide or lactam, or
$R_7$ and R % together with the nitrogen to which they are attached form a saturated, partially saturated or aromatic monocyclic, bicyclic or tricyclic ring system containing from 3 to 14 carbon atoms and from 0 to 3 additional heteroatoms selected from nitrogen, oxygen or sulphur, wherein the ring system is optionally substituted with at least one $C_1$–$C_6$alkyl, aryl, aryl$C_1$–$C_6$alkyl, hydroxy, $C_1$–$C_6$alkyloxy, $C_1$–$C_6$-alkyloxy$C_1$–$C_6$alkyl, $C_1$–$C_6$alkyl-amino$C_1$–$C_6$alkyl or $NR_{11}R_{12}$, wherein the $R_{11}$ and $R_{12}$ are independently selected from hydrogen, $C_1$–$C_6$alkyl or $NR_{11}R_{12}$, wherein $R_{11}$ and $R_{12}$ are independently selected from hydrogen, $C_1$–$C_6$alkylcarboxy or aryl$C_1$–$C_6$alkylcarboxy; wherein the alkyl and aryl groups are optionally substituted as defined below;
wherein the optionally substituted alkyl groups are substituted with one or more groups independently selected from halo, cyano, nitro, trihalomethyl, carbamoyl, hydroxy, oxo, $COOR_3$, $C_1$–$C_6$alkyl, $C_1$–$C_6$alkyloxy, aryloxy, aryl$C_1$–$C_6$alkyloxy, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$alkylcarbonyl, $C_1$–$C_6$alkylcarboxy, arylcarboxy, aryl$C_1$–$C_6$alkylcarboxy, $C_1$–$C_6$alkylcarbonylamino, —$C_1$– $C_6$alkylaminoCOR$_{13}$, wherein $R_{13}$ is $C_1$–$C_6$alkyl, aryl, aryl$C_1$–$C_6$alkyl, $C_1$–$C_6$alkyloxy, aryloxy, aryl$C_1$–$C_6$alkyloxy, aryl$C_1$–$C_6$alkylcarbonylamino, tetrahydrofuranyl, morpholinyl, piperazinyl, or a selected or partially saturated cyclic 5, 6 or 7 membered amine, imide or lactam;
and wherein the optionally substituted aryl group is substituted with a group selected from halo, nitro, cyano, trihalomethyl, $C_1$–$C_6$alkyl, aryl, aryl$C_1$–$C_6$alkyl, hydroxy, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, $C_1$–$C_6$alkylamino, $C_1$–$C_6$alkylamino$C_1$–$C_6$alkyl, arylamino, aryl$C_1$–$C_6$alkylamino, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$alkyl, aryl$C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, aryl$C_1$–$C_6$alkylcarbonylamino, aryl$C_1$–$C_6$alkylcarbonylamino$C_1$–$C_6$alkyl;

or a salt thereof with a pharmaceutically acceptable acid or base, or any optical isomer or mixture of optical isomers, a racemic mixture, or any tautomeric form, or prodrug thereof.

\* \* \* \* \*